(12) United States Patent
Mezes et al.

(10) Patent No.: US 6,329,507 B1
(45) Date of Patent: Dec. 11, 2001

(54) DIMER AND MULTIMER FORMS OF SINGLE CHAIN POLYPEPTIDES

(75) Inventors: Peter S. Mezes; Ruth A. Richard; Joseph A. Affholter; Nicolas J. Kotite, all of Midland, MI (US)

(73) Assignee: The Dow Chemical Company, Midland, MI (US)

(*) Notice: Subject to any disclaimer, the term of this patent is extended or adjusted under 35 U.S.C. 154(b) by 0 days.

(21) Appl. No.: 07/935,695

(22) Filed: Aug. 21, 1992

(51) Int. Cl.$^7$ .................................................. C12P 21/08
(52) U.S. Cl. .................. 530/387.3; 536/23.1; 435/320.1
(58) Field of Search ............................ 530/387.3, 387.1; 435/320.1, 69.1; 536/23.1

(56) References Cited

U.S. PATENT DOCUMENTS

| | | | |
|---|---|---|---|
| 4,474,893 | 10/1984 | Reading et al. | 436/547 |
| 4,642,334 | 2/1987 | Moore et al. | 530/388 |
| 4,714,681 | 12/1987 | Reading | 435/240.27 |
| 4,946,778 | 8/1990 | Ladner et al. | 435/69.6 |
| 5,130,297 | 7/1992 | Sharma et al. | 514/8 |
| 5,132,405 | 7/1992 | Huston et al. | 530/387.3 |

FOREIGN PATENT DOCUMENTS

8809344 * 12/1988 (WO).

OTHER PUBLICATIONS

Rodwell et al. Biotechnology vol. 3 1985 889.*
Walmann Science vol. 252. 1657 1991.*
Hird et al Genes and Cancer p. 183, 1990.*
SheeR et. al. Cancer Research 48, 6811–6818 Dec. 1988.*
Pantolianoet. al. Biochemistry 1991 30, 10117–10125.*
Huston et al., "Protein Engineering of Antibody Binding Sites: Recovery of Specific Activity in an Anti–digoxin Single–Chain Fv Analogue Produced in *Escherichia coli*", *Proc. Natl. Acad. Sci., Biochemistry*, vol. 85, pp. 5879–5883, Aug. 1988.
Larson, "Improved Tumor Targeting With Radiolabeled Recombinant, Single–Chain, Antigen–Binding Protein", *Journal of the National Cancer Institute*, vol. 82, No. 14, pp. 1173–1174, Jul. 18, 1990.
Colcher et al., In Vivo Tumor Targeting of a Recombinant Single–Chain Antigen–Binding Protein, *Journal of the National Cancer Institute*, vol. 82, No. 14, pp. 1191–1197, Jul. 18, 1990.
Bedzyk et al., "Immunological and Structural Characterization of a High Affinity Anti–fluorescein Single–chain Antibody", *The Journal of Biological Chemistry*, V. 265, No. 30, pp. 18615–18620, Oct. 25, 1990.
Winter et al., "Man–made Antibodies", *Nature*, vol. 349, pp. 293–299, Jan. 24, 1991.
Davis, "Single Chain Antibody (SCA) Encoding Genes: One–Step Construction and Expression in Eukaryotic Cells", *Biotechnology*, vol. 9, pp. 165–169, Feb. 1991.

Whitlow et al., "Single–Chain Fv Proteins and Their Fusion Proteins", *Methods: A Companion to METHODS in Enzymology*, vol. 2, No. 2, pp. 97–105, Apr. 1991.
Skerra et al., "The Functional Expression of Antibody $F_v$ Fragments in *Escherichia coli*: Improved Vectors and a Generally Applicable Purification Technique", *Biotechnology*, vol. 9, pp. 273–278, Mar. 1991.
Gibbs et al., "Construction and Characterization of a Single–Chain Catalytic Antibody", *Proc. Natl. Acad. Sci., U.S.A.*, vol. 88, pp. 4001–4004, May 1991.
Hodgson, "Making Monoclonals in Microbes", *Biotechnology*, vol. 9, pp. 421–425, May 1991.
Pluckthun, "Antibody Engineering: Advances From the Use of *Escherichia coli* Expression Systems", *Biotechnology*, vol. 9, pp. 545–550, Jun. 1991.
Bird et al., "Single Chain Antibody Variable Regions", *Trends in Biotechnology*, vol. 9, pp. 132–137 (1991).
Glockshuber et al., "A Comparison of Strategies to Stabilize Immunoglobulin $F_v$–Fragments", *Biochemistry*, vol. 29, pp. 1362–1367 (1990).
Denzin et al., "Single–chain Site–specific Mutations of Fluorescein–Amino Acid Contact Residues in High Affinity Monoclonal Antibody 4–4–20", *Journal of Biological Chemistry*, vol. 266, No. 21, pp. 14095–14103 (1991).
Pantoliano et al., "Conformational Stability, Folding, and Ligand–Binding Affinity of Single–Chain Fv Immunoglobulin Fragments Expressed in *Escherichia coli*", *Biochemistry*, vol. 30, pp. 10117–10125 (1991).
Gregoire et al., "Engineered Secreted T–Cell Receptor $\alpha\beta$ Heterodimers", *Proc. Natl. Acad., Sci., U.S.A.*, vol. 88, pp. 8077–8081, Sep. 1991.
Pack et al., "Miniantibodies: Use of Amphipathic Helices to Produce Functional, Flexibly Linked Dimeric $F_v$ Fragments with High Avidity in *Escherichia coli*", *Biochemistry*, vol. 31, No. 6, pp. 1579–1584 (1992).
Soo Hoo et al., "Characterization of a Single–chain T–cell Receptor Expressed in *Escherichia coli*", *Proc. Natl. Acad. Sci., U.S.A.*, vol. 89, pp. 4759–4763, May 1992.
Novotny et al., "A Soluble, Single–chain T–cell Receptor Fragment Endowed With Antigen–combining Properties", *Proc. Natl. Acad. Sci., U.S.A.*, vol. 88, pp. 8646–8650, Oct. 1991.
Williams et al., "The Immunoglobulin Superfamily–Domains for Cell Surface Recognition", *Ann. Rev. Immunol.*, vol. 6, pp. 381–405 (1988).

(List continued on next page.)

*Primary Examiner*—Sheela Huff
(74) *Attorney, Agent, or Firm*—Mark S. Scott; Karen L. Kimble

(57) ABSTRACT

The present invention discloses novel proteins which are dimers and multimers of single chain polypeptides. The single chain polypeptides having two domains derived from the immunoglobulin superfamily which are joined by a peptide linker. The dimers and multimers being formed by non-covalent linking of the single chain polypeptides.

18 Claims, 73 Drawing Sheets

OTHER PUBLICATIONS

Williams et al., "Structural Diversity in Domains of the Immunoglobulin Superfamily", Cold *Spring Harbor Symposia on Quantitative Biology*, *LIV*, pp. 637–647, 1989, Cold Spring Harbor Lab. Press.

Hunkapiller et al., "Implications of the Diversity of the Immunoglobulin Gene Superfamily", *Cold Spring Harbor Symposia on Quantitative Biology*, LIV, 1989, pp. 15–29, Cold Spring Harbor Laboratory Press.

Wraith et al., "T–cell Recognition as the Target for Immune Intervention in Autoimmune Disease", *Cell*, vol. 57, pp. 709–715, Jun. 2, 1989.

Adorini, et al., "New Perspectives on Immunointervention in Autoimmune Diseases", *Immunology Today*, vol. 11, No. 11, pp. 383–386 (1990).

Bird et al., "Single–Chain Antigen–Binding Proteins", *Science*, vol. 242, pp. 423–426, Oct. 21, 1988.

Skerra et. al., "Assembly of a Functional Immunoglobulin $F_v$ Fragment in *Escherichia coli*", *Science*, vol. 240, pp. 1038–1041, May 20, 1988.

Takkinen et al., "An Active Single–Chain Antibody Containing a Cellulase Linker Domain is Secreted by *Escherichia coli*", *Protein Engineering*, vol. 4, No. 7, pp. 837–841 (1991).

Traunecker et al., "Bispecific Single Chain Molecules (Janusins) Target Cytotoxic Lymphocytes on HIV Infected Cells", *The EMBO Journal*, vol. 10, No. 12, pp. 3655–3659 (1991).

\* cited by examiner

CONSTRUCTION OF PLASMID pSCFV31

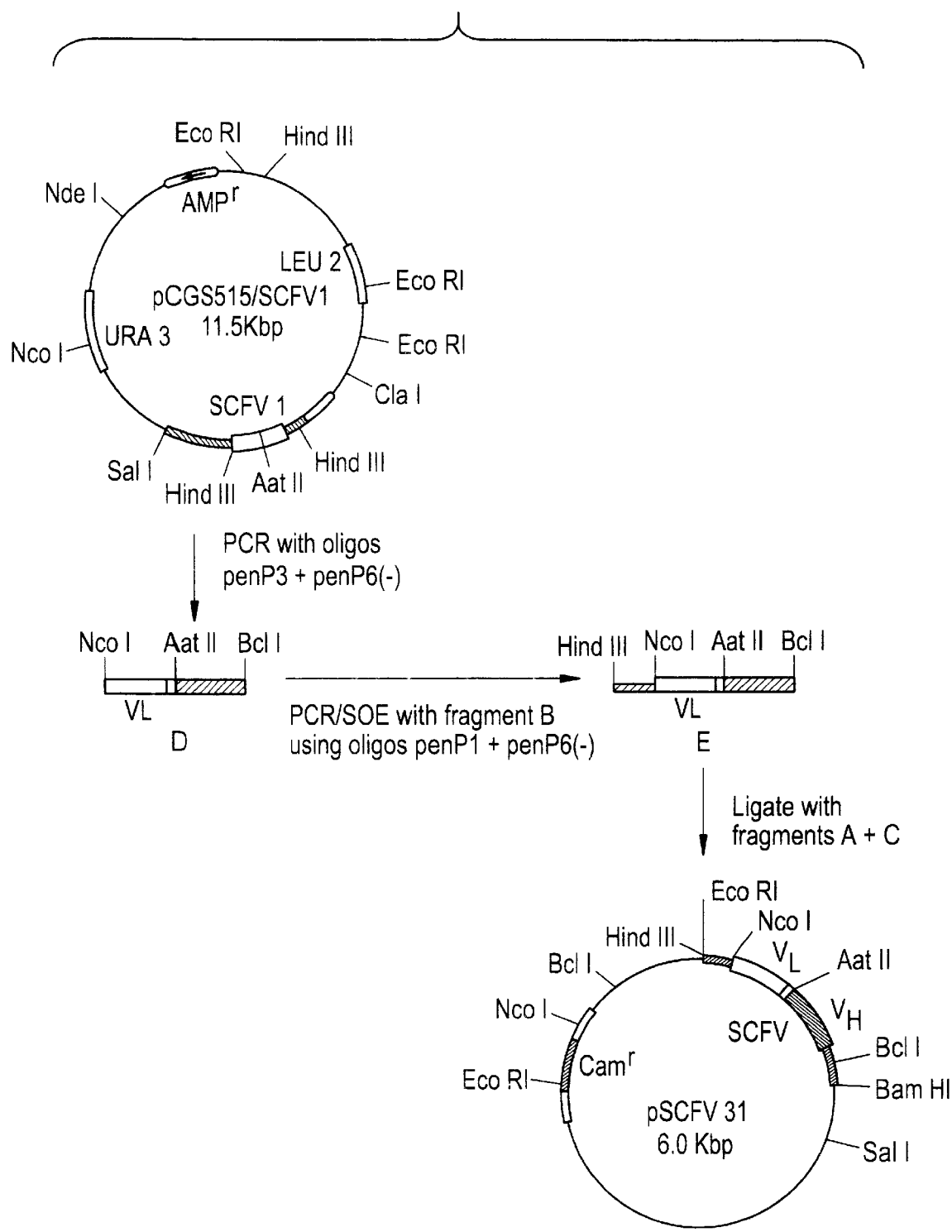

FIG. 3A

```
                                              Met Leu
              AAAAACTAT AAGCTCCATG ATG CTT

Leu Gln Ala Phe Leu Phe Leu Leu Ala
TTG CAA GCT TTC CTT TTC CTT TTG GCT

Gly Phe Ala Ala Lys Ile Ser Ala Asp
GGT TTT GCA GCC AAA ATA TCT GCA GAC

Ile Val Met Thr Gln Ser Pro Asp Ser
ATC GTG ATG ACC CAG TCT CCA GAC TCC

Leu Ala Val Ser Leu Gly Glu Arg Ala
CTG GCT GTG TCT CTG GGC GAG AGG GCC
                         |←――――――――CDR1L ―――
Thr Ile Asn Cys |Lys Ser Ser Gln Ser
ACC ATC AAC TGC |AAG TCC AGC TGC AAG

Val Leu Tyr Ser Ser Asn Asn Lys Asn
GTT TTA TAC AGC TCC AAC AAT AAG AAC
―――――――――――――→|
Tyr Leu Ala |Trp Tyr Gln Gln Lys Pro
TAC TTA GCT |TGG TAC CAG CAG AAA CCA

Gly Gln Pro Pro Lys Leu Leu Ile Tyr
GGA CAG CCT CCT AAG CTG CTC ATT TAC
|←――――――――CDR2L――――――――→|
|Trp Ala Ser Thr Arg Glu Ser| Gly Val
|TGG GCA TCT ACC CGG GAA TCC| GGG GTC

Pro Asp Arg Phe Ser Gly Ser Gly Ser
CCT GAC CGA TTC AGT GGC AGC GGG TCT
```

FIG. 3B

```
Gly Thr Asp Phe Thr Leu Thr Ile Ser
GGG ACA GAT TTC ACT CTC ACC ATC AGC

Ser Leu Gln Ala Glu Asp Val Ala Val
AGC CTG CAG GCT GAA GAT GTG GCA GTT
                 ←―――――――――CDR3L―――――――――
Tyr Tyr Cys |Gln Gln Tyr Tyr Ser Tyr
TAT TAC TGT |CAG CAA TAT TAT AGT TAT
―――――――――→
Pro Leu Thr |Phe Gly Gly Gly Thr Lys
CCT CTC ACT |TTC GGC GGA GGG ACC AAG

Val |Lys Glu Ser Gly Ser Val Ser Ser
GTG |AAG GAG TCA GGT TCG GTC TCC TCA
    ―――――――LINKER―――――――――――――――――
Glu Gln Leu Ala Gln Phe Arg Ser Leu
GAA CAA TTG GCC CAA TTT CGT TCC TTA
―――→
Asp |Val Gln Leu Gln Gln Ser Asp Ala
GAC |GTC CAG TTG CAG CAG TCT GAC GCT

Glu Leu Val Gly Pro Gly Ala Ser Val
GAG TTG GTG AAA CCT GGG GCT TCA GTG

Lys Ile Ser Cys Lys Ala Ser Gly Tyr
AAG ATT TCC TGC AAG GCT TCT GGC TAC
                 ←―――――――CDR1H―――――――→
Thr Phe Thr |Asp His Ala Ile His |Trp
ACC TTC ACT |GAC CAT GCA ATT CAC |TGG

Val Lys Gln Asn Pro Glu Gln Gly Leu
GTG AAA CAG AAC CCT GAA CAG GGC CTG
```

FIG.3C

```
                        |←——————————————————————————
Glu Trp Ile |Gly Tyr Phe Ser Pro Gly
GAA TGG ATT |GGA TAT TTT TCT CCC GGA
—————————————CDR2H ———————————————————
Asn Asp Asp Phe Lys Tyr Asn Glu Arg
AAT GAT GAT TTT AAA TAC AAT GAG AGG
——————————————→|
Phe Lys Gly |Lys Ala Thr Leu Thr Ala
TTC AAG GGC |AAG GCC ACA CTG ACT GCA

Asp Lys Ser Ser Ser Thr Ala Tyr Val
GAC AAA TCC TCC AGC ACT GCC TAC GTG

Gln Leu Asn Ser Leu Thr Ser Glu Asp
CAG CTC AAC AGC CTG ACA TCT GAG GAT
                                    |←———
Ser Ala Val Tyr Phe Cys Thr Arg |Ser
TCT GCA GTG TAT TTC TGT ACA AGA |TCC
————CDR3H ——————→|
Leu Asn Met Ala Tyr |Trp Gly Gln Gly
CTG AAT ATG GCC TAC |TGG GGT CAA GGA

Thr Ser Val Thr Val Ser
ACC TCA GTC ACC GTC TCC TAG TGA

AGCTTGGAAC ACCACACAAA CCATATCCAA A
```

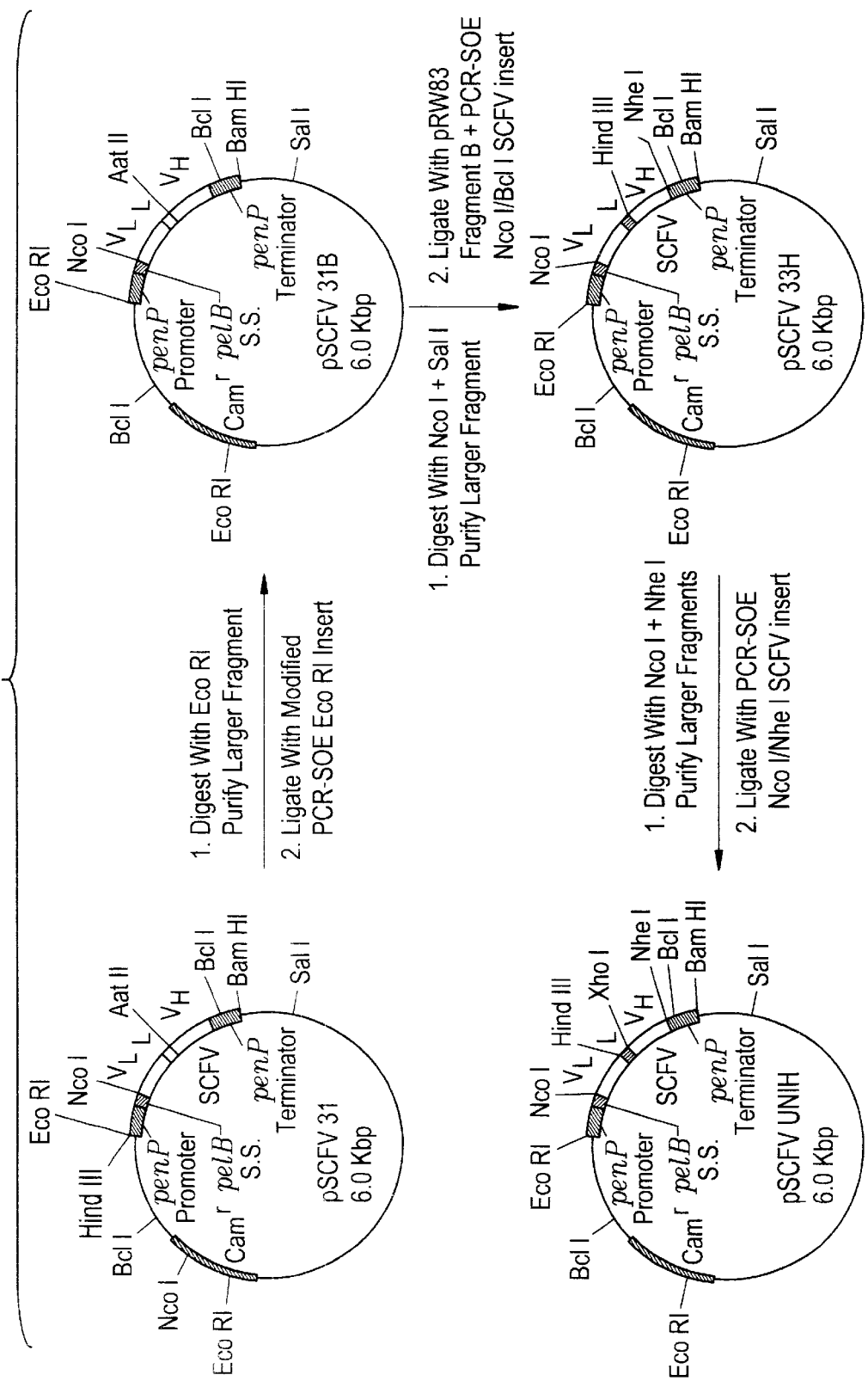

FIG. 5A

```
                                                                                                 3438
5' ATCGATAAAA TTTATTGAGA ATTTGTTTAT TATGATTAAC AGAGGTAAAA GCCAGTATAT
3' TAGCTATTTT AAATAACTCT TAAACAAATA ATACTAATTG TCTCCATTTT CGGTCATATA
   Cla I                                  *
                                                                                                 3498
TACTGATTAA TATAGGTAAA AGGCAGTTAA GAAATTGGGA ATGCTTTCTC TTCTGCTTTC
ATGACTAATT ATATCCATTT TCCGTCAATT CTTTAACCCT TACGAAAGAG AAGACGAAAG

3558
TTCTACGATG CACAAGGCGT TTCACATTTA TGCCCCTATG AAAATTACTA GGCTGTCCTA
AAGATGCTAC GTGTTCCGCA AAGTGTAAAT ACGGGGATAC TTTTAATGAT CCGACAGGAT

3618
GTCATTAGAT CTTTCAGCAG TTTGTAGTTT TAGAGCTTCT AAGTTGACTT CTGTCTTTTC
CAGTAATCTA GAAAGTCGTC AAACATCAAA ATCTCGAAGA TTCAACTGAA GACAGAAAAG

3678
TATTCATACA ATTACACATT CTGTGATGAT ATTTTTGGCT CTTGATTTAC ATTGGGTACT
ATAAGTATGT TAATGTGTAA GACACTACTA TAAAAACCGA GAACTAAATG TAACCCATGA
HUM1IN1 (-)

3738
TTCACAACCC ACTGCTCATG AAATTTGCTT TTGTACTACT GGTTGTTTTT GCATAGCCCC
AAGTGTTGGG TGACGAGTAC TTTAAACGAA AACATGATGA CCAACAAAAA CGTATCCGGG

3798
CTCCAGGCCA CGACCAGGTG TTTGGATTTT ATAAACGGGC CGTTTGCATT GTGAACTGAG
GAGGTCCGGT GCTGGTCCAC AAACCTAAAA TATTTGCCCG GCAAACGTAA CACTTGACTC

Met Val Leu Gln Thr Gln Val Leu Ile                                     3852
CTACAACAGG CAGGCAGGGG CAGCAAG ATG GTG TTG CAG ACC CAG GTC TTC ATT
GATGTTGTCC GTCCGTCCCC GTCGTTC TAC CAC AAC GTC TGG GTC CAG AAG TAA
```

FIG. 5B

```
Ser Leu Leu Leu Trp Ile Ser G Intron
TCT CTG TTG CTC TGG ATC TCT G GTGA GGAATTAAAA AGTGCCACAG TCTTTTCAGA     3908
AGA GAC AAC GAG ACC TAG AGA C CACT CCTTAATTTT TCACGGTGTC AGAAAAGTCT
                                                    HUMLIN2 (-)

GTAATATCTG TGTAGAAATA AAAAAAATTA AGATATAGTT GGAAATAAATG ACTATTTCCA      3968
CATTATAGAC ACATCTTTAT TTTTTTTAAT TCTATATCAA CCTTTATTAC TGATAAAGGT

Bam HI
ATATGGATCC AATTATCTGC TGACTTATAA TACTACTAGA AAGCAAATTT AAATGACATA      4028
TATACCTAGG TTAATAGACG ACTGAATATT ATGATGATCT TTCGTTTAAA TTTACTGTAT

TTTCAATTAT ATCTGAGACA GCGTGTATAA GTTTATGTAT AATCATTGTC CATTACTGAC      4088
AAAGTTAATA TAGACTCTGT CGCACATATT CAAATACATA TTAGTAACAG GTAATGACTG

+1
          ly Ala Tyr Gly Asp Ile Val Met Thr Gln Ser Pro Asp Ser Leu   4137
TACAG GT GCC TAC GGG GAC ACT GTG ATG ACC CAG TCT CCA GAC TCC CTG
ATGTC CA CGG ATG CCC CTG TAG CAC TAC TGG GTC AGA GGT CTG AGG GAC

Ala Val Ser Leu Gly Glu Arg Ala Thr Ile Asn Cys Lys Ser Ser Gln        4185
GCT GTG TCT CTG GGC GAG AGG GCC ACC ATC AAC TGC AAG TCC AGC CAG
CGA CAC AGA GAC CCG CTC TCC CGG TGG TAG TTG ACG TTC AGG TCG GTC
```

FIG.5C

```
  ----CDR 1----
Ser Val Leu Tyr Ser Ser Asn Asn Tyr Lys Asn Tyr Leu Ala Trp Tyr Gln
AGT GTT TTA TAC AGC TCC AAC AAT TAC AAG AAC TAC TTA GCT TGG TAC CAG    4233
TCA CAA AAT ATG TCG AGG TTG TTA TTC TTG ATG AAT CGA ACC ATG GTC
                        HUM1CDR1(-)
                                                      ----CDR 2----
Gln Lys Pro Gly Gln Pro Pro Lys Leu Leu Ile Tyr Trp Ala Ser Thr
CAG AAA CCA GGA CAG CCT CCT AAG CTG CTC ATT TAC TGG GCA TCT ACC        4281
GTC TTT GGT CCT GTC GGA GGA TTC GAC GAG TAA ATG ACC CGT AGA TGG

Arg Glu Ser Gly Val Pro Asp Arg Phe Ser Gly Ser Gly Ser Gly Thr
CGG GAA TCC GGG GTC CCT GAC CGA TTC AGT GGC AGC GGG TCT GGG ACA        4329
GCC CTT AGG CCC CAG GGA CTG GCT AAG TCA CCG TCG CCC AGA CCC TGT

Asp Phe Thr Leu Thr Ile Ser Ser Leu Gln Ala Glu Asp Val Ala Val
GAT TTC ACT CTC ACC ATC AGC AGC CTG CAG GCT GAA GAT GTG GCA GTT        4377
CTA AAG TGA GAG TGG TAG TCG TCG GAC GTC CGA CTT CTA CAC CGT CAA
                     ----CDR 3----
Tyr Tyr Cys Gln Gln Tyr Tyr Ser Tyr Pro Leu Thr Phe Gly Gly Gly
TAT TAC TGT CAG CAA TAT TAT AGT TAT CCT CTC ACT TTC GGC GGA GGG        4425
ATA ATG ACA GTC GTT ATA ATA TCA ATA GGA GAG TGA AAG CCG CCT CCC
```

FIG.5D

```
Thr Lys Val Val Ile Lys A                                         Hind III
ACC AAG GTG GTG ATC AAA C GTAAGTACAC TTTTCT AAG CTT 3'  human Cκ 4466
TGG TTC CAC CAC TAG TTT G CATTCATGTG AAAAGA TTC GAA 5'  insert
```

ANTI TAG-72 SINGLE CHAIN ANTIBODY
EXPRESSION PLASMIDS AND PRODUCTS

SINGLE CHAIN Fv MONOMER
(scFv)

SINGLE CHAIN Fv Dimer
(Fv2)

FIG.7A

DNA AND AMINO ACID SEQUENCES OF H4V$_L$-CC49 V$_H$ SCFV

```
         Cla I      EcoR I
5'·C TCA TGT TTG ACA GCT TAT CAT CGA TGA ATT CCA TCA CTT CCC TCC    46

GTT CAT TTG TCC CCG GTG GAA ACG AGG TCA TCA TTT CCT TCC GAA AAA    94

ACG GTT GCA TTT AAA TCT TAC ATA TAT AAT ACT TTC AAA GAC TAC ATT   142

TGT AAG ATT TGA TGT TTG AGT CGG CTG AAA GAT CGT ACG TAC CAA TTA   190

TTG TTT CGT GAT TGT TCA AGC CAT AAC ACT GTA GGG ATA GTG GAA AGA   238

GTG CTT CAT CTG GTT ACG ATC AAT CAA ATA TTC AAA CGG AGG GAG ACG   286

334
                                         Gly Leu Leu Leu
                                         GGA TTG TTA TTA

-22
    Met Lys Tyr Leu Leu Pro Thr Ala Ala Ala Gly
ATT TTG ATG AAA TAC CTA TTG CCT ACG GCA GCC GCT GGA
        Nco I
                 +1
                 Met Ala Asp Ile Val Met Thr Gln Ser Pro           382
                 ATG GCC GAC ATC GTG ATG ACC CAG TCT CCA
                                      20

Leu Ala Ala Gln Pro
CTC GCT GCC CAA CCA
      10
Asp Ser Leu Ala Val Ser Leu Gly Glu Arg Ala Thr Ile Asn Cys Lys   430
GAC TCC CTG GCT GTG TCT CTG GGC GAG AGG GCC ACC ATC AAC TGC AAG
```

FIG. 7B

```
                              30                              40
Ser Ser Gln Ser Val Leu Tyr Ser Ser Asn Asn Lys Asn Tyr Leu Ala
TCC AGC CAG AGT GTT TTA TAC AGC TCC AAC AAT AAG AAC TAC TTA GCT    478
                      50
Trp Tyr Gln Lys Pro Gly Gln Pro Pro Lys Leu Leu Ile Tyr Trp
TGG TAC CAG AAA CCA GGA CAG CCT CCT AAG CTG CTC ATT TAC TGG        526
              60                                      70
Ala Ser Thr Arg Glu Ser Gly Val Pro Asp Arg Phe Ser Gly Ser Gly
GCA TCT ACC CGG GAA TCC GGG GTC CCT GAC CGA TTC AGT GGC AGC GGG    574
                              80
Ser Gly Thr Asp Phe Thr Leu Thr Ile Ser Ser Leu Gln Ala Glu Asp
TCT GGG ACA GAT TTC ACT CTC ACC ATC AGC AGC CTG CAG GCT GAA GAT    622
Val Ala Val Tyr Tyr Cys Gln Gln Tyr Tyr Ser Tyr Pro Leu Thr Phe
GTG GCA GTT TAT TAC TGT CAG CAA TAT TAT AGT TAT CCT CTC ACT TTC    670
                      90                                 100
                                           110                           120
                                                         Hind III
Gly Gly Gly Thr Lys Val Val Ile Lys Leu Ser Ala Asp Asp Ala Lys
GGC GGA GGG ACC AAG GTG GTG ATC AAG CTT AGT GCG GAC GAT GCG AAA    718
```

FIG. 7C

```
                                                                                130
Lys Asp Ala Ala Lys Lys Asp Asp Ala Lys Lys Asp Ala Lys Lys
AAG GAT GCT GCG AAG AAG GAT GAC GCT AAG AAA GAC GAT GCT AAG AAG         766

Xho I  140                              150
Asp Leu Glu Val Gln Leu Gln Ser Asp Ala Glu Leu Val Lys Pro
GAC CTC GAG GTT CAG TTG CAG TCT GAC GCT GAG TTG GTG AAA CCT             814

160
Gly Ala Ser Val Lys Ile Ser Lys Cys Lys Ala Ser Gly Tyr Thr Phe Thr
GGG GCT TCA GTG AAG ATT TCC TGC AAG GCT TCT GGC TAC ACC TTC ACT         862

180
Asp His Ala Ile His Trp Val Lys Gln Asn Pro Glu Gln Gly Leu Glu
GAC CAT GCA ATT CAC TGG GTG AAA CAG AAC CCT GAA CAG GGC CTG GAA         910

200
Trp Ile Gly Tyr Phe Ser Pro Gly Asn Asp Asp Phe Lys Tyr Asn Glu
TGG ATT GGA TAT TTT TCT CCC GGA AAT GAT GAT TTT AAA TAC AAT GAG         958

210
Arg Phe Lys Gly Lys Ala Thr Leu Thr Ala Asp Lys Ser Ser Ser Thr
AGG TTC AAG GGC AAG GCC ACT CTG ACT GCA GAC AAA TCC AGC ACT            1006
```

FIG.7D

```
                                       220                                                          230
Ala Tyr Val Gln Leu Asn Ser Leu Thr Ser Glu Asp Ser Ala Val Tyr
GCC TAC GTG CAG CTC AAC AGC CTG ACA TCT GAG GAT TCT GCA GTG TAT    1054

Phe Cys Thr Arg Ser Leu Asn Met Ala Tyr Trp Gly Gln Gly Thr Ser
TTC TGT ACA AGA TCC CTG AAT ATG GCC TAC TGG GGT CAA GGA ACC TCA    1102
                         240
                                        Nhe I
Val Thr Val Ser Ser ***         ─────────────
GTC ACC GTC TCC TCA TAA AAA GCT AGC GAT GAA TCC GTC AAA ACA TCA    1150
 250

TCT TAC ATA AAG TCA CTT GGT GAT CAA GCT CAT ATC ATT GTC CGG CAA    1198

TGG TGT GGG CTT TTT TTG TTT TCT ATC TTA AAG ATC ATG TGA AGA AAA    1246

AAC GGG AAA ATC GGT CTG CGG GAA AGG ACC GGG TTT TTG TCG AAA TCA    1254
                                                  BamH I
                                                 ─────────────
TAG GCG AAT GGG TTG GAT TGT GAC AAA ATT CGG ATC C-3'               1291
```

FIG. 8A

DNA AND AMINO ACID SEQUENCES OF CC49 SCFV SPECIES

```
                          Cla I       EcoR I
5'·C TCA TGT TTG ACA GCT TAT CAT CGA TGA ATT CCA TCA CTT CCC TCC     46

GTT CAT TTG TCC CCG GTG GAA ACG AGG TCA TCA TTT CCT TCC GAA AAA   94

ACG GTT GCA TTT AAA TCT TAC ATA TAT AAT ACT TTC AAA GAC TAC ATT  142

TGT AAG ATT TGA TGT TTG AGT CGG CTG AAA GAT CGT ACG TAC CAA TTA  190

TTG TTT CGT GAT TGT TCA AGC CAT AAC ACT GTA GGG ATA GTG GAA AGA  238

GTG CTT CAT CTG GTT ACG ATC AAT CAA ATA TTC AAA CGG AGG GAG ACG  286

-22
        Met Lys Tyr Leu Leu Pro Thr Ala Ala Gly Leu Leu Leu
    ATT TTG ATG AAA TAC CTA TTG CCT ACG GCA GCC GCT GGA TTG TTA TTA  334

Nco I    +1
        Leu Ala Ala Gln Pro Ala Met Ala Asp Ile Val Met Ser Gln Ser Pro
        CTC GCT GCC CAA CCA ATG GCC GAC ATC GTG ATG TCA CAG TCT CCA    382
                                             20
        Ser Ser Leu Pro Val Ser Val Gly Glu Lys Val Thr Leu Ser Cys Lys
        TCC TCC CTA CCT GTG TCA GTT GGC GAG AAG GTT ACT TTG AGC TGC AAG 430
         10
```

FIG.8B

```
                    Ser Ser Leu Tyr Ser Gly Asn Gln Lys Asn Tyr Leu Ala
                30                                  40
Ser Ser Gln Ser Leu Tyr Ser Gly Asn Gln Lys Asn Tyr Leu Ala       478
TCC AGT CAG AGC CTT TAT AGT GGT AAT CAA AAG AAC TAC TTG GCC

Trp Tyr Gln Lys Pro Gly Gln Ser Pro Lys Leu Leu Ile Tyr Trp       526
TGG TAC CAG AAA CCA GGG CAG TCT CCT AAA CTG CTG ATT TAC TGG
                        50
                                                70
Ala Ser Ala Arg Glu Ser Gly Val Pro Asp Arg Phe Ser Gly Ser Gly   574
GCA TCT GCT AGG GAA TCT GGG GTC CCT GAT CGC TTC ACA GGC AGT GGA
                                    80

Ser Gly Thr Asp Phe Thr Leu Ser Ile Ser Ser Val Lys Thr Glu Asp   622
TCT GGG ACA GAT TTC ACT CTC TCC ATC AGC AGT GTG AAG ACT GAA GAC
                                                        100
Leu Ala Val Tyr Tyr Cys Gln Gln Tyr Tyr Ser Tyr Pro Leu Thr Phe   670
CTG GCA GTT TAT TAC TGT CAG CAG TAT TAT AGC TAT CCC CTC ACG TTC
            90
                                            Hind III          120
                                        Lys Leu Ser Ala Asp Asp Ala Lys
Gly Ala Gly Thr Lys Leu Val Leu Ser Ala Asp Asp Ala Lys           718
GGT GCT GGG ACC AAG CTG GTG CTG AAG CTT AGT GCG GAC GAT GCG AAA
                    110
```

FIG. 8C

```
     Lys Asp Ala Ala Lys Lys Asp Asp Ala Lys Lys Asp Ala Lys Lys
     AAG GAT GCT GCG AAG AAG GAT GAC GCT AAG AAA GAC GAT GCT AAA AAG    766
                       130                             150
      Xho I
     Asp Leu Glu Val Gln Leu Gln Gln Ser Asp Ala Glu Leu Val Lys Pro
     GAC CTC GAG GTT CAG CTG CAG CAG TCT GAC GCT GAG TTG GTG AAA CCT    814
         140                          160

Gly Ala Ser Val Lys Ile Ser Lys Ala Ser Gly Tyr Thr Phe Thr
     GGG GCT TCA GTG AAG ATT TCC AAG GCT TCT GGC TAC ACC TTC ACT        862
                 170                             180

Asp His Ala Ile His Trp Val Lys Gln Asn Pro Glu Gln Gly Leu Glu
     GAC CAT GCA ATT CAC TGG GTG AAA CAG AAC CCT GAA CAG GGC CTG GAA    910
                             190                         200

Trp Ile Gly Tyr Phe Ser Pro Gly Asn Asp Asp Phe Lys Tyr Asn Glu
     TGG ATT GGA TAT TTT TCT CCC GGA AAT GAT GAT TTT AAA TAC AAT GAG    958
                                         210

Arg Phe Lys Gly Lys Ala Thr Leu Thr Ala Asp Lys Ser Ser Ser Thr
     AGG TTC AAG GGC AAG GCC ACA CTG ACT GCA GAC AAA TCC TCC AGC ACT    1006
                                     220                       230

Ala Tyr Val Gln Leu Asn Ser Leu Thr Ser Glu Asp Ser Ala Val Tyr
     GCC TAC GTG CAG CTC AAC AGC CTG ACA TCT GAG GAT TCT GCA GTG TAT    1054
```

FIG.8D

```
                      240
     Phe Cys Thr Arg Ser Leu Asn Met Ala Tyr Trp Gly Gln Gly Thr Ser
     TTC TGT ACA AGA TCC CTG AAT ATG GCC TAC TGG GGT CAA GGA ACC TCA    1102
         250
S1.  Val Thr Val Ser Ser ***                                           1120
     GTC ACC GTC TCC TCA TAA
         250
S2.  Val Thr Val Ser Pro Glu Asp Tyr Asp Ser ***                       1135
     GTC ACC GTC TCC CCT GAG GAC TAT GAC TCC TAA
         250                                     260
S3.  Val Thr Val Ser Pro Glu Asp Pro Glu Asp Tyr Asp ***               1141
     GTC ACC GTC TCC CCT GAA GAC CCT GAA GAC TAT GAC TAA
           Nhe I
     AAA GCT AGC GAT GAA TCC GTC AAA ACA TCA TCT TAC ATA AAG TCA CTT    1189
     GGT GAT CAA GCT CAT ATC ATT GTC CGG CAA TGG TGT GGG CTT TTT TTG    1237
     TTT TCT ATC TTT AAA GAT CAT GTG AAG AAA AAC GGG AAA ATC GGT CTG    1285
     CGG GAA AGG ACC GGG TTT TTG TCG AAA TCA TAG GCG AAT GGG TTG GAT    1333
              BamH I
     TGT GAC AAA ATT CGG ATC C-3'      1354(A) ; 1369(B) ; 1375(C)
```

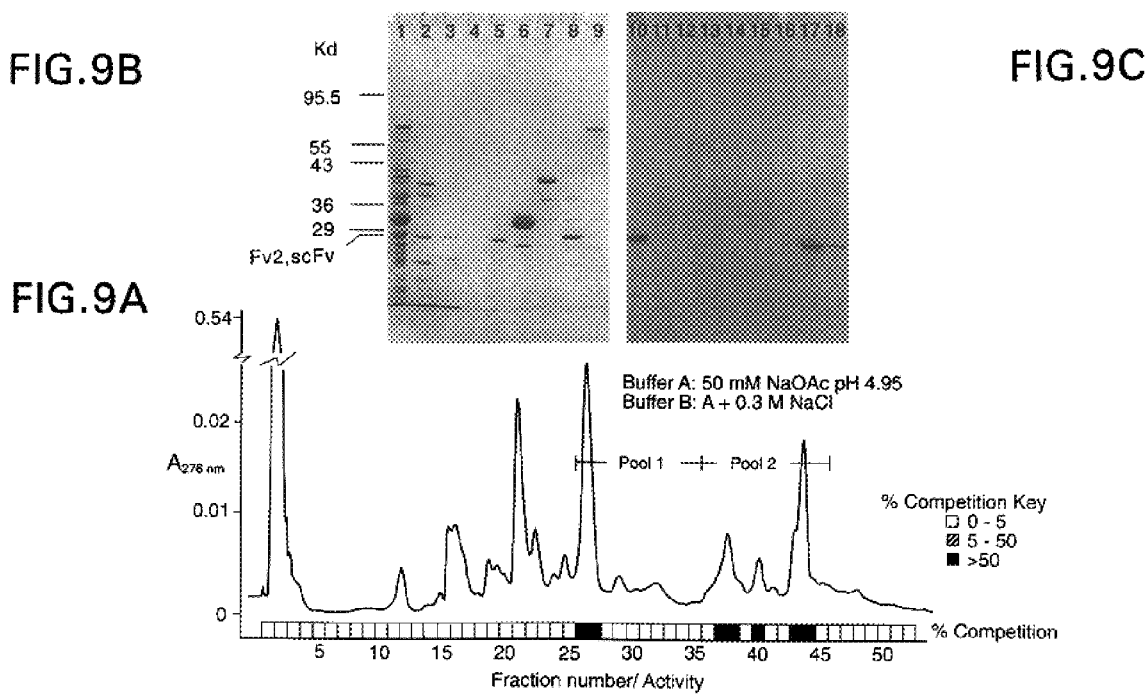

ANION EXCHANGE CHROMATOGRAPHY & SDS-PAGE OF MONO S
POOL 2 *E.COLI* pSCFV UHM 8.1 PERIPLASMIC FRACTION
FIG. 10A
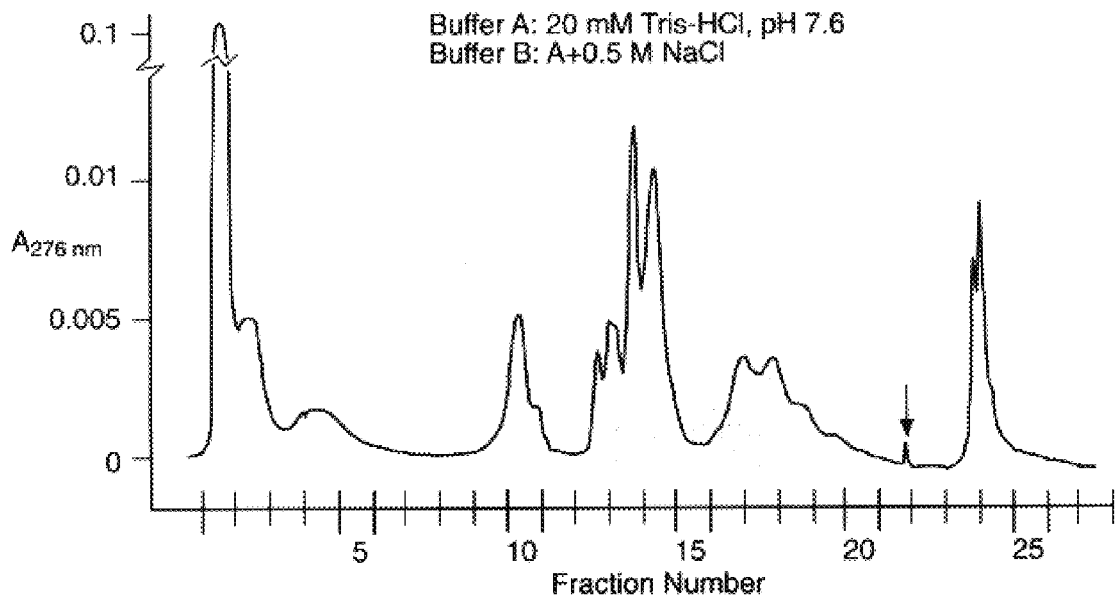
FIG. 10B
FIG. 10C
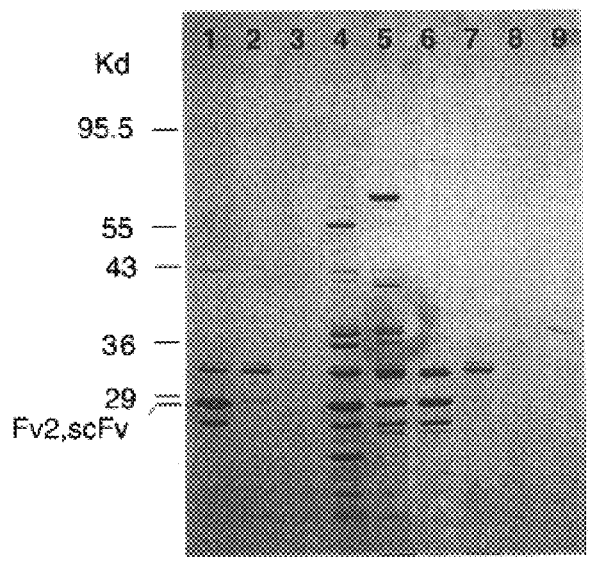
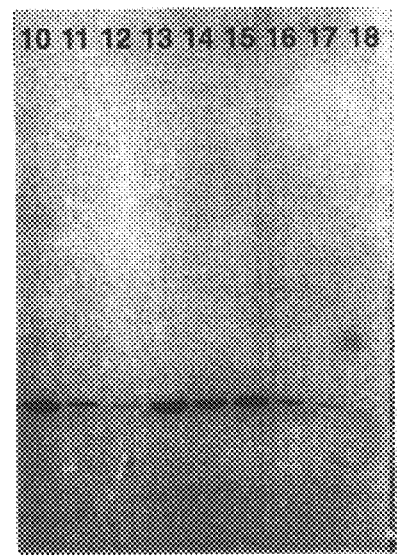

GEL FILTRATION, SDS-PAGE & IEF CORRELATION IN THE DISCOVERY OF FV2

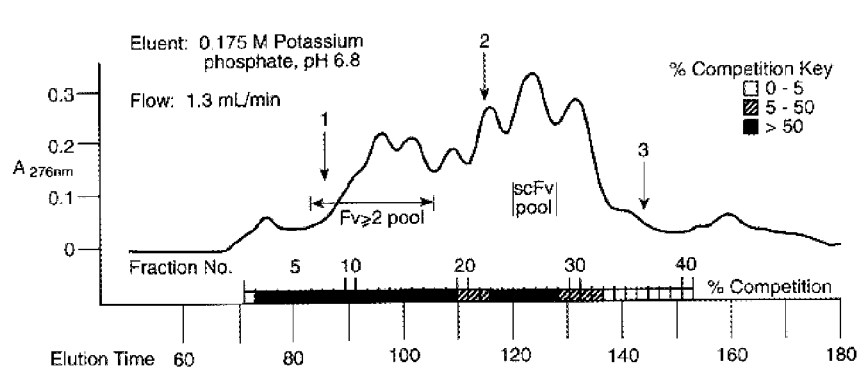
FIG.12A
GEL FILTRATION CHROMATOGRAPHY, ACTIVITY & SDS-PAGE
OF E.COLI pSCFVUHM 5.2 PERIPLASMIC FRACTION
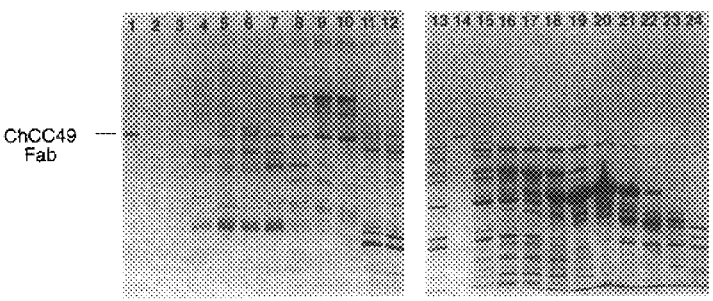
FIG.12B
FIG.12C

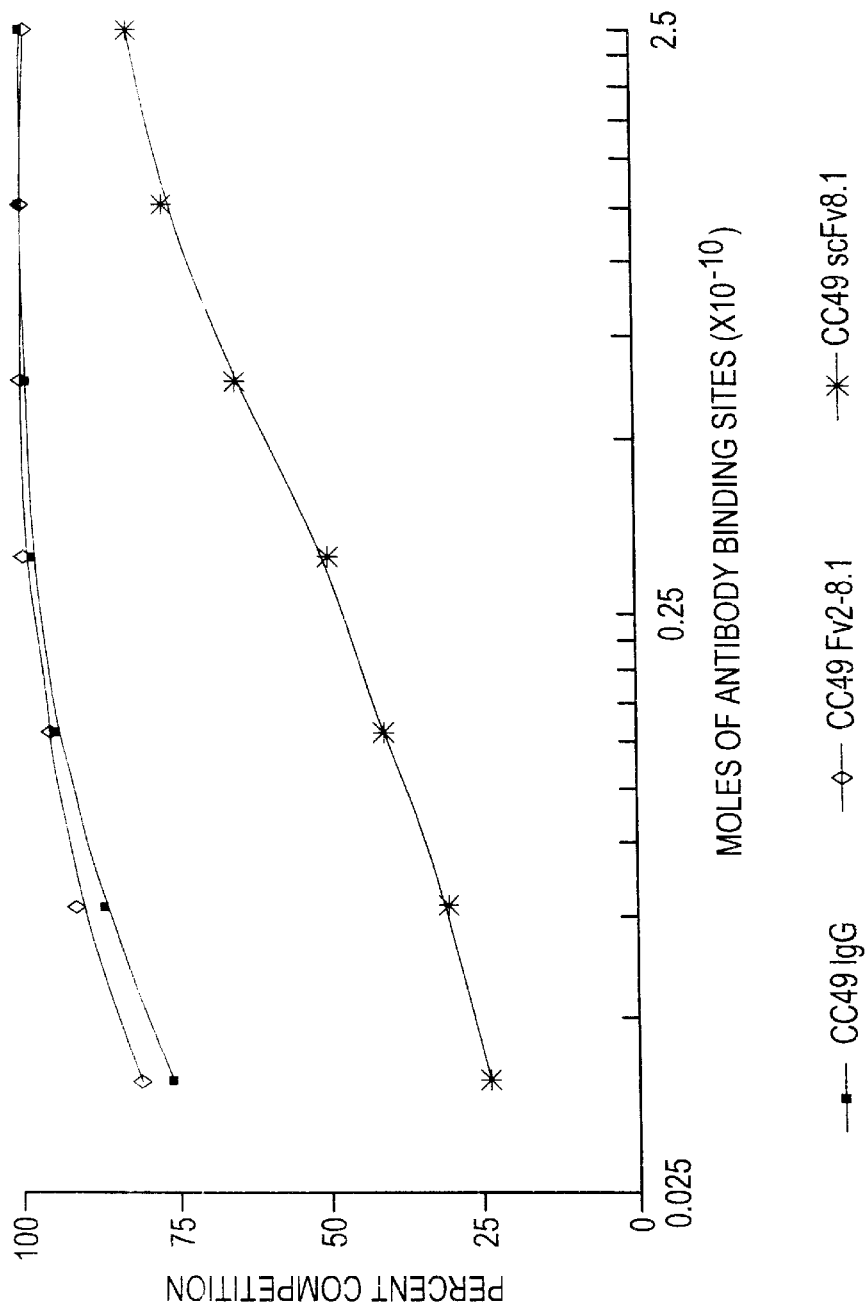

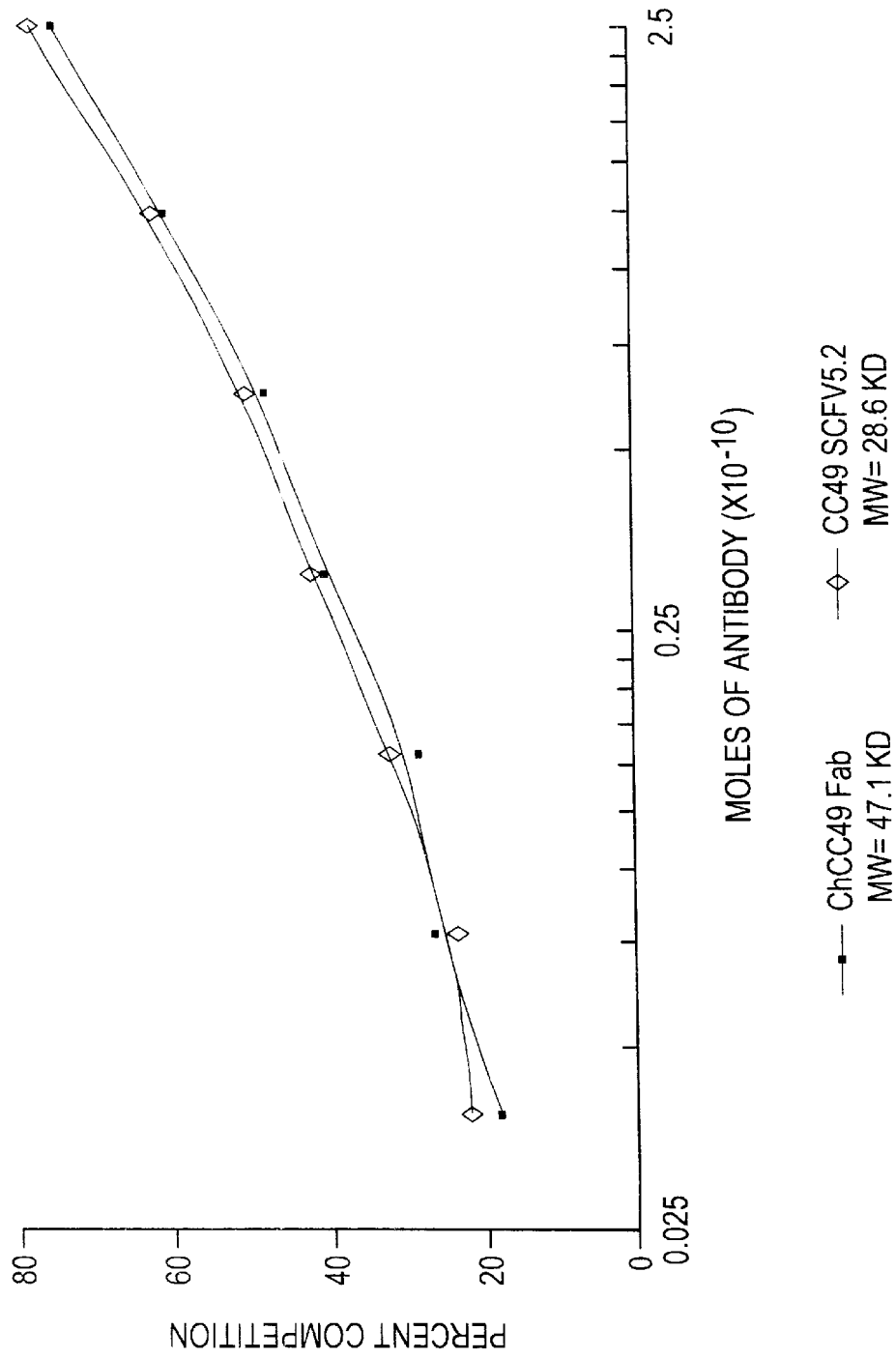

PLASMID CONSTRUCTION LEADING TO pPY31 & pPY32

PLASMID CONSTRUCTION LEADING TO pPY31 & pPY32

PLASMID CONSTRUCTION LEADING TO pPY31 & pPY32

PLASMID CONSTRUCTION LEADING TO pPY31 & pPY32 pPY1 →(Digest with EcoR V / Ligate with annealed linker)→ pPY2

PLASMID CONSTRUCTION LEADING TO pPY31 & pPY32 pPY2 →(Digest with BstB I + BamH I / Ligate with CC49 scFv PCR products)→ pPY21 & 22

PLASMID CONSTRUCTION LEADING TO pPY31 & pPY32 pPY21 & pPY22 →(Digest with Sst I + Sal I / Ligate with pHIL-S1 vector fragment from A)→ pPY31 & 32

FIG. 16A

DNA AND AMINO ACID SEQUENCE OF CC49 SCFV IN pPY21 & pPY22

```
                    AOX1P                                BstB I
        TTTAACGACAACTTGAGAAGATC ------- (AAAAAACAAC) TAATTATTC        9
5'-AOX1-----------------------------------(AAAAAACAAC)-----------
        -22
        Met Lys Tyr Met Leu Leu Gln Ala Phe Leu Phe Leu Leu Ala
GAA ACG ATG AAA TAC ATG CTT TTG CAA GCT TTC CTT TTC CTT TTG GCT     57
                EcoR V           +1
        Gly Phe Ala Ala Lys Ile Ser Ala Asp Ile Val Met Ser Gln Ser Pro
        GGT TTT GCA GCT AAG ATA TCT GCT GAC ATT GTG ATG TCA CAG TCT CCA  105
                                 10                     20
        Ser Ser Leu Pro Val Ser Val Gly Glu Lys Val Thr Leu Ser Cys Lys
        TCC TCC CTA CCT GTG TCA GTT GGC GAG AAG GTT ACT TTG AGC TGC AAG  153
                                                                40
        Ser Ser Gln Ser Leu Leu Tyr Ser Gly Asn Gln Lys Asn Tyr Leu Ala
        TCC AGT CAG AGC CTT TTA TAT AGT GGT AAT CAA AAG AAC TAC TTG GCC  201
                         30                      50
                TAGVLFR2
        Trp Tyr Gln Gln Lys Pro Gly Gln Ser Pro Lys Leu Leu Ile Tyr Trp
        TGG TAC CAG CAG AAA CCA GGG CAG TCT CCT AAA CTG CTG ATT TAC TGG  249
```

FIG. 16B

```
                60                                   70
Ala Ser Ala Arg Glu Ser Gly Val Pro Asp Arg Phe Thr Gly Ser Gly
GCA TCC GCT AGG GAA TCT GGG GTC CCT GAT CGC TTC ACA GGC AGT GGA    297

80
Ser Gly Thr Asp Phe Thr Leu Ser Ile Ser Ser Val Lys Thr Glu Asp
TCT GGG ACA GAT TTC ACT CTC TCC ATC AGC AGT GTG AAG ACT GAA GAC    345

TAGVLCDR3
                    A              T
             90   GT CAG CAG TAT TAT AGC TAT CC
Leu Ala Val Tyr Tyr Cys Gln Gln Tyr Tyr Ser Tyr Pro Leu Thr Phe
CTG GCA GTT TAT TAC TGT CAG CAG TAT TAT AGC TAT CCC CTC ACG TTC    393

Hind III             120
                          110
Gly Ala Gly Thr Lys Leu Val Leu Lys Leu Ser Ala Ser Ala Asp Ala Lys
GGT GCT GGG ACC AAG CTG GTG CTG AAG CTT AGT GCG GAC GAT GCG AAA    441

Lys Asp Ala Ala Lys Lys Asp Asp Ala Lys Lys Asp Asp Ala Lys Lys
AAG GAT GCT GCG AAG AAG GAT GAT GCT AAG AAA GAC GAT GCT AAA AAG    489

Xho I      140                              150
Asp Leu Glu Val Gln Leu Gln Ser Asp Ala Glu Leu Val Lys Pro
GAC CTC GAG GTT CAG TTG CAG CAG TCT GAC GCT GAG TTG GTG AAA CCT    537
```

FIG. 16C

```
                                                                                         A
Gly Ala Ser Val Lys Ile Ser Cys Lys Ala Ser Gly Tyr Thr Phe Thr       585
GGG GCT TCA GTG AAG ATT TCC TGC AAG GCT TCT GGC TAC ACC TTC ACT
                    160                                180

Asp His Ala Ile His Trp Val Lys Gln Asn Pro Glu Gln Gly Leu Glu       633
GAC CAT GCA ATT CAC TGG GTG AAA CAG AAC CCT GAA CAG GGC CTG GAA
    170

TAGVHCDR2            190
           TGG ATT GGA TAT TTT TCT CC
Trp Ile Gly Tyr Phe Ser Pro Gly Asn Asp Asp Phe Lys Tyr Asn Glu       681
TGG ATT GGA TAT TTT TCT CCC GGA AAT GAT GAT TTT AAA TAC AAT GAG
                                                200
                                    210

Arg Phe Lys Gly Lys Ala Thr Leu Thr Ala Asp Lys Ser Ser Ser Thr       729
AGG TTC AAG GGG AAG GCC ACA CTG ACT GCA GAC AAA TCC AGC AGC ACT
                220

Ala Tyr Val Gln Leu Asn Ser Leu Thr Ser Glu Asp Ser Ala Val Tyr       777
GCC TAC GTG CAG CTC AAC AGC CTG ACA TCC GAG GAT TCT GCA GTG TAT
                                                    230

Phe Cys Thr Arg Ser Leu Asn Met Ala Tyr Trp Gly Gln Gly Thr Ser       825
TTC TGT ACA AGA TCC CTG AAT ATG GCC TAC TGG GGT CAA GGA ACC TCA
                            240
```

FIG. 16D

```
         250                              260
S1. Val Thr Val Ser Pro Glu Asp Pro Glu Asp Tyr Asp *** ***
    GTC ACC GTC TCC CCT GAA GAC CCT GAA GAC TAT GAC TAA TAG    867

250
S2. Val Thr Val Ser Tyr *** ***
    GTC ACC GTC TCC TAC TAA TAG                                846

BamH I
GGATCCTTAG----------------------------AOX1 TERMINATOR-3'  877/856
```

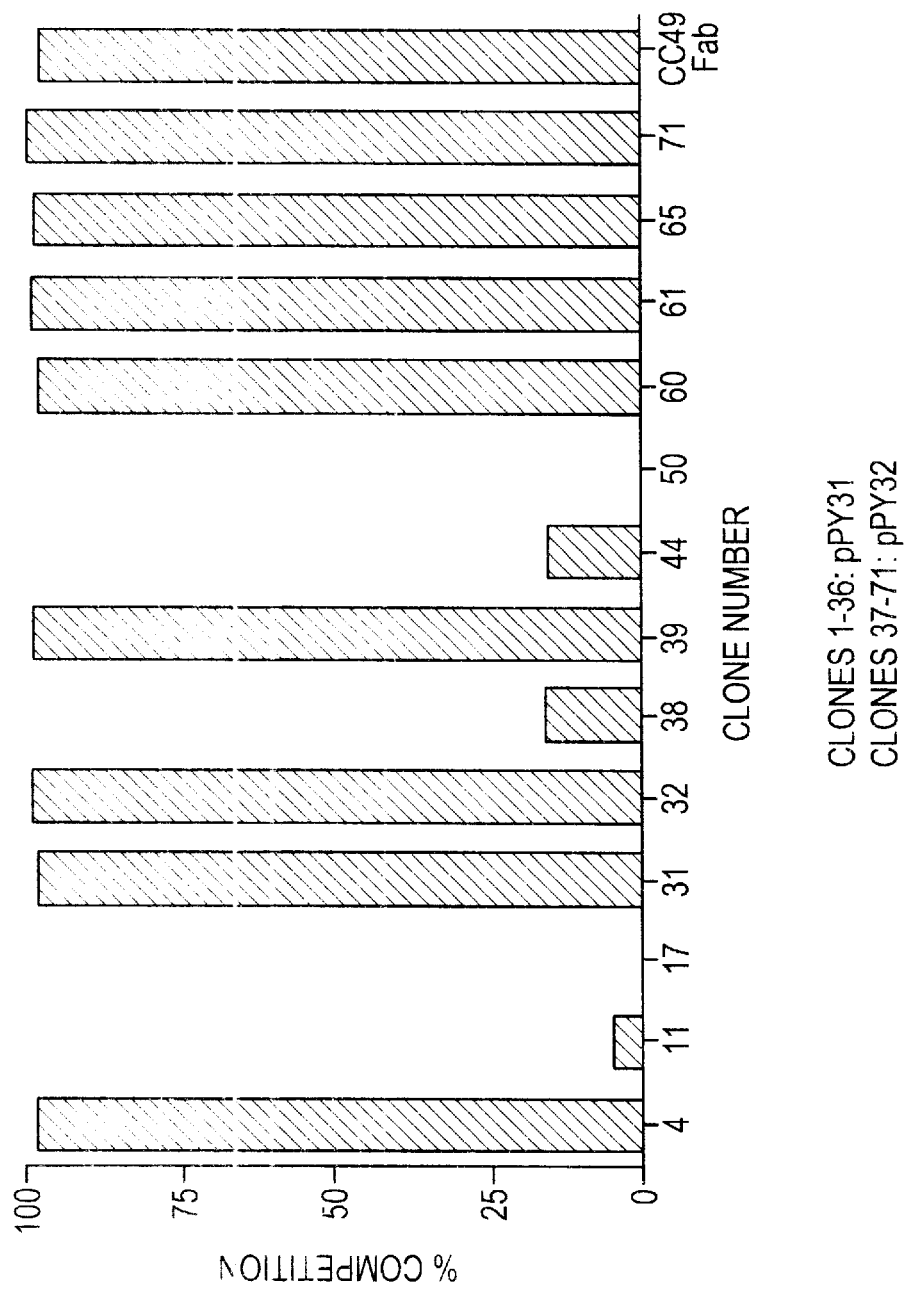

GEL FILTRATION & SDS-PAGE ANALYSIS OF *PICHIA* CC49 scFv
pI = 5.2 SPECIES

ANION EXCHANGE CHROMATOGRAPHY & SDS-PAGE OF
*PICHIA* CC49 scFv SPECIES

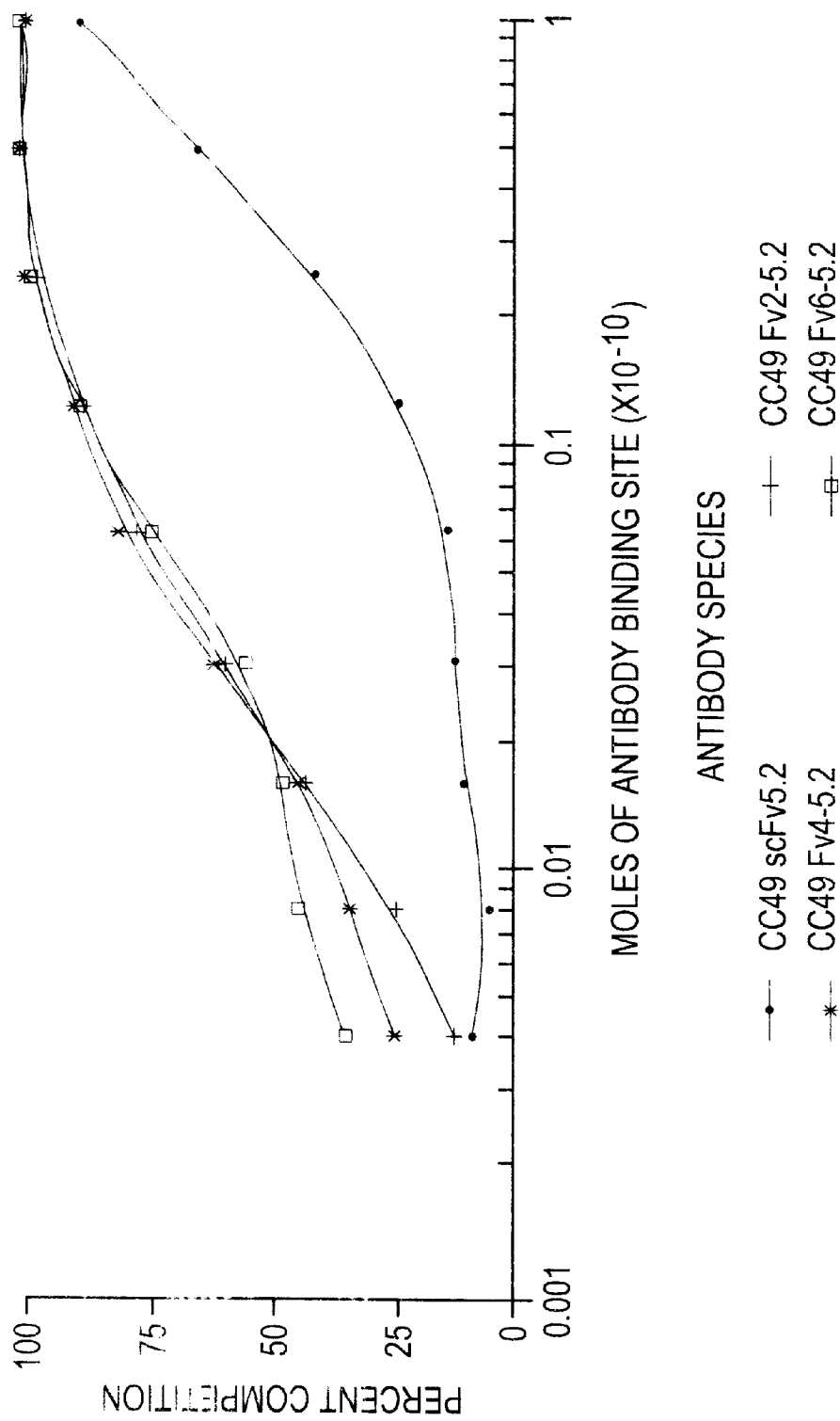

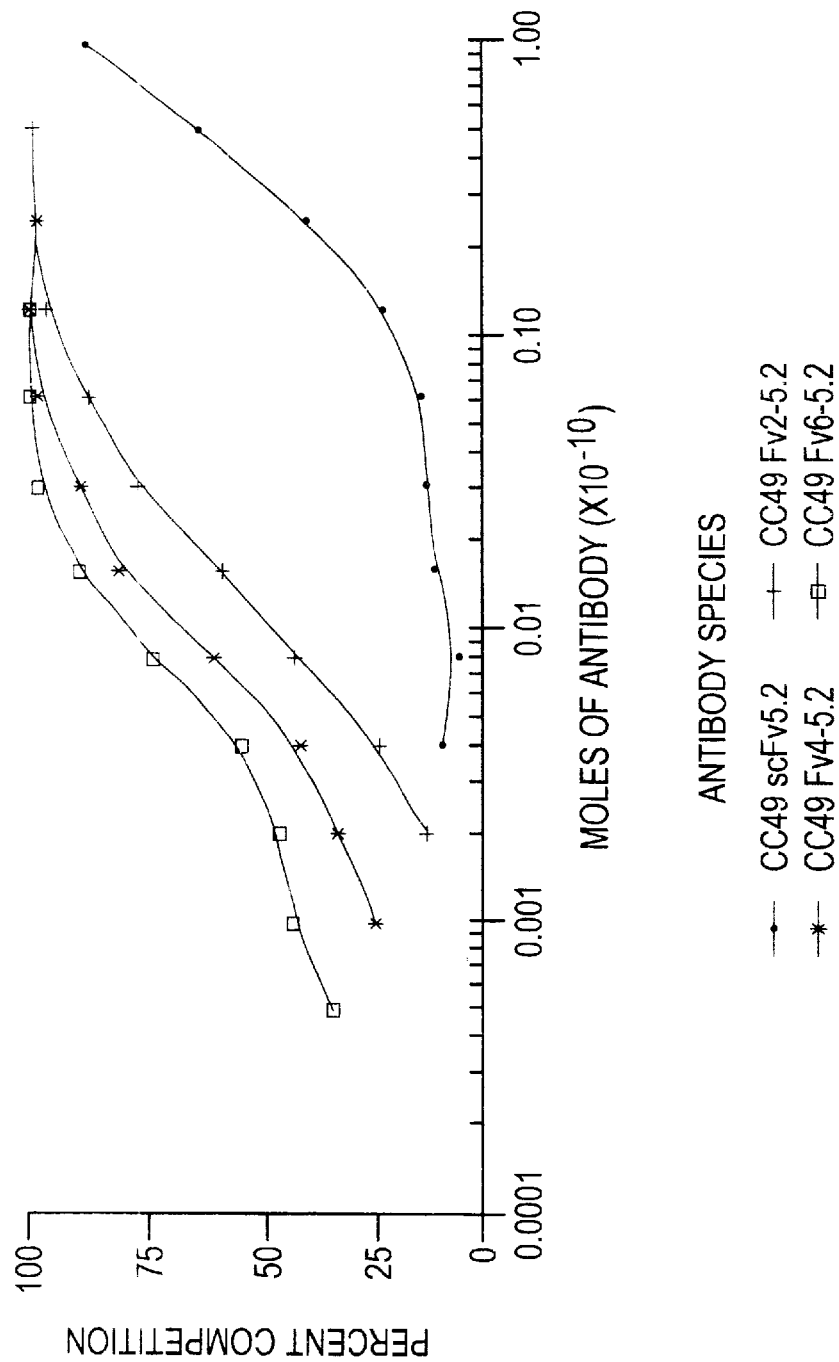

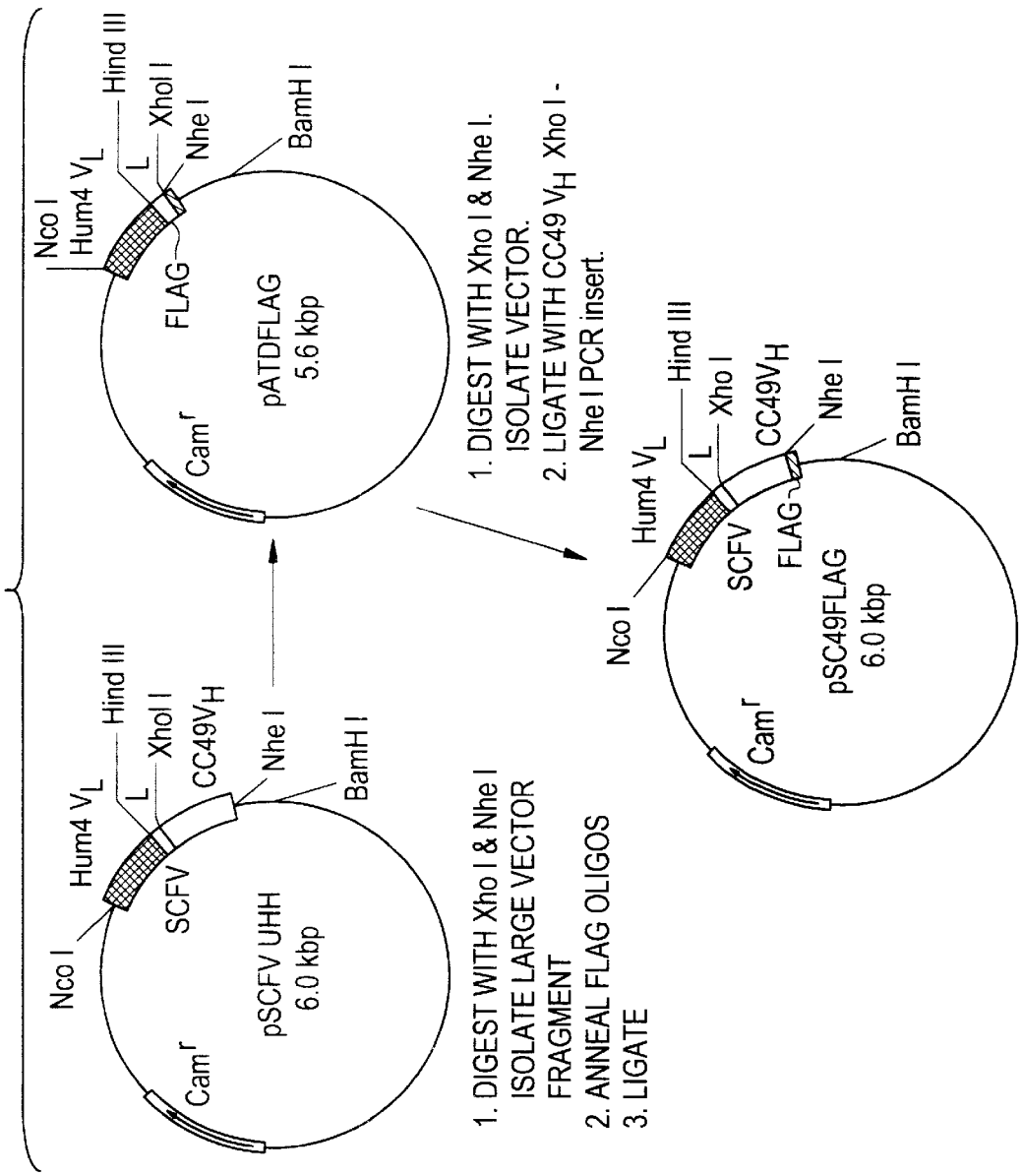

FIG. 23A

DNA AND AMINO ACID SEQUENCE IN pATDFLAG

```
           Cla I       EcoR I
5'-C TCA TGT TTG ACA GCT TAT CAT CGA TGA ATT CCA TCA CTT CCC TCC      46

GTT CAT TTG TCC CCG GTG GAA ACG AGG TCA TCA TTT CCT TCC GAA AAA       94

ACG GTT GCA TTT AAA TCT TAC ATA TAT AAT ACT TTC AAA GAC TAC ATT      142

TGT AAG ATT TGA TGT TGT TTG AGT CGG CTG AAA GAT CGT ACG CAA TTA      190

TTG TTT CGT GAT TGT TCA AGC CAT AAC ACT GTA GGG ATA GTG GAA AGA      238

GTG CTT CAT CTG GTT ACG ATC AAT CAA ATA TTC AAA CGG AGG GAG ACG      286

-22  Met Lys Tyr Leu Leu Pro Thr Ala Ala Ala Gly Leu Leu Leu
         ATG AAA TAC CTA TTG CCT ACG GCA GCC GCT GGA TTG TTA TTA      334

Nco I      +1
    Met Thr Gln Ser Pro
    Leu Ala Ala Gln Pro Ala Met Ala Asp Ile Val Met Thr Gln Ser Pro
    CTC GCT GCT CAA CCA GCC ATG GCC GAC ATC GTG ATG ACC CAG TCT CCA   382
                                    20

Asp Ser Leu Ala Val Ser Leu Gly Glu Arg Ala Thr Ile Asn Cys Lys
    GAC TCC CTG GCT GTG TCT CTG GGC GAG AGG GCC ACC ATC AAC TGC AAG   430
     10
```

FIG. 23B

```
                        30                              40
Ser Ser Gln Ser Val Leu Tyr Ser Ser Asn Asn Lys Asn Tyr Leu Ala
TCC AGC CAG AGT GTT TTA TAC AGC AAC AAT AAG AAC TAC TTA GCT      478

50
Trp Tyr Gln Lys Pro Gly Gln Pro Pro Lys Leu Leu Ile Tyr Trp
TGG TAC CAG AAA CCA GGA CAG CAG CCT CCT AAG CTC CTC ATT TAC TGG  526

60                                         70
Ala Ser Thr Arg Glu Ser Gly Val Pro Asp Arg Phe Ser Gly Ser Gly
GCA TCT ACC CGG GAA TCC GGG GTC CCT GAC CGA TTC AGT GGC AGC GGG  574

80
Ser Gly Thr Asp Phe Thr Leu Thr Ile Ser Ser Leu Gln Ala Glu Asp
TCT GGG ACA GAT TTC ACT CTC ACC ATC AGC AGC CTG CAG GCT GAA GAT  622

90                            100
Ala Ala Val Tyr Tyr Cys Gln Gln Tyr Tyr Ser Tyr Pro Leu Thr Phe
GCG GCA GTT TAT TAC TGT CAG CAA TAT TAT AGT TAT CCT CTC ACT TTC  670

110        Hind III           120
Gly Gly Gly Thr Lys Val Val Ile Lys Leu Ser Ala Asp Asp Ala Lys
GGC GGA GGG ACC AAG GTG GTG ATC AAG CTT AGT GCG GAC GAT GCG AAA  718
```

FIG. 23C

```
     Lys Asp Ala Ala Lys Lys Asp Asp Ala Lys Lys Asp Asp Ala Lys Lys
     AAG GAT GCT GCG AAG AAG GAT GAC GCT AAG AAA GAC GAT GCT AAA AAG    766
         Xho I                Nhe I
     Asp Leu Glu              Ala Ser Asp Tyr Lys Asp Asp Asp Asp Lys ***
     GAC CTC GAG ACAATGTCGCT AGC GAC TAC AAG GAC GAT GAC GAT AAA TAA    816
                                                                130
     AAA CCT AGC GAT GAA TCC GTC AAA ACA TCA TCT TAC ATA AAG TCA CTT    864
             PENTPSEQ: ←  G TTT TGT AGT AGA ATG TAT TTC

GGT GAT CAA GCT CAT ATC ATT GTC CGG CAA TGG TGT GGG CTT TTT TTG    912

TTT TCT ATC TTT AAA GAT CAT GTG AAG AAA AAC GGG AAA ATC GGT CTG    960

CGG GAA AGG ACC GGG TTT TTG TCG AAA TCA TAG GCG AAT GGG TTG GAT   1008
                 BamH I
     TGT GAC AAA ATT CGG ATC C-3'                                      1027
```

FIG. 24A  DNA AND AMINO ACID SEQUENCE OF pSC49FLAG

```
     ClaI         EcoRI
5'·C TCA TGT TTG ACA GCT TAT CAT CGA TGA ATT CCA TCA CTT CCC TCC        46

GTT CAT TTG TCC CCG GTG GAA ACG AGG TCA TCA TTT CCT TCC GAA AAA         94

ACG GTT GCA TTT AAA TCT TAC ATA TAT AAT ACT TTC AAA GAC TAC ATT        142

TGT AAG ATT TGA TGT TTG AGT CGG CTG AAA GAT CGT ACG TAC CAA TTA        190
                         PENPR1: AAC ACT GTA GGG ATA GTG GAA →

TTG TTT CGT GAT TGT TCA AGC CAT AAC ACT GTA GGG ATA GTG GAA AGA        238

GTG CTT CAT CTG GTT ACG ATC AAT CAA ATA TTC AAA CGG AGG GAG ACG        286
                         PENPR2: ← TAT AAG TTT GCC TCC CTC TG

Gly Leu Leu Leu
                                                          GGA TTG TTA TTA  334
              -22
              Met Lys Tyr Leu Leu Pro Thr Ala Ala Ala
              ATG AAA TAC CTA TTG CCT ACG GCA GCC GCT
                                          Nco I       +1
                                                                    20
                          Asp Ile Val Met Thr Gln Ser Pro
                          GAC ATC GTG ATG ACC CAG TCT CCA            382

Leu Ala Ala Gln Pro Ala Met Ala
CTC GCT GCC CAA CCA ATG GCC

10                                    Thr Ile Asn Cys Lys
Asp Ser Leu Ala Val Ser Leu Gly Glu Arg Ala Thr Ile Asn Cys Lys
GAC TCC CTG GCT GTG TCT CTG GGC GAG AGG GCC ACC ATC AAC TGC AAG        430
```

FIG. 24B

```
         Pro Ser Gln Ser Val Leu Tyr Ser Ser Asn Asn Lys Asn Tyr Leu Ala
         CCC AGC CAG AGT GTT TTA TAC AGC TCC AAC AAT AAG AAC TAC TTA GCT    478
                              30                                  40
TAGVLFR2:
         Trp Tyr Gln Gln Lys Pro Gly Gln Pro Pro Lys Leu Leu Ile Tyr Trp
         TGG TAC CAG CAG AAA CCA GG →
         TGG TAC CAG CAG AAA CCA GGA CAG CCT CCT AAG CTG CTC ATT TAC TGG    526
                                      50
         Ala Ser Thr Arg Glu Ser Gly Val Pro Asp Arg Phe Ser Gly Ser Gly
         GCA TCT ACC CGG GAA TCC GGG GTC CCT GAC CGA TTC AGT GGC AGC GGG    574
                      60                                  70
         Ser Gly Thr Asp Phe Thr Leu Thr Ile Ser Ser Leu Gln Ala Glu Asp
         TCT GGG ACA GAT TTC ACT CTC ACC ATC AGC AGC CTG CAG GCT GAA GAT    622
                                      80
         Ala Ala Val Tyr Tyr Cys Gln Gln Tyr Tyr Ser Tyr Pro Leu Thr Phe
         GCG GCA GTT TAT TAC TGT CAG CAA TAT TAT AGT CCT CTC ACT TTC        670
                      90                                  100
                                                  Hind III
         Gly Gly Gly Thr Lys Val Val Ile Lys Leu Ser Ala Asp Asp Ala Lys
         GGC GGA GGG ACC AAG GTG GTG ATC AAG CTT AGT GCG GAC GAT GCG AAA    718
                                      110                         120
```

FIG. 24C

```
UHVHSEQ:
      Lys Asp Ala Ala Ala Lys Lys Asp Ala Lys Lys Asp Asp Ala Lys Lys
      AAG GAT GCT GCG GCG AAG AAG GAT GAC GCT AAG AAA GAC GAT GCT AAA AAG   766
                                         G → 130
      Xho I   140                                      150
      Asp Leu Glu Val Gln Leu Gln Gln Ser Asp Ala Glu Leu Val Lys Pro
      GAC CTC GAG GTT CAG CTG CAG CAG TCT GAC GCT GAG TTG GTG AAA CCT       814
                                         160
      Gly Ala Ser Val Lys Ile Ser Cys Lys Ala Ser Gly Tyr Thr Phe Thr
      GGG GCT TCA GTG AAG ATT TCC TGC AAG GCT TCT GGC TAC ACC TTC ACT       862
                                                180       TAGVHCDR2: A
      Asp His Ala Ile His Trp Val Lys Gln Asn Pro Glu Gln Gly Leu Glu
      GAC CAT GCA ATT CAC TGG GTG AAA CAG AAC CCT GAA CAG GGC CTG GAA       910
      170
      Trp Ile Gly Tyr Phe Ser Pro Gly Asn Asp Asp Phe Lys Tyr Asn Glu
      TGG ATT GGA TAT TTT TCT CC →  GGA AAT GAT GAT TTT AAA TAC AAT GAG    958
                                                                    200
                                         210
      Arg Phe Lys Gly Lys Ala Thr Leu Thr Ala Asp Lys Ser Ser Ser Thr
      AGG TTC AAG GGC AAG GCC ACA CTG ACT GCA GAC AAA TCC TCC AGC ACT       1006
```

FIG. 24D

```
                     220                                                  230
Ala Tyr Val Gln Leu Asn Ser Leu Thr Ser Glu Asp Ser Ala Val Tyr
GCC TAC GTG CAG CTC AAC AGC CTG ACA TCT GAG GAT TCT GCA GTG TAT   1054

TAGVHFR4: AC TGG GGT CAA GGA ACC TCA
Phe Cys Thr Arg Ser Leu Asn Met Ala Tyr Trp Gly Gln Gly Thr Ser
TTC TGT ACA AGA TCC CTG AAT ATG GCC TAC TGG GGT CAA GGA ACC TCA   1102

G → 250          Nhe I                               260
Val Thr Val Ser Ser Ala Ser Asp Tyr Lys Asp Asp Asp Asp Lys ***
GTC ACC GTC TCC TCA GCT AGC GAT TAC AAG GAC GAT GAT GAC AAA TAA   1150

AAA CCT AGC GAT GAA TCC GTC AAA ACA TCA TCT TAC ATA AAG TCA CTT   1198

GGT GAT CAA GCT CAT ATT GTC CGG CAA TGG TGT GGG CTT TTT TTG       1246

TTT TCT ATC TTT AAA GAT CAT GTG AAG AAA ATC GGT CTG                1294

CGG GAA AGG ACC GGG TTT TTG TCG AAA TCA TAG GCG AAT GGG TTG GAT   1342

BamH I
TGT GAC AAA ATT CGG ATC C-3'                                       1361
```

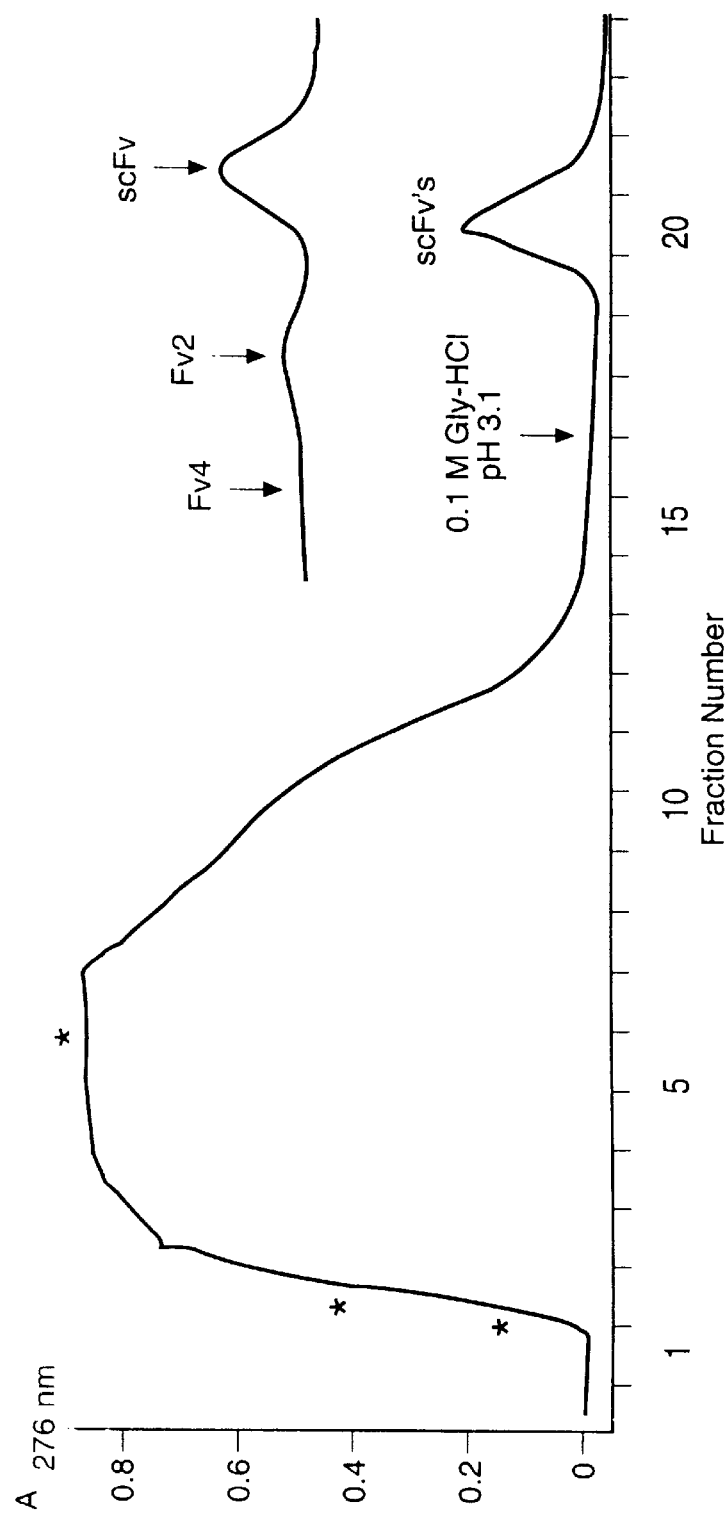
FIG. 25A  PURIFICATION AND CHARACTERIZATION OF H4L49HF scFv's

PURIFICATION AND CHARACTERIZATION OF H4L49HF scFv's

ELISA on TAG-72 Purified H4L49HF Monomer, Dimer, and Tetramer

ELISA on TAG-72 of *E.Coli* pSC49FLAG

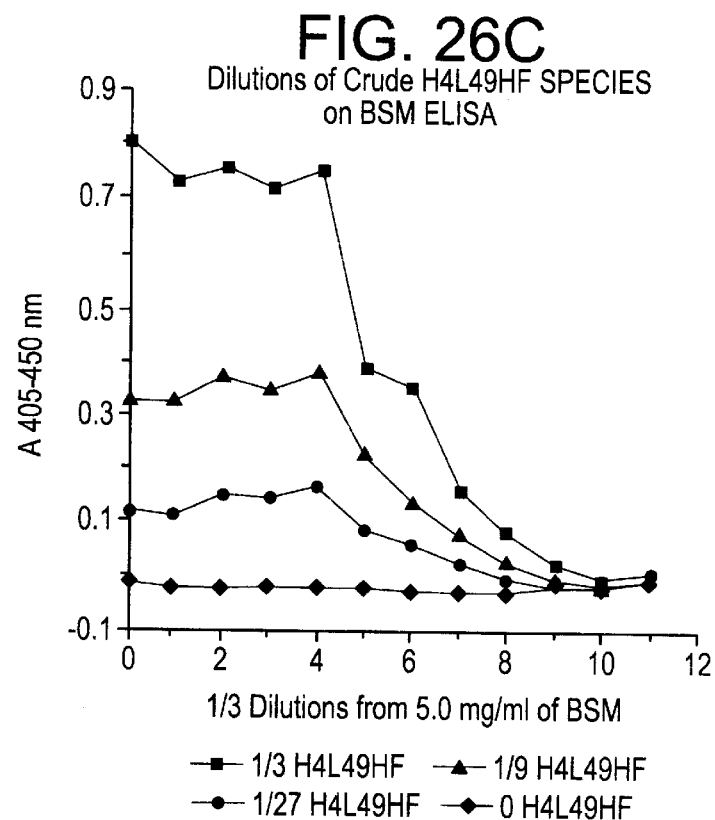
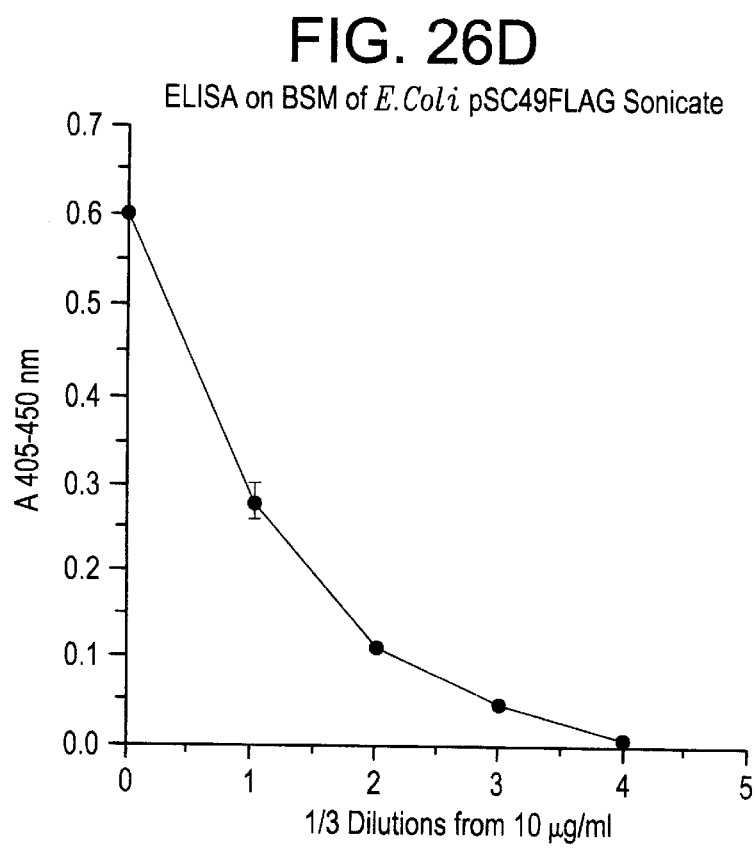

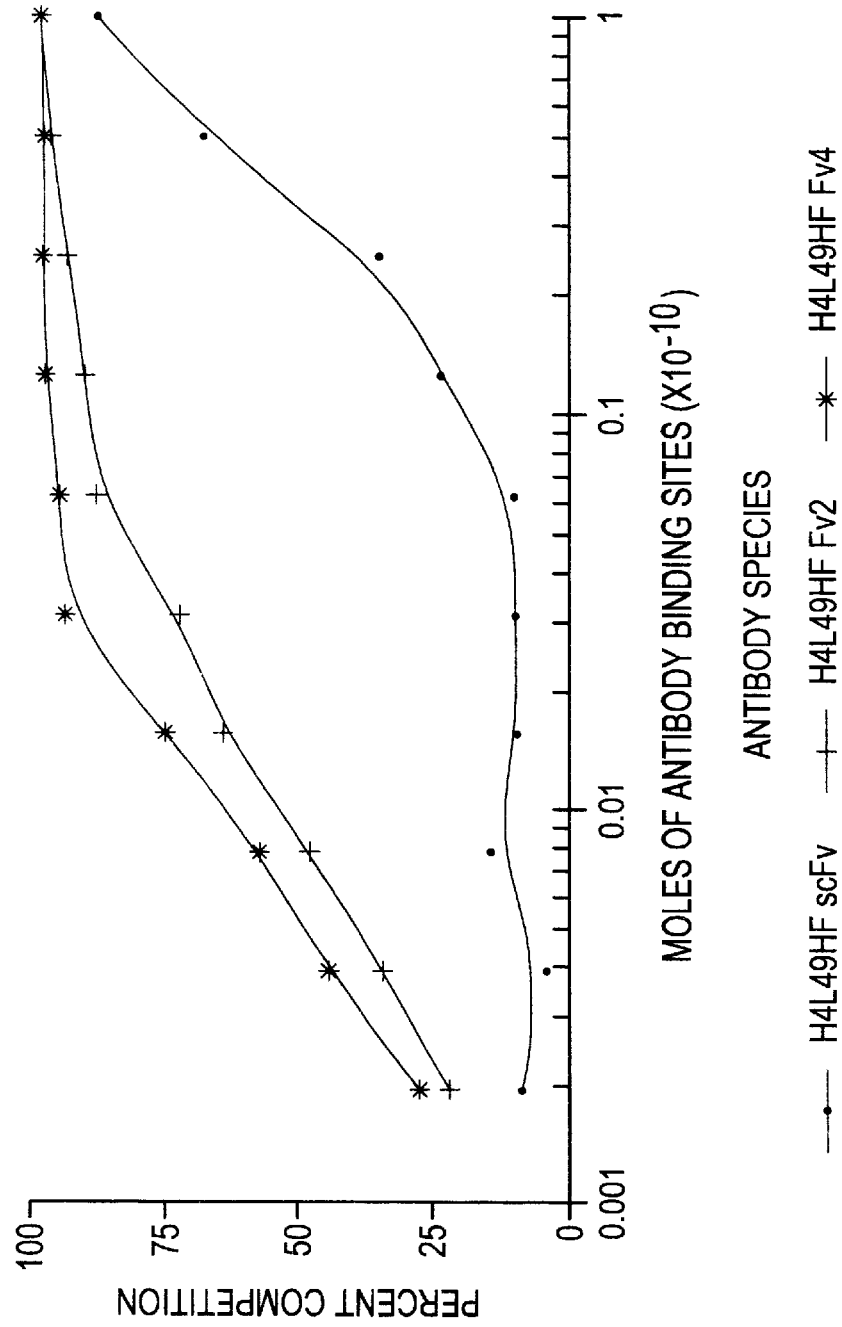

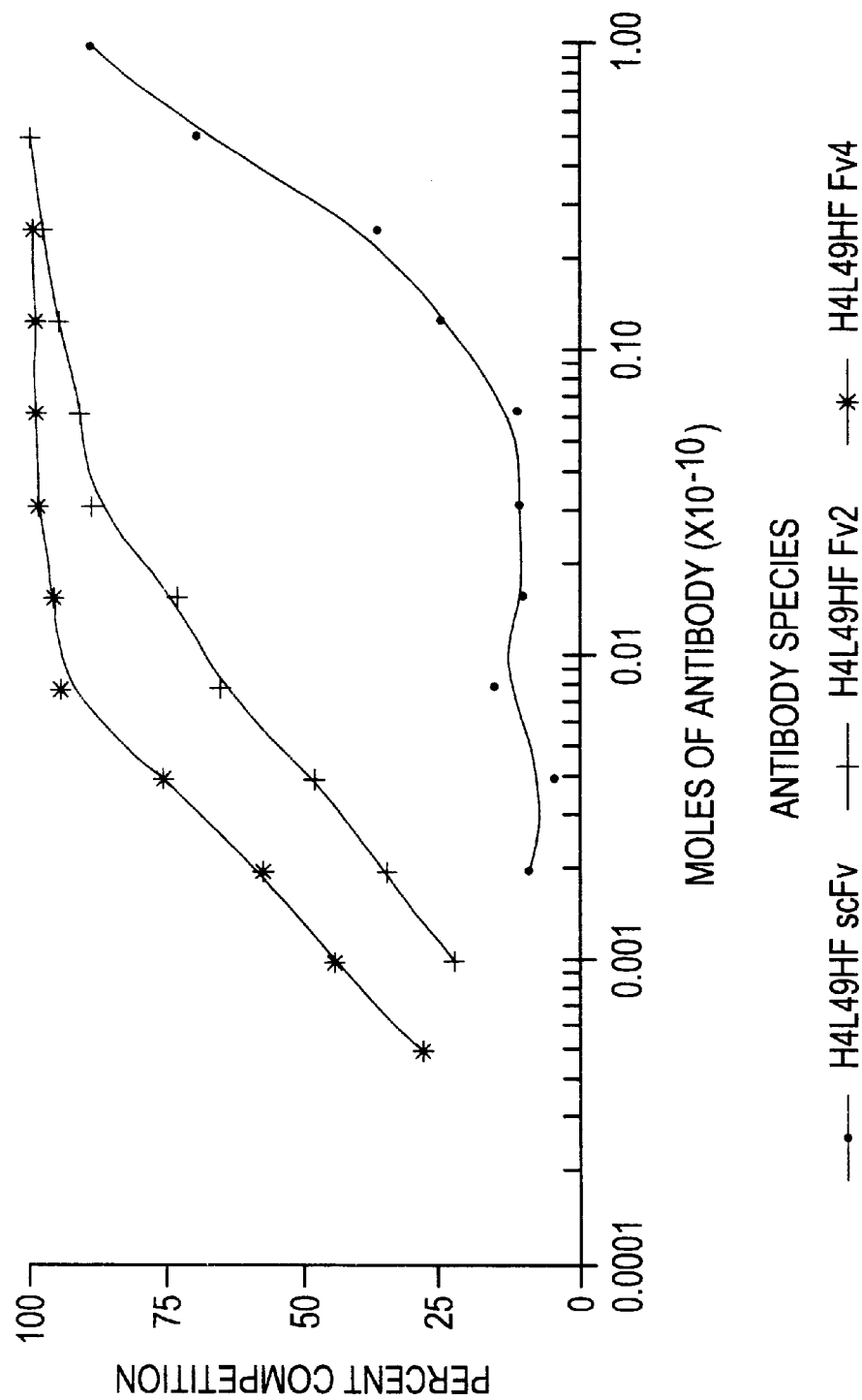

FIG. 30A

DNA AND AMINO ACID SEQUENCES OF scDRβ11/α-FLAG SPECIES

```
         Cla I        EcoR I
5'·C TCA TGT TTG ACA GCT TAT CAT CGA TGA ATT CCA TCA CTT CCC TCC    46

GTT CAT TTG TCC CCG GTG GAA ACG AGG TCA TCA TTT CCT TCC GAA AAA    94

ACG GTT GCA TTT AAA TCT TAC ATA TAT AAT ACT TTC AAA GAC TAC ATT   142

TGT AAG ATT TGA TGT TTG AGT CGG CTG AAA GAT CGT ACG TAC CAA TTA   190

TTG TTT CGT GAT TGT TCA AGC CAT AAC ACT GTA GGG ATA GTG GAA AGA   238

GTG CTT CAT CTG GTT ACG ATC AAT CAA ATA TTC AAA CGG AGG GAG ACG   286

-22
     Met Lys Tyr Leu Leu Pro Thr Ala Ala Ala Gly Leu Leu Leu
ATT TTG ATG AAA TAC CTA TTG CCT ACG GCA GCC GCT GGA TTG TTA TTA   334
                              Nco I
                                        +1
     Leu Ala Ala Gln Pro Ala Met Ala Gly Asp Thr Arg Pro Arg Phe Leu
     CTC GCT GCC CAA CCA GCC ATG GCC GGG GAC ACC CGA CCA CGT TTC TTG   382
      *                                          20

Trp Gln Leu Lys Phe Glu Cys His Phe Phe Asn Gly Thr Glu Arg Val
     TGG CAG CTT AAG TTT GAA TGT CAT TTC TTC AAT GGG ACG GAG CGG GTG   430
```

FIG.30B

```
                                                                40
Arg Leu Glu Arg Cys Ile Tyr Asn Gln Glu Ser Val Arg Phe
CGG TTG CTG GAA AGA TGC ATC TAT AAC CAA GAG TCC GTG CGC TTC     478

Asp Ser Asp Val Gly Glu Tyr Arg Ala Val Thr Glu Leu Gly Arg Pro
GAC AGC GAC GTG GGG GAG TAC CGG GCG GTG ACG GAG CTG GGG CGG CCT 526
                            *
                      60
Asp Ala Glu Tyr Trp Asn Ser Gln Lys Asp Leu Leu Glu Gln Arg Arg
GAT GCC GAG TAC TGG AAC AGC CAG AAG GAC CTC CTG GAG CAG AGG CGG 574
                                80
Ala Ala Val Asp Thr Tyr Cys Arg His Asn Tyr Gly Val Gly Glu Ser
GCC GCG GTG GAC ACC TAC TGC AGA CAC AAC TAC GGG GTT GGT GAG AGC 622
  *                                                Hind III
Phe Thr Val Gln Arg Arg Val Glu Pro Lys Val Thr Val Tyr Lys Leu
TTC ACA GTG CAG CGG CGA GTT GAG CCT AAG GTG ACT GTG TAT AAG CTT 670
                            *                100              120
Ser Ala Asp Asp Ala Lys Lys Asp Ala Ala Lys Lys Asp Asp Ala Lys
AGT GCG GAC GAT GCG AAA AAG GAT GCT GCG AAG AAG GAT GAC GCT AAG 718
```

FIG.30C

```
                Xho I
     Lys Asp Ala Lys Lys Asp Leu Glu Ile Lys Glu Glu His Val Ile Ile
     AAA GAC GCT AAA AAG GAC CTC GAG ATC AAA GAA GAA CAT GTG ATC ATC     766
                       140
                                              *
     Gln Ala Glu Phe Tyr Leu Asn Pro Asp Gln Ser Gly Glu Phe Met Phe
     CAG GCC GAG TTC TAT CTG AAT CCT GAC CAA TCA GGC GAG TTT ATG TTT     814
                              160
     Asp Phe Asp Gly Asp Glu Ile Phe His Val Asp Met Ala Lys Lys Glu
     GAC TTT GAT GGT GAT GAG ATT TTC CAT GTG GAT ATG GCA AAG AAG GAG     862
       *                                      180
     Thr Val Trp Arg Leu Glu Glu Phe Gly Arg Phe Ala Ser Phe Glu Ala
     ACG GTC TGG CGG CTT GAA GAA TTT GGA CGA TTT GCC AGC TTT GAG GCT     958
                                *                            200
     Gln Gly Ala Leu Ala Asn Ile Ala Val Asp Lys Ala Asn Leu Glu Ile
     CAA GGT GCA TTG GCC AAC ATA GCT GTG GAC AAA GCC AAC CTG GAA ATC     1006
                       210                         Nhe I
     Met Thr Lys Arg Ser Asn Tyr Thr Pro Ile Thr Asn Ala Ser Asp Tyr
     ATG ACA AAG CGC TCC AAC TAT ACT CCG ATC ACC AAT GCT AGC GAC TAC     1054
              *
     Lys Asp Asp Asp Lys ***
     AAG GAC GAT GAC AAA TAA AAA TAA AAA CCT AGC GAT GAA TCC GTC          1102
```

FIG.30D

```
AAA ACA TCT TAC ATA AAG TCA CTT GGT GAT CAA GCT CAT ATC ATT  1150

GTC CGG CAA TGG TGT GGG CTT TTT TTG TTT TCT ATC TTT AAA GAT CAT  1198

GTG AAG AAA AAC GGG AAA ATC GGT CTG CGG GAA AGG ACC GGG TTT TTG  1246

BamH I
TCG AAA TCA TAG GCG AAT GGG TTG GAT TGT GAC AAA ATT CGG ATC C-3'  1292
```

FIG.31A

DNA AND AMINO ACID SEQUENCES OF scDRβ42/α–FLAG SPECIES

```
        Cla I       EcoR I
5'-C TCA TGT TTG ACA GCT TAT CAT CGA TGA ATT CCA TCA CTT CCC TCC    46

GTT CAT TTG TCC CCG GTG GAA ACG AGG TCA TCA TTT CCT TCC GAA AAA    94

ACG GTT GCA TTT AAA TCT TAC ATA TAT AAT ACT TTC AAA GAC TAC ATT   142

TGT AAG ATT TGA TGT TTG AGT CGG CTG AAA GAT CGT ACG TAC CAA TTA   190

TTG TTT CGT GAT TGT TCA AGC CAT AAC ACT GTA GGG ATA GTG GAA AGA   238

GTG CTT CAT CTG GTT ACG ATC AAT CAA ATA TTC AAA CGG AGG GAG ACG   286
    -22
    Met Lys Tyr Leu Leu Pro Thr Ala Ala Gly Leu Leu Leu
ATT TTG ATG AAA TAC CTA TTG CCT ACG GCA GCT GGA TTG TTA TTA       334
            Nco I              +1
    Leu Ala Ala Gln Pro Ala Met Ala Gly Asp Thr Arg Pro Arg Phe Leu
    CTC GCT GCC CAA CCA ATG GCC GGG GAC ACC CGA CCA CGT TTC TTG   382
    *                                              20
    Glu Gln Val Lys His Phe Phe Asn Gly Thr Glu Arg Val
    GAG CAG GTT AAA CAT TTC TTC AAC GGG ACG GAG CGG GTG           430
```

FIG. 31B

```
                                                                         *                          40
Arg Phe Leu Asp Arg Tyr Phe Tyr His Gln Glu Glu Tyr Val Arg Phe
CGG TTC CTG GAC AGA TAC TTC TAT CAC CAA GAG GAG TAC GTG CGC TTC         478

*
Asp Ser Asp Val Gly Glu Tyr Arg Ala Val Thr Glu Leu Gly Arg Pro
GAC AGC GAC GTG GGG GAG TAC CGG GCG GTG ACG GAG CTG GGG CGG CCT         526

60                                        *
Asp Ala Glu Tyr Trp Asn Ser Gln Lys Asp Ile Leu Glu Asp Glu Arg
GAT GCC GAG TAC TGG AAC AGC CAG AAG GAC ATC CTG GAA GAC GAG CGG         574

Sac II                              80
Ala Ala Val Asp Thr Tyr Cys Arg His Asn Tyr Gly Val Val Glu Ser
GCC GCG GTG GAC ACC TAC TGC AGA CAC AAC TAC GGG GTT GTG GAG AGC         622

*                                                  100       Hind III
Phe Thr Val Gln Arg Arg Val Tyr Pro Lys Val Thr Val Tyr Lys Leu
TTC ACA GTG CAG CGG CGA GTC TAT CCT AAG GTG ACT GTG TAT AAG CTT         670

*                       120
Ser Ala Asp Asp Ala Lys Lys Asp Ala Ala Lys Lys Asp Asp Ala Lys
AGT GCG GAC GAT GCG AAA AAG GAT GCC GCG AAG AAG GAT GAC GCT AAG         718
```

FIG. 31C

```
                          Xho I
Lys Asp Ala Lys Lys Asp Leu Glu Ile Lys Glu His Val Ile Ile
AAA GAC GCT AAA AAG GAC CTC GAG ATC AAA GAA GAA CAT GTG ATC ATC    766
                140

Gln Ala Glu Phe Tyr Leu Asn Pro Asp Gln Ser Gly Glu Phe Met Phe
CAG GCC GAG TTC TAT CTG AAT CCT GAC CAA TCA GGC GAG TTT ATG TTT    814
                                    160                      *

Asp Phe Asp Gly Asp Glu Ile Phe His Val Asp Met Ala Lys Lys Glu
GAC TTT GAT GGT GAT GAG ATT TTC CAT GTG GAT ATG GCA AAG AAG GAG    862
                                                    180

Thr Val Trp Arg Leu Glu Glu Phe Gly Arg Phe Ala Ser Phe Glu Ala
ACG GTC TGG CGG CTT GAA GAA TTT GGA CGA TTT GCC AGC TTT GAG GCT    958
    *                                   *                      200

Gln Gly Ala Leu Ala Asn Ile Ala Val Asp Lys Ala Asn Leu Glu Ile
CAA GGT GCA TTG GCC AAC ATA GCT GTG GAC AAA GCC AAC CTG GAA ATC    1006
                                            210               Nhe I

Met Thr Lys Arg Ser Asn Tyr Thr Pro Ile Thr Asn Ala Ser Asp Tyr
ATG ACA AAG CGC TCC AAC TAT ACT CCG ATC ACC AAT GCT AGC GAC TAC    1054
                                *

Lys Asp Asp Asp Lys ***
AAG GAC GAT GAT GAC AAA TAA AAA TAA AAA CCT AGC GAT GAA TCC GTC    1102
```

FIG.31D

```
AAA ACA TCA TCT TAC ATA AAG TCA CTT GGT GAT CAA GCT CAT ATC ATT  1150

GTC CGG CAA TGG TGT GGG CTT TTT TTG TTT TCT ATC TTT AAA GAT CAT  1198

GTG AAG AAA AAC GGG AAA ATC GGT CTG CGG GAA AGG ACC GGG TTT TTG  1246

BamH I
TCG AAA TCA TAG GCG AAT GGG TTG GAT TGT GAC AAA ATT CGG ATC C-3' 1292
```

FIG. 32A

DNA AND AMINO ACID SEQUENCES OF scDRβ48/α-FLAG SPECIES

```
        Cla I     EcoR I
5'-C TCA TGT TTG ACA GCT TAT CAT CGA TGA ATT CCA TCA CTT CCC TCC    46

GTT CAT TTG TCC CCG GTG GAA ACG AGG TCA TCA TTT CCT TCC GAA AAA    94

ACG GTT GCA TTT AAA TCT TAC ATA TAT AAT ACT TTC AAA GAC TAC ATT   142

TGT AAG ATT TGA TGT TGT TTG AGT CGG CTG AAA GAT CGT ACG CAA TTA   190

TTG TTT CGT GAT TGT TCA AGC CAT AAC ACT GTA GGG ATA GTG GAA AGA   238

GTG CTT CAT CTG GTT ACG ATC AAT CAA ATA TTC AAA CGG AGG GAG ACG   286

-22
        Met Lys Tyr Leu Pro Thr Ala Ala Ala Gly Leu Leu Leu
ATT TTG AAA TAC CTA TTG CCT ACG GCA GCC GCT GGA TTG TTA TTA       334

NcoI          +1
Leu Ala Ala Gln Pro Ala Met Ala Gly Asp Thr Arg Pro Arg Phe Leu
CTC GCT GCC CAA CCA GCC ATG GCC GGG GAC ACC CGA CCA CGT TTC TTG   382
                                           20
 *
Glu Gln Val Lys His Glu Cys His Phe Phe Asn Gly Thr Glu Arg Val
GAG CAG GTT AAA CAT GAG TGT CAT TTC TTC AAC GGG ACG GAG CGG GTG   430
```

FIG.32B

```
                                                          *                                40
Arg Phe Leu Asp Arg Phe Tyr His Gln Glu Tyr Val Arg Phe
CGG TTC CTG GAC AGA TTC TAT CAC CAA GAG TAC GTG CGC TTC    478

*
Asp Ser Asp Val Gly Glu Tyr Arg Ala Val Thr Glu Leu Gly Arg Pro
GAC AGC GAC GTG GGG GAG TAC CGG GCG GTG ACG GAG CTG GGG CGG CCT    526

60                        Xho I    *
Asp Ala Glu Tyr Trp Asn Ser Gln Lys Asp Leu Glu Gln Arg Arg
GAT GCC GAG TAC TGG AAC AGC CAG AAG GAC CTC GAG CAG AGG CGG    574

Sac II                                    80
Ala Ala Val Asp Thr Tyr Cys Arg His Asn Tyr Gly Val Gly Glu Ser
GCC GCG GTG GAC ACC TAC TGC AGA CAC AAC TAC GGG GTT GGT GAG AGC    622

*                                              100         Hind III
Phe Thr Val Gln Arg Arg Val Glu Pro Lys Val Thr Val Tyr Lys Leu
TTC ACA GTG CAG CGG CGA GTT GAG CCT AAG GTG ACT GTG TAT AAG CTT    670

*                                                   120
Ser Ala Asp Asp Ala Lys Lys Asp Ala Ala Lys Lys Asp Asp Ala Lys
AGT GCG GAC GAT GCG AAA AAG GAT GCT GCG AAG AAG GAT GAC GCT AAG    718
```

FIG. 32C

```
         Xho I
Lys Asp Ala Lys Lys Asp Leu Glu Ile Lys Glu Glu His Val Ile Ile
AAA GAC GCT AAA AAG GAC CTC GAG ATC AAA GAA GAA CAT GTG ATC ATC   766
                     140

Gln Ala Glu Phe Tyr Leu Asn Pro Asp Gln Ser Gly Glu Phe Met Phe
CAG GCC GAG TTC TAT CTG AAT CCT GAC CAA TCA GGC GAG TTT ATG TTT   814

Asp Phe Asp Gly Asp Glu Ile Phe His Val Asp Met Ala Lys Lys Glu
GAC TTT GAT GGT GAT GAG ATT TTC CAT GTG GAT ATG GCA AAG AAG GAG   862
                        160                          180

Thr Val Trp Arg Leu Glu Glu Phe Gly Arg Phe Ala Ser Phe Glu Ala
ACG GTC TGG CGG CTT GAA GAA TTT GGA CGA TTT GCC AGC TTT GAG GCT   958

Gln Gly Ala Leu Ala Asn Ile Ala Val Asp Lys Ala Asn Leu Glu Ile
CAA GGT GCA TTG GCC AAC ATA GCT GTG GAC AAA GCC AAC CTG GAA ATC   1006
                                                         200
                                                          Nhe I
Met Thr Lys Arg Ser Asn Tyr Thr Pro Ile Thr Asn Ala Ser Asp Tyr
ATG ACA AAG CGC TCC AAC TAT ACT CCG ATC ACC AAT GCT AGC GAC TAC   1054
                     210

Lys Asp Asp Asp Lys ***
AAG GAC GAT GAT GAC AAA TAA AAA TAA AAA CCT AGC GAT GAA TCC GTC   1102
```

FIG. 32D

```
AAA ACA TCA TCT TAC ATA AAG TCA CTT GGT GAT CAA GCT CAT ATC ATT   1150

GTC CGG CAA TGG TGT GGG CTT TTT TTG TTT TCT ATC TTT AAA GAT CAT   1198

GTG AAG AAA AAC GGG AAA ATC GGT CTG CGG GAA AGG ACC GGG TTT TTG   1246

BamH I
TCG AAA TCA TAG GCG AAT GGG TTG GAT TGT GAC AAA ATT CGG ATC C-3'   1292
```

FIG. 33A

DNA AND AMINO ACID SEQUENCES OF scDRβ41/α-FLAG SPECIES

```
                  Cla I      EcoR I
5'·C TCA TGT TTG ACA GCT TAT CAT CGA TGA ATT CCA TCA CTT CCC TCC    46

GTT CAT TTG TCC CCG GTG GAA ACG AGG TCA TCA TTT CCT TCC GAA AAA    94

ACG GTT GCA TTT AAA TCT TAC ATA TAT AAT ACT TTC AAA GAC TAC ATT   142

TGT AAG ATT TGA TGT TTG AGT CGG CTG AAA GAT CGT ACG TAC CAA TTA   190

TTG TTT CGT GAT TGT TCA AGC CAT AAC ACT GTA GGG ATA GTG GAA AGA   238

GTG CTT CAT CTG GTT ACG ATC AAT CAA ATA TTC AAA CGG AGG GAG ACG   286

Leu Pro Thr Ala Ala Gly Leu Leu Leu
                                    CTT CCT ACG GCA GCC GCT GGA TTG TTA TTA   334
       -22
    Met Lys Tyr Leu                                                            
ATT TTG ATG AAA TAC CTA TTG                                                    
          NcoI                 +1
Leu Ala Ala Gln Pro Ala Met Ala Gly Asp Thr Arg Pro Arg Phe Leu
CTC GCT GCC CAA CCA ATG GCC GGG GAC ACC CGA CCA CGT TTC TTG           382
    *                              20

Glu Gln Val Lys His Glu Cys His Phe Phe Asn Gly Thr Glu Arg Val
GAG CAG GTT AAA CAT GAG TGT CAT TTC TTC AAC GGG ACG GAG CGG GTG       430
```

FIG. 33B

```
                                                                              40
    Arg Phe Leu Asp Arg Tyr Phe Tyr His Gln Glu Tyr Val Arg Phe
    CGG TTC CTG GAC AGA TAC TTC TAT CAC CAA GAG TAC GTG CGC TTC     478
                              *
    Asp Ser Asp Val Gly Glu Tyr Arg Ala Val Thr Glu Leu Gly Arg Pro
    GAC AGC GAC GTG GGG GAG TAC CGG GCG GTG ACG GAG CTG GGG CGG CCT  526
                 60                          Xho I     *
    Asp Ala Glu Tyr Trp Asn Ser Gln Lys Asp Leu Leu Glu Gln Lys Arg
    GAT GCC GAG TAC TGG AAC AGC CAG AAG GAC CTC CTC GAG CAG AAG CGG  574
    Sac II                              80
    Ala Ala Val Asp Thr Tyr Cys Arg His Asn Tyr Gly Val Gly Glu Ser
    GCC GCG GTG GAC ACC TAC TGC AGA CAC AAC TAC GGG GTT GGT GAG AGC  622
            *                                            100        Hind III
    Phe Thr Val Gln Arg Arg Val Tyr Pro Lys Val Thr Val Tyr Lys Leu
    TTC ACA GTG CAG CGG CGA GTC TAT CCT AAG GTG ACT GTG TAT AAG CTT  670
                     *                                   120
    Ser Ala Asp Asp Ala Lys Lys Asp Ala Ala Lys Lys Asp Asp Ala Lys
    AGT GCG GAC GAT GCG AAA AAG GAT GCT GCG AAG AAG GAT GAC GCT AAG  718
```

FIG. 33C

```
                    Xho I
Lys Asp Ala Lys Lys Asp Leu Glu Ile Lys Glu His Val Ile Ile
AAA GAC GCT AAA AAG GAC CTC GAG ATC AAA GAA CAT GTG ATC ATC    766
                140
                                         *
Gln Ala Glu Phe Tyr Leu Asn Pro Asp Gln Ser Gly Glu Phe Met Phe
CAG GCC GAG TTC TAT CTG AAT CCT GAC CAA TCA GGC GAG TTT ATG TTT    814
            160
Asp Phe Asp Gly Asp Glu Ile Phe His Val Asp Met Ala Lys Lys Glu
GAC TTT GAT GGT GAT GAG ATT TTC CAT GTG GAT ATG GCA AAG AAG GAG    862
     *                                  180
Thr Val Trp Arg Leu Glu Glu Phe Gly Arg Phe Ala Ser Phe Glu Ala
ACG GTC TGG CGG CTT GAA GAA TTT GGA CGA TTT GCC AGC TTT GAG GCT    958
                           *                                200
Gln Gly Ala Leu Ala Asn Ile Ala Val Asp Lys Ala Asn Leu Glu Ile
CAA GGT GCA TTG GCC AAC ATA GCT GTG GAC AAA GCC AAC CTG GAA ATC    1006
                    210                            Nhe I
Met Thr Lys Arg Ser Asn Tyr Thr Pro Ile Thr Asn Ala Ser Asp Tyr
ATG ACA AAG CGC TCC AAC TAT ACT CCG ATC ACC AAT GCT AGC GAC TAC    1054
                                *
Lys Asp Asp Asp Lys ***
AAG GAC GAT GAT GAC AAA TAA AAA CCT AGC GAT GAA TCC GTC    1102
```

FIG.33D

```
AAA ACA TCA TCT TAC ATA AAG TCA CTT GGT GAT CAA GCT CAT ATC ATT  1150

GTC CGG CAA TGG TGT GGG CTT TTT TTG TTT TCT ATC TTT AAA GAT CAT  1198

GTG AAG AAA AAC GGG AAA ATC GGT CTG CGG GAA AGG ACC GGG TTT TTG  1246
                                                  BamH I
TCG AAA TCA TAG GCG AAT GGG TTG GAT TGT GAC AAA ATT CGG ATC C-3' 1292
```

DIMER AND MULTIMER FORMS OF SINGLE CHAIN POLYPEPTIDES

BACKGROUND OF THE INVENTION

This invention relates to the field of molecular biology and production of single chain polypeptides.

The immunoglobulin (Ig) superfamily is a group of proteins having as a common denominator an adhesion function or binding function that triggers a subsequent event at a cell surface. The molecules of the Ig superfamily have a diversity of functions, including involvement in immune response and in controlling the behavior of cells in various tissues. See, for example, Williams et al., *Ann. Rev. Immunol.*, 6, 381–405 (1988); Williams, *Immunology Today*, 8, 298–303 (1987); and Matsunaga, *Immunology Today*, 6, 260–263 (1985).

The Ig superfamily includes such functionally-important members as the antigen receptors of lymphocytes [e.g., immunoglobulins, T-cell receptor (TCR) molecules, and Class I and Class II molecules of the major histocompatability complex (MHC)]. Lymphocytes are divided broadly into cells that mature in the thymus (T-lymphocytes or T-cells) and cells that mature without passing through the thymus (B lymphocytes or B cells). T-cells can be divided into a number of subtypes such as T-helper cells or cytotoxic T-cells. Helper T-cells respond only to antigen that is on the surface of an antigen presenting cell that also expresses a class II MHC. Cytotoxic T-cells destroy other cells that have been infected by an organism, such as a virus, by recognizing foreign antigen presented in the context of the class I MHC molecule on the surface of the infected cell.

A structural feature that characterizes members of the Ig superfamily is the presence of one or more regions homologous to the basic structural unit of immunoglobulins, the immunoglobulin homology unit. These regions are usually between 10 and 110 amino acid residues in length and are characterized by a series of anti-parallel β sheets that generate a compact sandwich of two β sheets or a single large sheet in the case of MHC proteins. This structure is stabilized by a small series of conserved residues, particularly, two virtually invariant cysteine residues that generate a signature disulfide bond holding the faces of the β sheet sandwich together. The loop sequences connecting the β strands are less significant for the basic homology unit structure and therefore, can accommodate extensive variability.

The Ig superfamily contains distinct classes of immune receptors, molecules that interact directly with an antigen including: (1) antibodies, (2) T-cell receptors, (3) MHC class I, (4) MHC class II; (5) Immunoglobulin Fc receptors (including CD16, CD23, CDw32, etc.) and (6) some cell-surface adhesion molecules (including but not limited to CD4 and CD8 and β1 integrin family of proteins). Antibodies can be expressed either on the cell surface or humorally; that is secreted into the blood to carry out their functions at a distance from the cell of origin. T-cells synthesize only a surface-bound antigen receptor. There are two classes of receptors encoded within the MHC. Class I MHC molecules are present in varying amounts on virtually all somatic cells. Class II MHC molecules are expressed only on particular antigen-presenting cells such as macrophages and B cells. Class I and class II MHC play a role in presenting antigens in a form which can be recognized by the T-cell receptors. Immunoglobulin Fc receptors are expressed on a variety of hematopoietic cells and function in antibody-dependent T-cell killing and in mast cell degranulation. Adhesion molecules are cell surface proteins involved in regulating the adhesion, migration and overall trafficking of lymphocytes necessary for their immunological function.

The basic structure of an antibody is a tetramer composed of two identical heterodimers each consisting of a light and a heavy chain. The antibody molecule is divided into variable (V) domains that are responsible for binding specificity and constant (C) domains that carry out various effector functions. The V domain is constructed of one V homology unit from both the light and heavy chains, designated $V_L$ and $V_H$ respectively. The variable region can be further subdivided into framework regions (FR) and complementarity determining regions (CDR), also designated as hypervariable regions. The FR maintain the structural integrity of the variable region domain. The CDR are the polypeptide segments within the variable region that mediate binding to the antigen. As the antibody contains two heterodimers, it has two antigen binding sites (divalent).

The T-cell antigen receptor is a heterodimer with one V domain involved in antigen recognition and one C domain that interacts with a membrane-bound protein complex, CD3, presumably involved in signal transduction. See for example Davis, *Annu. Reu. Immunol.*, 3, 537- (1985); Kronenberg et al., *Annu. Rev. Immunol.*, 4, 529- (1986). The majority of T-cells responsible for general antigen recognition use α and β chains. A small subset of T-cells employ T-cell receptors composed of γ and δ chains. As with antibodies, the V domain contains hypervariable regions which are the primary sequences responsible for antigenic interaction. Unlike antibodies, however, these hypervariable regions are not subject to somatic mutation during T-cell selection and maturation.

Class I MHC molecules are transmembrane, glycosylated polymorphic polypeptide chains in close, non-covalent association with a β2 microglobulin. The glycosylated polypeptide chain is divided into five distinct regions: three extracellular domains, a transmembrane region, and a cytoplasmic domain; the three extracellular domains designated α1, α2 and α3. Most of the sequence diversity of class I MHC molecules lies in the α1 and α2 domains with little sequence diversity in the α3 domain. The α1 and α2 domains interact to form a tertiary structure that is capable of binding a wide array of peptides. In this way, the α1/α2 interface is analogous to the $V_H/V_L$ interface of antibodies of the Vα/Vβ interface of the T-cell receptor.

Class II MHC molecules including the I-E, I-A molecules in the mouse, the HLA-DP, DQ and DR molecules in man and equivalent molecules in other mammals) are heterodimeric cell surface proteins composed of α and β chain polypeptides. With the exception of I-E, HLA-DR and their equivalent genes in other organisms, both the α and β chains of class II MHC proteins are highly polymorphic. Both chains have two extracellular domains, α1 and α2 for the achain, and β1 and β2 for the β chain. In each chain, there is also a transmembrane segment and a short intracytoplasmic domain. The α2 and β2 resemble immunoglobulin constant region domains. The highest degree of sequence variation occurs in the β1 domain with the α1 and β1 domains forming the recognition site for binding antigen.

By using current techniques in molecular biology, it is possible to clone polypeptide chains. The more complex the molecules, e.g., the multichain immune receptors of the Ig superfamily, the more difficult they are to produce in a single foreign host. Genes coding for each chain of a complex molecule can be cloned and expressed in separate hosts but the aggregation and refolding of the resultant polypeptides into a biologically active entity is difficult to achieve. Multiple chains expressed by multiple genes within the same host have an advantage in aggregating and refolding into native structure but their expression in stoichiometric amounts is difficult to regulate. Thus, neither approach has proven to be efficient.

Since it is the variable regions of light and heavy chain antibodies that interact with an antigen, single chain polypeptides have been created with one $V_L$ and one $V_H$ joined by a peptide linker (U.S. Pat. No. 4,946,778). This single chain fragment (Fv) is univalent and is one of the smallest structures necessary for antigen binding activity having all 6 CDR regions of a $V_L$–$V_H$ combination. Similarly, the formation of single chain polypeptides containing the variable domains of αβ T-cell antigen receptors have also been reported. Novotny et al., *Proc. Natl. Acad. Sci. USA*, 88, 8646–8650 (1991); Soo Hoo et al., *Proc. Natl. Acad. Sci. USA*, 89, 4759–4763 (1992). The ability to produce as single chain polypeptides the antigenic or ligand binding portions of antibodies and αβ T-cell antigen receptors reduces the difficulties discussed above which are encountered when producing multichain polypeptides.

The use of the functional smaller polypeptides which maintain an antigen recognition site are also advantageous when used for therapeutic purposes in mammals in that the smaller molecules are capable of rapidly localizing in the target tissue, such as single chain antibodies localizing in cancerous tissue or single chain T-cell receptors localizing to the inflammatory sites of patients suffering from such T-cell dependent pathological conditions as acute or chronic graft rejection, graft-vs-host disease, rheumatoid arthritis and other autoimmune diseases. Similarly, soluble single chain MHC molecules (perhaps bound to the disease-propagating antigens) could localize to and block pathologic antigen presentation at sites of T-cell dependent inflammation. However, while being able to penetrate the desired tissue, polypeptides with a molecular weight of less than about 50,000 daltons have the disadvantage of being retained within the glomerulus of the kidney. This is particularly disadvantageous when the polypeptide is bound with a carrier, such as a radioisotope or toxin, as the isotope or toxin will also accumulate in the kidneys.

Single chain polypeptides also suffer from the disadvantage of having only one binding site, thereby reducing their avidity.

It would therefore be advantageous to obtain constructions of the Ig superfamily which retain their antigen or ligand recognition properties, are of sufficient molecular weight to enhance retention at the target site with reduced retention in the kidney, and have a multiplicity of binding sites to enhance the avidity of the polypeptide. In addition, it would be beneficial if the single chain immunoglobulin superfamily proteins could be rendered bispecific to allow for recognition of different epitopes on the target tissue (or lymphocyte) or to allow for antibody-based recruitment of other immune effector functions (i.e., complement proteins, cytotoxic lymphocytes, etc.).

SUMMARY OF THE INVENTION

Surprisingly it has been found that single chains of the Ig superfamily will non-covalently associate to form dimers and multimers. In one embodiment, the invention is a protein comprising a dimer or multimer of single chain polypeptides wherein the polypeptides are non-covalently linked and each polypeptide comprises (a) a first polypeptide comprising an antigen binding portion of a variable domain from a member of the immunoglobulin superfamily; (b) a second polypeptide comprising an antigen binding portion of a variable domain from a member of the immunoglobulin superfamily; and (c) a peptide linker linking the first and second polypeptides (a) and (b) into a single chain polypeptide having affinity for the antigen. In particular, the invention is a protein comprising a dimer or multimer of single chain polypeptides wherein the polypeptides are non-covalently linked and each polypeptide comprises (a) a first polypeptide comprising an antigen binding portion of a light chain variable region of an antibody, an α-chain variable region of a T-cell receptor or the α1 domain of either a class I or class II major histocompatibility complex molecule;

(b) a second polypeptide comprising the antigen binding portion of a heavy chain variable region of an antibody; a β-chain variable region of a T-cell receptor or the β1 domain of a class I or class II major histocompatibility complex molecule; and (c) a peptide linker linking the first and second polypeptides (a) and (b) into a single chain polypeptide.

In another aspect the present invention includes the aforementioned dimer or multimers conjugated to an imaging marker or therapeutic agent. The invention also includes a composition comprising the dimer or multimer conjugated to an imaging marker or therapeutic agent in a pharmaceutically acceptable carrier.

The invention is also directed to a method for in vivo diagnostics of cancer which comprises administering to an animal containing a tumor expressing a recognizable marker, a pharmaceutically effective amount of a composition containing a dimer or multimer of single chain polypeptides wherein the first and second polypeptide are specific for the recognizable marker.

In another embodiment, the invention is a method for intraoperative therapy which comprises (a) administering a pharmaceutically effective amount of the aforementioned composition containing di- or multimers of a single chain antibody against a recognizable marker to a patient containing a tumor expressing this recognizable marker, whereby the tumor is localized and (b) excising the localized tumor.

In another aspect, the invention is related to a method for the prevention and/or treatment of pathological T-cell dependent inflammatory disorders comprising administering to a patient a pharmaceutically effective amount of the aforementioned composition containing dimers or multimers of single chain antibodies, T-cell receptor or MHC molecules.

In still another embodiment, the invention concerns a process for preparing and expressing the aforementioned dimer and multimers of single chain polypeptides. Such an exemplary process comprises:

(i) providing a genetic sequence coding for a single chain polypeptide;

(ii) transforming a host T-cell with the genetic sequence;

(iii) expressing the genetic sequence in the host T-cell; and (iv) recovery of single chain polypeptides which have non-covalently linked to form dimers and multimers.

BRIEF DESCRIPTION OF THE DRAWINGS

FIG. 2 shows the construction of plasmid pSCFV31.

FIG. 3 illustrates the nucleotide sequence (SEQ ID NO:1) and amino acid sequence (SEQ ID NO:2) of SCFV1.

FIGS. 4 shows the construction of plasmid pSCFV UNIH.

FIG. 5 illustrates the nucleotide sequence (SEQ ID NO:3) and amino acid sequence (SEQ ID NO:4) of Hum4 $V_L$ gene Cla I-Hind III segment in pRL1001.

FIG. 7 illustrates the nucleotide sequence (SEQ ID NO:5) and amino acid sequence (SEQ ID NO:6) of a Human Subgroup 4 variable light chain (H4$V_L$) and a murine variable having chain single chain Fv immunoglobulin fragment.

FIG. 8 illustrates the DNA sequence and amino acid sequence of CC49 SCFV species with a pI of 8.1(A), 5.8(B) and 5.2(C).

FIG. 9 shows the results of a cation exchange chromatograph activity, SDS-PAGE and Western Blot of *E. coli* pSCFV UHM8.1 periplasmic fraction.

FIG. 10 shows the results of an anion exchange chromatograph, SDS-PAGE and Western Blot of Pool 2 (FIG. 9) of *E. coli* pSCFV UHM8.1 periplasmic fraction.

FIG. 12 shows the results of a gel filtration chromatograph, activity SDS-PAGE and Western Blot of *E. coli* pSCFV UHM5.2 periplasmic fraction.

FIG. 13 illustrates the results of a CC49 antibody competition based on moles of antibody binding sites.

FIG. 14 illustrates the results of a competition ELISA read one hour after addition of substrate.

FIG. 16 illustrates the DNA sequence and amino acid sequence of CC49 SCFV in pPY21(A) and pPY22(B).

FIG. 17 shows the relative activity of CC49 CFV species obtained from Pichia pP431 and pP432 clones.

FIG. 21, i.e. FIGS. 21A and 21B, illustrates the results of a competition ELISA based on (A) moles of antibody sites and (B) moles of antibody.

FIG. 22 shows the construction of plasmids pATDFLAG and pSC49FLAG.

FIG. 23 illustrates the nucleotide sequences (SEQ ID NO:19) and amino acid sequences (SEQ ID NO:20) in plasmid pATDOFLAG.

FIG. 24 illustrates the nucleotide sequences (SEQ ID NO:21) and amino acid sequences (SEQ ID NO:22) in plasmid pSC49FLAG.

FIG. 27 illustrates the results of a competition assay based on moles of antibody binding sites of H4L49F single chain species.

FIG. 28 illustrates the results of a competition assay based on moles of H4L49F single chain species.

FIG. 30 illustrates the nucleotide sequence (SEQ ID NO:23) and amino acid sequence (SEQ ID NO:24) of the pscDRβ11/α-FLAG transcriptional unit.

FIG. 31 illustrates the nucleotide sequence (SEQ ID NO:25) and amino acid sequence (SEQ ID NO:26) of the pscDRβ42/α-FLAG transcriptional unit.

FIG. 32 illustrates the nucleotide sequence (SEQ ID NO:27) and amino acid sequence (SEQ ID NO:28) of the pscDRβ48/α-FLAG transcriptional unit.

FIG. 33 illustrates the nucleotide sequence (SEQ ID NO:29) and amino acid sequence (SEQ ID NO:30) of the pscDRβ41 /α-FLAG transcriptional unit.

DETAILED DESCRIPTION OF THE INVENTION

Figure 1:
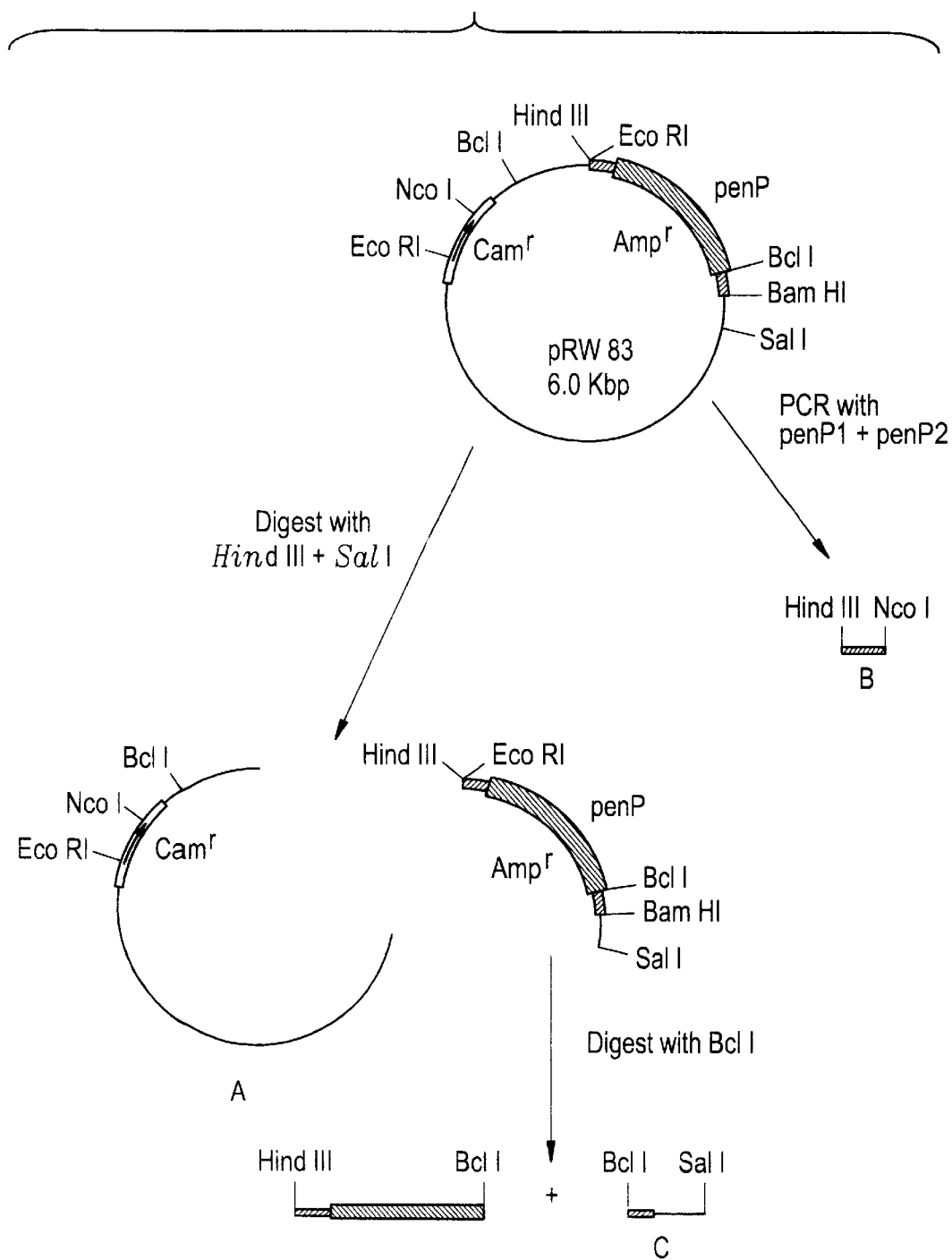
FIG. 1 shows the digestion of pRW83 to produce vectors used in the construction of plasmid pSCFV31.

The entire teaching of all references cited herein are hereby incorporated by reference.

Nucleic acids, amino acids, peptides, protective groups, active groups and such, when abbreviated, are abbreviated according to the IUPAC IUB (Commission on Biological Nomenclature) or the practice in the fields concerned.

As used herein, the term "non-covalently linked" means a polypeptide that will be separated on the basis of its molecular weight by size exclusion chromatography when done under non-reducing or reducing conditions, but will dissociate into two or more polypeptides when subjected to denaturing conditions such as heating and sodium dodecyl sulfate.

The term "single chain polypeptide" as used herein means a polypeptide from two original peptides linked by a peptide linker where the two original peptides are domains from the immunoglobulin superfamily and is capable of binding an antigenic determinant or receptor. "Domain" is a segment of protein that assumes a discrete function, such as antigen binding or antigen recognition.

The "immunoglobulin superfamily" means a family of proteins containing one or more domains that resemble an immunoglobulin domain. Proteins of the immunoglobulin superfamily include antibodies, T-cell receptors, CD1, CD2, CD3, CD7, CD8, Thy-1, Tp44, class I MHC molecules such as human leukocyte antigen (HLA) -A, -B, -C, -E; class II MHC molecules such as HLA-DP, -DZ, -DX, -DQ and -DR; immunoglobulin Fc receptors such as CD16, CD23, CDw32; and cell-surface adhesion molecules such as Cd4, CD8 and the β1 integrin family of proteins.

A "dimer" is two single chain polypeptides which are non-covalently linked and the term "multimer" means an even number of dimers which are non-covalently linked. "Vector" means a DNA element used as a vehicle for cloning a fragment of foreign DNA.

The single chain polypeptides which form dimers and multimers in the present invention can be obtained from any member of the Ig superfamily. Preferably, the two original peptides in the single chain are selected from a light and heavy chain variable region of an antibody, and α1 and α2 domains of a class I MHC molecule or α1 and β1 domains of a class II MHC molecule. More preferred are single chain polypeptides where the two original peptides in the single chain are selected from a light and heavy chain variable region of an antibody. Alternatively, it may be desirable to produce dimers and multimers of single polypeptides where the two original peptides are derived from the same domain (e.g., $V_L$-linker-$V_L$ or $V_H$-linker-$V_H$). The present invention also includes the formation of dimers and multimers wherein one single chain polypeptide is directed against one antigen and the second or additional polypeptides are directed against a different antigen.

The dimers and multimers of the present invention formed by domains of the Ig superfamily are advantageous for therapeutic purposes in mammals as they retain their antigenic recognition properties, contain multiple binding sites and are of larger molecular weight than the single chain monomers thereby reducing their retention in the kidneys.

Isolation of an Appropriate DNA Sequence

To prepare a vector containing the DNA sequence for an antigen binding portion of an Ig superfamily protein, a source of the genes encoding for these regions will be required. The appropriate DNA sequence can be obtained from published sources or can be obtained by standard procedures known in the art. For example, Kabat et al., *Sequences of Proteins of Immunological Interest* 4th ed., (1991), published by The U.S. Department of Health and Human Services, discloses sequences of most of the Ab and TCR variable regions which have been described to date. Kabat et al. also discloses nucleotide and amino acid sequences of class I and class II MHC proteins, CD4, CD8 and some Fc receptor sequences. A list of known human class II HLA sequences is contained in the report by Marsh, S. G. E. and Bodmer, J. G., entitled "HLA Class II Nucleotide Sequences" in *Immunobiology*, 182; 369–403 (1991). Up-to-date lists of other MHC sequences are also found in volume 182 of *Immunobiology*. WO 90/04410 published May 3, 1990 discloses a DNA sequence for variable regions of antibodies against tumor associated antigen (TAG).

When the genetic sequence is unknown, it is generally possible to utilize cDNA sequences obtained from mRNA by reverse transcriptase medicated synthesis as a source of DNA to clone into a vector. For antibodies, the source of mRNA can be obtained from a wide range of hybridomas. See, for example, the catalogue *ATCC Cell Lines and Hybridomas*, American Type Culture Collection, 20309 Parklawn Drive, Rockville Md., USA (1990). Hybridomas secreting monoclonal antibodies reactive with a wide variety of antigens are listed therein, are available from the collection, and usable in the present invention. These cell lines and others of similar nature can be utilized as a source of mRNA coding for the variable region or to obtain protein to determine amino acid sequence from the monoclonal antibody itself. The specificity of the antibody to be engineered will be determined by the original selection process. The class of antibody can be determined by criteria known to those skilled in the art.

Variable regions of antibodies can also be derived by immunizing an appropriate vertebrate, normally a domestic animal, and most conveniently a mouse. The immunogen will be the antigen of interest, or where a hapten, an antigenic conjugate of the hapten to an antigen such as keyhole limpet hemocyanin (KLH). The immunization may be carried out conventionally with one or more repeated injections of the immunogen into the host mammal, normally at two to three week intervals. Usually three days after the last challenge, the spleen is removed and dissociated into single cells to be used for cell fusion to provide hybridomas from which mRNA can readily be obtained by standard procedures known in the art.

Unlike the immunoglobulin locus which contains in excess of 100 $V_L$ and $V_H$ germline genes and which undergoes extensive somatic mutation, the TCR Vβ and Vα loci are much less diverse (especially true in humans) and do not undergo somatic mutation. For this reason, the T-cell receptor V region genes which have been studied to date fall into discrete subfamilies which differ significantly (<80 percent sequence identity between different subfamilies) in sequence. For human Vβ, there appears to be approximately 25–30 such subfamilies. For human Vα there appears to be slightly fewer subfamilies. One skilled in the art can se this sequence information to devise a number of assays for determining which T-cell receptor subfamilies are being expressed in the lymphocytes of a given sample. For example, oligonucleotide probes can be made which are specific for each of the subfamilies. By isolating lymphocytes from either peripheral blood or from a lymphocyte-rich infiltrate at an inflammatory site (i.e., synovial fluid in rheumatoid arthritis patients), one can isolate mRNA, reverse transcribe it to cDNA and use the subfamily-specific probes to detect the presence or absence of various T-cell receptor V regions in the cDNA from the site of interest. By such an approach it becomes possible to identify T-cell receptor subfamilies which may be important in the disease process.

After identifying a target T-cell receptor subfamily (or subfamilies), the V regions can be isolated using strategies essentially identical to those used for antibodies. For example, oligonucleotide primers can be synthesized which will allow the V regions of interest to be amplified, digested and ligated into an appropriate expression vector.

Class I and class II MHC molecules of interest are generally defined in the literature by epidemiological studies linking the presence of a given MHC molecule with a high incidence of a given disease. For example, rheumatoid arthritis is associated with a high incidence of HLA-DRβ1*0401, 0408 and 0101 alleles. In addition, one skilled in the art can use mixed lymphocyte reactions and similar assays to define MHC incompatibilities (i.e., target MHC molecules) in patients experiencing graft rejection or graft vs. host disease. Again, the MHC class II α1 and β1 (or class 1 α1 and α2) domains can be selectively amplified either from cDNA of cell lines expressing the appropriate alleles or from peripheral blood of patients. Given the appropriate restriction sites on the PCR primers, the amplified cDNA can be inserted into the expression vector as with antibody $V_H$s and $V_L$s.

T-cell receptor cDNA and cDNA of Class I and Class II MHC can be obtained in a manner similar to that used for obtaining cDNA of the light and heavy variable regions of an antibody. For example, peripheral blood, various lymphoid tissues, or inflammatory filtrate samples from an appropriate vertebrate can be obtained, lymphocytes isolated and either used directly or allowed to proliferate transiently (24 hours to 6 weeks) in culture before use. Isolation of the desired lymphocytes can be accomplished by standard techniques known in the art, for example, affinity purification, density gradient centrifugation, or by use of a flourescence-activated cell sorter. From the cultured lymphocytes, mRNA can be obtained which in turn is utilized to produce cDNA. From the pool of cDNA, the desired cDNA can be amplified using such techniques as polymerase chain reaction. Polymerase chain reaction (PCR) or PCR with splicing by overlap extension (PCR-SOE). PCR in essence involves exponentially amplifying DNA in vitro using sequence specified 5' and 3' oligonucleotides. PCR is described in Mullins et al., *Meth. Enz.,* 155, 335–350 (1987); and *PCR Technology,* Erlich (ed.) (1989).

When an antibody or cell surface marker of interest is obtained, and only its amino acid sequence is known, it is possible to reverse translate the sequence.

To form the single chain polypeptides which form dimers and multimers it is necessary to have a suitable peptide linker which links the first and second polypeptides. Suitable linkers for joining the polypeptides are those which allow the separate polypeptide chains to fold into a single polypeptide chain which will have a three dimensional structure very similar to the original structure made of two polypeptide chains, and allows non-covalent linkage of single chains to form dimers and multimers of the single polypeptide chain. The linker must thus be (1) sufficiently large to span the distance between the two polypeptides; (2) sufficiently flexible to allow the association of the two polypeptides; and (3) relatively hydrophilic, being on the water-accessible surface of the molecule. Obtaining a similar three dimensional structure allows the resulting single chain polypeptide, dimer or multimer to recognize and react with the initial antigen or ligand molecule. Generally, a linker which allows separate polypeptide chains to fold into a single polypeptide chain with a three dimensional structure similar to the original structure made of two polypeptide chains should also allow formation of dimer and multimers. Linkers having the desired properties can be obtained by the method disclosed in U.S. Pat. No. 4,946,778, the disclosure of which is hereby incorporated by reference. From the polypeptide sequences generated by the methods described in the U.S. Pat. No. 4,946,778, genetic sequences coding for the polypeptide can be obtained.

It is also necessary that the linker peptide be attached to the peptides such that the binding of the linker to the individual polypeptides does not interfere with the binding capacity of the antigen recognition site.

A preferred linker is the helical linker designated 205 as disclosed in Pantoliano et al. *Biochem.,* 30, 10117–10125 (1991).

The linker is generally about 10 to about 50 amino acid residues. Preferably the linker is about 10 to about 30 amino acid residues. More preferably the linker is about 12 to about 30 amino acid residues. Most preferred is a linker of about 15 to about 25 amino acid residues.

Expression vehicles for production of the molecules of the invention include plasmids or other vectors. In general, such vectors contain replicon and control sequences which are derived from species compatible with a host cell. The vector ordinarily carries a replicon site, as well as specific genes which are capable of providing phenotypic selection in transformed cells. For example, *E. coli* is readily transformed using pBR322 [Bolivar et al., *Gene,* 2, 95- (1977), or Sambrook et al., *Molecular Cloning,* Cold Spring Harbor Press, New York, 2nd Ed. (1989)], a plasmid derived from an *E. coli* species which contains genes for ampicillin and tetracycline resistance, and thus provides an easy means for identifying transformed cells. Expression vectors compatible with procaryotic cells are well known in the art and are available from commercial sources, e.g., pBR325 from Gibco Biological Research Laboratories. Typical of vector plasmids suitable for procaryotic cells are pUC8, pUC9, pBR322 and PBR329 available from Biorad Laboratories (Richmond, Calif.) and pPL and pKK222 available from Pharmacia-LKB (Piscataway, N.J.), and the Bluesript SK/KS vectors from Stratagene (LaJolla, Calif.).

Plasmids suitable for eukaryotic microbes may also be used. *S. cerevisiae,* or common baker's yeast, is the most commonly used among eukaryotic microorganisms although a number of other strains, such as *Pichia pastoris,* are available. Cultures of cells derived from multicellular organisms such as Sp2/0 or Chinese Hamster Ovary (CHO), which are available from the ATCC, may also be used as hosts. Typical of vector plasmids suitable for eukaryotic cells are pSV2neo and pSV2gpt (ATCC); pSVL and pKSV-10 (Pharmacia), pBPV-1/pML2d (International Biotechnology, Inc.).

The use of viral expression vectors to express the genes for polypeptides of the present invention is also contemplated. As used herein, the term "viral expression vector" refers to a DNA molecule that includes a promoter sequence derived from the long terminal repeat (LTR) region of a viral genome. Exemplary phage include λ phage and fd phage (See, Sambrook et al., supra; McCafferty et al., *Nature,* 6301, 552–554 (1990).

It is preferred that the expression vectors and the inserts which code for the single chain polypeptides have compatible restriction sites at the insertion junctions and that those restriction sites are unique to the areas of insertion. Both vector and insert are treated with restriction endonucleases and then ligated by any of a variety of methods such as those described in Sambrook et al., supra.

Preferred genetic constructions of vectors for production of dimers and multimers of the present invention are those which contain a constitutively active transcriptional promoter, a region encoding signal peptide which will direct synthesis/secretion of the nascent single chain polypeptide out of the cytoplasm into either an intracellular compartment (in eukaryotes) or the cell exterior (or periplasm in prokaryotes). Preferably, the expression rate is commensurate with the transport, folding and assembly steps to avoid accumulation of the polypeptide as insoluble material. In addition to the replicon and control sequences, additional elements may also be needed for optimal synthesis of single chain polypeptide. These elements may include splice signals, as well as transcription promoter, enhancers, and termination signals.

Vectors which are commercially available can easily be altered to meet the above criteria for a vector. Such alterations are easily performed by those of ordinary skill in the art in light of the available literature and the teachings herein.

Additionally, it is preferred that the cloning vector contain a selectable marker, such as a drug resistance marker or other marker which causes expression of a selectable trait by the host microorganism. Such a drug resistance or other selectable marker is intended in part to facilitate in the selection of transformants. Additionally, the presence of a selectable marker, such as a drug resistance marker, may be of use in keeping contaminating microorganisms from multiplying in the culture medium. In this embodiment, such a pure culture of the transformed host microorganisms would be obtained by culturing the microorganisms under conditions which require the induced phenotype for survival.

Recovery and purification of the dimers and multimers of the present invention can be accomplished using standard techniques known in the art. For example, if the polypeptides are excreted into the culture medium, the polypeptides can be concentrated by ultrafiltration and then separated from monomers by gel filtration. When the polypeptides are transported to the periplasmic space of a host cell, purification can be accomplished by osmotically shocking the cells, and proceeding with ultrafiltration, antigen affinity column chromatography or column chromatography using an ion exchange chromatography and gel filtration. Polypeptides which are insoluble and present as refractile bodies, also called inclusion bodies, can be purified by lysis of the cells, repeated centrifugation and washing to isolate the inclusion bodies, solubilization, such as with guanidine-HCl, and then passage of the solubilized material through a gel filtration column.

While not wishing to be bound by theory, it is believed the dimers and multimers of the present invention form as a result of two discrete physicochemical states (isoforms) of the single chain polypeptide. In one transition state (A) or folding intermediate, only monomers will be formed. In the second transition state (B) only dimers, or multiples thereof will be formed. The transition states are believed to be related to a conformational or charge equilibrium at a single residue or region in either polypeptide of the single chain polypeptide or even in the linker joining the two. During synthesis, since the single chain polypeptide has not yet assumed a final stable three dimensional structure, the single chain polypeptide is thought to be fairly random in configuration. Single chain polypeptides in this later transition state are capable of forming interchain dimers, a dimer being capable of non-covalently linking to another dimer or multimer.

The activity of the single chain polypeptides can be measured by standard assays known in the art, for example competition assays, enzyme-linked immunosorbant assay (ELISA), and radioimmunoassay (RIA).

Uses

The dimers and multimers of the present invention provide unique benefits for use in therapeutics, such as for use in a variety of cancer treatments and treatment of autoimmune diseases such as rheumatoid arthritis. In particular, the dimers and multimers are useful for, but not limited to, in vivo and in vitro uses in diagnostics, therapy, imaging and biosensors.

The dimers and multimers may be incorporated into a pharmaceutically acceptable carrier. Injectable compositions of the present invention may be either in suspension or solution form. In solution form the complex (or when desired the separate components) is dissolved in a pharmaceutically acceptable carrier. Such carriers comprise a suitable solvent, preservatives such as benzyl alcohol, if needed, and buffers. Useful solvents include, for example, water, aqueous alcohols, glycols, and phosphonate or carbonate esters. Such aqueous solutions generally contain no more than 50 percent of the organic solvent by volume.

Dimers and multimers composed of antigen specific antibody domains are particularly advantageous for use in the diagnosis and/or therapy of diseases, such as cancer, where target antigens are often expressed on the surface of cells. For diagnostic and/or therapeutic uses, the dimers or multimers can be conjugated with an appropriate imaging or therapeutic agent. Examples of antibodies from which the $V_L$ and $V_H$ domains can be obtained to produce dimers or multimers are CC antibodies, such as CC49, disclosed in published PCT Application WO 89/00692 on Jan. 26, 1989 and published PCT Application WO 90/04410 on May 3, 1990.

Methods for preparing and administering conjugates of the dimers and multimers are accomplished by methods well known or readily determined, as described, for example, in Goldenberg et al., New England J. Med., 298, 1384–1388 (1978); Goldenberg et al.,Gastroenterol., 84, 524–532 (1983); Siccardi et al., Cancer Res., 46, 4817–4822 (1986); Keenan et al., J. Nucl. med., 25, 1197–1203 (1984); Meares et al., Anal. Biochem., 142, 68–78 (1984). Moreover, suitable dosages will depend on the age and weight of the patient and the therapeutic agent employed and are well known or readily determined.

Conjugates of the dimers and multimers and an imaging marker are administered in a pharmaceutically effective amount for the inviuo diagnostic assays, and then detecting the presence of the imaging marker by appropriate detection means. Generally, the dosage should be effective to visualize or detect tumor sites, distinct from normal tissues. Preferably, a one-time dosage will be between 0.1 mg to 200 mg of the conjugate of the dimer or multimer and imaging marker per patient.

Examples of imaging markers which can be conjugated to the dimers and multimers are well known and include substances which can be detected by diagnostic imaging using a gamma scanner or hand held gamma probe, and substances which can be detected by nuclear magnetic resonance imaging using a nuclear magnetic resonance spectrometer.

Suitable but not limiting examples of substances which can be detected using a gamma scanner include $^{125}I$, $^{131}I$, $^{123}I$, $^{111}In$, $^{105}Rh$, $^{153}Sm$, $^{67}Cu$, $^{67}Ga$, $^{166}Ho$, $^{177}Lu$, $^{186}Re$, $^{188}Re$ and $^{99m}Tc$. An example of a substance which can be detected using a nuclear magnetic resonance spectrometer is gadolinium.

A pharmaceutically effective amount of a composition containing dimers and multimers of antibodies is that which should be sufficient to achieve effective binding with the antigens against which the antibodies have specific affinity.

Examples of antibody-therapeutic agent conjugates which can be used in therapy include dimers or multimers of antibodies coupled to radionuclides, such as $^{131}I$, $^{90}Y$, $^{105}Rh$, $^{47}Sc$, $^{67}Cu$, $^{212}Bi$, $^{211}At$, $^{67}Ga$, $^{125}I$, $^{186}Re$, $^{188}Re$, $^{177}Lu$, $^{99m}Tc$, $^{153}Sm$, 123I and $^{111}In$; to drugs such as methotrexate, adriamycin; to biological response modifiers, such as interferon and to toxins, such as ricin.

Methods of preparing and administering conjugates of the dimers and multimers of antibodies and a therapeutic agent are well known or readily determined. The pharmaceutical composition may be administered in a single dose or multiple dosage form. Moreover, suitable dosages will depend on the age and weight of the patient and the therapeutic agent employed and are well known or readily determined.

Dimers and multimers containing single chain antibodies are particularly suitable for radioimmunoguided surgery (RIGS). In RIGS, an antibody labeled with an imaging marker is injected into a patient having a tumor that expresses a target antigen. The antibody localizes to the tumor and is detected by a hand-held gamma detecting probe (GDP). The tumor is then excised (see, Martin et al. *Amer. J. Surg.*, 156, 386–392 (1988); Martin et al., *Hybridoma*, 5, S97–S108). An exemplary GDP is the Neoprobe™ scanner, commercially available from Neoprobe Corporation, Columbus, Ohio.

Dimers and multimers of T cell receptors, MHC molecules and other members of the immunoglobulin gene superfamily are particularly suitable for immunotherapy of chronic inflammatory diseases such as chronic graft rejection, graft-vs-host disease, rheumatoid arthritis and other autoimmune diseases. In these diseases, dimers and multimers of the single chain proteins would have extended serum half-lives which would enhance the overall bioavailability of the therapeutic agent while simultaneously reducing the frequency with which the drug must be administered. In addition, the increased avidity achieved by multiple antigen binding sites should allow for prolonged duration of action (i.e., increased stability of the therapeutic at its desired site of action at the surface of the lymphocyte or antigen presenting cell).

The administration of compositions containing dimers and multimers of T cell receptors, MHC molecules and other members of the immunoglobulin gene superfamily are the same as those described above for single chain antibodies.

The invention will be further clarified by a consideration of the following examples, which are intended to be purely exemplary of the present invention.

| ABBREVIATIONS | |
|---|---|
| BCIP | 5-bromo-4-chloro-3-indoyl phosphate |
| bp | base pair |
| Bis-Tris propane | (1,3-bis[tris(hydroxymethyl)-methylamino]-propane) |
| BSA | bovine serum albumin |
| CDR | Complementarity determining region |
| ELISA | enzyme linked immunosorbent assay |
| Fv2 | non-covalent single chain Fv dimer |
| IEF | isoelectric focusing |
| Kbp | kilo base pair |
| LB | Luria-Bertani medium |
| Mab | monoclonal antibody |
| MES | 2-(N-Morpholino)ethane sulfonic acid |
| MW | molecular weight |
| NBT | nitro blue tetrazolium chloride |
| PAG | polyacrylamide gel |
| PAGE | poiyacrylamide gel electrophoresis |
| PBS | phosphate buffered saline |
| PCR | polymerase chain reaction |
| pSCFV | plasmid containing DNA sequence coding for SCFV |
| RIGS | radioimmunoguided surgery |
| RIT | radioimmunotherapy |
| scFv | single chain Fv immunoglobulin fragment |
| SDS | sodium dodecyl sulfate |
| TBS | Tris-buffered saline |
| Tris | (Tris[hydroxymethyl]aminomethane) |
| TTBS | Tween-20 wash solution |
| $V_H$ | immunoglobulin heavy chain variable domain |
| $V_L$ | immunoglobulin light chain variable domain |

Antibodies

CC49: A murine monoclonal antibody specific to the human tumor-associated glycoprotein 72 (TAG-72) deposited as ATCC No. HB9459.

CC49 FAB: An antigen binding portion of CC49 consisting of an intact light chain linked to the N-terminal portion of the heavy chain.

ChCC49: Chimeric CC49 has the murine constant regions of the CC49 antibody replaced with the corresponding human constant regions.

CC49 scFv(X): Single chain antibody fragment consisting of two variable domains of CC49 antibody joined by a peptide linker. X refers to the theoretical pI of the scFv (e.g., CC49 scFv8.1).

CC49 Fv2: Two CC49 scFv non-covalently linked to form a dimer. The number after Fv refers to the number of monomer subunits of a given molecule, e.g., CC49 Fv6 refers to the hexamer multimers.

Hum4 $V_L$ or H4VL: Variable domain of the human Subgroup IV kappa light chain.

SCFV UHM(X): SCFV consisting of a CC49 variable light chain and a CC49 variable heavy chain joined by a 25 amino acid linker named UNIHOPE (SEQ ID NO:31). (X) refers to the theoretical pI of the SCFV which changes as amino acids are added to the C terminus, e.g., scFv UHM8.1; scFv UHM5.2 and scFv UHM5.2.

SCFV UHH: SCFV consisting of a Hum4 $V_L$ and a CC49 variable heavy chain joined by a 25 amino acid linker named UNIHOPE (SEQ ID NO:31).

EXAMPLES

General Experimental

Procedures for molecular cloning are as those described in Sambrook et al., *Molecular Cloning*, Cold Spring Harbor Press, New York, 2nd Ed. (1989) and Ausubel et al., *Current Protocols in Molecular Biology*, John Wiley and Sons, New York (1992), the disclosures of which are hereby incorporated by reference.

All water used throughout was deionized distilled water.

Oligonucleotide Synthesis and Purification

All oligonuclotides (oligos) were synthesized on either a Model 380A or a Model 391 DNA Synthesizer from Applied Biosystems (Foster City, Calif.) using standard β-cyanoethyl phosphoramidites and synthesis columns. Protecting groups on the product were removed by heating in concentrated ammonium hydroxide at 55° C. for 6 to 15 hours. The ammonium hydroxide was removed through evaporation and the crude mixtures were resuspended in 30 to 40 μL of sterile water. After electrophoresis on polyacrylamide-urea gels, the oligos were visualized using short wavelength ultraviolet (UV) light. DNA bands were excised from the gel and eluted into 1 mL of 100 mM Tris-HCl, pH 7.4, 500 mM NaCl, 5 mM EDTA over 2 hours at 65° C. Final purification was achieved by applying the DNA to Sep-Pac™ C-18 columns (Millipore, Bedford, Mass.) and eluting the bound oligos with 60 percent methanol. The solution volume was reduced to approximately 50 μL and the DNA concentration was determined by measuring the optical density at 260 nm ($OD_{260}$).

Bacterial Strains

Both *Eschericia coli* (*E. coli*) RR1 and *E. coli* GM 161 (dam⁻), containing the plasmid pRW83, were obtained from Dr. J. O. Lampen (Rutgers University, New Brunswick, N.J.) *E. coli* DH1 was purchased from Invitrogen (San Diego, Calif.) and competent *E. coli* AG1 was purchased from Stratagene (La Jolla, Calif.). The plasmid pCGS515 was obtained from Collaborative Research, Inc. (Bedford, Mass.).

Restriction Enzyme Digests

All restriction enzyme digests were performed using Bethesda Research Laboratories (Gaithersburg, Md.), or New England Biolabs, Inc. (Beverly, Mass.) enzymes and buffers following the manufacturer's recommended procedures. Digested products were separated by polyacrylamide gel electrophoresis (PAGE). The gels were stained with ethidium bromide, the DNA bands were visualized using long wavelength UV light and the DNA bands were then excised. The gel slices were placed In dialysis tubing (Union Carbide Corp., Chicago) containing 5 mM Tris, 2.5 mM acetic acid, 1 mM EDTA, pH 8.0 and eluted using a Max Submarine electrophoresis apparatus (Hoefer Scientific Instruments, Calif.). Sample volumes were reduced on a Speed Vac Concentrator (Savant Instruments, Inc., NY). The DNA was ethanol precipitated and redissolved in sterile water.

Enzyme Linked Immunosorbent Assay (ELLSA)

TAG-72 antigen, prepared substantially as described by Johnson et al, *Can. Res.*, 46, 850–857 (1986), was adsorbed onto the wells of a polyvinyl chloride 96 well microtiter plate (Dynatech Laboratories, Inc., Chantilly, Va.) by drying overnight. The plate was blocked with 1 percent BSA in PBS for 1 hour at 31° C. and then washed 3 times with 200 μL of PBS, 0.05 percent Tween-20. 25 μL of test antibodies and 25 μL of biotinylated CC49 (1/20,000 dilution of a 1 mg/mL solution) were added to the wells and the plate incubated for 30 minutes at 31° C. The relative amounts of TAG-72 bound to the plate, biotinylated CC49, streptavidin-alkaline phosphatase, and color development times were determined empirically in order not to have excess of either antigen or biotinylated CC49, yet have enough signal to detect competition by scFv. Positive controls were CC49 at 5 µg/mL and CC49 Fab at 10 µg/mL. Negative controls were 1 percent BSA in PBS and/or concentrated LB. Unbound proteins were washed away. 50 µL of a 1:1000 dilution of streptavidin conjugated with alkaline phosphatase (Southern Biotechnology Associates, Inc., Birmingham, Ala.) were added and the plate was incubated for 30 minutes at 31° C. The plate was washed 3 more times. 50 µL of a para-nitrophenyl-phosphate solution (Kirkegaard & Perry Laboratories, Inc., Gaithersburg, Md.) were added and the color reaction was allowed to develop for a minimum of 20 minutes. The relative amount of scFv binding was measured by optical density scanning at 404–450 nm using a microplate reader (Molecular Devices Corporation, Manlo Park, Calif.). Binding of the scFv resulted in decreased binding of the biotinylated CC49 with a concomitant decrease in color development.

Amino-Terminal Sequence Analysis

Amino terminal amino acid sequencing was performed by the Edman degradation procedure using an Applied Biosystems model 470A Protein Sequencer (Foster City, Calif.). Fractions were analyzed with an interface to an Applied Biosystems Model 120A Analyzer (Hewrick, M. W. et al.). Protein samples (about 10 µg each) were prepared by removing PBS present in the sample by 2 cycles of water dilution and concentration using a Centrican 30 device (Amicon).

SDS-PAGE and Western Blotting

Samples for SDS-PAGE analysis (20 µL) were prepared by boiling in a non-reducing sample preparation buffer-Seprasol I (Integrated Separation Systems (ISS), Natick, Mass.) for 5 minutes and loaded on 10–20 percent gradient polyacrylamide Daiichi Minigels as per the manufacturer's directions (ISS).

Electrophoresis was conducted using a Mini 2-gel apparatus (ISS) at 55 mA per gel at constant current for approximately 75 minutes. Gels were stained in Coomassie Brilliant Blue R-250 (Bio-Rad, Richmond, Calif.) for at least 1 hour and destained. Molecular weight standards were prestained (Mid Range Kit, Diversified Biotech, Newton Center, Mass.) and included the following proteins: Phosphorylase b, glutamate dehydrogenase, ovalbumin, lactate dehydrogenase, carbonic amhydrase, B-lactoglobulin and cytochrome C. The corresponding MWs are: 95,500, 55,000, 43,000, 36,000, 29,000, 18,400, and 12,400, respectively.

When Western analyses were conducted, a duplicate gel was also run. After electrophoresis, one of the gels was equilibrated for 15–20 minutes in anode buffer #1 (0.3 M Tris-HCl pH 10.4). An Immobilon-P PVDF (polyvinylidene dichlorine) membrane (Millipone, Bedford, Mass.) was treated with methanol for 2 second, and immersed in water for 2 minutes. The membrane was then equilibrated in anode buffer #1 for 3 minutes. A Milliblot-SDE apparatus (Millipore) was utilized to transfer proteins in the gel to the membrane. A drop of anode buffer #1 was placed in the middle of the anode electrode surface. A sheet of Whatman 3MM filter paper was soaked in anode buffer #1 and smoothly placed on the electrode surface. Another filter paper soaked in anode buffer #2 (25 mM tris pH 10.4) was placed on top of the first one. A sandwich was made by next adding the wetted PVDF membrane, placing the equilibrated gel on top of this and finally adding a sheet of filter paper soaked in cathode buffer (25 mM Tris-HCl, pH 9.4 in 40 mM glycine). The screws for the cathode were firmly secured. Transfer was accomplished in 30 minutes using 250 mA constant current (initial voltage ranged from 8–20 volts).

After blotting, the membrane was rinsed briefly in water and placed in a dish with 20 mL blocking solution (1 percent bovine serum albumin (BSA) (Sigma, St. Louis, Mo.) in Tris-buffered saline (TBS)). TBS was purchased from Pierce Chemical (Rockford, Ill.) as a preweighed powder such that when 500 mL water is added, the mixture gives a 25 mM Tris, 0.15 M sodium chloride solution at pH 7.6. The membranes were blocked for a minimum of 1 hour at ambient temperature and then washed 3 times for 5 minutes each using 20 mL 0.5 percent Tween-20 wash solution (TTBS). To prepare the TTBS, 0.5 mL of Tween 20 (Sigma) was mixed per liter of TBS. The probe antibody used was 20 mL biotinylated FAID14 solution (10 µg per 20 mL antibody buffer). Antibody buffer was made by adding 1 g BSA per 100 mL of TTBS. After probing for 30–60 minutes at ambient temperature, the membrane was washed 3 times with TTBS, as above.

Next, the membrane was incubated for 30–60 minutes at ambient temperature with 20 mL of a 1:500 dilution in antibody buffer of streptavidin conjugated with alkaline phosphatase (Southern Biotechnology Associates, Birmingham, Ala.). The wash step was again repeated after this, as above. Prior to the color reaction, membranes were washed for 2 minutes in an alkaline carbonate buffer (20 mL). This buffer is 0.1 M sodium bicarbonate, 1 mM $MgCl_2 \cdot H_2O$, pH 9.8. To make up the substrate for alkaline phosphatase, nitroblue tetrazolium (NBT) chloride (50 mg, Sigma) was dissolved in 70 percent dimethylformamide. 5-Bromo-4-chloro-3-indoyl phosphate (BCIP) (25 mg, Sigma) was separately dissolved in 100 percent dimethyl-formamide. 5-Bromo-4-chloro-3-indoyl phosphate (BCIP) 25 mg, Sigma) was separately dissolved in 100 percent dimethylformamide. These solutions are also commercially available as a Western developing agent sold by Promega. These solutions were stored at 4° C. in the dark for up to 3 months. For color development, 120 µL of each were added to the alkaline solution above and allowed to react for 15 minutes before they were washed from the developed membranes with water.

Biotinylated FAID14

FAID14 is a murine anti-idiotypic antibody (IgG2a, K isotype) deposited as ATCC No. CRL 10256 directed against CC49. FAID14 was purified using a Nygene Protein A affinity column (Yonkers, N.Y.). The manufacturer's protocol was followed, except that 0.1 M sodium citrate, pH 3.0 was used as the elution buffer. Fractions were neutralized to pH ~7 using 1.0 M Tris-HCl pH 9.0. The biotinylation reaction was set up as follows. FAID14 (1 mg, 100 µL in water) was mixed with 100 µL of 0.1 M $Na_2CO_3$ pH 9.6. Biotinyl-ε-amino-caproic acid N-hydroxy succinimide ester (Biotin-X-NHS) (Calbiochem, LaJolla, Calif.) (2.5 mg) was dissolved in 0.5 mL dimethylsulfoxide. Biotin-X-NHS solution (20 µL) was added to the FAID14 solution and allowed to react at 22° C. for 4 h. Excess biotin and impurities were removed by gel filtration, using a Pharmacia Superose 12 HR10/30 column (Piscataway, N.J.). At a flow rate of 0.8 mL/min, the biotinylated FAID14 emerged with a peak at 16.8 min. The fractions making up this peak were pooled and stored at 4° C. and used to detect the CC49 idiotype as determined by the CC49 $V_L$ and $V_H$ CDRs.

Isoelectric Focusing (IEF) and Western Analysis

Isoelectric points (pI's) were predicted using a computer program called PROTEIN-TITRATE, available through DNASTAR (Madison, Wis.). Based on amino acid composition with an input sequence, a MW value is given, in addition to the pI. Since Cys residues contribute to the charge, the count was adjusted to 0 for Cys, since they are all involved in disulfide bonds.

Experimentally, pI's were determined using Isogel agarose IEF plates, pH range 3–10 (FMC Bioproducts, Rockland, Me.). A Biorad Bio-phoresis horizontal electrophoresis cell was used to run the IEF, following the-directions of both manufacturers. The electrophoresis conditions were: 500 volts (limiting), at 20 mA current and 10 W of constant power. Focusing was complete in 90 min. IEF standards were purchased from Biorad; the kit included phycocyanin, β-lactoglobulin B, bovine carbonic anhydrase, human carbonic anhydrase, equine myoglobin, human hemoglobins A and C, 3 lentil lectins and cytochrome C, with pI values of 4.65, 5.10, 6.00, 6.50, 7.00, 7.10 and 7.50, 7.80, 8.00, and 8.20 and 9.60 respectively. Gels were stained and destained according to the directions provided by FMC.

For IEF Westerns, duplicate gels were electrophoresed. Focused proteins in the second gel were transferred to PVDF membranes, as above, using a Biorad Model 483 slab dryer hooked up to a dry ice trap and vacuum pump. A piece of filter paper wetted in water was placed on the drier surface, followed by a prepared PVDF membrane, and then by the gel itself, with its solid support facing up. The plastic cover of the drier was then placed on top of this "sandwich". The drier was operated under vacuum without heat for 20 min to transfer the proteins in the gel to the membrane. Following the transfer, the blotted membrane was blocked and subsequently probed with biotinylated FAID 14 as described above for SDS-PAGE.

Quantitation of CC49 Antibody Species

Purified CC49 antibodies were quantitated by measuring the absorbance of protein dilutions at 280 mm using matching 1.0 mL 1.0 cm pathlength quartz cuvettes (Hellma) and a Perkin-Elmer UV/VIS Spectrophotometer, Model 552A. Molar absorptivities ($E_m$) were determined for each antibody by using the following formula:

$E_m$=(number Trp)×5,500+(number Tyr)×1,340+(number (Cys)2)×150+(number Phe)×10

The values are based on information given by D. B. Wetlaufer, *Advances in Protein Chemistry*, 17, 375–378).

High Performance Liquid Chromatography

All high performance liquid chromatography (HPLC) was performed using an LKB HPLC system with titanium or teflon tubing throughout. The system consists of the Model 2150 HPLC pump, model 2152 controller, UV CORD SII model 2238 detection system set at an absorbance of 276 nm and the model 2211 SuperRac fraction collector.

Example 1

Formation of Single Chain Antibody Dimers in *E. coli*

A. Preparation of pSCFV 31

A vector was prepared from plasmid pRW 83 containing a chloramphenicol resistance ($Cam^r$) gene for clone selection, and a penP gene with a penP promoter and terminator (see Mezes, et al. (1983), *J. Biol. Chem.*, 258, 11211–11218) and the pelB signal sequence [see Lei et al., *J. Bact.*, 169, 4379–4983 (1987)]. The vector designated Fragment A (see FIG. 1) was prepared by removal of the penP gene with a Hind III/Sal I digest.

The penP promoter and pelB signal sequence were obtained by a PCR using pRW 83 as a template and oligonucleotides penP1 and penP2 as primers. The fragment was designated Fragment B (see FIG. 1). A Nco I enzyme restriction site was introduced at the 3' end of the signal sequence region by the penP2 oligonucleotide.

penP1 (SEQ ID NO:32):
5'-CGATAAGCTTGAATTCCATCACTTCC-3' penP2 (SEQ ID NO:33):
5'-GGCCATGGCTGGTTGGGCAGCGAGTAATAACAA-TCCAGCG GCTGCCGTAGGCAATAGGTATTTCAT-CAAAATCGTCTCCCTCCGTTTGAA-3'

A scFv comprised of a Hum4 $V_L$, a CC49 $V_H$, and an 18 amino acid linker (Lys Glu Ser Gly Ser Val Ser Ser Glu Gln Leu Ala Gln Phe Arg Ser Leu Asp) was obtained from pCGS515/SCFV1 by PCR using oligonucleotides penP3 and penP6. This fragment was designated Fragment D (see FIG. 2). The complete nucleotide sequence (SEQ ID NO:1) and amino acid sequence (SEQ ID NO:2) of pCGS515/SCFV1 is given in FIG. 3. A Bcl I site was introduced at the 3' end of the $V_H$ region by the penP6 oligonucleotide.

penP3 (SEQ ID NO:34):
5'-GCTGCCCAACCAGCCATGGCCGACATCGTGATG-ACCCAGTCTCC-3' penP6(−) (SEQ ID NO:35):
5'-CTCTTGATCACCAAGTGACTTTATGTAAGATGAT-GTTTTG ACGGATTCATCGCAATGTTTTTATTTGC-CGGAGACGGTGACTGAGGTTCC-3'

Fragments B and D were joined by SOE-PCR (splicing by overlap extention-polymerase chain reaction) using oligonucleotides penP1 and penP6, following the procedures of Horton et al., *Gene* 77, 61–68 (1989). The new fragment was designated E (See FIG. 2).

Fragment C, containing the penP termination codon, was isolated by digesting pRW 83 with Bcl I and Sal I. pRW 83 was isolated from *E. coli* strain GM161, which is DNA methylase minus or dam⁻.

Plasmid pSCFV 31 (see FIG. 2) was created with a three part ligation of Fragments A, C, and E.

B. Preparation of PSCFV 31b

The Nco I restriction enzyme site within the $Cam^r$ gene and the Hind III site located at the 5' end of the penP promoter in pSCFV 31 were destroyed through a PCR DNA amplification using oligonucleotides Nco1.1 and Nco1.3(−) to generate an Eco RI to Nco I fragment and oligonucleotides Nco1.2 and Nco1.4c(−) to generate a Nco I to Eco RI fragment. These two fragments were joined by PCR-SOE using oligonucleotides Nco1.1 and Nco1.4c(−). The oligonucleotides are set forth below:

Nco1.1 (SEQ ID NO:36):
5'-TCCGGAATTCCGTATGGCAATGA-3'

Nco1.3(−) (SEQ ID NO:37):
5'-CTTGCGTATAATATTTGCCCATCGTGAAAACGG-GGGC-3'

Nco1.2 (SEQ ID NO:38):
5'-ATGGGCAAATATTATACGCAAG-3'

Nco1.4c(−) (SEQ ID NO:39):
5'-CACTGAATTCATCGATGATAAGCTGTCAAACAT-GAG-3' pSCFV 31 was digested with Eco RI and the larger fragment was isolated by polyacrylamide gel electrophoresis. To prevent self ligation, the DNA was dephosphorylated using calf intestinal alkaline phosphatase according to the teachings of Sambrook et al., supra.

A two part ligation of the larger pSCFV 31 digested fragment and the PCR-SOE fragment, described above, resulted in the creation of pSCFV 31b (see FIG. 4).

C. Preparation of pSCFV 33H pSCFV 31b was digested with Nco I and Sal I and a fragment containing the Cam$^r$ gene was isolated.

The Hum4 $V_L$ was obtained by PCR DNA amplification using pCGS515/SCFV1 (See FIG. 3) as a template and oligonucleotides 104BH1 and 104BH2(−) as primers.

104BH1 (SEQ ID NO:40):
5'-CAGCCATGGCCGACATCGTGATGACCCAGTCTCCA-3'

104BH2(−) (SEQ ID NO:41):
5'-AAGCTTGCCCCATGCTGCTTTAACGTTAGTTTTATCTGCTGGGACAGAGTGCCTTCTGCCTCCACCTTGGTCCCTCCGCCGAAAG-3'

The CC49 $V_H$ was obtained by PCR using p49$_\gamma$1-2.3 (PCT WO 90/04410) as a template and oligonucleotides 104B3 and 104B4(−) as primers. A Nhe I enzyme restriction site was introduced just past the termination codon in the 3' end (before the Bcl I site) by oligonucleotide 104B4(−).

104B3 (SEQ ID NO:42):
5'-GTTAAAGCAGCATGGGGCAAGCTTATGACTCAGTTGCAGCAGTCTGACGC-3'

104B4(−) (SEQ ID NO:43):
5'-CTCTTGATCACCAAGTGACTTTATGTAAGATGATGTTTTGACGGATTCATCGCTAGCTTTTTATTTGCCATAATAAGGGGAGACGGTGACTGAGGTTCC-3'

In the PCR which joined these two fragments using oligonucleotides 104BH1 and 104B4(−) as primers, a coding region for a 22 amino acid linker was formed.

A fragment C (same as above) containing the penP termination codon was isolated from pRW 83 digested with Bcl I and Sal I.

Plasmid pSCFV 33H (see FIG. 4) was created with a three part ligation of the vector, fragment C, and the SCFV fragment described above.

D. Preparation of pSCFV UNIH

To create a vector for any SCFV with the desired restriction sites in place, a plasmid designated UNIH was created by digesting pSCFV 33H with NcoI and NheI, and isolating the DNA fragment containing the Cam$^r$ gene.

Hum4 $V_L$ was obtained by PCR DNA amplification using pRL1001 as a template and oligonucleotides UNIH1 and UNIH2(−) as primers. The DNA sequence (SEQ ID NO:3) in pRL1001 coding for the Hum4 $V_L$ is given in FIG. 5. Oligonucleotides for the PCR were:

UNIH1 (SEQ ID NO:44):
5'-CAGCCATGGCC GACATTGTGATGTCACAGTCTCC-3'

The Nco I site is in bold and the hybridizing sequence is underlined.

UNIH2(−) (SEQ ID NO:45):
5'-GAGGTCCGTAAGATCTGCCTCGCTACCTAGCAAAAGGTCCTCAAGCTTGATCACCACCTTGGTCCCTCCGC-3'

The Hind III site is in bold.

The CC49 $V_H$ was obtained by a PCR using p49$_\gamma$1-2.3 as a template and oligonucleotides UNI3 and UNI4(−) as primers.

UNI3 (SEQ ID NO:46):
5'-AGCGAGGCAGATCTTACGGACCTCGAG GTTCAGTTGCAGCAGTCTGAC-3'.

The Xho I site is in bold and the hybridizing sequence is underlined.

UNI4(−) (SEQ ID NO:47):
5=-CATCGCTAGC TTTTTATGAGGAGACGGTGACTGAGGTTCC-3'.

The Nhe I site is in bold and the hybridizing sequence is underlined.

Oligonucleotides UNIH1 and UNI4(−) were used in the PCR-SOE amplification which joined the Hum4 $V_L$ and CC49 $V_H$ fragments and formed a coding region for a negatively charged fifteen amino acid linker. The DNA was digested with Nhe I and Nco I and ligated with the vector fragment from the Nco I-Nhe I digest of pSCFV 33H. The resultant plasmid was designated pSCFV UNIH (see FIG. 4).

With the construction of pSCFV UNIH, a universal vector for any SCFV was created with all the desired restriction enzyme sites in place.

E. Preparation of pSCFV UHH and pSCFV UHM pSCFV UNIH was digested with Hind III/Xho I, and the large DNA fragment containing the Cam$^r$ gene, Hum4 $V_L$ and CC49 $V_H$ was isolated.

A fragment coding for a 25 amino acid linker, UNIHOPE, was made by annealing the two oligonucleotides shown below. Annealing conditions were as follows: 10 µg of each oligo were added to Bethesda Research Laboratories (Gaithersburg, Md.) enzyme Buffer #2 for a total volume of 53 µL, the mixture was heated to 98° C. for one minute, cooled slowly to 40° C. and placed at 4° C. overnight. Following digestion with Hind III/Xho I, the linker was electrophoresed through a 6 percent PAG. The DNA bands were excised from the gel and the DNA was electroeluted for five minutes at 200 volts. The DNA was pelleted by ethanol precipitation and dissolved in water. The linker UNIHOPE is based on 205C SCA™ linker (see Whitlow et al., *Methods: A Companion to Methods in Enzymology*, 2, 97–105 (1991), but the first amino acid was changed from serine to leucine and the twenty-fifth amino acid were changed from glycine to leucine, to accommodate the Hind III and Xho I restriction sites, respectively. The nucleotide sequence encoding the linker UNIHOPE is set forth below:

UNIHOPE (SEQ ID NO:48) (Top Strand):
5'-TATAAAGCTTAGTGCGGACGATGCGAAAAAGGATGCTGCGAAGAAGGATGACGCTAAGAAAGACGATGCTAAAAAGGACCTCGAGTCTA-3'

UNIHOPE(−) (SEQ ID NO:49) Bottom Strand:
5'TAGACTCGAGGTCCTTTTTAGCATCGTCTTTCTTAGCGTCATCCTTCTTCGCAGCATCCTTTTTCGCATCGTCCGCACTAAGCTTTATA-3'

The resulting annealed strand was digested with Hind III/Xho I and ligated into the vector, thus generating the plasmid pSCFV UHH (shown in FIG. 6). Plasmid pSCFV UHH expresses a biologically active, TAG-72 binding SCFV consisting of the Hum4 $V_L$ and CC49 $V_H$. The expression plasmid utilizes the β-lactamase penP promoter, pectate lyase pelB signal sequence and the penP terminator region. Different immunoglobulin light chain variable regions can be inserted in the Nco I-Hind III restriction sites, different SCFV linkers can be inserted in the Hind III-Xho I sites and different immunoglobulin heavy chain variable regions can be inserted in the Xho I-Nhe I sites.

F. Preparation of pSCFV UNIM and PSCFV UHM pSCFV UNIM was created in conjunction with pSCFV UNIH. It differs in that the DNA sequence coding for the CC49$V_L$ is incorporated into UNIM as opposed to the DNA sequence coding for the Hum4 $V_L$. The sequence for murine CC$^{49}V_L$ is disclosed in PCT WO 90/04410, published May 3, 1990, and was produced by PCR using the oligos UNIM1 and UNIM2(−) as primers. The CC49 $V_H$ and the vector fragment were obtained by the manner described above for pSCFV UNIH. The SCFV insert was generated by PCR-SOE using oligos UNIM1 and UNI4(−) to join the light and heavy chains and form a coding region for a negatively charged fifteen amino acid linker.

Following NheI and NcoI digestion and purification of the vector and insert, a ligation of the two pieces produced pSCFV UNIM.

UNIM1 (SEQ ID NO:50):
5'CAGCCATGGCCGACATTGTGATGTCACAGTCTCC-3'

UNIM2(-) (SEQ ID NO:51):
5'GAGGTCCGTAAGATCTGCCTCGCTACCTAGCAA-AAGGTCCTCAAGCTTCAGCACCAGCTTGGTCC-CAGCAC-3 pSCFV UHM was generated by digesting pSCFV UNIM with HindIII and XhoI, isolating the vector fragment with the Cam$^r$ gene by 4 percent PAG, and ligating the twenty five amino acid linker, UNIHOPE, into the vector DNA fragment piece. The procedure was the same as described for pSCFV UHH. pSCFV UHM contains DNA sequence coding for an scFv having the CC49 $V_L$ and CC49 $V_H$ with a computer predicted pI of 8.1. Hence, this plasmid was named pSCFV UHM8.1. Hence, this plasmid was named pSCFV UHM8.1

Figure 6A:
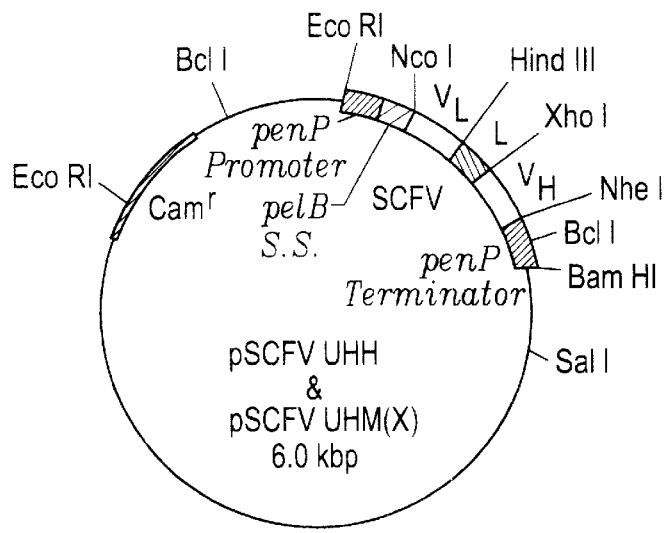
FIG. 6A illustrates the plasmid pSCFV VHH and plasmid pSCFV UHM. (B) and (C) illustrate a schematic representation of a single chain Fv monomer and single chain Fv dimer, respectively. The darkened areas represent the complimentarity determining regions.
Figure 6B:
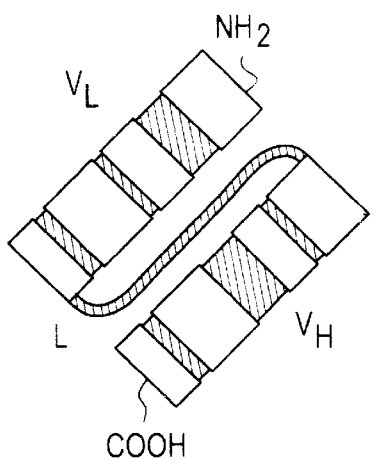
Figure 6C:
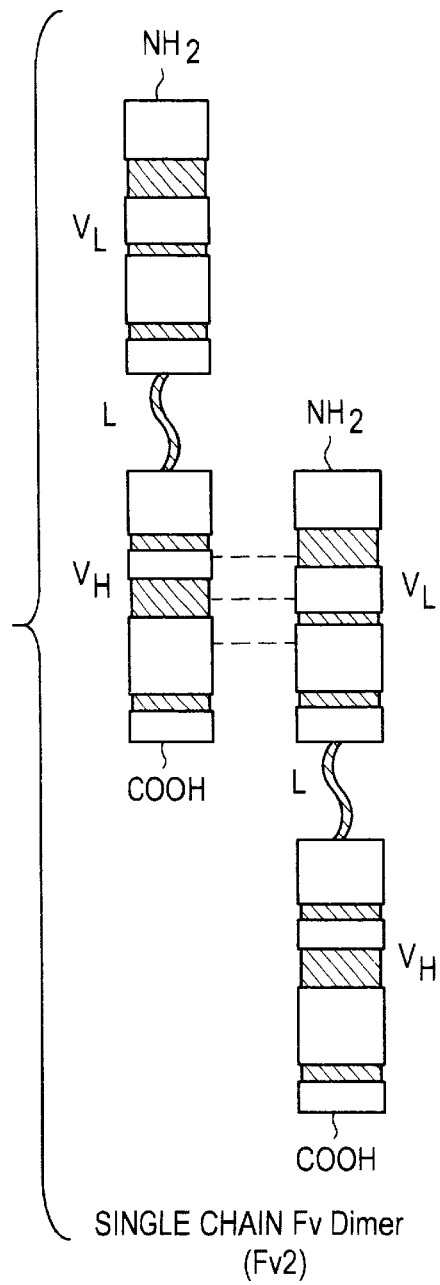

The plasmid map of pSCFV UHH and pSCFV UHM are illustrated in FIG. 6A. For pSCFV UHH, $V_L$ is Hum4 $V_L$, the linker (L) is UNIHOPE and $V_H$ is CC49 $V_H$. For the pSCFV UHM series, $V_L$ is CC49 $V_H$, the linker is UNIHOPE and $V_H$ is CC4$^9$$V_H$. For the pSCFV UHM(X) series, X indicates the pI of the monomer product (pI=8.1, 5.8 or 5.2) as described herein. FIGS. 6B and 6C illustrate the monomeric (scFv) and dimeric (Fv2) forms, respectively, of the products. The CDR regions are indicated schematically by the black bands.

The DNA (SEQ ID NO:5) and amino acid (SEQ ID NO:6) sequences of the scFv obtained from pSCFV UHH constructions are given in FIG. 7. The UNIHOPE linker sequence is indicated in bold and underlined, while the CDR regions are in bold and italicized. The amino terminus of the mature scFv product is indicated by +1.

*E. coli* AG1 (Statagene, La Jolla, Calif.) cells were transformed with pSCFV UHH and pSCFV UHM8.1 by following the manufacturer's instructions. Competent cells were thawed on ice and gently mixed by hand before 50 μL aliquots were dispensed into 15 mL polypropylene tubes. A fresh dilution of β-mercaptoethanol was added to the tubes for a final concentration of 25 mM. The cells were swirled gently every two minutes for ten minutes. Either 1 μL or 5 μL of the prepared DNA was added to the tubes. The cells and DNA sat on ice for 30 minutes, were heat pulsed in a 42° C. water bath for 45 seconds and put back on ice for two minutes. SOC medium (450 μL) (medium containing bacto-tryptone, bacto-yeast extract, NaCl MgCl$_2$ and glucose) was added to each tube and the tubes were incubated at 37° C. for one hour with shaking. Either 100 μL or 200 μL of transformed cells were plated on LB agar containing 20 μg/ml chloramphenicol. Plates were incubated at 37° C. overnight.

From each transformation, twelve to eighteen bacterial colonies were selected for overnight growth at 37° C. in 2 mL of LB/CAM 20. A portion of the overnight culture (1.2 mL) was used for a small scale plasmid preparation following the boiling method adapted from Holmes and Quigley (Sambrook et al, 1989, supra). Plasmid DNA was digested with restriction enzymes and the resultant fragments with size analyzed by agarose gel electrophoresis using ethidium bromide and long wavelength UV for visualization. The remaining 0.8 mL of overnight culture was sonicated (Soniprep 150, MSE Ltd., Sussex), then microcentrifuged for 3 minutes to pellet the debris. The supernatant was reduced in volume by 50 to 80 percent using a Centricon 10 microconcentrator device (Amicon, Beverly, Mass.) and tested for biological activity against TAG-72.

(G) Construction of pSCFV UHM5.8 and pSCFV UHM5.2

Two Plasmids, pSCFV UHM5.8 and pSCFV UHM5.2 were constructed to express CC49 scFvs and CC49 Fv2s having computer predicted pI's of 5.8 and 5.2, respectively. Extra negatively charged amino acids were added to the carboxyl terminus of the CC49 $V_H$, by synthesizing two oligonucleotides (oligos) and using them for a polymerase chain reaction (PCR) amplification of the CC49 $V_L$-linker-CC49 $V_H$ DNA present in pSCFV UHM8.1. These oligos for the 3' end of the target are as follows. For the 5.8 construction, a 58-mercalled SCUHPM 5.8 was made. For the 5.2 construction, a 64-mercalled SCUHPM 5.2 was made.

SCUHPM 5.8 (SEQ ID NO:52)
5'-AACA GCTAGC TTT TTA GGA GTC ATA GTC CTC AGG GGA GAC GGT GAC TGA GGT TCC TTG-3'

SCUHPM 5.2 (SEQ ID NO:53)
5'-AACA GCTAGC TTT TTA CTC ATA CTC TTC AGG GTC TTC AGG GGA GAC GGT GAC TGA GGT TCC TTG-3'

The nucleotides representing Nhe I restriction sites are indicated in bold. These oligos were purified from a 14 percent polyacrylamide gel containing urea (Sambrook et al., supra). The 5' oligo for the PCR was a 34 mer designated UNIM1 (sequence given above).

The nucleotides representing an Nco I restriction site are indicated in bold. For the PCR's, 100 pmol of the 5'(UNIM1) and 3' (SCUHPM 5.8) oligos were used to generate the CC49 scFv 5.8 DNA product insert, while 100-pmol of each of UNIM1 and SCUHPM 5.2 were used to generate the CC49 scFv 5.2 DNA product insert. The target DNA for the oligos in the PCR reaction (100 uL) was 1.0 ng of pSCFV UHM8.1. The reaction was performed using a programmable thermal controller (MJ Research Inc., Watertown, Mass.) and Taq polymerase according to the directions provided by Perkin Elmer Cetus (Norwalk, Conn.). There were 30 cycles consisting of 40 seconds at 94° C., 70 seconds at 45° C. and 75 seconds at 72° C. For the final cycle, the temperature was held at 72° C. for 2 minutes. The PCR products were analyzed on a 1.0 percent agarose gel containing ethidium bromide and found to be the expected sizes of 788 bp and 794 bp for the 5.8 and 5.2 CC49 scFv constructions, respectively. The DNA was preparatively purified from a 4 percent polyacrylamide gel, digested with Nco I (from BRL, Gaithersburg, Md.) and Nhe I (from New England Biolabs) using New England BioLabs 10×buffer #2 (10 mM Tris-Hcl, 10 mM MgCl$_2$, 50 mM NaCl, 1 mM OTT, pH 7.9).

The resulting trimmed Nco I and Nhe I oligonucleotides fragment of the correct size were purified away from the DNA inserts by electrophoresis in a 4 percent polyacrylamide gel. The CC49 scFv inserts were electroeluted and ethanol precipitated (Sambrook). The vector for ligation with these inserts had been prepared from pSCFV33H digested with Neo I and Nhe I. Competent *E. coli* AG1 cells (Strategene, La Jolla, Calif.) were transformed with the ligated DNA and plated on LB plates containing 20 μg/mL chloramphenicol.

Four clones were chosen from each transformation to prepare miniprep plasmid DNA (Sambrook) for restriction enzyme analysis. Based on these results single clones were chosen; *E. coli* AG1/pSCFV UHM5.8 *E. coli* and AG1/pSCFV UHM5.2.

The DNA and amino acid sequences of the CC49 species, PSCFV UHM8.1 (SEQ ID NO:7 and NO:8) (A), 5.8 (SEQ ID NO:9 and NO:10) (B) and 5.2 (SEQ ID NO:11 and NO:12) (C), are given in FIG. 8.

Preparation of Total Cellular Protein and *Escherichia coli* Periplasimic Shockates For analysis of total cell CC49 scFv activity or preparation of samples for sodium dodecyl sulfate polyacrylamide gel electrophonesis (SDS-PAGE), *E. coli* (pSCFV UHM8.1; pSCFV 5.8; or pSCFV 5.2) liquid cultures (2.5 mL LB supplemented with 20 µg/mL chloramphenicol) were grown overnight at 37° C. Cells from 1.5 mL of culture were pelleted in a microcentrifuge, the supernatant discarded, and the cell pellets resuspended in 0.5 mL phosphate buffered saline (PBS) (Sigma Chemical). Sample tubes were placed in an ethanol ice bath before sonication (MSE Soniprep 150, UK) using 3 cycles of disruption at 14 microns amplitude for 15 seconds each and cool down for 45 seconds in between. The sonicated cell debris was pelleted in a microcentrifuge, and the supernatant, representing the total, soluble protein fraction, was filtered through a Millex-GV 0.22µ filter disc (Millipore, Bedford, Mass.).

For purification of the CC49 scFv$^{(x)}$ derivatives, where x=8.1, 5.8 and 5.2, *E. coli* periplamsic fractions were prepared from 1.0 L overnight cultures. A 1.0 L culture was divided into 4×250 mL portions and centrifuged at 5,000 rpm, for 10 minutes in a Sorvall GS-3 rotor. The pelleted cells were washed and resuspended in 100 mL each of 10 mM Tris-HCl pH 7.3 containing 30 mM NaCl. The cells were again pelleted at 5,000 rpm for 10 minutes. Cells were washed with a total of 100 mL of 30 mM Tris-HCl (pH 7.3) and pooled into 1 tube. To this was added 100 mL of 30 mM Tris-HCl pH 7.3 containing 40 percent w/v sucrose and 2.0 mL of 10 mM EDTA, pH 7.5. The mixture was kept at ambient temperature, with occasional shaking for 10 minutes. The hypertonic cells were centrifuged as above. The cells where then quickly resuspended in ice cold 0.5 mM MgCl$_2$ and the suspension kept on ice for 10 minutes with occasional shaking. The cells were centrifuged as above and the shockate, containing the *E. coli* periplasmic fraction was further clarified by passing through a 0.2µ filter apparatus (Nalge Co., Rochester, N.Y.). This material was concentrated using Centriprep 30 and Centricon 30 ultrafiltration devices (Amicon Beverly, Mass.) to a final volume of 1–2 mL.

For isolation and analysis of just cytoplasmic proteins, previously shocked *E. coli* cells (0.5–1.0 mg-wet weight) were resuspended in 0.5 mL PBS and sonicated as above. The cytosol was recovered by microcentrifugation and filtered through a 0.2µ filter device.

Prior to further purification, the shockate was dialyzed against 50 mM sodium acetate buffer, pH 4.95, using a System 500 microdialyzer unit (Pierce Chemical, Rockford, Ill.), with 3–4 exchange of buffer. An 8,000 molecular weight (MW) out-off membrane was used.

Purification of CC49 Single Chain Monomer and Dimer Species

The general purification of the single chain antibody species is given in Scheme 1. The procedure under column 1 was initially used for purification of antibodies from pSCFV UHM8.1 and was later modified as given under column 2. Single chain antibody species derived from pSCFV UHM5.2 were purified as given under column 3. Final purification of the pSCFV UHM5.8 products was not completed.

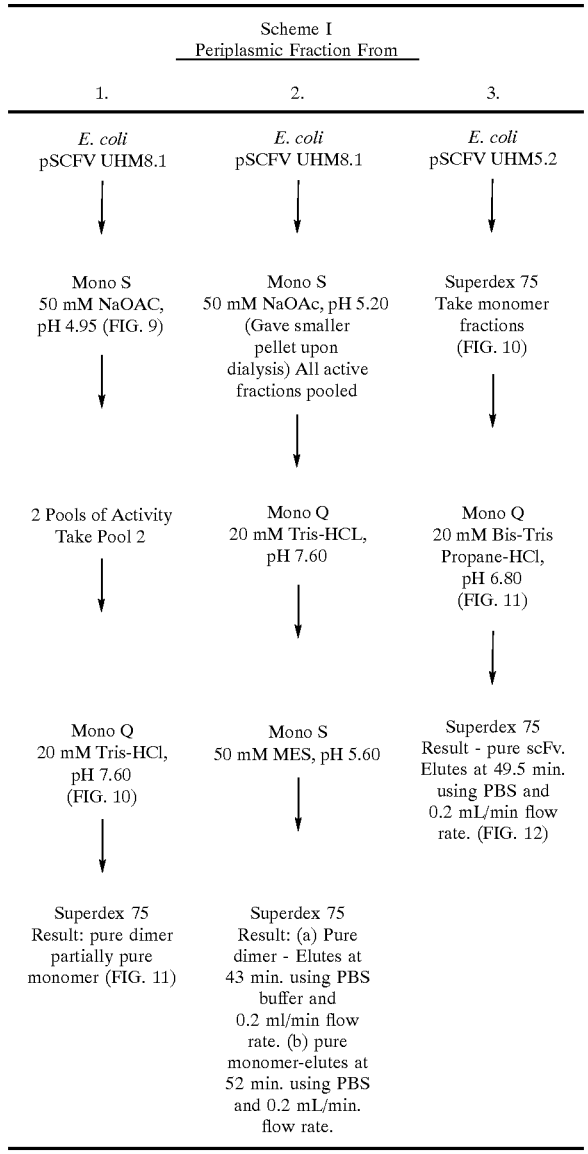

A. CC49 scFv 8.1

For single chain antibody species from pSCFV UHM8.1, about half of the *E. coli* AG1/pSCFV UHM8.1 periplasmic shockate prepared from 1 L of culture as described above was dialyzed overnight against 50 mM sodium acetate buffer, pH 4.95. Precipitated proteins were pelleted by microcentrifugation and the supernatant was applied to a cation exchange column (Mono S HR5/5 HPLC column, Pharmacia, Piscataway, N.J.). A linear gradient program utilizing 50 mM sodium acetate pH 4.95 as buffer A and 50 mM sodium acetate pH 4.95 containing 0.3 M NaCl as buffer B was run as follows:.

| Time (min) | Flow Rate (mL/min) | Percent B |
|---|---|---|
| 0 | 1.5 | 0 |
| 5.0 | 1.5 | 0 |
| 35.0 | 1.5 | 30 |

-continued

| Time (min) | Flow Rate (mL/min) | Percent B |
|---|---|---|
| 40.0 | 1.5 | 50 |
| 45.0 | 1.5 | 100 |
| 50.0 | 1.5 | 100 |
| 55.0 | 1.5 | 0 |

When the periplasmic fraction was chromatographed over Mono S, two areas of activity were observed (FIG. 9) and the two pools kept separate for the next step. The lanes 1–9 for SDS-PAGE correspond to a crude periplasmic fraction (lane 1) and fractions 1, 2, 3, 12, 16, 21, 26 and 43, lanes 2–9 respectively, with a Western transfer of the samples from a duplicate gel, indicate product in fractions 26 and 43 (lanes 17 and 18).

Pool 2 from the Mono S purification was concentrated to below 250 μL using a Centricon 30 device and dialyzed against buffer A (20 mM Tris-HCl, pH 7.60) for rechromatography on the Mono Q HR5/5 anion exchange column (Pharmacia, Piscataway, N.J.). Buffer B was the same as buffer A, but in 0.5 M NaCl. The gradient program used was the same as for the Mono S run above, but for this Mono Q run the Mono S pool 2 sample was changed to 100 percent B the gradient was at 16 percent B.

The anion exchange chromatography and SDS-PAGE of the Mono S Pool 2 sample is given in FIG. 10. The arrow on the chromatogram indicates the point in the gradient of Buffer B (16 percent) where the percent of B was changed to 100 and held for 5 minutes. Lanes 1–9 correspond to fractions 1–3 of a similar chromatography (not shown) done on Pool 1 (FIG. 9); a sample of Pool 1; a sample of Pool 2; and fractions 1–4 from the anion exchange chromatography of Pool 2. Lanes 10–18 represent the same fractions as in lanes 1–9 in a Western transfer from a duplicate gel.

Figure 11A:
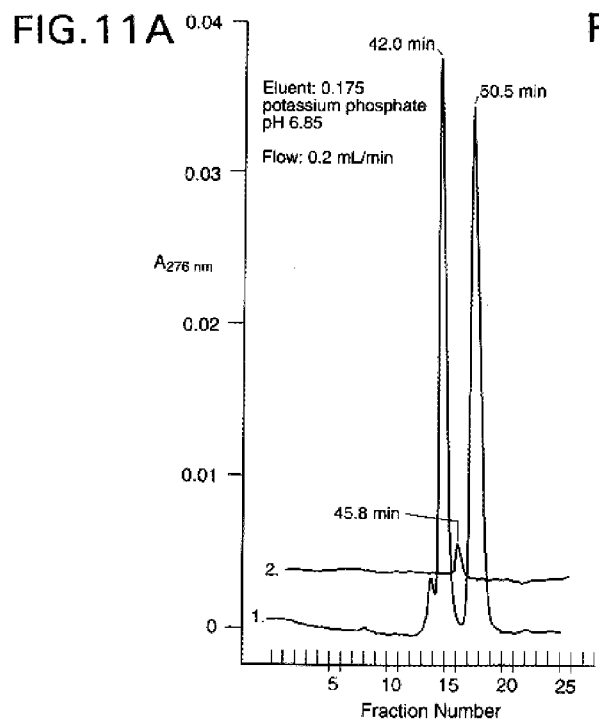
FIG. 11(A–C) shows the results of a gel filtration chromatograph SDS-PAGE and isoelectric focusing (IEF) from fraction 1 of the anionic exchange (FIG. 10).
Figure 11B:
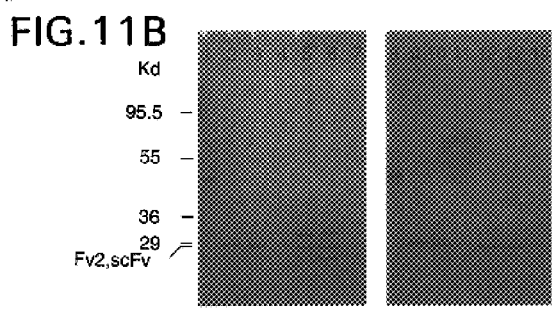

The final step in the purification utilized a Superdex 75 HR10/30 gel filtration column (Pharmacia). Potassium phosphate buffer (0.175 M, pH 6.85) was used as the mobile phase, at a flow rate of 0.2 mL/min. Fraction 1 from the Mono Q purification was applied to the Superdex column and the resulting chromatogram is shown in FIG. 11A-1. Both peaks emerging at 42 and 50.5 minutes were active in the competition assay, with considerably more activity being observed in the first peak (42 minutes). On SDS-PAGE and Western transfer FIG. 11B) a band for the correct molecular weight of monomeric single chain antibody was observed. Lanes B1 and 8 are ChCC49 Fab; lanes 2 and 9, fraction 14; lanes 3 and 10, fraction 15; lanes 4 and 11 fraction 16; lanes 5 and 12, fraction 17,; lanes 6 and 13, fraction 18; and lanes 7 and 14, fraction 19. Application of a ChCC49 Fab fragment to the gel filtration column (FIG. 11A-2), using the same conditions as for the scFv sample, indicated that the scFv peak emerging at 42 minutes contained a protein that was larger than the Fab, which emerged at 45.8 minutes. When the peak emerging at 42 minutes was subjected to the reducing condition of SDS-PAGE, a monomeric unit on the gel and Western was seen, indicating a con-covalently linked dimeric (Fv2) form of the single chain antibody. Further evidence of a unique dimeric entity was obtained when an IEF gel was run.

Figure 11C:
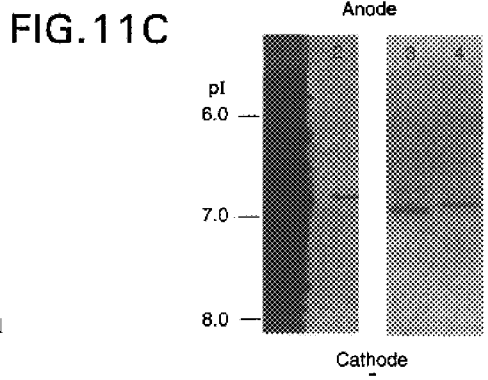

IEF of fractions 15 (lanes C1 and C3) and 17 (lanes C2 and C4), indicates there is a distinct difference between the pI of the Fv2 (lanes 1 and 3) and the monomeric scFV (lanes 2 and 4). Samples in lanes 1 and 2 were stained with Coomassie Brilliant Blue R-250, while lanes 3 and 4 represent a Western transfer of the corresponding lanes of a duplicate IEF gel. The faint FAID14 positive band in FIG. 11C, lane 3, above the main Fv2 band is not known. It could be a trace degradation product or some higher multimer.

A second purification system was then developed to optimize the purification of the monomer, dimer and multimer species of the pI 8.2 single chain antibodies. The procedure is outlined in column two of Scheme 1. The buffer system for purification with the Mono S cation exchange column was also changed to 50 mM sodium acetate pH 5.2 and 50 mM 2-(N-morpholino)ethane sulfonic acid (MES).

The protocol which afforded pure CC49 scFv and Fv2 8.2 was as follows: A periplasmic fraction was dialyzed and applied to mono S using a 50 mM sodium acetate buffer system, as before, but at pH 5.20. At this pH less protein precipitated than at pH 4.95 but the results were much the same in terms of the chromatography. Next, the Mono Q column was utilized as above. After this, a second Mono S run was introduced for the active Mono Q fractions. The buffer system used was: buffer A (50 mM MES, pH 5.6) and buffer B being the same as buffer A in 0.5 M NaCl. The monomer and dimer were finally purified using the Superdex 75 HR10/30 column and PBS as the buffer.

B. CC49 scFv5.2 and Fv2-5.2

The periplasmic shockate from a 1.0 liter culture was prepared as described above. The strategy for purification used here was to separate the monomer from the dimer in a gel filtration step first. A Superdex 75 prep grade HR 26/60 preparative column was used. The concentrated crude sample (0.5 mL) was chromatographed at a flow rate of 1.3 mL/min. using 0.175 M potassium phosphate buffer pH 6.8. See FIG. 12 for the chromatogram. The elution times for the molecular weight standards: (1) bovine IgG (Pharmacia), MW=153 Kd; (2) chicken ovalbumin, MW=44 Kd; and (3) horse myoglobin, MW 17 Kd from a separate run are as indicated by the arrows.

SDS-PAGE analysis of the fractions was as follows: lanes 1 and 14, ChCC49 Fab; lanes 2–13 correspond to fractions 3, 8, 10, 12, 14, 16, 18, 19, 20, 22, 23 and 24 respectively and lanes 15–24 correspond to fractions 25–33 and 35, respectively.

Both the resulting dimer and monomer pools were concentrated to 300 μL with centricon 30 devices and dialyzed overnight against 20 mM (1,3-bis[tris(hydroxymethyl)-methylamino]propane (Bis-Tris propane)-Cl pH 6.8 buffer and applied to the Mono Q HR5/5 column for the monomer and dimer purification. The same gradient program was used as described earlier with buffer B being 20 mM Bis-Tris propane-Cl pH 6.8 in 0.5 M NaCl. The active Mono Q fractions were pooled and concentrated to 130 μL. The sample was applied to the Superdex 75 HR 10/30 column to verify purity of the monomer and exchange the buffer to PBS.

Antibody Competition

Using purified monomer and dimer, it was possible to quantitate them accurately (Table 1) and compare them directly in a competition assay to a Fab, which is monovalent, and the CC49 whole antibody, which is divalent. The results of this study are given in FIG. 13. The results indicate the dimer and whole IgG have similar activity. These results further support the data of the existence of the dimer, indicating the dimer is folding in a way that gives two active, accessible binding sites.

TABLE 1

Characterization of CC49 Antibody Species

| Amino Acid Composition | SCFV UHM 8.1 | Fv2 8.1 | SCFV UHM 5.8 | Fv2 5.8 | SCFV UHM 5.2 | Fv2 5.2 | SCFV UHH | ChCC49 $V_L^1$ | ChCC49 $V_H$ $(83C_H1)^1$ | CC49 $V_L^2$ | CC49 $V_H^2$ |
|---|---|---|---|---|---|---|---|---|---|---|---|
| -Ala | 20 | 40 | 20 | 40 | 20 | 40 | 21 | 12 | 15 | 10 | 24 |
| -Cys | 4 | 8 | 4 | 8 | 4 | 8 | 4 | 5 | 5 | 5 | 12 |
| -Asp | 18 | 36 | 20 | 40 | 21 | 42 | 19 | 9 | 8 | 11 | 18 |
| -Glu | 9 | 18 | 10 | 20 | 11 | 22 | 9 | 10 | 6 | 9 | 22 |
| -Phe | 8 | 16 | 8 | 16 | 8 | 16 | 8 | 7 | 8 | 7 | 19 |
| -Gly | 17 | 34 | 17 | 34 | 17 | 34 | 18 | 13 | 17 | 13 | 21 |
| -His | 2 | 4 | 2 | 4 | 2 | 4 | 2 | 2 | 4 | 2 | 11 |
| -Ile | 6 | 12 | 6 | 12 | 6 | 12 | 8 | 4 | 3 | 7 | 15 |
| -Lys | 24 | 48 | 24 | 48 | 24 | 48 | 22 | 16 | 14 | 15 | 32 |
| -Leu | 21 | 42 | 21 | 42 | 21 | 42 | 18 | 20 | 15 | 17 | 23 |
| -Met | 2 | 4 | 2 | 4 | 2 | 4 | 3 | 1 | 1 | 2 | 6 |
| -Asn | 7 | 14 | 7 | 14 | 7 | 14 | 8 | 7 | 9 | 10 | 21 |
| -Pro | 9 | 18 | 10 | 20 | 11 | 22 | 9 | 11 | 11 | 11 | 34 |
| -Gln | 15 | 30 | 15 | 30 | 15 | 30 | 14 | 14 | 10 | 11 | 21 |
| -Arg | 4 | 8 | 4 | 8 | 4 | 8 | 5 | 5 | 4 | 6 | 7 |
| -Ser | 35 | 70 | 35 | 70 | 34 | 68 | 32 | 35 | 32 | 35 | 47 |
| -Thr | 16 | 32 | 16 | 32 | 16 | 32 | 17 | 15 | 20 | 18 | 40 |
| -Val | 16 | 32 | 16 | 32 | 16 | 32 | 16 | 18 | 20 | 14 | 41 |
| -Trp | 5 | 10 | 5 | 10 | 5 | 10 | 5 | 3 | 4 | 4 | 9 |
| -Tyr | 15 | 30 | 16 | 32 | 16 | 32 | 15 | 13 | 9 | 13 | 13 |
| TOTAL | 253 | 506 | 258 | 516 | 260 | 520 | 253 | 220 | 215 | 220 | 436 |
| $E_{280}$ | 47,980 | 95,960 | 49,320 | 98,640 | 49,320 | 98,640 | 47,980 | 68,880 | | 215 | 750 |
| $E_{280}$ 0.1% | 1.73 | 1.73 | 1.74 | 1.74 | 1.72 | 1,72 | 1.73 | 1.46 | | 1.49 | |
| $MW^3$ | 27,749 | 55,498 | 28,369 | 56,738 | 28,623 | 57,246 | 27,736 | 24,125 | 22,956 | 24,294 | 48,037 |
| $P^I$ | 8.12 | 8.29–8.46 | 5.84 | 6.10–6.38 | 5.23 | 5.35 | 6.39 | 8.67 | 9.22 | 8.21 | 7.22 |

[1]The MW of the ChCC49 Fab from these components is 47,081 daltons.
[2]The MW of the CC49 IgG1 from these components is 144,662 daltons. Carbohydrate weight was not included.
[3]The values given are adjusted for disulfide bond formation between Cys residues.

The activity of the purified CC49 scFv5.2 was compared with the ChCC49 Fab in a competition assay (FIG. 14) and the scFv was found to be equivalent to the Fab. This indicates one can add certain features to the carboxyl terminus of a scFv construction, as in this case the addition of Pro-Glu-Asp-Pro-Glu-Asp-Tyr-Asp, that do not affect the binding site. Therefore, other modifying sequences can be contemplated which alter the overall characteristics of the molecule.

Amino-Terminal Amino Acid Analysis

The amino terminal sequencing data gave the following result: $NH_2$-?-I-V-M-S-Q-S-P-S?-T?-L. The first residue couldn't be unequivocally assigned, but its positioning indicates that signal peptidase had cleaved at the end of the pel B signal sequence, and released a correctly processed mature product. The residues indicated at positions 2–11 correspond to the sequence predicted by the DNA sequence (See FIG. 8). The yields for Ser and Thr at positions 9 and 10 were low, but in general, Ser and Thr yields are known to be lower than for the other amino acids. Based on these data, one can conclude that the pel B signal sequence is effective in directing the secretion of the single chain products to the *E. coli* periplasm. It is apparent that one need not be limited to using the pel B leader, and that the same results, as far as processing and secretion of the product is concerned, can be obtained by using other signal sequences such as omp A and pen PC, and others. One can include these sequences in the PCR oligo when making the construction upstream from the mature protein.

Temperature Stability Study of CC49 Fv2 8.1

Approximately 3 μg aliquots of CC49 Fv2 8.1 kept at 37° C. were analyzed at intervals over 24 hours by gel filtration chromatography. A Superdex 75 HR10/30 column was utilized, using PBS as the mobile phase, at a flow rate of 0.5 mL/min.

The results of samples taken at various time points over 24 hours at 37° C. indicated that the Fv2 remained intact (eluted at the same position as the starting material), and that no degradation products were observed.

Example 2

Cloning of CC49 Single Chain Antibody Species into the Yeast *Pichia pastoris*

For expression of single chain antibody species in yeast, the strain *Pichia pastoris* GTS115 HIS4 (NRRL Y-15851) carrying a defective histidine dehydrogenase gene was used as a host cell. The plasmid pHIL-S1, available from Phillips Petroleum Company, was used as the expression plasmid modified as described below. The original sequence (SEQ ID NO:54) and features in the 5' region of pHIL-S1 are as follows:

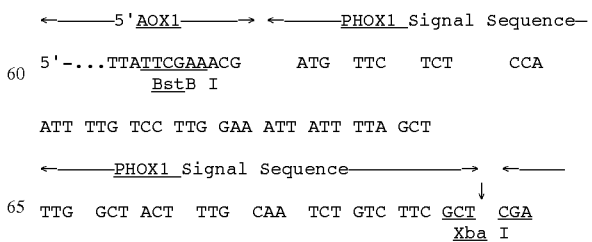

```
-continued

Multi Cloning Sites————→  ←1——3'AOX1
GAA TCC   CCC GGG ATC CTT AGA CAT ....-3'
 EcoR I    Sma I BamH I
↓
 indicates the signal peptide cleavage site.
```

DNA Sequencing

The dideoxy chain termination method of Sanger so (Samibrook et al. supra) was used for DNA sequencing of the CC49 scfv genes present in pPY21 and pPY22. A Sequenase™ sequencing kit (United States Biochemical, Cleveland, Ohio) was used for the sequencing reactions, according to the manufacturer's directions. The radiolabel used was α-P32 dATP (3,000 Ci/mmol) obtained from Amersham (Arlington Heights, Ill.), lot no. AC9048. Double loadings were done using a BRL Model S2 sequencing apparatus and a premixed 6% Gel-Mix sequencing gel (BRL). After electrophoresis, gels were dried for 30 min using a Model 483 Slab Gel Dryer (Biorad, Richmond, Calif.) and exposed to Kodak X-OMat film (Sigma Chemical, St. Louis, Mo.) for 1–24 h. The sequencing oligonucleotides used for priming (0.5 pmol each) were:

1) AOXLP (SEQ ID NO:13) (23-mer), 5'-TTTAACCACAACTTGAGAAGATC-3';

2) TAGVLFR2 (SEQ ID NO:55) (20-mer), 5'-TGGTACCAGCAGAAACCAGG-3';

3) TAGVLCDR3 (SEQ ID NO:56) (Mixed 22-mer), 5'-CTCAGCA(AG)TATTATAG(CT)TATCC-3' and;

4) TAGVHCDR2 (SEQ ID NO:57) (21-mer), 5'-ATGGATTGGATAITTTTCTCC-3'

Construction of pPY1

Figure 15A:
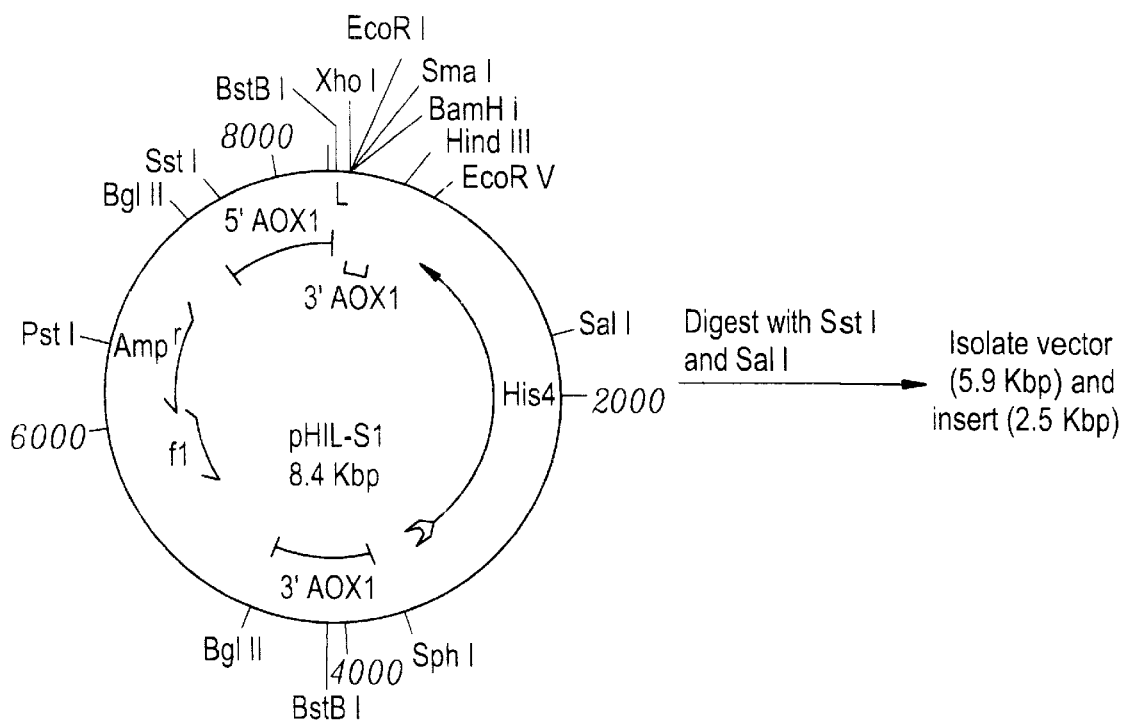
FIG. 15(A–F) shows the construction of plasmids pP41, pP42, pP421, pP422, pP431 and pP432.

A clone of *E. coli* AG1 transformed with pHIL-S1 was used to isolate purified pHIL-S1 plasmid using Qiagen's midi plasmid prep procedure (Chatsworth, Calif.). Three micrograms of purified pHIL-S1 were treated with SstI (Biological Research Laboratories, BRL) (10 units) in a volume of 40 µL for 45 minutes and then 2 µL of 1.5 M NaCl and 20 units (2 µL) of SalI (BRL) were added (see FIG. 15A). After the reaction proceeded for about 45 minutes, the sample was loaded onto a (16×18 cm) 4 percent polyacrylamide gel (PAG).

Figure 15B:
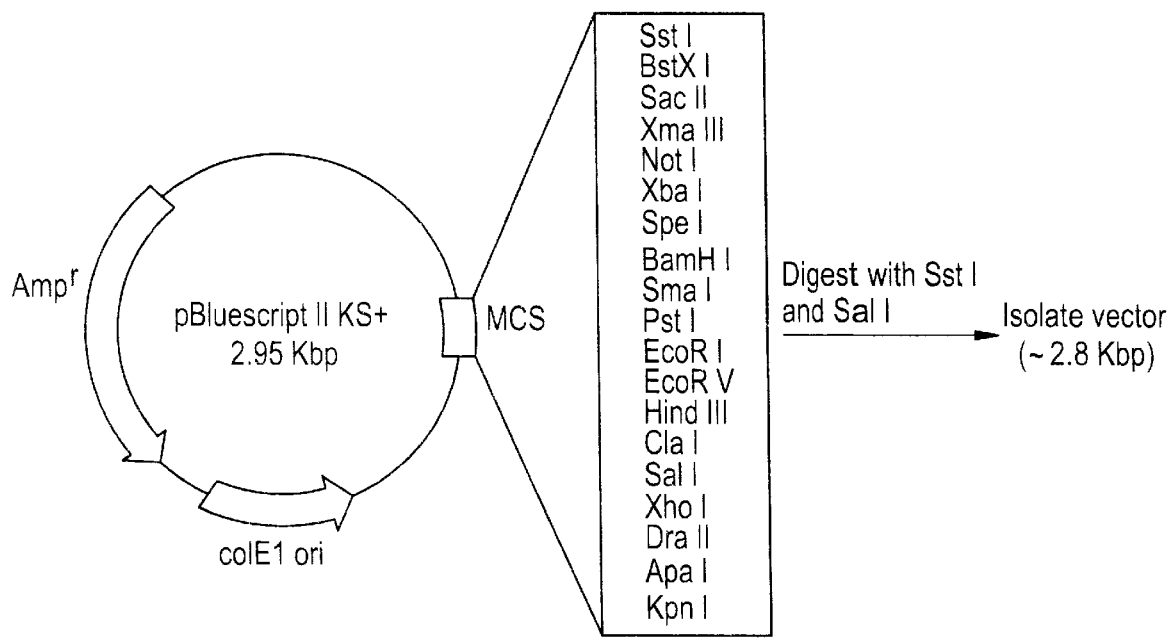

In a separate reaction, pBluescript II KS+ (5 µg) purchased from Stratagene, was treated with SstI (12.5 units) in a volume of 40 µL for 45 min. (see FIG. 15B). The buffer was then modified to favor SalI activity, by adding 2λ of 1.5 M NaCl, and then 25 units of SalI Vere added. After another 45 min at 37° C., this sample was also loaded on the 4 percent PAG. DNA fragments were separated by electrophoresis at 90 volts over 2.5 h.

pHIL-S1 gave 2 fragments, a larger one at 5.9 Kbp containing the ampicillin resistance gene and a smaller fragment at 2.5 Kbp containing most of the 5'AOX1 region and multiple cloning site. Both fragments were cut out of the gel and isolated by electroelution and ethanol precipitation.

Figure 15C:
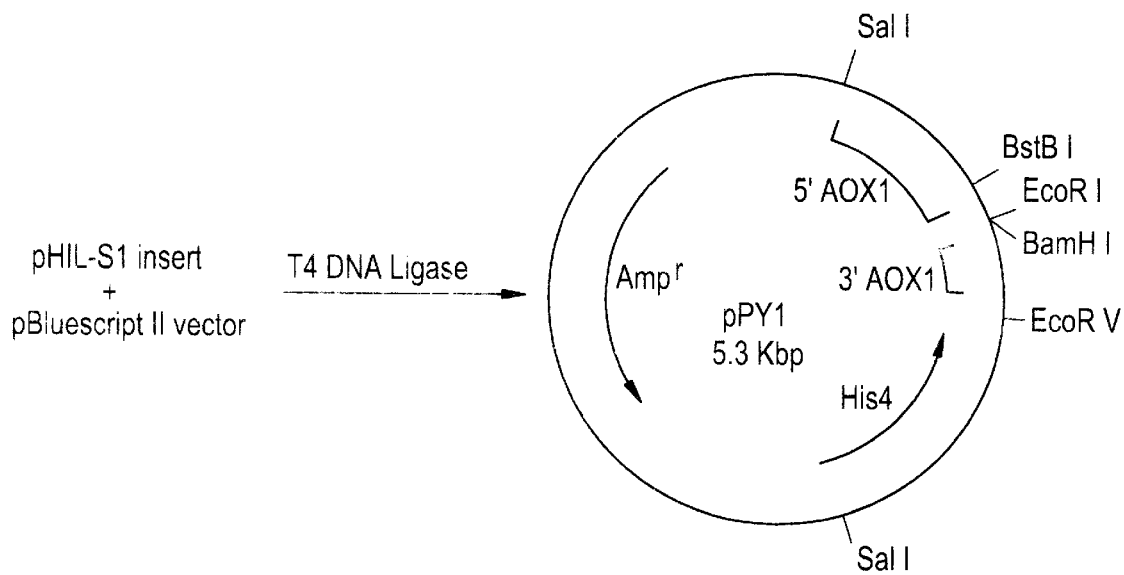

For the pBluescript II digest, 2 bands were visualized, one corresponding to the vector piece at about 2.8 Kbp and a small fragment from the multiple cloning site. The 2.8 Kbp fragment was recovered as above. To make pPY1 (FIG. 15C), the pbluescript II SstI/SalI 2.8 Kbp fragment (~100 mg) was used in a ligation reaction with the 2.5 Kbp pHIL-S1 fragment (~100 mg). The ligation kit components were from Stratagene, while the T4 DNA ligase was a New England Biolabs product. Ligation commenced at 18° C., with a cooling gradient down to 4° C. overnight. *E. coli* SURE (Stratagen, LaJolla, Calif.) was transformed with this ligation mix (1 µL and 5 µL samples). After overnight growth on Luria Broth (Sambrook et al., Supra) plates containing 100 µg/mL ampicillin, uncolored colonies (plasmids containing inserts) out-numbered blue colonies (without inserts) by roughly 10:1. Five of the uncolored colonies were picked for plasmid screening with SstI and SalI. All 5 gave the restriction pattern expected based on the plasmid construction (2 bands at 2.8 Kbp and 2.5 Kbp). The plasmid from a clone designated #4 was tested further and found to have the correct sites for BstB I, XhoI (2 sites), EcoR V and BamH I, and was thus picked as the representative clone for PPY1.

Construction of pPY2

Using the plasmid mini prep DNA of pPY1 from above, 2.5 µg were treated with 20 units of EcoR V (BRL) in a reaction volume of 45 µL at 37° C. for 30 min. A single linearized DNA fragment at 5.3 Kbp was purified from a 3.75 percent PAG as described above. A linker DNA fragment with single EcoR I and NotI sites was then ligated into the blunt ended EcoR V site as follows.

Figure 15D:
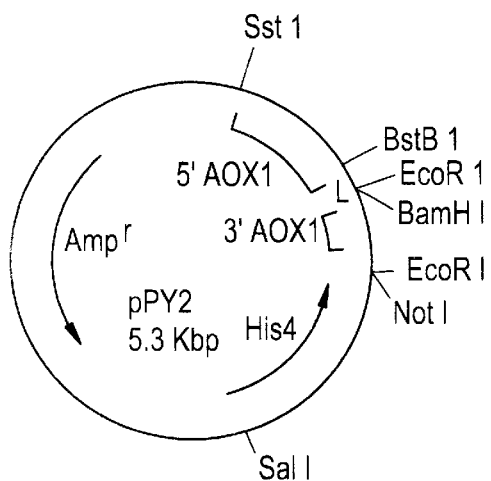

The oligos ECONOT (SEQ ID NO:58), a 20-mer: 5'-GAATTCTTAGCGGCCGCTTG-3' for the top strand and TONOCE (SEQ ID NO:59), a 20-mer: 5'-CAAGCGGCCGCTAAGAATTC-3' for the bottom strand were synthesized and purified for annealing. A 60 fold molar excess of annealed linker over the EcoR V treated pPY1 fragment ($5.7 \times 10^{-14}$ moles -20 mg) were ligated using T4 DNA ligase and temperature conditions as above. Competent *E. coli* AG1 cells were transformed with aliquots (1 and 5 µL) of this ligation mix and plated (75 or 150 µL) onto LB agar plates containing 100 µg/mL ampicillin. Twelve clones were picked for plasmid screening with EcoR I. Out of these, 10 clones had the correct two EcoR I fragments of roughly 600 bp and 4.7 Kbp. Four of these clones were selected for DNA sequencing of their plasmids for verification and orientation of the linker sequence. The oligo used for the sequencing (0.5 pmol) was ECOVNHE-SEQ (SEQ ID NO:60), a 19-mer: 5'-TGCGCATAGAAATTGCATC-3'. Two of the plasmids had the correct sequence and desired orientation, one was chosen as the representative pPY2 clone (see FIG. 15D).

Construction of pPY21 and pPY22

A common vector derived from pPY2 was used to generate both pPY21 and pPY22. Two micrograms of pPY2 mini-prep DNA were treated with 24 units of BstB I (New England Biolabs) in a 20 µL reaction volume at 65° C. for 15 min. At this point, 1.5 M NaCl was added (1.2 µL). with 12 units (1.2 µL) of BamH I (New England Biolabs) and the reaction allowed to proceed for 15 min at 37° C. This sample was loaded on a 4 percent PAG, and the pPY2 fragment with BstB I and BamH I ends of roughly 5.2 Kbp was recovered by electroelution and ethanol precipitation.

The PCRs to generate 2 CC49 scFv inserts for the pPY2 vector were performed as follows. Oligos (100 pmol each) targeting PSCFV UHM5.2, perpared as described in Example 1 (5 ng) were:

1) PY49VLI (SEQ ID NO:61), a 92-mer, 5'-ACATTTCAAACGATGCTTTTGCAAGCTTTCCTT-TTCCTTTTGCTGGTTTTGCAGCTAAGATATCTGC-TCACATTGTGATGTCACAGTCTC-3'; and 2) pPY523(SEQ ID NO:62), a 36-mer, 5'-AAATGGATC-CTATTAGTCATAGTCTTCACGGTCTTC-3'.

Taq polymerase was purchased from Perkin Elmer Cetus (Norwalk, Conn.) and used in conjunction with the Gene-Amp™ kit, according to the manufacturer's directions. The conditions for the PCR were: 30 cycles of 94° C. for 30 sec, 52° C. for 30 sec and 72° C. for 1 min. On the final cycle, the last elongation step (72° C.) was 2 min. An MJ Research (Watertown, Mass.) thermal cycler was used.

For the PCR of the second CC49 scFv insert, oligos (100 pmol each) targeting pSCFV UHM8.1 (see example 1) (5 ng) were:
1) PY49VL$_1$ (SEQ ID NO:61), as above; and
2) PSC49VH (SEQ ID NO:63), a 40-mer, 5'-ATGTGGATCCCTATTAGTAGGAGACGGTGACT-GAGGTTCC-3'.

The reaction was set up and carried out as described for pSCFV UHM5.2, above. The PCR products were purified free of reactants by electropboresis in a 4 percent PAG. The desired bands from the pSCFV UHM5.2 and pSCFV UHM8.1 targets were visualized at the expected 875 bp and 854 bp sizes respectively. The DNA was recovered by electroelution and ethanol precipitation.

Figure 15E:
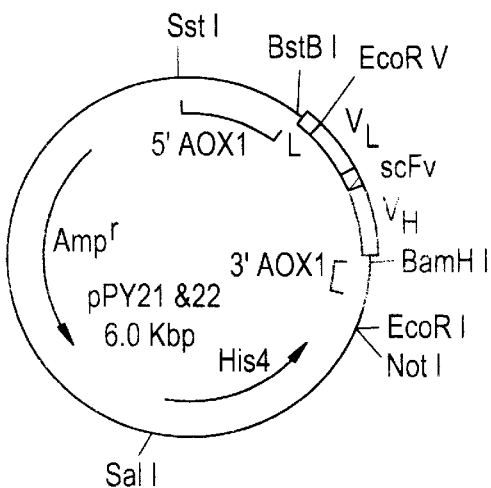

The PCR inserts were prepared for ligation by trimming the ends off of each with BstB I at the 5' ends and BamH I at the 3' ends, using the same reaction conditions as described above for the pPY2 vector. After this treatment, the DNA inserts were again purified using a 4 percent PAG, subsequent electroelution and ethanol precipitation. The DNA inserts generated from pSCFV UHM5.2 and pSCFV UHM8.1 were used to make pPY21 and pPY22, respectively (FIG. 15E). The ligation reactions regenerating pPY21 and pPY22 were set up (20 μL total volume) using 100 mg of pPY2 vector for each, and a 1:1 stoichiometric equivalent of the prepared PCR inserts from pSCFV UHM5.2 and pSCFV UHM8.1 respectively. The ligation kit components and T4 DNA ligase were from Stratagene and used according to their directions. The ligation reactions were incubated at 15° C. for 2 hours, and 2 μL from each used to transform $E.$ $coli$ AG1 competent cells. Samples were plated onto LB agar containing 100 μg/mL ampicillin. Seven clones each for pPY21 and pPY22 were picked for screening of their plasmid DNAs, using the BstB I-BamH I double digest described above. A single clone (#6) was obtained with the correct DNA fragments for pPY21, while four clones (#11–14) were obtained for pPY22. The clone for pPY21 and pPY22 clone #12 were selected for DNA sequencing of the insert DNAs containing the CC49 scFv constructions. Both clones contained the correct sequence for CC49 scFv, 5.2 (pPY21) and 8.1 (pPY22), respectively, and were used for the final expression plasmid constructions.

The DNA and amino acid sequences of CC49 scFv in pPY21 (SEQ ID NO:14 and NO:15) and pPY22 (SEQ ID NO:16 and NO:17) are given in FIG. 16. In these scFv constructions, the V$_L$ gene came first followed by the V$_H$ and was joined by a 25 amino acid linker which is in bold and underlined. The oligonucleotides used as DNA sequencing primers are shown above the DNA sequence lines. Restriction enzyme sites are as indicated, and underlined. The SUC2 signal peptide is underlined; the putative first amino acid of these mature products is indicated by (+1). Complementarity determining CDRs regions segments for the CC49V$_L$ and CC49V$_H$ are italicized in bold. Sequences for pPY21, giving negatively charged proteins (CC49, scFv5.2, Fv(2n)-5.2) are indicated by sequence A; and sequences for pPY22, giving close to neutrally charged scFv products (CC49, scFv8.1P, Fv-(2n)-8.1P) are represented by sequence B.

Construction of pPY31 and pPY32

Figure 15F:
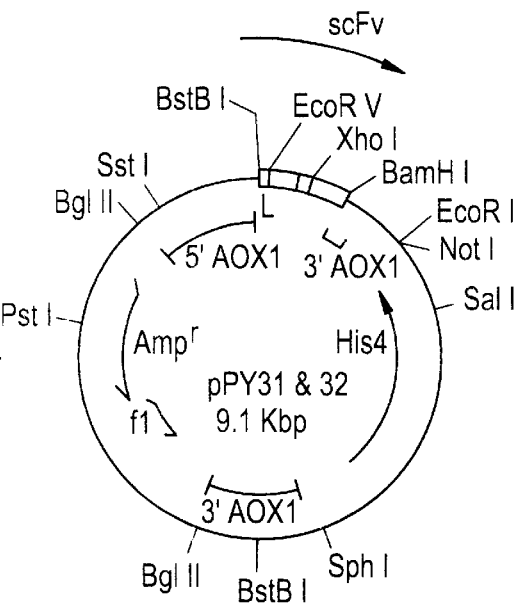

The SstI-SalI DNA fragments of pPY21 and pPY22 containing the CC49 scFv constructions were isolated and purified, to be used as inserts with the pHIL-S1 vector fragment (5.9 Kbp) already described above. Three micrograms of pPY21 and pPY22 plasmid mini-prep DNAs from above (same clones as were sequenced) were treated with 9 units each of SstI(BRL) in a 30 μL reaction at 37° C. for 20 min. The samples were electrophoresed on a 4 percent PAG. The resulting bands at 3.2 Kbp (containing the DNA of interest) and at 2.8 Kbp were isolated together, since the resolution was not adequate for good resolution on the FAG. These pairs of DNA inserts were then ligated with the pHIL-S1 SstI-SalI vector fragment (100 mg) in a 1:1 stoichiometric ratio, in a 20 μL reaction volume for 2 h at 15° C. to form pPY31 and pPY32 (FIG. 15F). Competent $E.$ $coli$ AG1 cells were transformed with 2.5 μL aliquots of the ligation mixes and plated onto LB agar plates containing 100 μg/mL ampicillin. Six potential clones each of pPY31 and pPY32 were selected for plasmid screening. The resulting mini-prep DNAs were digested with an SstI-SalI double digest, as described above for the insert preparation. Three clones had the correct 2 bands (3.2 Kbp and 5.9 Kbp) for pPY31, one was chosen as the pPY31 representative. Two clones had the correct bands for pPY32 and one of them was chosen as the representative for transformation into Pichia.

Transformation of $Pichia$ $pastoris$ GTS115 with pPY31 and pPY32

The procedure of Becker and Guarente for [$Methods$ $in$ $Enzymeogy$, 194. 182 (1990)]. electroporation of yeast cells was followed with some modifications, as described below, to introduce the CC49 scFv genes into Pichia. Yeast extract peptone glucose (YEiD) medium (125 mL) was inoculated for overnight culture at 30° C. from a stock of $P.$ $pastoris$ GTS115 stored at 4° C. The cells were harvested the next day when the O.D.$_{600\ nm}$ was between 0.8–0.9. After washing with sterile water and 1M sorbitol, the cells were resuspended in ice-cold 1 M sorbitol (150 μL) and held on ice. Aliquots of pPY31 or pPY32 (2 μg/μL) linearized with BglII, totaling 5 μg and 10 μg were added to 40 μL each of the Picha electro competent cells and transferred to pre-chilled (on ice) 0.2 cm sterile electroporation cuvettes (Biorad). Each sample was pulsed at 1.5 kV, 25 μF and 200 ohms, using a Biorad Gene Pulser with Pulse Controller. The time interval of the pulsers was 4.7–4.8 msec. Immediately after each pulse, 1.0 mL of cold 1M sorbitol was added to the cuvette, and three RDB plates for each of the 4 transformations (see U.S. Pat. Nos. 4,855,231, 4,879,231 and 4,808,537) were plated (200 μL each). Plates were incubated at 30° C. Four days later, 36 colonies (numbered 1–36) transformed with pPY31 and 35 colonies (numbered 37–71) transformed with pPY32 were randomly picked and inoculated into 2.0 mL of BMGY media and streaked on MD and MM plates. All were grown at 30° C. BMGY is buffered minimal glycerol-complex medium containing 1 m potassium phosphate (pH 6.0); 13.4 g/L yeast nitrogen base with ammonium sulfate; 400 μg/L biotin; 10 g/L yeast extract; and 20 g/L peptone. MD is a medium containing 13.4 g/L yeast nitrogen base; 400 μg/L biotin; and 20 g/L dextrose. MM is the same as MD with 5 mL/L of methanol substituted for the dextrose.

Clones able to grow on MM pates are not AOX$^-$, implying that the Bg1 II fragment did not incorporate at the AOX1 locus, but at some other chromosomal location. The MM plates have only methanol as a carbon source. After 2 days of growth in the BMGY medium, 9 potential AOX$^-$ mutant lines (observed by slow growth on the MM plate, 3 for PPY31, designated Nos. 4, 31, 32 and 6 for pPY32, designated Nos. 39, 44, 60, 61, 65 and 71 and an AOX$^+$ control (Clone No. 11, from the pPY31 set) were transferred to BMY medium (2.0 mL each). BMMY medium is the same as BMGY with 5 ml/L methanol substituted for glycerol. Aliquots of methanol (20 μL) were added to each tube, roughly every 10–14 h. Samples (100 μL) from each culture were taken 32 h after methanol induction and the biological activity determined by a competition assay described in Example 1. SDS-PAGE 10–20 percent gradient gels were run on 10 μL aliquots taken 32 and 100 h post induction. Western transfer and detection by biotinylated FAID14 was also done for the 100 hour samples.

The relative anti TAG-72 activities were evaluated for the methanol slow (AOX⁻) clones, along with some normal growing clones on MM medium. Biotinylated CC49 was used as the competitor in a competition assay. The results are presented in FIG. 17, where the percent competition for a given sample was calculated based on $OD_{405\,nm} - OD_{450\,nm}$ readings of the average of triplicate samples assayed using the following formula:

$$\frac{\text{zero competition} - \text{Sample} \times 100}{\text{zero competition} - 100\% \text{ competition}} = \% \text{ competition}$$

The zero competition value was obtained from a 0.2 micron filtered BMKY medium sample, while the 100 percent competition value was obtained using a 25 μL sample of CC49 IgG at 5 μg/mL. The Pichia samples for assay were prepared by microcentrifugation of the culture sample and filtration through a 0.22μ filter. For pPY31 the results indicated that the methanol slow clones 4 and 32 competed very well (FIG. 17) as did clone 31, which by observation of growth on the MM plate could not be categorized as methanol slow. Clones 11 and 17 were producing little or no scFv. For pPY32, the methanol slow clones 39, 60, 61, 65 and 71 all gave excellent competition. Clones 38, 44 and 50 gave little or no competition.

The SDS-PAGE-Western data corroborated the competition ELISA results. The main product of the crude Pichia culture supernatant observed on SDS-PAGE-Western was the scFv product. The Pichia products correlated well with the previously obtained *E. coli* product equivalents in terms of size on the SDS-PAGE and activity in the competition assay. In the case of the pI 8.1 Pichia products, a very slightly slower mobility was observed relative to the Western positive band representing the *E. coli* CC49 scfv I8.1 product. This is due to the increase in molecular weight of the Pichia product due to the carboxyl terminal tyrosine residue weighing approximately 78 daltons more than the corresponding serine residue at the same position in the *E. coli* product.

Purification of Single Chain Antibody Species from *P. pastoris* GCTS115 pPY31 Culture

*Pichia pastoris* carrying the plasmid pPY31 produces a CC49 single chain antibody having a pI of about 5.2. Starter cultures (20 mL BMGY medium) was inoculated (Clone #4 above) and grown for 26.5 hours at 30° C. This was used then to inoculate 800 mL BMGY medium in a 2.8 L Fernbach flask. The culture was grown at 30° C. for 24 hours with shaking at 150 rpm. The Pichia cells were pelleted at 10° C. using 2 tubes and a G53 rotor (Sorvall) run at 5,000 rpm for 10 minutes. The cells from each tube were aseptically resuspended in BMMY medium (40 mL) to which 75 μL of methanol were added and continued to shake at 30° C. Methanol (200 μL) was added approximately every 12 hours over a 36 hour growth period.

Figure 18A:
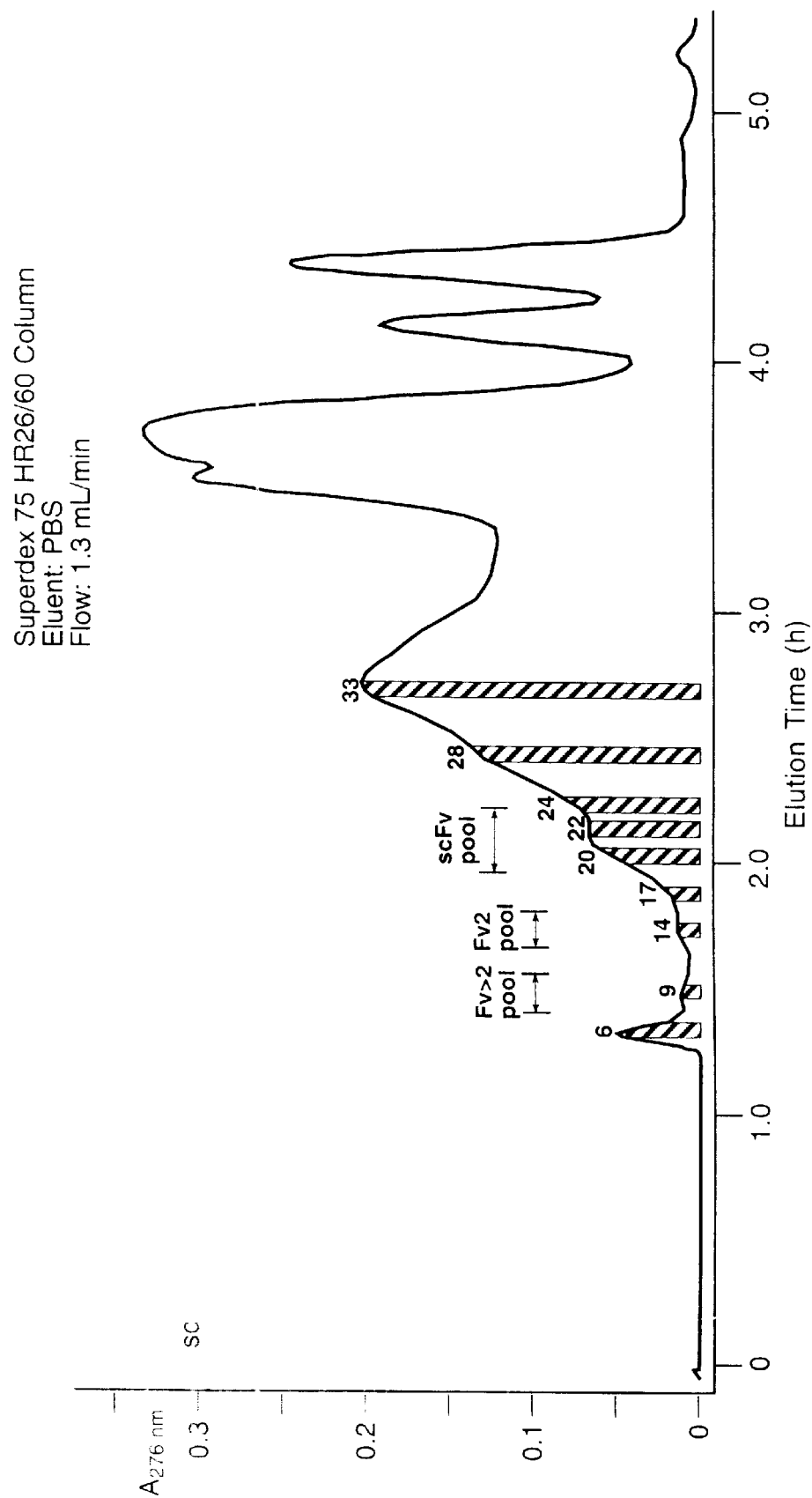
FIG. 18 shows the results of gel filtration and SDS-PAGE analysis of Pichia CC49 scFv species having a pI of 5.2.
Figure 18B:
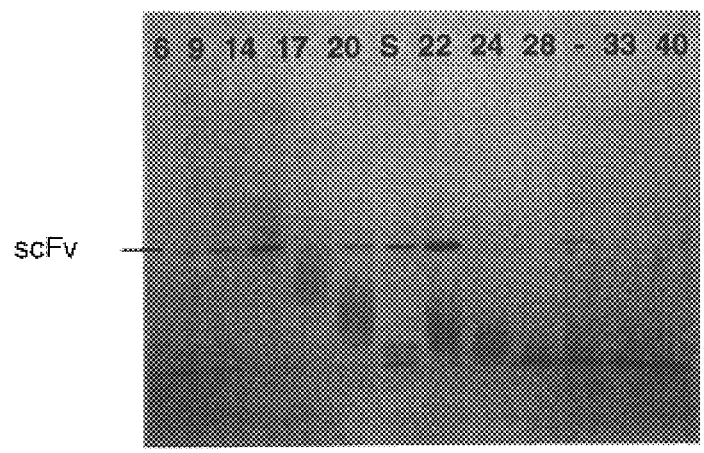

Culture supernatants (containing the single chain antibody products) were harvested by spinning the cultures at 5,500 rpm in a SS34 rotor (Sorvall) for 5 minutes. The supernatant (about 66 mL) was further clarified by filtering through a 0.22μ pore size filter device (Nalge) and then concentrated to 10 mL using a Centriprep 10 device (Amicon). Half of this material was applied to a Superdex 75 HR26/60 gel filtration column (Pharmacia), at a flow rate of 1.3 mL/min using PBS as the buffer. The gel filtration profile (See FIG. 18) gave three pools of single chain species indicating the formation of monomeric single chain antibody (scfv, fraction 19–23), dimers (scFv2, fractions 13–15) and multimeric forms (scFv(2n) where n>1, fractions 8–10). On the SDS-PAGE insert, lane "S" indicates the identical purified protein standard CC49 scFv5.2 derived from *E. coli* pSCFYV UHM5.2 (Example 1). In the processing of running SDS-PAGE, the nou-covalent interactions in a dimer or multimer are caused to break apart, showing that the dimer and multimer forms correspond to the same size as the basic monomeric unit.

TABLE I

GEL FILTRATION ANALYSIS OF CC49 SCFV PI = 5.2 SPECIES[1]

| Single Chain Antibody Species | Elution Time (min.) | Elution Volume (mL) | $K_{av}$[2] | Predicted MW (Kd) | Observed MW (Kd) | Notes |
|---|---|---|---|---|---|---|
| A. Monomer: scFv | 21.1 | 12.66 | .320 | 28.6 | 30.5 | Derived from fractions 26 and 27, Figure 2A, pool 1 |
| B. Dimer: Fv2 | 18.8 | 11.28 | .237 | 57.2 | 68 | Derived from fractions 41 and 42, Figure 2B, pool 2 |
| C. Tetramer: Fv4 | 17.5 | 10.5 | .191 | 114.5 | 120 | Derived from fractions 40 and 41, Figure 2Ca, pool 3 |
| D. Hexamer: Fv6 | 17.0 | 10.2 | .173 | 171.7 | 180 | Derived from fractions 42 and 43, Figure 2Cb, pool 4 |
| E. Octomer: Fv8 and above? | _3 | _3 | _3 | 229.0 | _3 | Derived from fraction 44, Figure 2Cc |

[1]Buffer used was PBS, at a flow rate of 0.6 mL/min. In each case, all peaks were indicative of a pure species with <10 percent of any contamination from other forms or products.
[2]Based on a void volume of 7.32 mL (thyroglobulin, MW = 670 Kd) and a column volume of 24 mL. $K_{av}$ values for the MW standards borine IgG at 158 Kd daltons, ovalbumin at 44 Kd daltons, myoglobulin at 17 Kd daltons and cyanocobalamin at 1,350 daltons were 0.178, 0.284, 0.381 and 0.644, respectively.
[3]All of the above samples were run twice, except this one which was only run once. Using a different Superdex 75 column at that time the elution times for the species ScFv, Fv2, Fv4, Fv6 and this putative Fv8 were 16.74, 14.10, 12.78, 12.46 and 12.2 minutes, respectively. No gel filtration standards were run at the same time so that a MW for the putative Fv8 could not be determined. 12.78, 12.46 and 12.2 min., respectively. no gel filtration standards were run at the same time so that a Each of the single chain antibody pools was further purified by use of a Mono Q HR5/5 anion exchange column as described in Example 1. Each of the various species was then re-chromatographed on an analytical gel filtratiom column (Superdex 75 HR10/30, Pharmacia-LKB). Table II gives the elution time, elution volume, Kav values and molecular weights determined for the monomeric and various multimeric forms. The predicted molecular weights were predicted by DNASTAR™ protein titrate computer program using the amino acid composition of the polypeptide.

Figure 19A:
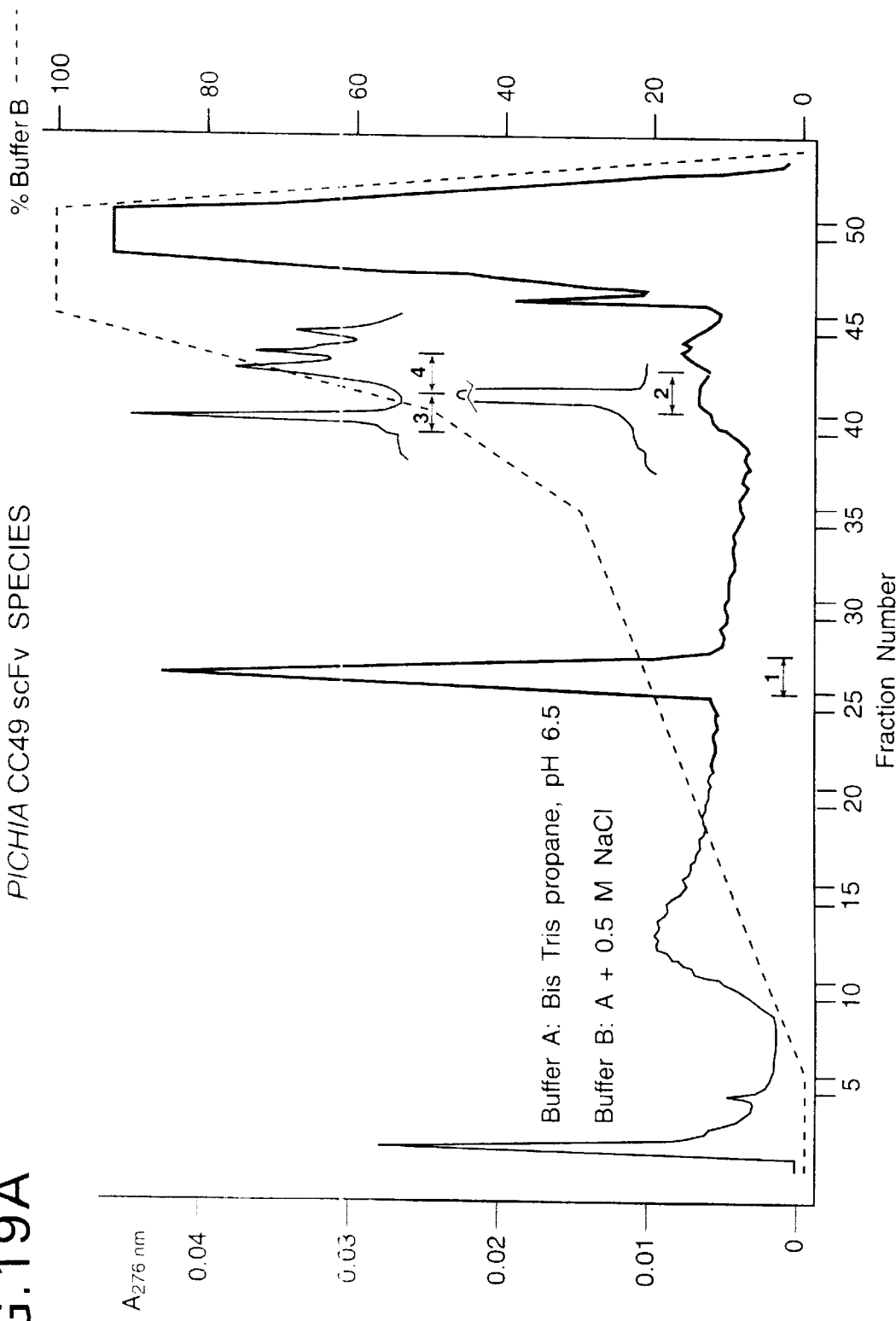
FIG. 19 shows the results of an anion exchange chromatography and SDS-PAGE of Pichia CC49 scFv species having a pI of 5.2.
Figure 19B:
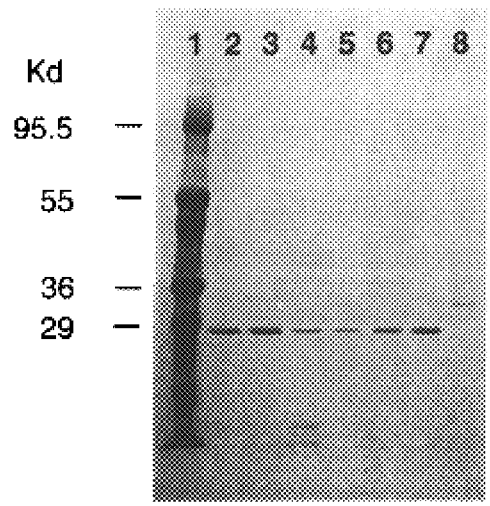

The Anion Exchange Chromatography and SDS-PAGE are given in FIG. 19. Relevant parts A, B, and C correspond to the monomer, dimer and higher multimer forms of the scFv speciesy respectively. The buffer system used and the gradient of Buffer B are also shown. The SDS-PAGE insert (D) has the following samples: molecular weight markers (lane 1); monomer and dimer (lanes 2 and 3); and E. coli derived CC49 scFv 5.2 standard (lane 4); tetramer, hexamer and putative octamer (lanes 5, 6, and 7, respectively) and an approximately 34 Kd impurity (lane 8) derived from fraction 45.

Figures 20A, 20B:
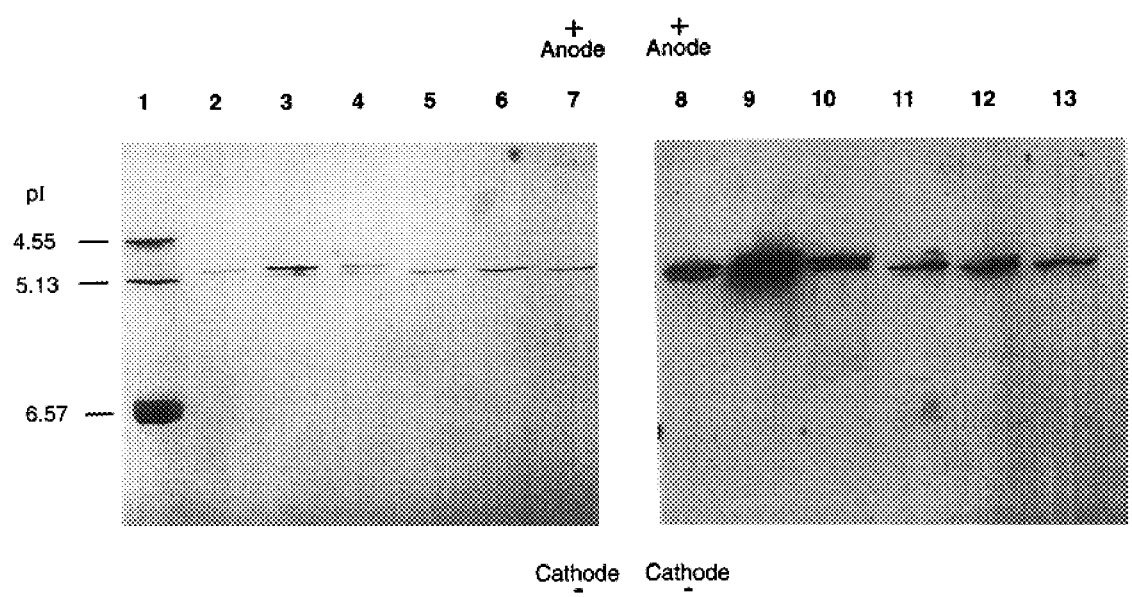
FIG. 20 shows the results of an isoelectric focusing and Western Blot of Pichia scFv species having a pI of 5.2.

The IEF gel and Western, shown in FIG. 20 indicate that the monomer and various multimer forms have distinct pI values. Both the E. coli and Pichia derived monomer forms, have a pI of 4.92 (derived from a graph of distance from cathode vs. pI of the standards), with a minor band at pI 4.97, which is the same as the pI for all multimers. That 2 bands seen in the monomer (lanes 3 and 9) support the hypothesis that there are two charge forms for the monomer in equilibrium, where the pI 4.97 form has a tendency to dimerize. In FIG. 20, lanes 1–7 represent bands stained with Coomassie Brilliant Blue R-250 and lanes 8–13 represent a Western transfer of samples corresponding to lanes 2–7. The pI markers (lane 1) were from Sigma: soybean trypsin inhibitor, pI 4.55; bovine β-lactoglobulin A, pI 5.13; and human erythrocyte carbonic anhydrase B, pI 6.57. Lanes 2 and 8 show purified CC49 scFv5.2 derived from E. coli pSCFV UHK5.2; lanes 3 and 9 show the same product derived from Pichia. Lanes 4 and 10 show a sample of crude culture supernatant from Pichia containing all the CC49 single chain antibody species present. Lanes 5 and 11, 6 and 12, and 7 and 13 indicate the Pichia dimer, tetramer and hexamer species, respectively.

Purification of Single Chain Antibody Species of Pichia pastoris GTS115/pPY32

P. pastoris having the plasmid pPY32 produces CC49 single chain antibodies having a pI of about 8.1. The growth, harvesting and induction of the AOX1 promoter were the same as for the pPY31 clone above.

The purity of the 8.1 monomer and dimer (multimeric forms were not analyzed) was verified by SDS-PAGE. The IEF pattern of these molecules indicated that except for carboxyl terminal Ser residue present in the E. coli derived CC49 scFv8.1 and Fv28.1, the corresponding Pichia products have the same pI values. In Pichia the carboxyl terminal residue is Tyr.

The N-terminal amino acid sequencing results indicated that the invertase signal sequence used in constructing these single chain antibodies was accurately being removed by signal peptidase. For the CC49 scFv8.1P and Fv2-8.1P proteins, the following $NH_2$ terminal residues were determined: Asp-Ile-Val-Met-Ser-Gln-Ser-Pro-Ser-Ser, which matches the predicted amino acid sequence of the mature form, from the DNA sequence (see FIG. 16). For the CC49 Fv2-5.2 product, the same results were obtained as above, except that the first and tenth amino acids could not be unequivocally assigned. Based on the above results with the 8.1 pI system, it is reasonable to assume for the 5.2 pI products that the unassigned residues are the same.

From the competition ELISA results (FIGS. 21A and 21B), it can be observed that the avidity of the single chain species, increases with higher multimer forms. It is possible that the effects seen for the tetramer and hexamer are underestimated and that different concentrations or densities of TAG-72 on the ELISA plate may influence the results. The availability of antigen to some of the binding faces of the hexamer and octamer, for example, may not be sterically available.

Example 3

Biodistribution Characteristics of $^{125}$I Labeled CC49 Single Chain Fv Species The biodistribution of four CC49 single chain antibody species, two monomeric species: CC49 scFv with a pI of 8.1 obtained from Pchia (scFv 8.1P) and CC49 with a pI of 5.2 also obtained from Pichia (scFv 5.2); and two dimeric species: CC49 Fv2 with a pI of 8.1 obtained from Pichia (Fv2-8.1P) and CC49 Fv2 with a pI of 5.2 obtained from E. coli (Fv2-5.2), was determined. This was compared with ChCC49 Fab and IgG. The single chain species were labeled with $^{125}$I using the Iodo-Beads™ (Pierce, Rockford, Ill.) method using N-chloro-benzenesulfonamide derivatited polystyrene beads (Iodo-Beads™, Pierce, Rockford, Ill.). To label the antibodies, initially 3 Iodo-Beads™ were incubated at room temperature for 5 minutes in PBS and 150 μCi carrier-free I-125 (Nordion, 100.9 pCi/μL). At this point, the antibody (0.3 mg in PBS) was added and allowed to react for 8 minutes. Unincorporated isotope and reaction by-products were removed by gel filtration chromatography (Pharmacia Superdex 75 HR10/30 column), using PBS as the buffer at a flow rate of 0.6 mL/minute. An aliquot of the purified protein peak was measured in each case at $A_{280\ nm}$ and quantitated according to the $E^{1\%}_{280\ nm}$ values as described in Example 1 for the respective proteins. Levels of radioactivity were determined by measurement in a Capintec Counter, set for reading I-125.

SDS-PAGE and IEF analyses were performed as previously described. Gels were dried and radioactive bands detected by exposure to Kodak XAR X-OMAT film. The observed pI values for the 8.1P species, as determined by IEF are 7.1 and 7.25 for monomer and dimer, respectively, and for the 5.2 species, 4.9 and 5.0 for the monomer and dimer, respectively. Differences between the calculated values (after which the species are officially called) and the observed values indicate that the tertiary structure of these molecules play a role in charge-charge interactions and/or hydrogen bonding which will determine the observed pI values.

Five test groups, each containing 5 female nu/nu (CD-1) mice (obtained from Charles River Breeding Laboratories) bearing LS174T human tumor xenografts, were used to measure the biodistribution of $^{125}$I labeled antibody species. The biodistribution of the compounds was measured at various time intervals over 48 hours, after intravenous (tail vein) injection of the compounds. Animals were housed and identified by group as outlined in Section 4.0 of Standard Operation Manual for the Care of Laboratory Animals (SOP-PTG). At the appropriate time, the mice were euthanatized and the radioactivity remaining in samples of blood, liver, spleen, kidney, tumor, lung, GI tract, tail, and remaining carcass were quantified as outlined in Section 4.0 and Section 5.0 of SOP-PTG. The LS174T tumors were produced in the mice according to the procedure set forth in Section 2.0 of SOP-PTG.

For metabolite studies, groups of Balb/c mice were injected intravenously with 1 μCi of one of the antibody species. Mice from each group were anesthetized after 30 minutes, 2 h and 5 h, urine removed from the bladder, urine counted for radioactivity and then kept frozen at −70° C. until HPLC analysis. A Pharmacia Superdex 75 gel filtration HR10/30 column was used for chromatography, using PBS as the eluent at 1.5 mL/minute. The volumes of the injected urine varied from 20–80 μL. The column eluent passed through a dual detector for absrbance at 280 nm and for radioactivity.

Gamma Counter #2 (Searle/ND-66) was used to measure radioactivity in standards and tissue samples. Biodistribution of radioactivity in the collected tissues was analyzed using template TEMPL as outlined in Section 5.0 of SOP-PTG. Experimental outliers were treated as outlined in Section 6.0 of SOP-PTG.

Table IV gives the amount of protein and activity of each species injected into the mice for biodistribution studies.

Tables IV, V. VI, VII, VIII, and IX give the biodistribution of $^{125}$I CC49 species of scFv5.2, Fv2-5.2, and scFv8.1P, Fv2-8.1P, ChFab and IgG, respectively, based on percent injected dose per organ. Percent injected dose per organ is calculated by determining the $^{125}$I in counts per minute (CPM) in each tissue, divided by the injected dose (CPM) multiplied by 100 to give percent.

TABLE III

Summary of Protein and Radioactivity Amounts Used to Inject Nude Mice Bearing LS174T Tumor Xenografts

| Sudy No. | seFV5.2 N9103 | FV2-5.2 N9103 | seFV8.1P N9105 | FV2-8.1P N9105 | Ch Fab N9102 | IgG. N9101 |
|---|---|---|---|---|---|---|
| reg. protein Per mouse | 6.85 | 7.75 | 5.15 | 3.85 | 27.25 | 21.95 |
| uCi I-125 per mouse | 1.12 | 1.60 | 1.00 | 0.75 | 12.5 | 4.32 |
| Percent Activity (as determined by BSM binding) | 64 | 895 | 91 | 68 | 64 | 96 |
| Specific Activity (Ci/g) | 0.163 | 0.21 | 0.19 | 0.19 | 0.46 | 0.20 |

TABLE IV

Biodistribution of $^{125}$I Injected as $^{125}$I-CC49 scFv Monomer, pI 5.2 (scFV5.2) Values as Percent Injected Dose/Gram (n = 5)

| | 20 Minutes | | 2 hours | | 5 Hours | | 24 Hours | | 48 Hours | |
|---|---|---|---|---|---|---|---|---|---|---|
| Tissue | Mean | Standard | Mean | Standard | Mean | Standard | Mean | Standard | Mean | Standard |
| Blood | 5.87 | 0.58 | 2.43 | 0.39 | 1.53 | 0.22 | 0.02 | 0.01 | 0.01 | 0.00 n = 4, a |
| Liver | 4.08 | 0.42 | 1.77 | 0.16 | 1.16 | 0.08 | 0.28 | 0.05 | 0.17 | 0.02 |
| Spleen | 3.35 | 0.80 | 1.77 | 0.09 | 1.17 | 0.13 | 0.19 | 0.03 | 0.14 | 0.03 |
| Kidney | 155.25 | 17.46 | 51.58 | 6.37 | 34.25 | 0.53 | 15.76 | 1.33 | 9.62 | 1.69 |
| Tumor | 2.80 | 0.34 | 2.24 | 0.13 n = 4, a | 1.72 | 0.25 | 0.58 | 0.09 | 0.40 | 0.08 |
| Lung | 5.72 | 0.88 | 2.91 | 0.72 | 1.014 | 0.27 | 0.13 | 0.11 | 0.01 | 0.00 |
| Tumor Weight | 0.20 | 0.04 | 0.19 | 0.05 | 0.27 | 0.07 | 0.13 | 0.07 | 0.17 | 0.04 |

TABLE V

Biodistribution of $^{125}$I Injected as $^{125}$I-CC49 scFv Dimer, pI 5.2 (Fv2-5.2) Values as Percent Injected Dose/Gram (n = 5)

| | 20 Minutes | | 2 hours | | 5 Hours | | 24 Hours | | 48 Hours | |
|---|---|---|---|---|---|---|---|---|---|---|
| Tissue | Mean | Standard | Mean | Standard | Mean | Standard | Mean | Standard | Mean | Standard |
| Blood | 29.47 | 3.26 | 12.47 | 1.81 | 3.95 | 1.37 | 0.014 | 0.02 | 0.01 | 0.01 |
| Liver | 10.24 | 0.35 n = 4, a | 5.51 | 0.79 | 2.87 | 0.54 | 0.55 | 0.014 | 0.30 | 0.09 |
| Spleen | 9.63 | 2.56 | 5.45 | 0.73 | 2.31 | 0.30 | 0.34 | 0.08 | 0.22 | 0.12 |
| Kidney | 30.56 | 0.89 n = 4, a | 15.85 | 1.07 | 8.63 | 1.22 | 3.12 | 0.26 | 2.07 | 0.51 |
| Tumor | 3.57 | 0.16 n = 4, a | 8.91 | 1.58 | 8.52 | 2.35 | 7.66 | 1.74 | 4.96 | 2.08 |
| Lung | 8.65 | 0.78 | 4.84 | 0.80 | 2.09 | 0.52 | 0.07 | 0.02 | 0.01 | 0.01 |
| Tumor Weight | 0.17 | 0.02 | 0.25 | 0.11 | 0.27 | 0.04 | 0.18 | 0.10 | 0.14 | 0.06 |

TABLE VI

Biodistribution of $^{125}$I Injected as $^{125}$I-CC49 scFv Monomer, pI 8.1 (scFv8.1P)
Values as Percent Injected Dose/Gram

| Tissue | 20 Minutes n = 3 | | 2 hours n = 5 | | 5 Hours n = 5 | | 24 Hours n = 5 | | 48 Hours n = 5 | |
| --- | --- | --- | --- | --- | --- | --- | --- | --- | --- | --- |
| | Mean | Standard | Mean | Standard | Mean | Standard | Mean | Standard | Mean | Standard |
| Blood | 5.31 | 0.77 | 2.43 | 0.81 | 2.36 | 0.75 | 0.01 | 0.00 | 0.01 | 0.00 |
| Liver | 5.80 | 0.96 | 1.30 | 0.33 | 1.05 | 0.41 | 0.07 | 0.01 | 0.04 | 0.01 |
| Spleen | 3.79 | 0.03 | 1.81 | 0.51 | 1.42 | 0.42 | 0.05 | 0.02 | 0.02 | 0.01 |
| | | n = 2, a | | | | n = 4, a | | | | |
| Kidney | 150.74 | 34.76 | 5.91 | 0.71 | 3.05 | 0.70 | 0.37 | 0.03 | 0.23 | 0.02 |
| Tumor | 3.06 | 0.38 | 2.19 | 0.28 | 2.09 | 0.35 | 0.64 | 0.06 | 0.40 | 0.03 |
| | | | | | | | | | | n = 4, a |
| Lung | 6.75 | 1.01 | 7.25 | 0.86 | 1.34 | 0.32 | 0.02 | 0.01 | 0.00 | 0.00 |
| | | | | n = 4, a | | | | n = 4, a | | |
| Tumor Weight | 0.24 | 0.03 | 0.16 | 0.04 | 0.25 | 0.10 | 0.18 | 0.06 | 0.16 | 0.03 |

TABLE VII

Biodistribution of $^{125}$I Injected as $^{125}$I-CC49 scFv Dimer, pI 8.1 (Fv2-8.1P)
Values as Percent Injected Dose/Gram

| Tissue | 20 Minutes n = 4 | | 2 hours n = 5 | | 5 Hours n = 5 | | 24 Hours n = 5 | | 48 Hours n = 5 | |
| --- | --- | --- | --- | --- | --- | --- | --- | --- | --- | --- |
| | Mean | Standard | Mean | Standard | Mean | Standard | Mean | Standard | Mean | Standard |
| Blood | 20.55 | 3.26 | 3.30 | 0.60 | 1.91 | 0.51 | 0.01 | 0.00 | 0.00 | 0.00 |
| Liver | 15.74 | 2.00 | 3.92 | 0.146 | 1.81 | 0.28 | 0.23 | 0.03 | 0.11 | 0.02 |
| Spleen | 10.52 | 1.94 | 3.71 | 0.82 | 1.73 | 0.17 | 0.19 | 0.07 | 0.09 | 0.04 |
| Kidney | 31.40 | 2.16 | 4.90 | 0.63 | 1.71 | 0.30 | 0.12 | 0.02 | 0.05 | 0.01 |
| Tumor | 1.70 | 0.145 | 3.18 | 0.89 | 2.23 | 0.40 | 1.56 | 0.35 | 0.93 | 0.18 |
| | | | | | | n = 4, a | | | | |
| Lung | 5.77 | 1.26 | 3.05 | 0.86 | 1.15 | 0.33 | 0.03 | 0.04 | 0.00 | 0.00 |
| Tumor Weight | 0.25 | 0.13 | 0.21 | 0.08 | 0.35 | 0.08 | 0.14 | 0.02 | 0.15 | 0.05 |

TABLE VIII

Biodistribution of $^{125}$I Injected as 125I ChCC49 Fab (Ch Fab),
Values as Percent Injected Dose/Gram

| Tissue | 15 Minutes n = 4 | | 30 Minutes n = 3 | | 2 Hours n = 5 | | 5 Hours n = 5 | | 24 Hours n = 5 | |
| --- | --- | --- | --- | --- | --- | --- | --- | --- | --- | --- |
| | Mean | Standard | Mean | Standard | Mean | Standard | Mean | Standard | Mean | Standard |
| Blood | 17.11 | 3.85 | 6.06 | 0.63 | 4.68 | 0.42 | 1.96 | 0.39 | 0.16 | 0.02 |
| Liver | 6.82 | 0.45 | 4.32 | 0.38 | 2.78 | 0.58 | 1.19 | 0.26 | 0.43 | 0.02 |
| | | | | | | | | | | n = 4, a |
| Spleen | 5.92 | 1.54 | 3.28 | 0.80 | 2.84 | 0.77 | 1.13 | 0.31 | 0.24 | 0.00 |
| | | | | | | | | | | n = 4, a |
| Kidney | 154.17 | 22.39 | 167.64 | 9.52 | 23.81 | 7.39 | 5.46 | 1.23 | 1.29 | 0.06 |
| | | | | | | | | | | n = 4, a |
| Tumor | 2.54 | 0.56 | 2.36 | 0.19 | 3.03 | 0.13 | 1.75 | 0.20 | 1.03 | 0.10 |
| Lung | 6.08 | 9.47 | 4.94 | 1.02 | 2.56 | 0.17 | 1.27 | 0.31 | 0.13 | 0.02 |
| Tumor Weight | 0.26 | 0.14 | 0.36 | 0.10 | 0.33 | 0.12 | 0.20 | 0.09 | 0.11 | 0.02 | a One tissue value rejected due to Outlier Statistic >p-95 value.

TABLE IX

Biodistribution of 125I Injected as 125I-IgG
Values as Percent Injected Dose/Gram

| Tissue | 5 Hours n = 5 | | 24 Hours n = 5 | | 48 Hours n = 4 | | 120 Hours n = 5 | |
|---|---|---|---|---|---|---|---|---|
| | Mean | Standard | Mean | Standard | Mean | Standard | Mean | Standard |
| Blood | 22.13 | 1.05 | 13.73 | 1.25 | 10.24 | 0.91 | 8.114 | 0.35 n = 4, a |
| Liver | 7.87 | 0.58 | 3.96 | 0.22 n = 4, a | 2.77 | 0.12 | 2.13 | 0.09 n = 4, a |
| Spleen | 5.06 | 0.45 | 3.05 | 0.62 | 2.14 | 0.22 | 1.56 | 0.26 |
| Kidney | 3.52 | 0.65 | 1.58 | 0.141 | 1.77 | 0.02 n = 3, a | 1.53 | 0.12 n = 4, a |
| Tumor | 10.85 | 2.51 | 30.12 | 10.09 | 55.49 | 1.50 n = 3, a | 58.21 | 12.56 |
| Lung | 6.04 | 0.56 | 3.80 | 0.62 | 3.11 | 0.39 | 2.18 | 0.34 n = 4, a |
| Tumor Weight | 0.19 | 0.03 | 0.17 | 0.03 | 0.17 | 0.02 | 0.18 | 0.07 |

[a]One tissue value rejected due to Outlier Statistic >p-95 value.
[b]One tumor value rejected-outside acceptable weight range.

The differences in pharmacokinetics for the various sizes and charges of the CC49 antibody species are demonstrated by the data in tables IV–IX. In general, the smaller the molecule, the faster it clears the blood. The 25–50 K dalton size molecules (all except the IgG) clear the blood within 24 hours. The negatively charged Fv2-5.2 dimer has the greatest amount in the blood at 2 hour (Table V). Both dimers accumulate in the tumor to the largest extent over a 24 hour time period (Tables V and VII), excluding the IgG.

A major difference between the antibody species is observed in retention by the kidneys. The negatively charged monomer species, CC49 scFv5.2, clears the most slowly (Table IV). This is surprising in that the negative charge should have prevented electrostatic interaction with the negatively charged glomerular cells of the kidney. The nominally neutral charged species, scFv8.1P cleared more quickly (Table VI). This trend was also true for the two dimers, but clearance was much better for these relative to the monomers. It is unexpected that the negatively charged dimer would have the best tumor localization values (Table V). The data also shows that a relatively small molecule (58 Kd) has staying power on the tumor. Both dimers out performed the monomers and chimeric CC49 Fab molecule in this regard.

Results from metabolic studies indicated that after injection with $^{125}$I labeled scFv 5.2 and Fv2-5.2, only one radioactive metabolite was observed in the urine, free $^{125}$I, as determined by gel filtration chromatography. No larger peptides are observed at any of the time points. These data indicate that dehalogenation is occurring within the body and that free I-125 is able to be readily excreted into the urine.

The tumor to tissue ratios 8 to 24 hours post injection indicated the dimers would be effective in radioimmunoguided surgery procedures. Surgery may be performed in a more timely fashion, rather than 2 to 3 weeks post injection, as is presently necessitated by the biodistribution kinetics of whole antibody.

Example 4

Construction, Purification and Characterization of Anti TAG-72 Single Chain Antibody Species with the Human Subgroup IV $V_L$ To provide for a rapid and convenient procedure to determine the effectiveness of the single chain dimers and multimers of the present invention, a unique octapeptide sequence -NH$_2$-Asp-Tyr-Lys-Asp-Asp-Asp-Asp-Lys-COOH, called the FLAG™ peptide (a trademark of International Biotechnologies Inc., Conn.) was used. This sequence is recognized by International Biotechnology Incorporated's (IBI) mouse M2 monoclonal antibody. Placing the FLAG™ sequence on two annealing oligonucleotides in pSCFV UHR leads to a single chain antibody having the human subgroup 4 $V_L$ and CC49 $V_H$ with the FLAG peptide attached at the carboxyl terminus.

The final plasmid derived from pSCFV UHK containing FLAG™ is designated pSC49FLAG. The nomenclature for the single chain proteins produced from pSC49FLAG is as follows: for the monomer-H4L49HF scFv, for the dimer-H4L49HF Fv2 and for the tetramer-H4L49HF Fv4. The "H4L" portion refers to the human Subgroup IV light chain $V_L$ region, "49H" refers to the CC49 $V_H$ and "F" indicates that the FLAG™, peptide is attached.

Construction of pSC49FLAG

A general outline for obtaining the plasmid pSC49FLAG is shown in FIG. 22 and the procedure described below.

a) Isolation of pSCFVUHH Xho I/Nhe I Vector Fragment

Approximately 5 μg of plasmid pSCFV UHH (Example 1) in 15 μL of water was used from the Magic Mini-prep system (Promega). To this was added 5.4 μL of 10× Buffer #2 (New England Biolabs), 45 units of Xho I (New England Biolabs), 15 units of Nhe I and 24 μL of water. The reaction proceeded for 1 hour at 37° C. The sample was then loaded with running dyes on a 4 percent polyacrylamide gel, electrophoresed and purified by electroelution (Sambrook et al, supra). The obtained DNA pellet was dissolved in 20 μL of water.

b) Construction of pATDFLAG

Plasmid pSCFV URI treated with Xho I and Nhe I from above was used in a ligation reaction with annealed FLAG and FLAGNC oligos.

FLAGC (SEQ ID NO:64):
5'-TCGAGACAATGICGCTAGCGACTACAAGGACGA-TGATGACAAATAAAAAC-3'

FLAGNC (SEQ ID NO:65):
5'-CTAGGTTTTTATTTGTCATCATCGTCCTT;TAGTC-GCTAGCGACATTGTC-3'

Equimolar amounts (3 μM of each of the oligos) FLAGC and FLAGNC in a total volume of 62.5 μL) were mixed together using a ligation buffer diluted to 1x(Stratagene). The sample was heated to 95° C. for 2 min and was allowed to cool to below 35° C. over 10 min before use in the ligation reaction below.

The reaction was carried out using the components and amounts indicated above. Starting at 18° C., and then being cooled gradually to 4° C. overnight. Competent *E. coli* Ag1 cells (Stratagene) were transformed with 3 µl of the above ligation reaction and colonies

| COMPONENT | AMOUNT |
|---|---|
| pSCFVUHH XhoI/NheI vector (~100 ng) | 1.0 µL |
| ANNEALED FLAGC/FLAGNC | 0.85 µL |
| 10X Ligation buffer | 2 µL |
| T4 DNA Ligase | 1 µL |
| 10 MM ATP | 2 µL |
| ddH$_2$O | 13.2 µL | selected using LB/CAM 20 plates. A clone having the appropriate Nhe I/Xho I and Nhe I/Xho I restriction patterns was selected for DNA sequencing.

The oligonucleotide used to verify the sequence of the FLAG™ linker in pATDFLAG was called PENPTSEQ (SEQ ID NO:66): 5'-CTTTATGTAAGATGATGTTTTG-3'. This oligonucleotide is derived from the non-coding strand of the penP terminator region (See FIG. 23). FIG. 23 gives the amino acid (SEQ ID NO:20) and DNA sequence (SEQ ID NO:19) in pATDFLAG. The amino acid sequence corresponding to the FLAG™ peptide is given in bold italics. The FLAG™ peptide is out of frame relative to the H4V$_L$-linker sequence which ends at the Xho I site. The DNA sequencing primer, PENPTSEQ, is shown in bold. Nucleotides 824–478 inclusive were verified using the PENPTSEQ primer. At position 624, a 'T' nucleotide present in the original H4V$_L$ sequence has been changed to a 'C' nucleotide resulting in a Val to Ala amino acid residue 89 substitution. These differences are indicated in shadow. The CDR amino acid sequences of H$_4$VL are shown in bold, while the UNIHOPE linker sequence is in bold and underlined. DNA sequencing was performed using the Sequenase™ sequencing kit (U.S. Biochemical, Cleveland, Ohio) following the manufacturer's directions.

c) Generation of pSC49FLAG

The plasmid pATDFLAG (approximately 5 µg, purified from a 2.5 mL culture by the Magic Miniprep system (Promega) was treated at 37° C. for 1 h as indicated in the protocol given below:

DNA—17 µL
10xbuffer (New England Biolabs #2)—6 µL
Xho I (New England Biolabs)—2.5 µL (25 units)
Nhe I (New England Biolabs)—3.5 µL (17.5 units)
H$_2$O—31 µL The resulting vector fragment was purified from a 4 percent PAG, electroeluted and ethanol precipitated. The obtained DNA was dissolved in 20 µL water.

The CC49 V$_H$ insert DNA was obtained from a PCR amplification protocol (Perkin Elmer Cetus) as instructed by the manufacturer. The target DNA (uncut) containing the CC49 V$_H$ was pSCFV UHM 8.1 (Example 1) (0.5 mg). The 5' oligo used for the PCR (100 pmol) was UNI-3 (SEQ ID NO:46) (Example 1). The 3' oligo used (100 pmol) was called SC49FLAG (SEQ ID NO:67), a 33-mer as follows:

Nhe I
5'-TATTGCTAGCTGA GGA GAC GGT GAC TGA GGT TC-3'.

The resulting amplified DNA was purified from a 4 percent PAG, dissolved in 20 µL water, and then treated at 37° C. for 1 h as indicated in the protocol given below:

DNA—10 µL (~2 µg)
10xbuffer (New England Biolabs #2)—6 µL
Xho I (New England Biolabs)—2.5 µL (25 units)
Nhe I (New England Biolabs)—3.5 µL (17.5 units)
water—38 µL The resulting insert fragment was purified and dissolved in 20 µL water. The vector and insert fragments from above were set up in a ligation reaction at 18° C. going down to 4° C. overnight as follows:

DNA vector (pATDFLAG-Xho I/Nhe I)—1.5 µL
DNA insert (PCR amplified CC49 V$_H$-Xho I/Nhe I)-0.8 µL
10xligation buffer (Stratagene)—2 µL
10 mM ATP—2 µL
T4 DNA ligase—1 µL
water—12.7 µL Competent *E. coli* AG1 cells (Stratagene) were transformed using the ligation reaction from above, as directed by the manufacturer. Clone number 1, was selected for further work, and for verification of the constructed DNA sequence. The oligos used as primers for the DNA sequencing were as follows:

1) PENPR1 (SEQ ID NO:68), a 21-mer: 5'-AAC ACT GTA GGG ATA GTG GAA-3';
2) PENPR2 (SEQ ID NO:69), a 20-mer: 5'-GTC TCC CTC CGT TTG AAT AT-3';
3) TAGVLFR2 (SEQ ID NO:55), a 20-mer: 5'-TGG TAC CAG CAG AAA CCA GG-3;
4) UHVHSEQ (SEQ ID NO:70), a 22-mer: 5'-GAT GCT GCG AAG AAG GAT GAC G-3';
5) TAGVHCDR2 (SEQ ID NO:57), a 21-mer: 5'-ATGG ATT GGA TAT TTT TCT CC-3' and;
6) TAG VH FR4 (SEQ ID NO:71), a 21-mer: 5'-ACT GGG GTC AAG GAA CCT CAG-3'.

The DNA (SEQ ID NO:21) and amino acid sequence (SEQ ID NO:22) of pSC49FLAG is given in FIG. 24. Asp=1 indicates the first amino acid from H4V$_L$ of the mature single chain antibody species. The UNIHOPE linker is in bold and underlined. The complimentarity determining region sequences are shown in bold, while the PLAG peptide is in bold italics. Nucleotides corresponding to the Nhe I site in pSCFV UHH are in bold and underlined (position 1154–1159). The 'C' at position 1155 and the 'A' at position 1157 are italicized within this sequence and indicate differences from the published penP terminator sequence. The DNA sequencing was carried out using the Sequenase™ kit mentioned above.

The predicted pI and molecular weight (MW) of each of the protein species produced was obtained from the DNAS-TAR™ Protein-Titrate computer program (Madison, Wis.).

Purification of H4L49HF Single Chain Products

A 10 mL M2 antibody affinity column was prepared (gel purchased from IBI) and incorporated on the HPLC system described under general experimental procedures. The H4L49HF crude protein sample was prepared as follows. One liter (2x500 mL) of *E. coli* AG1/pSC49FLAG was grown overnight at 37° C. in LB broth containing 20 µg/mL chloramphenicol. The cells were recovered by centrifugation of the culture at 5,000 rpm for 10 min at 5° C. in a Sorvall GS-3 rotor (duPont). The cell pellet was resuspended in 100 mL of PBS, and subjected to sonication (MSE Soniprep 150) for 5 bursts at 14 microns amplitude lasting for 15 seconds each, and cooling in an ethanol-ice bath for 1 minute in between. The sonicate was ultracentrifuged at 26,000 rpm for 2 hours in a Type Ti30 rotor (Beckman Instruments). The resulting supernatant was filtered through a 0.22 membrane device (Nalge Co., Rochester, N.Y.) and finally concentrated to 22 mL using Centriprep 30 (Amicon) devices. The sonicate was pumped onto the affinity column at 2 mL/min with stops lasting for 1 min twice during the application, to allow interaction with the affinity ligand.

PBS was used to wash the column of any unbound material, and when the absorbance at 276 nm returned substantially to the baseline, the buffer was changed to 0.1M glycine-HCl, at pH 3.1. Elution of a peak began 4 minutes later, the fractions of which were immediately neutralized using 1 M Tris pH 8.8 and PANPEHA indicator (range 0–14) pH paper strips (Schleicher Schull). The eluted protein was concentrated to 200 $\mu$L using Centriprep 30 and Centricon 30 (Amicon) devices.

The resulting single chain antibody species were separated by gel filtration using a Pharmacia Superdex 75 Prep Grade HR 26/60 column and PBS as the eluent. The flow rate was initially 0.4 mL/min, and then increased to 1.2 mL/min during the chromatography. Three pools of fractions from this run were made, and then tested analytically on a Superdex 75 HR10/30 column for purity and characteristic elution time. Biorad gel filtration standards were also chromatographed on this column using the same buffer (PBS) and a 0.6 mL/min flow rate, to generate a standard curve for comparison with the elution times of the single chain antibody species. The three species obtained were concentrated, quantitated at OD 280 nm and stored frozen at $-20°$ C.

Figure 25B:
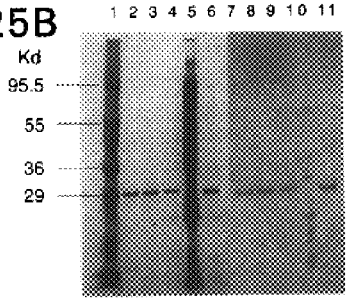
FIG. 25 shows the results of an M2 affinity chromatograph (A), analytical gel filtration (B), SDS-PAGE (C) and (D) Western Blot of H4L 49HF scFv's.
Figure 25C:
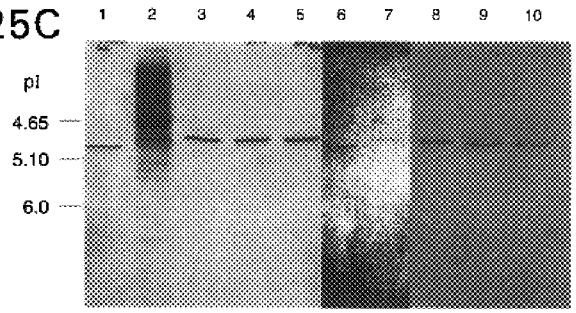

The results of the purification and characterization of the H4L49HF single chain products is given in FIG. 25. Panel A shows the M2 affinity chromatography profile for *E. coli* pSC49FLAG sonicate preparation. Stars (*) indicate points in the application of sample when the flow was stopped for 30 seconds. The arrow indicates the point at which the buffer was changed and the flow chart increased to 2.0 mL/min. Fractions were 2 minutes long.

Panel B represents an analytical gel filtration chromatogram obtained from application of 0.5 percent of the total pooled sample from fractions 19–21 shown in A.

Panel C shows a 10–20 percent gradient SDS-PAGE of samples stained with Coomassie Brilliant Blue R-250 (Lanes 1–6) or Western transferred (lanes 7–11) and probed with biotinylated FAID14. Lane 1: prestained molecular weight standards (Diversified Biotech); lanes 2–4 and 7–9 are purified H4L49RF scFv, Fv2 and Fv4, respectively; lanes 5 and 10; *E. coli* pSC49FLAG sonicate sample, the same as that as applied to M2 affinity column; and lanes 6 and 11, Pichia CC49scFv 5.2.

Amino Terminal Sequencing

Samples of the three protein species of H4L49HF (10 $\mu$g each) were desalted by 3 successive water washings using Centricon 30 devices and freeze-dried. Amino terminal sequencing was determined by standard Edman degradation techniques.

Determination of Anti TAG-72 Activity
  a) anti-PLAG ELISA
A. Tag Elisa

Binding activities of the purified monomer and is multimer forms of H4L49HF as well as sonicates of *E. coli* expressing these species were determined by ELISA (Enzyme Linked Immunosorbant Assay) on 96 well PVC plates coated with a 1/300 dilution of the TAG-72 prep (040191). The plates were prepared and blocked for two hours with 1 percent bovine serum albumin (BSA) in PBS with 0.025 percent sodium azide at 37° C. After blocking, the plates were washed three times with 0.025 percent Tween 20 solution and stored at 4° C.

Aliquots of 50 $\mu$L of sample at each concentration were added in duplicate to the 96 well plate. The starting concentrations for the purified monomer, dimer, and tetramer were 10 $\mu$g/mL for each, and 1:2 dilutions were made to a final concentration of 0.005 $\mu$g/mL. The samples added to the plate included the purified monomer, dimer, tetramer, and various crude sonicates.

After adding the samples, the plate went through a series of incubations at 37° C. The first incubation was for 1 hour with sample. The plate was washed five times with 0.025 percent Tween 20. Binding of FLAG™ containing single chain species was detected by subsequent incubations with murine anti-FLAG MAb, M2 (International Biotechnologies cat: IB13010) at 1/250 dilution. The plate was incubated for 1 hour removed, and washed. Alkaline phosphatase conjugated goat anti-mouse polyclonal antibody (GAMIG-ALPH, Southern Biotechnology Associates) was added at 50 $\mu$L per well. The plate was incubated for 1 hour, removed, and washed. The diluent for both antibodies was in 1 percent BSA in PBS with 0.025 percent sodium azide. The phosphatase substrate (Kirkegaard & Perry Laboratories, Inc.) was prepared by mixing 1 ml of 5xbuffer (Kirkegaard & Perry Kit), 4 mL water, and one substrate tablet (Kirkegaard & Perry Kit). To each well, 50 $\mu$L were added. Color development was terminated after 15 minutes with 50 $\mu$L/well of 1 M sodium hydroxide. The ELISA plate was read with the Molecular Devices Kinetic Microplate Reader using the Delta Soft® Computer program.

B. BSM ELISA

Bovine submaxillary mucin (BSM) was applied to a PVC plate at concentrations ranging from 5.0 mg/ml to 0.00008 mg/ml decreasing at 1:2 dilutions in water. A blank of 50 $\mu$L of PBS with 0.025 percent azide was added as a control. The plate was allowed to dry at room temperature overnight in a biological safety cabinet. The plate was blocked using 200 $\mu$L of 1 percent BSA in PBS. The plate was incubated at 37° C. for 50 minutes. The plate was removed from incubation and washed three times with 0.025 percent Tween 20. Dilutions (1/3, 1/9, 1/27) of a crude sonicate of pSC49FLAG were applied to the BSM control wells.

After obtaining results from the above ELISA, a BSM concentration of 60 $\mu$g/ml was selected for further plating. The diluent was water. The BSM at 60 $\mu$g/ml was loaded at 50 $\mu$L per well using a multi-channel pipet land dried and blocked as above. The plates were washed three times with 0.025 percent Tween 20 and stored at 4° C. Incubation and detection of FLAG-containing species was performed as above, using the M2 anti-FLAG antibody.

Figure 26A:
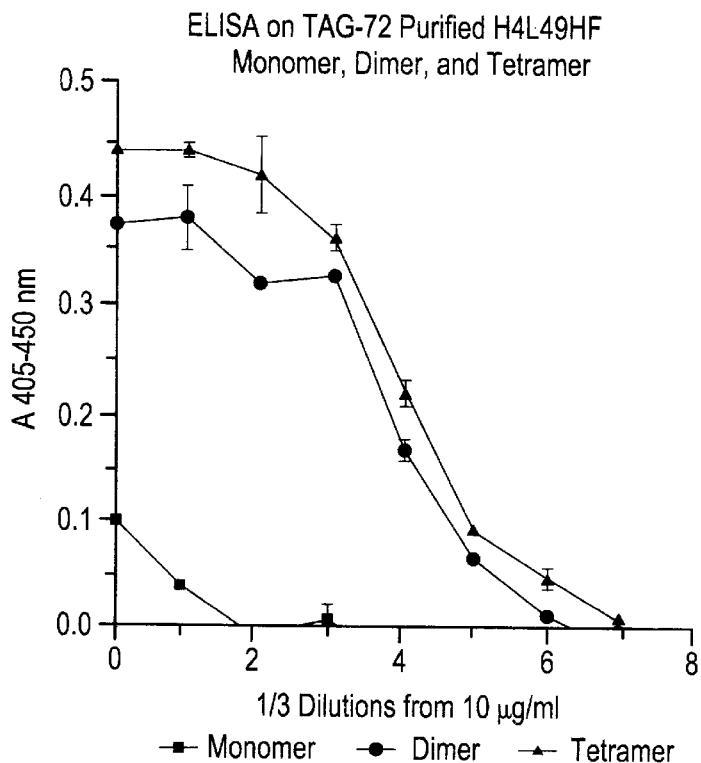
FIG. 26 illustrates the results of binding of H4L49HF single chain species by TAG ELISA (A, B and C) or BSM ELISA (D).
Figure 26B:
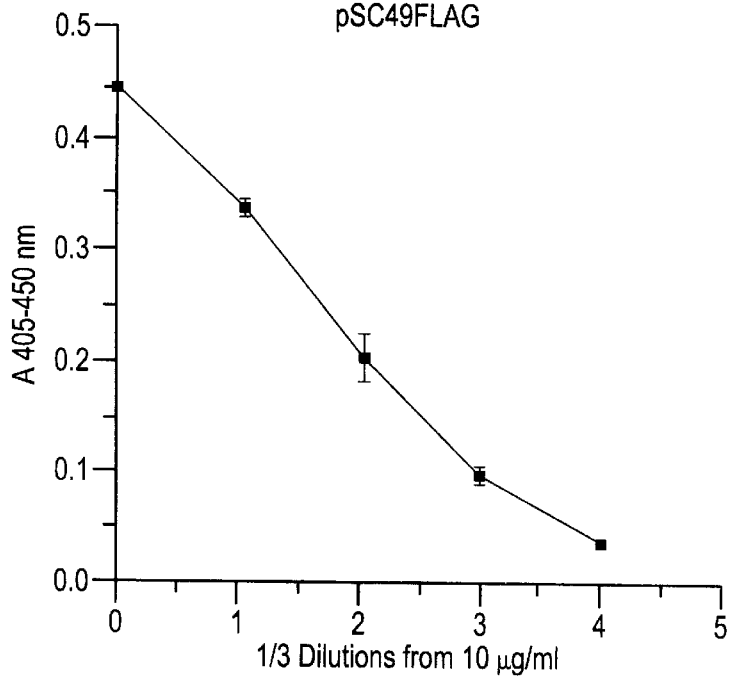

The relative binding of H4L49HF single chain species by TAG of BSM ELISA are given in FIG. 26. FIG. 26A shows results from TAG ELISA for purified monomer, dimer and tetramer. FIG. 26B shows results from TAG ELISA for *E. coli* pSC49FLAG sonicate containing monomer and multimer species. FIG. 26C shows results from various concentrations of the single chain species reacting with BSM. FIG. 26D is ELISA on BSM with pSC49FLAG sonicate.

In FIG. 26A, starting with concentrations of 10 ug/ml, 1:3 dilutions were performed and the relative binding to TAG-coated plates was determined. It can be seen that the tetramer species gave the greatest binding, followed by dimer, and eventually by monomer. Using DeltaSoft software (BioMetallics, Princeton, N.J.), and assuming the dimer as the standard curve, the tetramer activity was 1.3 to 5 times greater than the dimer activity. The monomer activity was only 0.5 to 0.8 percent of the dimer activity.

b) Competition ELISA

This assay was performed as described in Example 1. The formula used to calculate percent competition is as follows:

$$\frac{\text{No Competition} - \text{Sample reading}}{\text{No Competition} - \text{Background}} \times 100$$

Absorbance values for the samples were measured at 405 nm–450 nm. The average of duplicate readings was used. Initially samples (25 µL) were applied to the TAG-72 coated microliter plates at $2.0 \times 10^{31}$ $^{10}$/mL. Biotin CC49 (4 µg/µL diluted 1:20,000—used 25 µL) diluted the samples by a factor of 2. Serial dilutions (1:2) were performed, resulting in a total of 10 concentrations for each sample. The "no competition" sample consisted of 25 µL of antibody buffer (1 percent BSA in Tris buffered saline (Pierce Chemical Co.)+0.025 percent Tween and 25 µL of the biotinylated CC49 competitor. Background samples were formulated with either antibody buffer with no added CC49 biotin, or a 5 µg/mL solution of CC49 IgG in antibody buffer. Both give essentially the background reading.

The results of the competion ELISA are given in FIGS. 27 and 28, FIG. 27 based on moles of antibody binding site and FIG. 28 based on moles of antibody. These results show that the extra FLAGS binding sites on the dimer and tetramer did not skew the results in favor of the multimers.

Immunohistochemistry (IHC)

Specimens. A total of 7 specimens of colorectal adenocarcinoma, including four primary adenocarcinomas and three intra-abdominal metastases (two mesenteric metastases and one hepatic metastasis), were used in these studies. Areas of reactive or normal tissue were also present for assessment of immunoreactivity of non-neoplastic tissues. Sequential 5 µm thick sections were prepared. One section was stained with hematoxylin and eosin (H and E) with other sections used for the various IHC procedures.

The purified H4L49HF Fv2 product was used at 0.33, 1.7 and 8.3 µg/mL levels as the primary probing agent for the specimens. Sonication (as per Example 1) of a 2.5 mL overnight culture of E. coli pSC49FLAG provided a crude test probe material and was used for the specimens. These sonicates contained a mixture of H4L49HF scFv, Fv2, Fv4 etc. whose concentration and composition was not known.

Immunohistochemistry procedures (IHC). IHC was performed using a modification of the avidin-biotin-peroxidase complex (ABC) method (Hsu et al., J. Histochem. Cytochem. 29, 577–580, 1981). The method utilized a commercial anti-mouse IgG kit (Vectastain Peroxidase Mouse IgG, Vector Laboratories, Burlingame, Calif.). Briefly, the technique was as follows:

1) Sequential 5–6µ sections of the test tumors were deparaffinized, rebydrated, and endogenous peroxidase activity was quenched.

The sections were then sequentially flooded with the following reagents:

2) Normal equine blocking serum (Vectastain kit) for 20 minutes.

3) Add primary antibody for 45 minutes, either 200 µL of H4L49HF Fv2 or sonicate of E. coli pSC49FLAG (from 2.5 mL of overnight cell growth), and add to sequential sections of the tumor. Diluent (PBS containing 0.1 percent:BSA, Sigma Chemicals Co. St. Louis, Mo.) was used on one section from every tumor at this step to serve as a negative control.

4) M-2 (International Biotechnologies Inc., San Pedro, Calif.), murine anti-FLAG MAb, was then used at a dilution of 1:100 for 45 mintues.

5) Secondary antibody biotinylated anti-mouse IgG (Vectastain kit), for 45 minutes.

6) ABC reagent for 45 minutes.

7) The chromagen, 0.05 percent diaminobenzidine, in 0.02 percent $H_2O_2$ for 3.5 minutes.

8) The slides were counterstained with Meyer's hematoxylin (Sigma Diagnostics, St. Louis, Mo.), dehydrated, and coverslipped by routine methods.

All reactions were conducted at room temperature. The slides were rinsed between each step, except following step 2, in three washes of PBS for at least five minutes each; the final rinse contained 0.1 percent BSA. IHC reactivity was evaluated for both the acellular and cellular parts of the tumor as well as for adjacent non-neoplastic structures.

The H4L49HF purified dimer stained both cellular and a cellular areas of the test colon carcinomas. Mucinous acellular material from the neoplastic cells vas extensively reactive. Viable neoplastic cells had more variable reactivity with some tumors having high numbers of reactive cells and other tumors having few reactive cells. The specific cellular location of the staining was also variable within and between the different specimens. The atypical cytoplasm and/or (atypical) surface adjacent stained acellular material was most frequently stained. Lesser members of cells had diffuse cytoplasmic staining. There was little reactivity of H4L49H Fv2 with limited numbers of non-neoplasmic tissues examined except reactive colon mucosa immediately adjacent CRC. In this mucosa, the mucin vacuoles of goblet cells and the free mucin on the surface was reactive. The staining diminished with the distance from the tumor/reactive mucosa junction. Crude E. coli pSC49FLAG sonicate, containing all the H4L49HF scFv species (monomer, dimer, multimer, etc.) also gave similar results, indicating that these single chain antibodies are specific for tumor tissues. A control sonicate from E. coli pATDFLAG gave no staining of the TAG-72 positive areas.

Example 5

Synthesis and Expression of Genes Encoding Single Chain Species of HLA-DR

DNA and Oligonucleotides

Plasmids containing full length cDNAs encoding HLA alleles DRB1*0101, *0401, *0402 and *0408 and HLAα1 are derived as follows. Poly A+ mRNA is isolated from the peripheral blood lymphocytes of a number of volunteers. First strand cDNA synthesis is performed using oigo (dT) as the primer.

α Chain Amplification

Using the known sequence of the HLA-DR α chain [see, Schamboeck et al., Nucl. Acids Res. 11, 8663–8675 (1983)] a 5' end primer called HLADA5 and a 3' end primer called HLADA3 are synthesized to amplify the α chain sequence. These primers contain an Eco RI restriction enzyme site. The sequences of the primers being:

HLADA5 (SEQ ID NO:72):
5'-(TGACGAATTCGCCCAAGAAGAAAATGGCCA)-3'
HLADA3 (SEQ ID NO:73):
5'-(TCAGGAATTCTGGAAAACGCTGAAGATGAC)-3'

Amplifying the α chain from the single-stranded cDNA from above results in an approximately 1 Kb fragment, which is gel purified (GeneClean™ kit, La Jolla, Calif.), digested with Eco RI and gel purified again. The product is then subdloned into an Eco RI digested pUC18 vector. A clone designated pKEKα4 is chosen as the α chain clone.

β Chain Amplification

Using the known sequence of the HLA-DR β chains, [see, Hurley et al., *J. Immunology,* 140, 4019–4023 (1988)] a 5' end primer called HLADB5, and a 3' end primer called HLADB3.3 are synthesized to amplify the β chain sequence. Both of these primers contain an Eco RI restriction enzyme site, the sequences of the primers being:
HLADB5 (SEQ ID NO:74):
5'-(TGACGAATTCCTGTCCTGTTCTCCAGCATG)-3'
HLADB3.3 (SEQ ID NO:75):
5'-(GACTCTAGACCCGGGTACCAATGCTGGGACTT-CAGGCC)-3

Amplification products are digested with Eco RI and XbaI, gel purified and subcloned into and Eco RI/Xba I digested pUC18 vector. A number of clones are isolated, two of which contain rheum atoid arthritis (RA) associated alleles (DRB1*0401 and DRB1*1001) are isolated.

Two additional RA-associated alleles (DRB1*0101 and DRB1*0408) are generated via a semisynthetic approach using the pool of clones which were generated above. The DRB1*0101 clone is generated by removing a SacII/Bsu36I fragment from a clone containing DRB1*0102/DRB and inserting a small fragment generated by annealing the 0101F and 0101R oligonucleotides described below. The small inserted fragment changes amino acids 85 and 86 of DRB1*0102 to the amino acids encoded in the DRB1*0101 allele. The clone, designated pSYNβ60, contains a chimeric β chain cDNA encoding HLA-DRB1*0101.
0101F (SEQ ID NO:76):
5' (GGTGGACACCTATTGCAGACACAACTACGGGGT-TGGTGAGAGCTTCACAGTGCAGCGGCGAGTTG-AGCC)-3'
0101R (SEQ ID NO:77):
5'-(TTAGGCTCAACTCGCCGCTGCACTGTGAAGCTC-TCACCAACCCCGTAGTTGTGTCTGCAATAGGT-GTCCACCGC)-3'

The DRB1*0408 clone is generated by removing a EcoO 109I/Bsu36I fragment from a clone containing DRB1*0401 and inserting a small fragment generated by annealing two oligionucleotides DRβ-3AHV5' and DRβ-3AHV3'. The annealed fragment exchanges amino acids 71 through 86 from the DRB1*0401 allele to the DRB1*0408 allele.
DRβ-3AHV5' (SEQ ID NO:78):
5'-(GACCTCCTCGAGCAGAGGCGGGCCGCGGTGGA-CACCTACTGCCGGCACAACTACGGGGTTGGTGA-AAGCTTCACAGTGC)-3'
DRβ-3AHV3' (SEQ ID NO:79):
5'-TCAGGATAGACTCGCCGCTGCACTGTGAAGCTT-TCACCAACCCCGTAGTTGTGCCGGCAGTAGGTG-TCCACCGCGGCCCGCCTCTGCTCGAGGAG-3'

Figure 29:
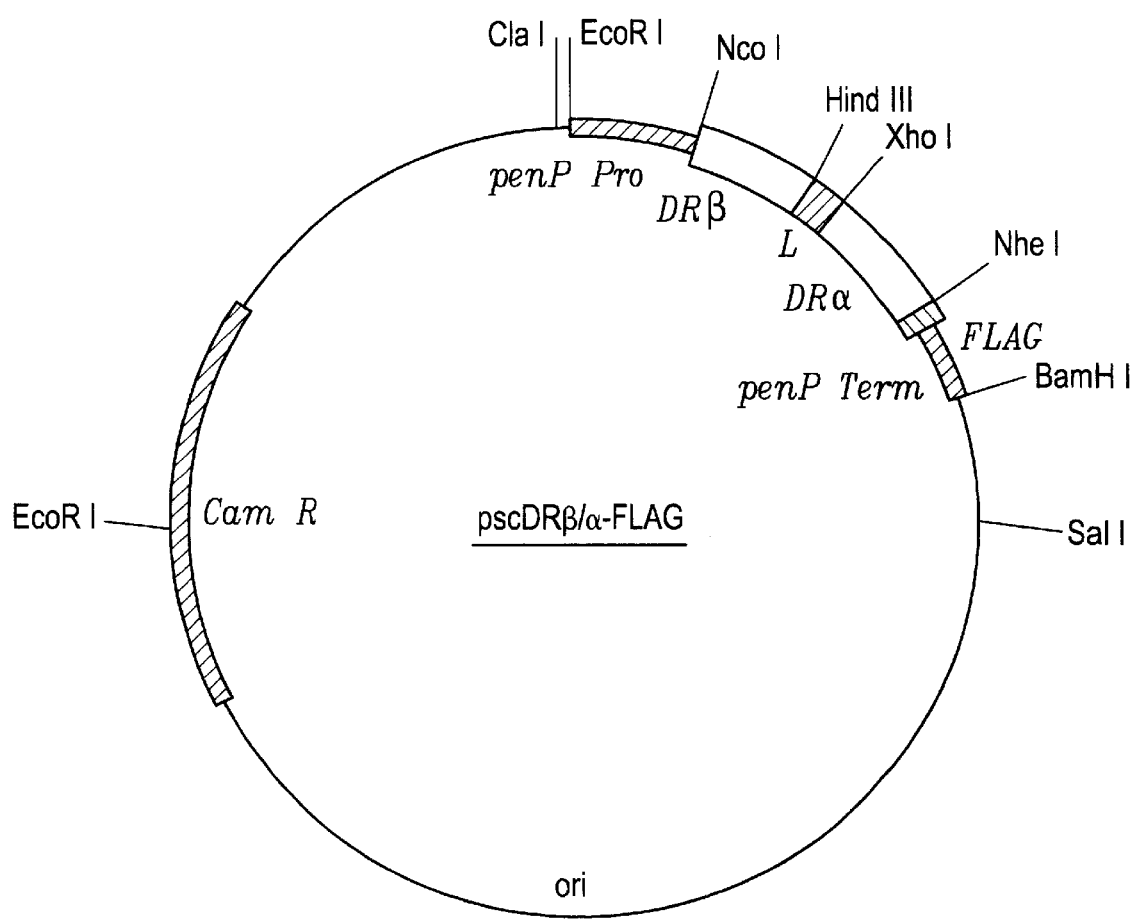
FIG. 29 illustrates the plasmid pscDRB/α-FLAG.

The scDRβ/α-FLAG expression vector (see FIG. 29) is based on the single chain antibody expression vector pATD-FLAG (Example 4).

The following oligonucleotides are used in PCR amplifications to generate cDNAs encoding the human α1 and β1 domains.
SCDRA5.1 (SEQ ID NO:80)
5'-GGACCTCGAGATCAAAGAAGAACATGTG-3'
SCDRA3.1 (SEQ ID NO:81)
5'-AGTCGCTAGCATTGGTGATCGGAGTATA-3'
SCDRB5.1 (SEQ ID NO:82)
5'-CCAGCCATGGCCGGGGACACCCGACCACGT-3'
SCDRB3.1 (SEQ ID NO:83)
5'-CACTAAGCTTATACACAGTCACCTTAGG-3'

Sequencing reactions of the pSL301 subclones containing either sdDRβ1 or sdDRα1 are done using the commercially available biotinylated T7 and T3 primers are used (New England Biolabs). Alternatively these domains are sequenced directly in the psdDRβ/-αFLAG expression vector using the following primers.
VLSEQ1 (SEQ ID NO:84)
5'-CTATTGCCTACGGCAGCC-3'
VLSEQ2 (SEQ ID NO:85)
5'-AGCGTCATCCTTCTTCGC-3'
VHSEQ1 (SEQ ID NO:86) 5'-GATGCTAAAAAGAC-3'
VHSEQ2 (SEQ ID NO:87)
5'-AGGTTTTTATTTGTCATCATC-3'

Primers used for sequencing the full length β-chain and α chain cDNA clones include the pUC/M13 forward (−40) and pUC/M13 reverse primers (New England Biolabs) and primers Aint1, Aint2, Bint1, Bint2, bint3, bint4.
Aint1 (SEQ ID NO:88) 5'(GGACGATTTGCCAGCTT)-3'
Aint2 (SEQ ID NO:89) 5'(CACCAGACCCACAGTCA)-3'
Bint1 (SEQ ID NO:90) 5'(GCTTCGACAGCGACGTG)-3'
Bint2 (SEQ ID NO:91) 5'(GTACACAGTCACCGTAG)3'
Bint3 (SEQ ID NO:92) 5'(ACCAGGAGGTTGTGGTG)-3'
Bint4 (SEQ ID NO:93) 5'(GCTCAGGAATCCTGTTG)-3'
PCR Amplification The reactions are performed in a Perkin-ElmerCetus PCR System 9600. The amplification program consists of 35 cycles of the following thermal profile: 94° C. for 30 seconds, 55° C. for 1 minute and 72° C. for 1 minute.

Gel Purification Of DNA Fragments: The DNA bands (restriction fragments or PCR products) are excised from agarose gels and DNA purified using either the Geneclean™ II DNA Isolation (for fragments >1000 bp) or MerMaid DNA Isolation kits (for fragments <1000 bp) using the manufacturer's protocols (BIO101, La Jolla, Calif.). The DNA is eluted from the glass beads using water.

DNA Sequencing: The sequence of the double stranded plasmid DNAs is determined following either the Sequenase™ Sequencing System (United States Biochemical, Cleveland, Ohio) or the TaqTrack™ Sequencing System (ProMega, Madison, Wis.) protocols. Nonradioactive sequencing using the biotinylated T7 and T3 primers is done using the UniPlex™ Luminescent Kit (Millipore, Bedford, Mass.). DNA analysis is performed on a Macintosh SE/30 using the MacVector™ programs of International Biotechnologies, Inc. (New Haven, Conn.).
Anti-FLAG Colony Screening Assay Colonies containing appropriate size inserts are selected from each transformation and streaked onto a hydrophilic PVDF (polyvinylidene difluroide) membrane. The membrane-bound colonies are grown overnight (approximately 16 hours) at 37° C. on an agar plate containing Luria nutrient broth (LB) and chloramphenicol at 25 μg/mL. Interspersed between the hydrophilic membrane and the agar/LB plate is a hydrophobic PVDF membrane. This second membrane actsas a "protein trap" which can be used to examine the protein secretion profile of each of the colonies on the overlying membrane. In most cases, this hydrophobic filter is developed using the anti-FLAG antibody M2 (International Biotechnologies, New Haven, Conn.) and anti-mouse alkaline-phosphatase conjugate according to standard procedures.
Protein Expression and Purification Single chain DRβ1/α1-FLAG proteins are expressed constitutively in recipient *E. coli* strains under the transcriptional control of the penicillinase P promoter from *Bacillus licheniformis* and contain the C-terminal octamer peptide referred to as FLAG™ (see Example 5). Lysates are analyzed for expression of FLAG-containing peptides directly by standard immunoblotting procedures using the anti-FLAG antibody M2. Lysates for either direct analysis or for purification are prepared as follows. Overnight cultures of plasmid containing colonies (approximately 2 mL for direct blotting; 100–500 mL for purification) are pelleted by centrifugation at approximately 5,000 rpm in an SS34 rotor at 4° C., resuspended in phosphate-buffered saline (PBS), sonicated through three 20 second cycles at a setting of 14 microns and pelleted by centrifugation at 10,000 rpm (SS34 rotor). For purification, the lysate is filtered through a 0.2 micron syringe-mounted filter. Affinity purification is accomplished through use of a 10 mL or 1 mL anti-FLAG™ affinity columns. Loading and washes are in PBS. Elution is with 0.10 M glycine pH 3.12. Fractions containing the eluted peak are neutralized and analyzed for the presence of FLAG-containing proteins by SDS-PAGE and immunoblotting with the anti-FLAG antibody.

Immune sera from mice immunized with mouse L cells expressing HLA-DRB*0101 is also used to probe membranes. The assay is conducted as described above for anti-FLAG except that anti-FLAG is replaced by a 1:80 dilution of serum isolated from an immunized mouse.

Enzyme-linked Immunosorbent Assays (ELISAs)

Commercially available anti-HLA-DR and anti-FLAG antibodies and supernatants from hybridomas derived from HLA-DR-immunized mice are assayed for the capacity to bind wells coated with the purified proteins according to standard procedures. Such as described in Caligan, S. E. et al., *Current Protocals in Immunology,* New York: John Wiley & Sons, Inc., (1991)

DR α1 and DRβ1 Amplification and Cloning

To isolate independently folding HLA-DRβ1 and -α1 domains and to intersperse them with a linker in such a way as to optimize their potential interaction in forming a class II MHC-like protein structure when expressed in microbial systems, an amino acid which is predicted to be in the region extending from the β1 domain to the β2 domain (or α1 to α2) as the C-terminal codon of the amplified product is selected [Brown et al., *Nature* 332, 845–850 (1988)]. For β1, amino acid 102 is selected and for α1, amino acid 84 is selected (Kabat et al., Supra)). Oligonucleotide primers are synthesized such that the N-terminal and C-terminal codons are flanked by restriction enzyme sites appropriate for cloning into the expression vector pATD-FLAG. Specifically, amplification with the β1-specific primers results in PCR products containing an Nco I site near the 5'-end and a Hind III site near the 3'-end. Amplification with the α1-specific primers (SCDRAS.1 and SCDRA3.1) gives products flanked by Xho I and Nhe I sites on the 5'- and 3'-ends, respectively.

The β1 domain is amplified from plasmids containing DRB1 alleles *0101, *0401, *0402 and *0408, (pcD-SYNβ60, pcD-RAEβ60, pcD-DAKβ21 and pcD-SYNβ65, respectively. Bands of approximately 320 bp are gel isolated, purified using the MerMaid kit, digested with Nco I and Hind III and gel purified again. For subcloning, the PCR products and the plasmid PATD-FLAG' are digested with Nco I and Hind III, purified and ligation reactions setup either with or without digested β-chain PCR DNA. Plasmid pATD-FLAG' differs from PATD-FLAG only in the Xho I-to-Nhe I spacer (see sequences below). In pATD-FLAG, this spacer contains of 8 bp of DNA, placing the FLAG peptide translationally out of frame with the linker, thereby preventing constructs containing only β1-encoding cDNA (between the Nco I and Hind III sites) from expressing the corresponding FLAG-containing polypeptide. In pATD-FLAG', this spacer contains of 18 bp of DNA which places the FLAG peptide in-frame with the DRαβ domain and linker allowing the constructs containing only the DRDβ1 insert to express a FLAG-containing protein.

pATD-FLAG Linker

```
     Xho I                   Nhe I    (SEQ ID NO:94)
   Leu Glu Thr Met     Ala Ser
  5'-CTC GAG ACA ATG TC GCT AGC
``` pTAD-FLAG' linker:

```
                                         (SEQ ID NO:95)
     Xho I                                      Nhe I
   Leu Glu Thr Thr Ser Ala Asp Asp Ala Ser (SEQ ID NO:96)
  5'-CTC GAG ACA ACT AGT GCG GAC GAC GCT AGC
```

Colonies containing appropriate size insert s (approximately 315 bp) are selected from each ligation and streaked on a hydrophilic PVDF membrane. The membrane-bound colonies are assayed for production of FLAG peptide and FLAG-positive colonies from each set selected for sequencing. The HLA-DRβ1 insert from each of these colonies is subcloned into pSL301 (Invitrogen Corporation, La Jolla, Calif.) and the nucleotide sequence determined nonradioactively using biotinylated T7- and T3-promoter primers and the Sequenase™ kit.

Subcloned Nco I/Hind III fragments are assigned names corresponding to their respective HLA-DR alleles; "sdDRβ11" for the (sd=single domain) β1-encoding domain of DRB1*0101, "sdDRβ41" for allele DRB1*0401, "sdDRβ42" for allele DRB1*0402 and "sdDRβ48" for allele DRB1*0408. DNA sequencing (FIGS. 30 (SEQ ID NO:23), 31 (SEQ ID NO:25), 32 (SEQ ID NO:27) and 33 (SEQ ID NO:29) for plamids containing sdDRβ11, sdDRβ42, sdDRβ48 and sdDRβ42, respectively) reveal that both sdDβ11 and sdDRβ42 contained nucleotide sequences identical to the parental HLA-DR cDNAs from which they had been amplified. The sequences extended from the first amino acid codon of the mature β1 domain (GGG=Gly) to amino acid codon number 102 (TAT=Tyr).

In FIGS. 30 through 33, the transcriptional unit consists of the *Bacillus licheniformis* penicillinase P promoter (nucleotides 2–292) and terminator nucleotides 1076–1292), the pel B signal peptide (nucleotides 292–352) and the corresponding scDRβ/α-FLAG protein-coding region (nucleotides 358–1072). The corresponding scDRβ/α-FLAG region is composed of the DRβ domain, encoded by nucleotides 358–664 (between the Nco I and Hind III sites), the linker regions (nucleotides 664–742; underlined), the corresponding DRα domain, encoded by nucleotides 743–1048 (between the Xho I and Nhe I sites) and the FLAG peptide-coding regions (nucleotides 1049–1072; dotted and underlined).

The psdDRβ-FLAG constructs lack the DRα coding domain and instead contain a linker formed by ligation of the annealed oligonucleotides XSN and NSX into the Xho I/Nhe I digested vector. The Xho I to Nhe I insertion is shown as follows:

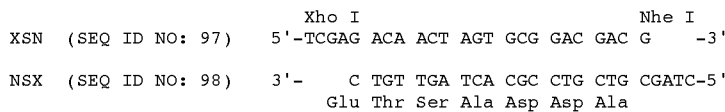

```
                     Xho I                                Nhe I
XSN  (SEQ ID NO: 97)  5'-TCGAG ACA ACT AGT GCG GAC GAC G     -3'

NSX  (SEQ ID NO: 98)  3'-    C TGT TGA TCA CGC CTG CTG CGATC-5'
                             Glu Thr Ser Ala Asp Asp Ala
```

The sdDRβ48 is originally intact only from codon 1 to codon 87, which is altered from GAA to GAG during semisynthesis of the HLA-DRB1*0408 cDNA). FIG. 32 shows the nucleotide and amino acid sequences after the missing codons 87–102 are replaced as follows. 25 Briefly, the change in codon 87 results in the generation of a Hind III site at codons 87–89 such that digestion of the DRβ48 PCR product with Nco I and Hind III gives a Nco I/Hind III fragment with a 3'-overhang at codon 88 instead of codon 103. Thus, it is necessary to reinsert the codons corresponding to amino acid residues 87–102. Because of the similarity between HLA-DRB1*0101 and HLA-DRB1*0408 in this region and because both alleles contain a Sac II site at codons 73–75, this is done by replacing the Sac II/Hind III region of the original (truncated) sdDRβ48 construct with the Sac II to Hind III region of sdDRβ11 (sdDRβ41 or sdDRβ42 may also be used). In the example shown (FIG. 32), the Sac II/Hind II region of sdDRβ11 is used to replace the missing codons. The β1 domain of the resulting construct differs in amino acid sequence from the native HLA-DRB1*0408 β1 domain only at amino acid 96 (glutamic acid) which in the native *0408 allele is a tyrosine. This difference lies outside the region of the class II MHC molecule thought to be involved in antigen-binding and is not expected to alter the overall functional properties of the encoded protein.

The α1 domain is amplified from the plasmid pcD-KEKα4 (the pCD vector is described in Okayama, H. et al., *Molecular and Cellular Biology*, 3, 280–289 (1983). The pCD-1 vector is identical to the original vector except that the Pst I-Kpn I multiple cloning site is replaced by ligating the Pst I/Kpn I digested the following annealed oligonucleotides
pCD-1 (SEQ ID NO:99) 5'GAGAATTCAGGTAC-3'
pCD-2 (SEQ ID NO:100) ACGTCTCTTAAGTCC-3'
A band of approximately 270 bp is gel isolated, purified using the Mermaid kit, digested with Xho I and Nhe I and gel purified again. For subloning, the PCR product and plasmids approximately 5–10 ng) encoding the β1 domains (inserted between the Nco I and Hind III sites of pATD-FLAG') are digested with Xho I and Nhe I, purified and ligation reactions set up either with or without (~20 ng)digested α-chain PCR DNA. Competent *E. coli* cells are transformed with 1–2 μl of ligation mix and plated on LB/chloramphenicol plates. When insert-containing ligation mixes give more colonies per plate than the negative control ligations, colonies are picked, grown overnight in 2 mL LB/chloramphenicol medium and plasmid DNA is isolated. Restriction digests (Xho I and Nco I or Nco I and Nhe I) confirm that a band of the right size has been inserted. The α-chain is excized using Xho I and Nhe I and subdloned into plasmid pSL301 and the nucleotide sequence determined.

sdDRβ11-FLAG Expression

Single-domain (sd) DRβ11-FLAG protein is purified by sonication and affinity chromatography as described above. The sdDRβ11-FLAG (and scDRβ42) protein elutes in a single peak. Fractions from the chromatographic elution are analyzed by SDS-PAGE and anti-FLAG immunoblotting. Coomassie-stained SDS-polyacrylamide gels show that the major Coomassie stained band in fractions in the purified preparation runs more quickly than the purified single-chain antibody sc49-FLAG (MW approximately 29.0 kD) and migrates at a MW of about 15,000. The immunoblot of the same gel shows that the purified band is recognized by anti-FLAG antibody. The Coomassie-stained gel also shows that the scDRβ11-FLAG protein constitutes a fairly minor component of the whole lysate (<1 percent) and the major protein (>50 percent) of the purified protein. Thus, sdDRβ11-FLAG (and sdDRβ42-FLAG; data not shown here) appears to be expressed as a stable protein with an apparent molecular weight of ~15,000 as expected for a molecule consisting of 141 amino acids (DRβ1 domain=102 amino acids; linker=26 amino acids; FLAG' filler region=3 amino acids; and the FLAG-peptide coding region including the Nhe I site=10 amino acids). Although these constructs contain the DRβ1 domain, a linker region and a FLAG-peptide coding region, it is unlikely that the latter two components contribute significantly to the overall stability of the scDRβ1 proteins. These regions can be removed by digestion of the psdDRβ-plasmids with Hind II and Nhe I and ligation of a linker which introduces a stop codon immediately after the Hind III site. One such linker is generated by ligation of the oligonucleotides sdDRtrunc1 and sdDRtrunc-2 into the digested psdDRβ-plasmid. Sequences of two such oligonucleotides are as follows:

sdDRtrunc-1 (SEQ ID NO:101) 5'AGCTTTAAG-3'
sdDRtrunc-2 (SEQ ID NO:102) 3'AATTCGATC-5'
where the stop codon (TAA) is shown in bold letters.

Figure 34:
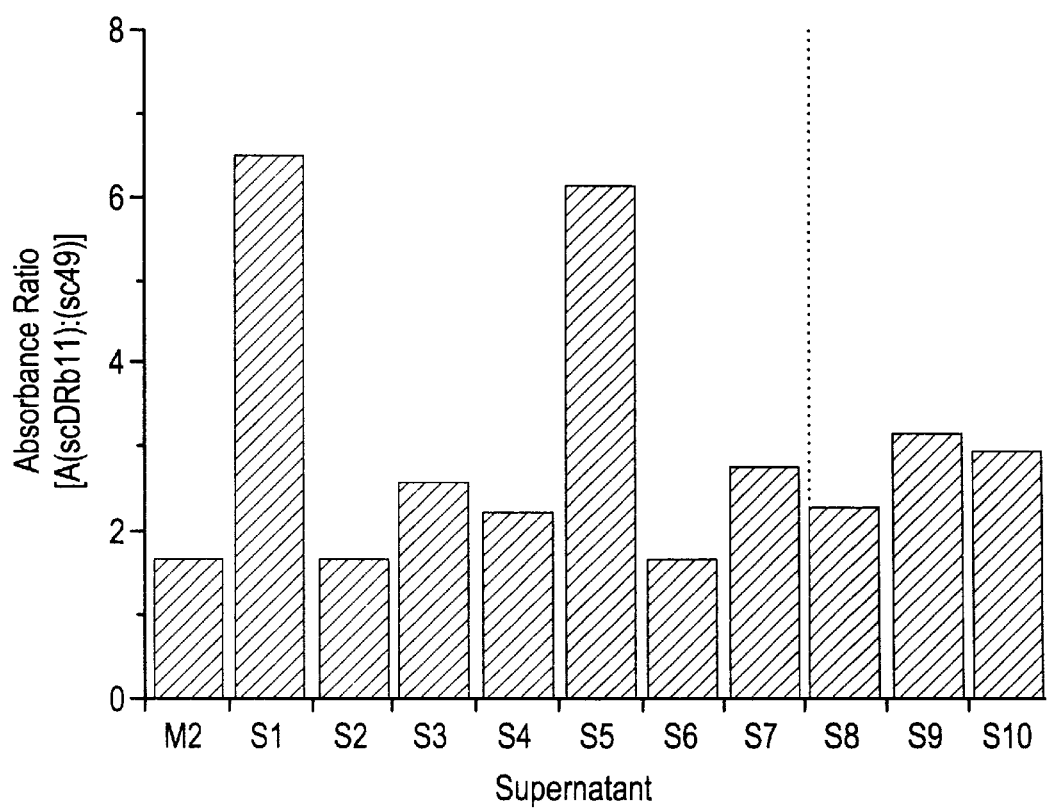
FIG. 34 illustrates the results of an ELISA showing the relative binding of 11 hybridoma supernatants to purified sdDRB11-FLAG protein.

To ascertain whether an immune response directed against HLA-DRB1*0101 might also recognize the sdDRβ11-FLAG protein, an immunoblot of the purified sdDRβ11 protein is developed using serum derived from a C3H mouse immunized with mouse L cells expressing the human HLA-DRB1*0101 protein. The immunoblot shows that the major band in this blot is the 15 kD sdDRβ11-FLAG. Thus, it appears the single domain DRβ1 proteins are stable and can be recognized by polyclonal immune serum raised against the native HLA-DRB1*0101 molecule. ELISA results (FIG. 34) shows that hybridomas generated by immunization of mice with cells expressing native HLA-DRB1*0101 can be found which are capable of binding the sdDRβ11-FLAG protein. These results suggest that the overall structure of the free sdDR11-FLAG protein is similar to that of the β1 domain of the nature molecule. This is of considerable value in the discovery of antibodies and other molecules capable of binding discrete subsets of Class II MHC proteins. It also suggests considerable utility of the free β1 domain as an immunogen as a potential therapeutic in suerantigen-dependent disorders.

Expression and Purification of Single-Chain DRβ/α-FLAG Proteins

As described for the sdDRβ11-FLAG above, scDRβ/α-FLAG proteins are also being expressed and purified from *E. coli* transformed with plasmids encoding these molecules. The scDRβ/α-FLAG proteins are similar in size to a single chain antibody (such as sc49-FLAG) and migrate at a MW of about 25 to 30 kD. The scDRβ/α-FLAG (single-chain DR) proteins can be purified by affinity chromatography in a manner similar to that described for the sdDRβ-FLAG proteins described above. Thus, a Coomassie-stained SDS-polyacrylamide gel will show that the purified protein migrates at a MW similar to that of purified sc49-FLAG. The affinity-purified protein represents the major protein component of the purified preparation. The similarity of the single-chain DR to the native HLA-DR molecule is being assessed in a number of ways. First, polyclonal immune sera raised in mice against cell surface HLA-DR is being used in immunoblotting experiments to determine whether antibodies raised against the native protein bind to the engineered single-chain molecule. Secondly, immunoblots and enzyme-linked immunosorbent assays (ELISA) are being used to assess the capacity of commercially available and public domain antibodies known to recognize HLA-DR to bind to the purified scDRβ/α-FLAG proteins. Thirdly, hybridomas derived from HLA-DR-immunized mice are being screened for the capacity to bind to the purified single-chain proteins. Functional activity of the scDRβ/α-FLAG molecules is being measured by competition-assays involving an influenza peptide (influenza hemagglutinin 307–319) known to bind a wide variety of class II MHC proteins. The data suggests that, like sdDRβ-FLAG proteins, the scDRβ/α-FLAG proteins are expressed as stable proteins in *E. coli*, that they migrate at the appropriate MW and are recognized on immunoblots by at least one publicly available antibody (L227) known to bind native HLA-DR.

Characterization of Dimers and Multimers of scDRβ/α-FLAG Proteins

The presence of dimers and multimers of single chain DRβ/α molecules (scDR(β/α)$_2$ and scDR(β/α)$_n$ respectively) is assessed using essentially the same techniques as described for single chain antibody molecules (Example 1). Briefly, the affinity purified scDRβ/α-FLAG preparation is subjected to size-exclusion (gel filtration) chromatograph on a column containing an appropriate matrix (such as Superdex 75). The presence of peaks at molecular weights corresponding to approximately 48,000, approximately 96,000 and approximately 144,000 kilodaltons indicates the presence of dimers, tetramers, hexamers as is the case with the scFv molecules. The absence of peaks at approximately 72,000, approximately 120,000 and approximately 168,000 kilodaltons indicates the lack of trimers, pentamers and heptamers, respectively.

Given the present model of multimer formation, the latter peaks are usually absent or very minor components. Isoelectric focusing (of the purified preparation or crude lysate) is also used to assess the presence of distinct charged forms of the scDRβ/α-FLAG indicating the influence of multimerization on the ionic properties of the single chain protein. Denaturing gel electrophoresis of the purified protein is used, like gel filtration, to confirm the presence of multimeric forms of scDRβ/α and to estimate the sizes of such multimeric forms.

Other embodiments of the invention will be apparent to those skilled in the art from a consideration of the specification or practice of the invention disclosed herein. It is intended that the specification and examples be considered as exemplary only, with the true scope and spirit of the invention being indicated by the following claims.

What is claimed is:

1. A protein comprising a dimer or multimer of single chain polypeptides wherein the polypeptides are non-covalently linked and each polypeptide comprises (a) a first polypeptide comprising an antigen binding portion of a variable domain of an antibody; (b) a second polypeptide comprising an antigen binding portion of a variable domain of an antibody and (c) a peptide linker linking the first and second polypeptides (a) and (b) into a single chain polypeptide having affinity for an antigen wherein the first and second polypeptide are from antibody CC49.

2. The protein of claim 1 wherein the first polypeptide is an antigen binding portion of a light chain variable region of an antibody and the second polypeptide is an antigen binding portion of a heavy chain variable region of an antibody.

3. The protein of claim 2 wherein the polypeptide is a dimer.

4. The protein of claim 1 conjugated to an imaging marker.

5. The protein of claim 4 wherein the first polypeptide is an antigen binding portion of a light chain variable region of an antibody and the second polypeptide is an antigen binding portion of a heavy chain variable region of an antibody.

6. The protein of claim 4 wherein the imaging marker is $^{125}I$, $^{131}I$, $^{111}In$, $^{105}Rh$, $^{153}Sm$ $^{67}Cu$, $^{67}Ga$, $^{166}Ho$, $^{177}Lu$, $^{186}Re$, $^{188}Re$ or $^{99m}Tc$.

7. The protein of claim 1 conjugated to a therapeutic agent.

8. The protein of claim 7 wherein the first polypeptide is an antigen binding portion of a light chain variable region of an antibody and the second polypeptide is an antigen binding portion of a heavy chain variable region of an antibody.

9. The protein of claim 7 wherein the therapeutic agent is a radionuclide, drug, or or toxin.

10. The protein of claim 9 wherein the radionuclide is $^{131}I$, $^{90}Y$, $^{105}Rh$, $^{47}Sc$, $^{67}Cu$, $^{212}Bi$, $^{211}At$, $^{67}Ga$, 125I, $^{186}Re$, $^{188}Re$, $^{177}Lu$, $^{99m}Tc$, $^{153}Sm$, 123I or 111In.

11. A composition comprising the protein of claim 1 in a pharmaceutically acceptable carrier.

12. The composition of claim 11 wherein the protein is conjugated to an imaging marker.

13. The composition of claim 11 wherein the protein is conjugated to a therapeutic agent.

14. The composition of claim 13 wherein the therapeutic agent is a radionuclide.

15. The protein of claim 1 wherein the peptide linker is encoded by a nucleotide sequence of 5'-CTTAGTGCGGACGATGCGAAAAAGGATGCTGC-GAAGAAGGATGACGCTAAGAAAGACGATGCTA-AAAAGGACCTC-3' (bases 431–450 of SEQ ID NO:14).

16. The protein of claim 15 wherein the variable domains are derived from CC49.

17. A method for producing a dimer or multimer of single chain polypeptides wherein the polypeptides are non-covalently linked and each polypeptide comprises (a) a first polypeplide comprising an antigen binding portion of a variable domain of an antibody; (b) a second polypeptide comprising an antigen binding portion of a variable domain of an antibody and (c) a peptide linker linking the first and second polypeptides (a) and (b) into a single chain polypeptide wherein the first and second polypeptide are from antibody CC49, the method comprising:

(i) providing a genetic sequence coding for a single chain polypeptide;

(ii) transforming a host cell with the genetic sequence;

(iii) expressing the genetic sequence in the host cell; and (iv) recovery of single chain polypeptides which have non-covalently linked to form dimers and multimers.

18. The method of claim 17 wherein genetic sequence coding for a single chain polypeptide contains a sequence encoding for a signal peptide which will direct secretion of the single chain polypeptide out of the cytoplasm of the host cell.

* * * * *

SEQUENCE LISTING

```
<160> NUMBER OF SEQ ID NOS:  102

<210> SEQ ID NO 1
<211> LENGTH: 836
<212> TYPE: DNA
<213> ORGANISM: Artificial Sequence
<220> FEATURE:
<221> NAME/KEY: SCFV1 from pCGS515
<222> LOCATION: 1..836
<223> OTHER INFORMATION: :

<400> SEQUENCE: 1
aaaaactata agctccatga tgcttttgca agctttcctt ttccttttgg ctggttttgc        60
agccaaaata tctgcagaca tcgtgatgac ccagtctcca gactccctgg ctgtgtctct       120
gggcgagagg gccaccatca actgcaagtc cagctgcaag gttttataca gctccaacaa       180
taagaactac ttagcttggt accagcagaa accaggacag cctcctaagc tgctcattta       240
ctgggcatct acccgggaat ccggggtccc tgaccgattc agtggcagcg ggtctgggac       300
agatttcact ctcaccatca gcagcctgca ggctgaagat gtggcagttt attactgtca       360
gcaatattat agttatcctc tcactttcgg cggagggacc aaggtgaagg agtcaggttc       420
ggtctcctca gaacaattgg cccaatttcg ttccttagac gtccagttgc agcagtctga       480
cgctgagttg gtgaaacctg gggcttcagt gaagatttcc tgcaaggctt ctggctacac       540
cttcactgac catgcaattc actgggtgaa acagaaccct gaacagggcc tggaatggat       600
tggatatttt tctcccggaa atgatgattt taaatacaat gagaggttca agggcaaggc       660
cacactgact gcagacaaat cctccagcac tgcctacgtg cagctcaaca gcctgacatc       720
```

```
tgaggattct gcagtgtatt tctgtacaag atccctgaat atggcctact ggggtcaagg    780
aacctcagtc accgtctcct agtgaagctt ggaacaccac acaaaccata tccaaa        836
```

```
<210> SEQ ID NO 2
<211> LENGTH: 260
<212> TYPE: PRT
<213> ORGANISM: Artificial Sequence
<220> FEATURE:
<221> NAME/KEY: SCFV1 from pCGS515
<222> LOCATION: 1..260
<223> OTHER INFORMATION: :

<400> SEQUENCE: 2
```

```
Met Leu Leu Gln Ala Phe Leu Phe Leu Leu Ala Gly Phe Ala Ala Lys
1               5                   10                  15

Ile Ser Ala Asp Ile Val Met Thr Gln Ser Pro Asp Ser Leu Ala Val
            20                  25                  30

Ser Leu Gly Glu Arg Ala Thr Ile Asn Cys Lys Ser Gln Ser Val
        35                  40                  45

Leu Tyr Ser Ser Asn Asn Lys Asn Tyr Leu Ala Trp Tyr Gln Gln Lys
    50                  55                  60

Pro Gly Gln Pro Pro Lys Leu Leu Ile Tyr Trp Ala Ser Thr Arg Glu
65                  70                  75                  80

Ser Gly Val Pro Asp Arg Phe Ser Gly Ser Gly Ser Gly Thr Asp Phe
                85                  90                  95

Thr Leu Thr Ile Ser Ser Leu Gln Ala Glu Asp Val Ala Val Tyr Tyr
                100                 105                 110

Cys Gln Gln Tyr Tyr Ser Tyr Pro Leu Thr Phe Gly Gly Gly Thr Lys
            115                 120                 125

Val Lys Glu Ser Gly Ser Val Ser Ser Glu Gln Leu Ala Gln Phe Arg
    130                 135                 140

Ser Leu Asp Val Gln Leu Gln Gln Ser Asp Ala Glu Leu Val Lys Pro
145                 150                 155                 160

Gly Ala Ser Val Lys Ile Ser Cys Lys Ala Ser Gly Tyr Thr Phe Thr
                165                 170                 175

Asp His Ala Ile His Trp Val Lys Gln Asn Pro Glu Gln Gly Leu Glu
                180                 185                 190

Trp Ile Gly Tyr Phe Ser Pro Gly Asn Asp Asp Phe Lys Tyr Asn Glu
            195                 200                 205

Arg Phe Lys Gly Lys Ala Thr Leu Thr Ala Asp Lys Ser Ser Ser Thr
    210                 215                 220

Ala Tyr Val Gln Leu Asn Ser Leu Thr Ser Glu Asp Ser Ala Val Tyr
225                 230                 235                 240

Phe Cys Thr Arg Ser Leu Asn Met Ala Tyr Trp Gly Gln Gly Thr Ser
                245                 250                 255

Val Thr Val Ser
            260
```

```
<210> SEQ ID NO 3
<211> LENGTH: 1088
<212> TYPE: DNA
<213> ORGANISM: Homo sapiens
<220> FEATURE:
<221> NAME/KEY: Human kappa subgroup IV VL (Hum4 VL) from pRL1001
<222> LOCATION: 1..1088
```

-continued

```
<400> SEQUENCE: 3
atcgataaaa tttattgaga atttgtttat tatgattaac agaggtaaaa gccagtatat    60
tactgattaa tataggtaaa aggcagttaa gaaattggga atgctttctc ttctgctttc   120
ttctacgatg cacaaggcgt ttcacattta tgccctatg aaaattacta ggctgtccta   180
gtcattagat ctttcagcag tttgtagttt tagagcttct aagttgactt ctgtcttttc   240
tattcataca attacacatt ctgtgatgat attttggct cttgatttac attgggtact   300
ttcacaaccc actgctcatg aaatttgctt ttgtactact ggttgttttt gcataggccc   360
ctccaggcca cgaccaggtg tttggatttt ataaacgggc cgtttgcatt gtgaactgag   420
ctacaacagg caggcagggg cagcaagatg gtgttgcaga cccaggtctt catttctctg   480
ttgctctgga tctctggtga ggaattaaaa agtgccacag tcttttcaga gtaatatctg   540
tgtagaaata aaaaaaatta agatatagtt ggaaataatg actatttcca atatggatcc   600
aattatctgc tgacttataa tactactaga agcaaattt aaatgacata tttcaattat   660
atctgagaca gcgtgtataa gtttatgtat aatcattgtc cattactgac tacaggtgcc   720
tacggggaca ctgtgatgac ccagtctcca gactccctgg ctgtgtctct gggcgagagg   780
gccaccatca actgcaagtc cagccagagt gtttttataca gctccaacaa taagaactac   840
ttagcttggt accagcagaa accaggacag cctcctaagc tgctcattta ctgggcatct   900
acccgggaat ccggggtgccc tgaccgattc agtggcagcg gtctgggac agatttcact   960
ctcaccatca gcagcctgca ggctgaagat gtggcagttt attactgtca gcaatattat  1020
agttatcctc tcactttcgg cggagggacc aaggtggtga tcaaacgtaa gtacactttt  1080
ctaagctt                                                           1088

<210> SEQ ID NO 4
<211> LENGTH: 133
<212> TYPE: PRT
<213> ORGANISM: Homo sapiens
<220> FEATURE:
<221> NAME/KEY: Human kappa subgroup IV VL (Hum4 VL) from pRL1001
<222> LOCATION: 1..133

<400> SEQUENCE: 4

Met Val Leu Gln Thr Gln Val Leu Ile Ser Leu Leu Trp Ile Ser
1               5                   10                  15

Gly Ala Tyr Gly Asp Ile Val Met Thr Gln Ser Pro Asp Ser Leu Ala
            20                  25                  30

Val Ser Leu Gly Glu Arg Ala Thr Ile Asn Cys Lys Ser Ser Gln Ser
        35                  40                  45

Val Leu Tyr Ser Ser Asn Asn Lys Asn Tyr Leu Ala Trp Tyr Gln Gln
    50                  55                  60

Lys Pro Gly Gln Pro Pro Lys Leu Leu Ile Tyr Trp Ala Ser Thr Arg
65                  70                  75                  80

Glu Ser Gly Val Pro Asp Arg Phe Ser Gly Ser Gly Ser Gly Thr Asp
                85                  90                  95

Phe Thr Leu Thr Ile Ser Ser Leu Gln Ala Glu Asp Val Ala Val Tyr
            100                 105                 110

Tyr Cys Gln Gln Tyr Tyr Ser Tyr Pro Leu Thr Phe Gly Gly Gly Thr
        115                 120                 125

Lys Val Val Ile Lys
    130
```

<210> SEQ ID NO 5
<211> LENGTH: 1330
<212> TYPE: DNA
<213> ORGANISM: Artificial Sequence
<220> FEATURE:
<221> NAME/KEY: Hum4VL-VH scFv from pSCFV UHH
<222> LOCATION: 1..1330
<223> OTHER INFORMATION: :

<400> SEQUENCE: 5

```
ctcatgtttg acagcttatc atcgatgaat tccatcactt ccctccgttc atttgtcccc      60
ggtggaaacg aggtcatcat ttccttccga aaaacggtt gcatttaaat cttacatata     120
taatactttc aaagactaca tttgtaagat ttgatgtttg agtcggctga agatcgtac     180
gtaccaatta ttgtttcgtg attgttcaag ccataacact gtaggatag tggaaagagt     240
gcttcatctg gttacgatca atcaaatatt caaacggagg gagacgattt tgatgaaata     300
cctattgcct acggcagccg ctggattgtt attactcgct gcccaaccag ccatggccga     360
catcgtgatg acccagtctc cagactccct ggctgtgtct ctgggcgaga gggccaccat     420
caactgcaag tccagccaga gtgttttata cagctccaac aataagaact acttagcttg     480
gtaccagcag aaaccaggac agcctcctaa gctgctcatt tactgggcat ctacccggga     540
atccggggtc cctgaccgat tcagtggcag cgggtctggg acagatttca ctctcaccat     600
cagcagcctg caggctgaag atgtggcagt ttattactgt cagcaatatt atagttatcc     660
tctcactttc ggcggaggga ccaaggtggt gatcaagctt agtgcggacg atgcgaaaaa     720
ggatgctgcg aagaaggatg acgctaagaa agacgatgct aaaaaggacc tcgaggttca     780
gttgcagcag tctgacgctg agttggtgaa acctggggct tcagtgaaga tttcctgcaa     840
ggcttctggc tacaccttca ctgaccatgc aattcactgg gtgaaacaga ccctgaaca     900
gggcctggaa tggattggat attttctcc cggaaatgat gattttaaat acaatgagag     960
gttcaaggc aaggccacac tgactgcaga caaatcctcc agcactgcct acgtgcagct    1020
caacagcctg acatctgagg attctgcagt gtatttctgt acaagatccc tgaatatggc    1080
ctactggggt caaggaacct cagtcaccgt ctcctcataa aaagctagcg atgaatccgt    1140
caaaacatca tcttacataa agtcacttgg tgatcaagct catatcattg tccggcaatg    1200
gtgtgggctt tttttgtttt ctatcttaaa gatcatgtga agaaaaacgg gaaaatcggt    1260
ctgcgggaaa ggaccgggtt tttgtcgaaa tcataggcga atgggttgga ttgtgacaaa    1320
attcggatcc                                                          1330
```

<210> SEQ ID NO 6
<211> LENGTH: 275
<212> TYPE: PRT
<213> ORGANISM: Artificial Sequence
<220> FEATURE:
<221> NAME/KEY: Hum4VL-VH scFv from pSCFV UHH
<222> LOCATION: 1..275
<223> OTHER INFORMATION: :

<400> SEQUENCE: 6

Met Lys Tyr Leu Leu Pro Thr Ala Ala Ala Gly Leu Leu Leu Leu Ala
1               5                   10                  15

Ala Gln Pro Ala Met Ala Asp Ile Val Met Thr Gln Ser Pro Asp Ser
            20                  25                  30

Leu Ala Val Ser Leu Gly Glu Arg Ala Thr Ile Asn Cys Lys Ser Ser
        35                  40                  45

```
Gln Ser Val Leu Tyr Ser Ser Asn Asn Lys Asn Tyr Leu Ala Trp Tyr
    50                  55                  60
Gln Gln Lys Pro Gly Gln Pro Pro Lys Leu Leu Ile Tyr Trp Ala Ser
 65              70                  75                  80
Thr Arg Glu Ser Gly Val Pro Asp Arg Phe Ser Gly Ser Gly Ser Gly
                85                  90                  95
Thr Asp Phe Thr Leu Thr Ile Ser Ser Leu Gln Ala Glu Asp Val Ala
            100                 105                 110
Val Tyr Tyr Cys Gln Gln Tyr Tyr Ser Tyr Pro Leu Thr Phe Gly Gly
            115                 120                 125
Gly Thr Lys Val Val Ile Lys Leu Ser Ala Asp Asp Ala Lys Lys Asp
        130                 135                 140
Ala Ala Lys Lys Asp Asp Ala Lys Lys Asp Asp Ala Lys Lys Asp Leu
145                 150                 155                 160
Glu Val Gln Leu Gln Gln Ser Asp Ala Glu Leu Val Lys Pro Gly Ala
                165                 170                 175
Ser Val Lys Ile Ser Cys Lys Ala Ser Gly Tyr Thr Phe Thr Asp His
            180                 185                 190
Ala Ile His Trp Val Lys Gln Asn Pro Glu Gln Gly Leu Glu Trp Ile
        195                 200                 205
Gly Tyr Phe Ser Pro Gly Asn Asp Asp Phe Lys Tyr Asn Glu Arg Phe
    210                 215                 220
Lys Gly Lys Ala Thr Leu Thr Ala Asp Lys Ser Ser Ser Thr Ala Tyr
225                 230                 235                 240
Val Gln Leu Asn Ser Leu Thr Ser Glu Asp Ser Ala Val Tyr Phe Cys
                245                 250                 255
Thr Arg Ser Leu Asn Met Ala Tyr Trp Gly Gln Gly Thr Ser Val Thr
            260                 265                 270
Val Ser Ser
        275

<210> SEQ ID NO 7
<211> LENGTH: 1331
<212> TYPE: DNA
<213> ORGANISM: Artificial Sequence
<220> FEATURE:
<221> NAME/KEY: SCFV UHM8.1
<222> LOCATION: 1..1331
<223> OTHER INFORMATION: :

<400> SEQUENCE: 7
ctcatgtttg acagcttatc atcgatgaat tccatcactt ccctccgttc atttgtcccc      60
ggtggaaacg aggtcatcat ttccttccga aaaacggttg catttaaat cttacatata     120 taatactttc aaagactaca tttgtaagat ttgatgtttg agtcggctga aagatcgtac    180
gtaccaatta ttgtttcgtg attgttcaag ccataccact gtagggatag tggaaagagt    240
gcttcatctg gttacgatca atcaaatatt caaacggagg gagacgattt tgatgaaata    300
cctattgcct acggcagccg ctggattgtt attactcgct gcccaaccag ccatggccga    360
cattgtgatg tcacagtctc catcctccct acctgtgtca gttggcgaga gggttacttt    420
gagctgcaag tccagtcaga gccttttata gtggtaat caaagaact acttggcctg      480 gtaccagcag aaaccagggc agtctcctaa actgctgatt tactgggcat ccgctaggga    540
atctggggtc cctgatcgct tcacaggcag tggatctggg acagtttca ctctctccat     600 cagcagtgtg aagactgaag acctggcagt ttattactgt cagcagtatt atagctatcc    660
```

-continued

```
cctcacgttc ggtgctggga ccaagctggt gctgaagctt agtgcggacg atgcgaaaaa    720
ggatgctgcg aagaaggatg acgctaagaa agacgatgct aaaaaggacc tcgaggttca    780
gttgcagcag tctgacgctg agttggtgaa acctgggggt tcagtgaaga tttcctgcaa    840
ggcttctggc tacaccttca ctgaccatgc aattcactgg gtgaaacaga accctgaaca    900
gggcctggaa tggattggat attttctcc cggaaatgat gattttaaat acaatgagag    960 gttcaaggc aaggccacac tgactgcaga caaatcctcc agcactgcct acgtgcagct    1020
caacagcctg acatctgagg attctgcagt gtatttctgt acaagatccc tgaatatggc    1080
ctactggggt caaggaacct cagtcaccgt ctcctcataa aaagctagcg atgaatccgt    1140
caaaacatca tcttacataa agtcacttgg tgatcaagct catatcattg tccggcaatg    1200
gtgtgggctt ttttgtttt ctatctttaa agatcatgtg aagaaaaacg ggaaaatcgg    1260
tctgcgggaa aggaccgggt ttttgtcgaa atcataggcg aatgggttgg attgtgacaa    1320
aattcggatc c                                                        1331
```

<210> SEQ ID NO 8
<211> LENGTH: 275
<212> TYPE: PRT
<213> ORGANISM: Artificial Sequence
<220> FEATURE:
<221> NAME/KEY: SCFV UHM8.1
<222> LOCATION: 1..275
<223> OTHER INFORMATION: :

<400> SEQUENCE: 8

```
Met Lys Tyr Leu Leu Pro Thr Ala Ala Ala Gly Leu Leu Leu Leu Ala
1               5                   10                  15

Ala Gln Pro Ala Met Ala Asp Ile Val Met Ser Gln Ser Pro Ser Ser
            20                  25                  30

Leu Pro Val Ser Val Gly Glu Lys Val Thr Leu Ser Cys Lys Ser Ser
        35                  40                  45

Gln Ser Leu Leu Tyr Ser Gly Asn Gln Lys Asn Tyr Leu Ala Trp Tyr
    50                  55                  60

Gln Gln Lys Pro Gly Gln Ser Pro Lys Leu Leu Ile Tyr Trp Ala Ser
65                  70                  75                  80

Ala Arg Glu Ser Gly Val Pro Asp Arg Phe Thr Gly Ser Gly Ser Gly
                85                  90                  95

Thr Asp Phe Thr Leu Ser Ile Ser Ser Val Lys Thr Glu Asp Leu Ala
            100                 105                 110

Val Tyr Tyr Cys Gln Gln Tyr Tyr Ser Tyr Pro Leu Thr Phe Gly Ala
        115                 120                 125

Gly Thr Lys Leu Val Leu Lys Leu Ser Ala Asp Asp Ala Lys Lys Asp
    130                 135                 140

Ala Ala Lys Lys Asp Asp Ala Lys Lys Asp Asp Ala Lys Lys Asp Leu
145                 150                 155                 160

Glu Val Gln Leu Gln Gln Ser Asp Ala Glu Leu Val Lys Pro Gly Ala
                165                 170                 175

Ser Val Lys Ile Ser Cys Lys Ala Ser Gly Tyr Thr Phe Thr Asp His
            180                 185                 190

Ala Ile His Trp Val Lys Gln Asn Pro Glu Gln Gly Leu Glu Trp Ile
        195                 200                 205

Gly Tyr Phe Ser Pro Gly Asn Asp Asp Phe Lys Tyr Asn Glu Arg Phe
    210                 215                 220
```

Lys Gly Lys Ala Thr Leu Thr Ala Asp Lys Ser Ser Thr Ala Tyr
225                 230                 235                 240

Val Gln Leu Asn Ser Leu Thr Ser Glu Asp Ser Ala Val Tyr Phe Cys
            245                 250                 255

Thr Arg Ser Leu Asn Met Ala Tyr Trp Gly Gln Gly Thr Ser Val Thr
                260                 265                 270

Val Ser Ser
        275

<210> SEQ ID NO 9
<211> LENGTH: 1346
<212> TYPE: DNA
<213> ORGANISM: Artificial Sequence
<220> FEATURE:
<221> NAME/KEY: SCFV UHM5.8
<222> LOCATION: 1..1346
<223> OTHER INFORMATION: :

<400> SEQUENCE: 9
ctcatgtttg acagcttatc atcgatgaat tccatcactt ccctccgttc atttgtcccc      60
ggtggaaacg aggtcatcat ttccttccga aaaaacggtt gcatttaaat cttacatata     120
taatactttc aaagactaca tttgtaagat ttgatgtttg agtcggctga agatcgtac      180 gtaccaatta ttgtttcgtg attgttcaag ccataccact gtagggatag tggaaagagt     240
gcttcatctg gttacgatca atcaaatatt caaacggagg gagacgattt tgatgaaata     300
cctattgcct acggcagccg ctggattgtt attactcgct gcccaaccag ccatggccga     360
cattgtgatg tcacagtctc catcctccct acctgtgtca gttggcgaga gggttacttt     420
gagctgcaag tccagtcaga gccttttata tagtggtaat caaaagaact acttggcctg     480
gtaccagcag aaaccagggc agtctcctaa actgctgatt tactgggcat ccgctaggga     540
atctggggtc cctgatcgct tcacaggcag tggatctggg acagatttca ctctctccat     600
cagcagtgtg aagactgaag acctggcagt ttattactgt cagcagtatt atagctatcc     660
cctcacgttc ggtgctggga ccaagctggt gctgaagctt agtgcggacg atgcgaaaaa     720
ggatgctgcg aagaaggatg acgctaagaa agacgatgct aaaaaggacc tcgaggttca     780
gttgcagcag tctgacgctg agttggtgaa acctggggct tcagtgaaga tttcctgcaa     840
ggcttctggc tacaccttca ctgaccatgc aattcactgg gtgaaacaga ccctgaaca      900 gggcctggaa tggattggat attttctcc cggaaatgat gatttaat acaatgagag        960 gttcaaggc aaggccacac tgactgcaga caaatcctcc agcactgcct acgtgcagct     1020
caacagcctg acatctgagg attctgcagt gtatttctgt acaagatccc tgaatatggc    1080
ctactggggt caaggaacct cagtcaccgt ctcccctgag gactatgact cctaaaaagc    1140
tagcgatgaa tccgtcaaaa catcatctta cataaagtca cttggtgatc aagctcatat    1200
cattgtccgg caatggtgtg ggctttttt gttttctatc tttaaagatc atgtgaagaa     1260
aaacgggaaa atcggtctgc gggaaaggac cgggtttttg tcgaaatcat aggcgaatgg    1320
gttggattgt gacaaaattc ggatcc                                         1346

<210> SEQ ID NO 10
<211> LENGTH: 280
<212> TYPE: PRT
<213> ORGANISM: Artificial Sequence
<220> FEATURE:
<221> NAME/KEY: SCFV UHM5.8
<222> LOCATION: 1..280
<223> OTHER INFORMATION: :

-continued

```
<400> SEQUENCE: 10

Met Lys Tyr Leu Leu Pro Thr Ala Ala Gly Leu Leu Leu Ala
1               5                   10                  15

Ala Gln Pro Ala Met Ala Asp Ile Val Met Ser Gln Ser Pro Ser Ser
            20                  25                  30

Leu Pro Val Ser Val Gly Glu Lys Val Thr Leu Ser Cys Lys Ser Ser
        35                  40                  45

Gln Ser Leu Leu Tyr Ser Gly Asn Gln Lys Asn Tyr Leu Ala Trp Tyr
    50                  55                  60

Gln Gln Lys Pro Gly Gln Ser Pro Lys Leu Leu Ile Tyr Trp Ala Ser
65                  70                  75                  80

Ala Arg Glu Ser Gly Val Pro Asp Arg Phe Thr Gly Ser Gly Ser Gly
                85                  90                  95

Thr Asp Phe Thr Leu Ser Ile Ser Ser Val Lys Thr Glu Asp Leu Ala
            100                 105                 110

Val Tyr Tyr Cys Gln Gln Tyr Tyr Ser Tyr Pro Leu Thr Phe Gly Ala
        115                 120                 125

Gly Thr Lys Leu Val Leu Lys Leu Ser Ala Asp Ala Lys Lys Asp
    130                 135                 140

Ala Ala Lys Lys Asp Asp Ala Lys Lys Asp Asp Ala Lys Lys Asp Leu
145                 150                 155                 160

Glu Val Gln Leu Gln Gln Ser Asp Ala Glu Leu Val Lys Pro Gly Ala
                165                 170                 175

Ser Val Lys Ile Ser Cys Lys Ala Ser Gly Tyr Thr Phe Thr Asp His
            180                 185                 190

Ala Ile His Trp Val Lys Gln Asn Pro Glu Gln Gly Leu Glu Trp Ile
        195                 200                 205

Gly Tyr Phe Ser Pro Gly Asn Asp Asp Phe Lys Tyr Asn Glu Arg Phe
    210                 215                 220

Lys Gly Lys Ala Thr Leu Thr Ala Asp Lys Ser Ser Ser Thr Ala Tyr
225                 230                 235                 240

Val Gln Leu Asn Ser Leu Thr Ser Glu Asp Ser Ala Val Tyr Phe Cys
                245                 250                 255

Thr Arg Ser Leu Asn Met Ala Tyr Trp Gly Gln Gly Thr Ser Val Thr
            260                 265                 270

Val Ser Pro Glu Asp Tyr Asp Ser
        275                 280

<210> SEQ ID NO 11
<211> LENGTH: 1352
<212> TYPE: DNA
<213> ORGANISM: Artificial Sequence
<220> FEATURE:
<221> NAME/KEY: SCFV UHM5.2
<222> LOCATION: 1..1352
<223> OTHER INFORMATION: :

<400> SEQUENCE: 11
ctcatgtttg acagcttatc atcgatgaat tccatcactt ccctccgttc atttgtcccc      60
ggtggaaacg aggtcatcat ttccttccga aaaacggtt gcatttaaat cttacatata      120
taatactttc aaagactaca tttgtaagat ttgatgtttg agtcggctga agatcgtac      180 gtaccaatta tgtttcgtg attgttcaag ccataccact gtagggatag tggaaagagt      240
gcttcatctg gttacgatca atcaaatatt caaacggagg gagacgattt tgatgaaata      300
cctattgcct acggcagccg ctggattgtt attactcgct gcccaaccag ccatggccga      360
```

-continued

```
cattgtgatg tcacagtctc catcctccct acctgtgtca gttggcgaga gggttacttt    420
gagctgcaag tccagtcaga gccttttata tagtggtaat caaaagaact acttggcctg    480
gtaccagcag aaaccagggc agtctcctaa actgctgatt tactgggcat ccgctaggga    540
atctggggtc cctgatcgct tcacaggcag tggatctggg acagatttca ctctctccat    600
cagcagtgtg aagactgaag acctggcagt ttattactgt cagcagtatt atagctatcc    660
cctcacgttc ggtgctggga ccaagctggt gctgaagctt agtgcggacg atgcgaaaaa    720
ggatgctgcg aagaaggatg acgctaagaa agacgatgct aaaaaggacc tcgaggttca    780
gttgcagcag tctgacgctg agttggtgaa acctggggct tcagtgaaga tttcctgcaa    840
ggcttctggc tacaccttca ctgaccatgc aattcactgg gtgaaacaga ccctgaaca    900 gggcctggaa tggattggat attttttctcc cggaaatgat gatttaaat acaatgagag    960 gttcaagggc aaggccacac tgactgcaga caaatcctcc agcactgcct acgtgcagct    1020
caacagcctg acatctgagg attctgcagt gtatttctgt acaagatccc tgaatatggc    1080
ctactggggt caaggaacct cagtcaccgt ctcccctgaa gaccctgaag actatgacta    1140
aaaagctagc gatgaatccg tcaaaacatc atcttacata aagtcacttg gtgatcaagc    1200
tcatatcatt gtccggcaat ggtgtgggct tttttgttt tctatctta aagatcatgt    1260 gaagaaaaac gggaaaatcg gtctgcggga aaggaccggg ttttttgtcga aatcataggc    1320 gaatggttg gattgtgaca aaattcggat cc                                   1352
```

<210> SEQ ID NO 12
<211> LENGTH: 282
<212> TYPE: PRT
<213> ORGANISM: Artificial Sequence
<220> FEATURE:
<221> NAME/KEY: SCFV UHM5.2
<222> LOCATION: 1..282
<223> OTHER INFORMATION: :

<400> SEQUENCE: 12

```
Met Lys Tyr Leu Leu Pro Thr Ala Ala Gly Leu Leu Leu Leu Ala
 1               5                  10                  15

Ala Gln Pro Ala Met Ala Asp Ile Val Met Ser Gln Ser Pro Ser Ser
                20                  25                  30

Leu Pro Val Ser Val Gly Glu Lys Val Thr Leu Ser Cys Lys Ser Ser
        35                  40                  45

Gln Ser Leu Leu Tyr Ser Gly Asn Gln Lys Asn Tyr Leu Ala Trp Tyr
    50                  55                  60

Gln Gln Lys Pro Gly Gln Ser Pro Lys Leu Leu Ile Tyr Trp Ala Ser
65                  70                  75                  80

Ala Arg Glu Ser Gly Val Pro Asp Arg Phe Thr Gly Ser Gly Ser Gly
                85                  90                  95

Thr Asp Phe Thr Leu Ser Ile Ser Ser Val Lys Thr Glu Asp Leu Ala
            100                 105                 110

Val Tyr Tyr Cys Gln Gln Tyr Tyr Ser Tyr Pro Leu Thr Phe Gly Ala
        115                 120                 125

Gly Thr Lys Leu Val Leu Lys Leu Ser Ala Asp Asp Ala Lys Lys Asp
    130                 135                 140

Ala Ala Lys Lys Asp Asp Ala Lys Lys Asp Ala Lys Lys Asp Leu
145                 150                 155                 160

Glu Val Gln Leu Gln Gln Ser Asp Ala Glu Leu Val Lys Pro Gly Ala
                165                 170                 175
```

```
Ser Val Lys Ile Ser Cys Lys Ala Ser Gly Tyr Thr Phe Thr Asp His
                180                 185                 190

Ala Ile His Trp Val Lys Gln Asn Pro Glu Gln Gly Leu Glu Trp Ile
            195                 200                 205

Gly Tyr Phe Ser Pro Gly Asn Asp Asp Phe Lys Tyr Asn Glu Arg Phe
            210                 215                 220

Lys Gly Lys Ala Thr Leu Thr Ala Asp Lys Ser Ser Ser Thr Ala Tyr
225                 230                 235                 240

Val Gln Leu Asn Ser Leu Thr Ser Glu Asp Ser Ala Val Tyr Phe Cys
                245                 250                 255

Thr Arg Ser Leu Asn Met Ala Tyr Trp Gly Gln Gly Thr Ser Val Thr
                260                 265                 270

Val Ser Pro Glu Asp Pro Glu Asp Tyr Asp
                275                 280
```

<210> SEQ ID NO 13
<211> LENGTH: 23
<212> TYPE: DNA
<213> ORGANISM: Artificial Sequence
<220> FEATURE:
<221> NAME/KEY: AOX1 Promoter
<222> LOCATION: 1..23
<223> OTHER INFORMATION: :

<400> SEQUENCE: 13

```
tttaacgaca acttgagaag atc                                             23
```

<210> SEQ ID NO 14
<211> LENGTH: 877
<212> TYPE: DNA
<213> ORGANISM: Artificial Sequence
<220> FEATURE:
<221> NAME/KEY: CC49 scFv from pPY21
<222> LOCATION: 1..877
<223> OTHER INFORMATION: :

<400> SEQUENCE: 14

```
aaaaaacaac taattattcg aaacgatgaa atacatgctt ttgcaagctt tccctttcct     60
tttggctggt tttgcagcta agatatctgc tgacattgtg atgtcacagt ctccatcctc    120
cctacctgtg tcagttggcg agaaggttac tttgagctgc aagtccagtc agagcctttt    180
atatagtggt aatcaaaaga actacttggc ctggtaccag cagaaaccag ggcagtctcc    240
taaactgctg atttactggg catccgctag ggaatctggg gtccctgatc gcttcacagg    300
cagtggatct gggacagatt tcactctctc catcagcagt gtgaagactg aagacctggc    360
agtttattac tgtcagcagt attatagcta tccccctcac gttcggtgct ggaccaagct    420
ggtgctgaag cttagtgcgg acgatgcgaa aaaggatgct gcgaagaagg atgacgctaa    480
gaaagacgat gctaaaaagg acctcgaggt tcagttgcag cagtctgacg ctgagttggt    540
gaaacctggg gcttcagtga agatttcctg caaggcttct ggctacacct tcactgacca    600
tgcaattcac tgggtgaaac agaaccctga cagggcctg aatggattg atatttttc      660 tcccggaaat gatgatttta aatacaatga gaggttcaag gggaaggcca cactgactgc    720
agacaaatcc tccagcactg cctacgtgca gctcaacagc ctgacatccg aggattctgc    780
agtgtatttc tgtacaagat ccctgaatat ggcctactgg ggtcaaggaa cctcagtcac    840
cgtctcccct gaagaccctg aagactatga ctaatag                              877
```

```
<210> SEQ ID NO 15
<211> LENGTH: 282
<212> TYPE: PRT
<213> ORGANISM: Artificial Sequence
<220> FEATURE:
<221> NAME/KEY: CC49 scFv from pPY21
<222> LOCATION: 1..282
<223> OTHER INFORMATION: :

<400> SEQUENCE: 15

Met Lys Tyr Met Leu Leu Gln Ala Phe Leu Phe Leu Leu Ala Gly Phe
1               5                   10                  15

Ala Ala Lys Ile Ser Ala Asp Ile Val Met Ser Gln Ser Pro Ser Ser
            20                  25                  30

Leu Pro Val Ser Val Gly Glu Lys Val Thr Leu Ser Cys Lys Ser Ser
        35                  40                  45

Gln Ser Leu Leu Tyr Ser Gly Asn Gln Lys Asn Tyr Leu Ala Trp Tyr
    50                  55                  60

Gln Gln Lys Pro Gly Gln Ser Pro Lys Leu Leu Ile Tyr Trp Ala Ser
65                  70                  75                  80

Ala Arg Glu Ser Gly Val Pro Asp Arg Phe Thr Gly Ser Gly Ser Gly
                85                  90                  95

Thr Asp Phe Thr Leu Ser Ile Ser Ser Val Lys Thr Glu Asp Leu Ala
            100                 105                 110

Val Tyr Tyr Cys Gln Gln Tyr Tyr Ser Tyr Pro Leu Thr Phe Gly Ala
        115                 120                 125

Gly Thr Lys Leu Val Leu Lys Leu Ser Ala Asp Asp Ala Lys Lys Asp
    130                 135                 140

Ala Ala Lys Lys Asp Asp Ala Lys Lys Asp Asp Ala Lys Lys Asp Leu
145                 150                 155                 160

Glu Val Gln Leu Gln Gln Ser Asp Ala Glu Leu Val Lys Pro Gly Ala
                165                 170                 175

Ser Val Lys Ile Ser Cys Lys Ala Ser Gly Tyr Thr Phe Thr Asp His
            180                 185                 190

Ala Ile His Trp Val Lys Gln Asn Pro Glu Gln Gly Leu Glu Trp Ile
        195                 200                 205

Gly Tyr Phe Ser Pro Gly Asn Asp Asp Phe Lys Tyr Asn Glu Arg Phe
    210                 215                 220

Lys Gly Lys Ala Thr Leu Thr Ala Asp Lys Ser Ser Ser Thr Ala Tyr
225                 230                 235                 240

Val Gln Leu Asn Ser Leu Thr Ser Glu Asp Ser Ala Val Tyr Phe Cys
                245                 250                 255

Thr Arg Ser Leu Asn Met Ala Tyr Trp Gly Gln Gly Thr Ser Val Thr
            260                 265                 270

Val Ser Pro Glu Asp Pro Glu Asp Tyr Asp
        275                 280

<210> SEQ ID NO 16
<211> LENGTH: 856
<212> TYPE: DNA
<213> ORGANISM: Artificial Sequence
<220> FEATURE:
<221> NAME/KEY: CC49 scFv from pPY22
<222> LOCATION: 1..856
<223> OTHER INFORMATION: :
```

<400> SEQUENCE: 16

```
aaaaaacaac taattattcg aaacgatgaa atacatgctt ttgcaagctt tcccttccct      60
tttggctggt tttgcagcta agatatctgc tgacattgtg atgtcacagt ctccatcctc     120
cctacctgtg tcagttggcg agaaggttac tttgagctgc aagtccagtc agagcctttt    180
atatagtggt aatcaaaaga actacttggc ctggtaccag cagaaaccag ggcagtctcc    240
taaactgctg atttactggg catccgctag ggaatctggg gtccctgatc gcttcacagg    300
cagtggatct gggacagatt tcactctctc catcagcagt gtgaagactg aagacctggc    360
agtttattac tgtcagcagt attatagcta tcccctcacg ttcggtgctg ggaccaagct    420
ggtgctgaag cttagtgcgg acgatgcgaa aaaggatgct gcgaagaagg atgacgctaa    480
gaaagacgat gctaaaaagg acctcgaggt tcagttgcag cagtctgacg ctgagttggt    540
gaaacctggg gcttcagtga agatttcctg caaggcttct ggctacacct tcactgacca    600
tgcaattcac tgggtgaaac agaaccctga acagggcctg gaatggattg gatattttc    660
tcccggaaat gatgatttta atacaatga gaggttcaag gggaaggcca cactgactgc    720
agacaaatcc tccagcactg cctacgtgca gctcaacagc ctgacatccg aggattctgc    780
agtgtatttc tgtacaagat ccctgaatat ggcctactgg ggtcaaggaa cctcagtcac    840
cgtctcctac taatag                                                    856
```

<210> SEQ ID NO 17
<211> LENGTH: 275
<212> TYPE: PRT
<213> ORGANISM: Artificial Sequence
<220> FEATURE:
<221> NAME/KEY: CC49 scFv from pPY22
<222> LOCATION: 1..275
<223> OTHER INFORMATION: :

<400> SEQUENCE: 17

```
Met Lys Tyr Met Leu Leu Gln Ala Phe Leu Phe Leu Leu Ala Gly Phe
 1               5                  10                  15

Ala Ala Lys Ile Ser Ala Asp Ile Val Met Ser Gln Ser Pro Ser Ser
            20                  25                  30

Leu Pro Val Ser Val Gly Glu Lys Val Thr Leu Ser Cys Lys Ser Ser
        35                  40                  45

Gln Ser Leu Leu Tyr Ser Gly Asn Gln Lys Asn Tyr Leu Ala Trp Tyr
    50                  55                  60

Gln Gln Lys Pro Gly Gln Ser Pro Lys Leu Leu Ile Tyr Trp Ala Ser
65                  70                  75                  80

Ala Arg Glu Ser Gly Val Pro Asp Arg Phe Thr Gly Ser Gly Ser Gly
                85                  90                  95

Thr Asp Phe Thr Leu Ser Ile Ser Ser Val Lys Thr Glu Asp Leu Ala
            100                 105                 110

Val Tyr Tyr Cys Gln Gln Tyr Tyr Ser Tyr Pro Leu Thr Phe Gly Ala
        115                 120                 125

Gly Thr Lys Leu Val Leu Lys Leu Ser Ala Asp Asp Ala Lys Lys Asp
    130                 135                 140

Ala Ala Lys Lys Asp Asp Ala Lys Lys Asp Ala Lys Lys Asp Leu
145                 150                 155                 160

Glu Val Gln Leu Gln Gln Ser Asp Ala Glu Leu Val Lys Pro Gly Ala
                165                 170                 175

Ser Val Lys Ile Ser Cys Lys Ala Ser Gly Tyr Thr Phe Thr Asp His
            180                 185                 190
```

```
Ala Ile His Trp Val Lys Gln Asn Pro Glu Gln Gly Leu Glu Trp Ile
        195                 200                 205
Gly Tyr Phe Ser Pro Gly Asn Asp Asp Phe Lys Tyr Asn Glu Arg Phe
        210                 215                 220
Lys Gly Lys Ala Thr Leu Thr Ala Asp Lys Ser Ser Ser Thr Ala Tyr
225                 230                 235                 240
Val Gln Leu Asn Ser Leu Thr Ser Glu Asp Ser Ala Val Tyr Phe Cys
                245                 250                 255
Thr Arg Ser Leu Asn Met Ala Tyr Trp Gly Gln Gly Thr Ser Val Thr
                260                 265                 270
Val Ser Tyr
        275

<210> SEQ ID NO 18
<211> LENGTH: 10
<212> TYPE: DNA
<213> ORGANISM: Artificial Sequence
<220> FEATURE:
<221> NAME/KEY: AOX1 Terminator
<222> LOCATION: 1..10
<223> OTHER INFORMATION: :

<400> SEQUENCE: 18
ggatccttag                                                              10

<210> SEQ ID NO 19
<211> LENGTH: 1027
<212> TYPE: DNA
<213> ORGANISM: Artificial Sequence
<220> FEATURE:
<221> NAME/KEY: Hum4 VL-UNIHOPE linker-FLAG peptide construct in
      pATDFLAG
<222> LOCATION: 1..1027
<223> OTHER INFORMATION: :

<400> SEQUENCE: 19
ctcatgtttg acagcttatc atcgatgaat tccatcactt ccctccgttc atttgtcccc       60
ggtggaaacg aggtcatcat ttccttccga aaaacggtt gcatttaaat cttacatata      120
taatactttc aaagactaca tttgtaagat ttgatgtttg agtcggctga agatcgtac      180
gtaccaatta ttgtttcgtg attgttcaag ccataacact gtagggatag tggaaagagt      240
gcttcatctg gttacgatca atcaaatatt caaacggagg gagacgattt tgatgaaata      300
cctattgcct acggcagccg ctggattgtt attactcgct gcccaaccag ccatggccga      360
catcgtgatg acccagtctc cagactccct ggctgtgtct ctgggcgaga gggccaccat      420
caactgcaag tccagccaga gtgttttata cagctccaac aataagaact acttagcttg      480
gtaccagcag aaaccaggac agcctcctaa gctgctcatt tactgggcat ctacccggga      540
atccggggtc cctgaccgat tcagtggcag cgggtctggg acagatttca ctctcaccat      600
cagcagcctg caggctgaag atgcggcagt ttattactgt cagcaatatt atagttatcc      660
tctcactttc ggcggaggga ccaaggtggt gatcaagctt agtgcggacg atgcgaaaaa      720
ggatgctgcg aagaaggatg acgctaagaa agacgatgct aaaaaggacc tcgagacaat      780
gtcgctagcg actacaagga cgatgatgac aaataaaaac ctagcgatga atccgtcaaa      840
acatcatctt acataaagtc acttggtgat caagctcata tcattgtccg gcaatggtgt      900
gggcttttt tgttttctat ctttaaagat catgtgaaga aaacgggaa atcggtctg      960
cgggaaagga ccgggttttt gtcgaaatca taggcgaatg ggttggattg tgacaaaatt     1020
cggatcc                                                              1027
```

<210> SEQ ID NO 20
<211> LENGTH: 171
<212> TYPE: PRT
<213> ORGANISM: Artificial Sequence
<220> FEATURE:
<221> NAME/KEY: Hum4 VL-UNIHOPE linker-FLAG peptide construct in pATDFLAG
<222> LOCATION: 1..171
<223> OTHER INFORMATION: :

<400> SEQUENCE: 20

```
Met Lys Tyr Leu Leu Pro Thr Ala Ala Gly Leu Leu Leu Ala
1               5                   10                  15

Ala Gln Pro Ala Met Ala Asp Ile Val Met Thr Gln Ser Pro Asp Ser
                20                  25                  30

Leu Ala Val Ser Leu Gly Glu Arg Ala Thr Ile Asn Cys Lys Ser Ser
            35                  40                  45

Gln Ser Val Leu Tyr Ser Ser Asn Asn Lys Asn Tyr Leu Ala Trp Tyr
        50                  55                  60

Gln Gln Lys Pro Gly Gln Pro Pro Lys Leu Leu Ile Tyr Trp Ala Ser
65                  70                  75                  80

Thr Arg Glu Ser Gly Val Pro Asp Arg Phe Ser Gly Ser Gly Ser Gly
                85                  90                  95

Thr Asp Phe Thr Leu Thr Ile Ser Ser Leu Gln Ala Glu Asp Ala Ala
            100                 105                 110

Val Tyr Tyr Cys Gln Gln Tyr Tyr Ser Tyr Pro Leu Thr Phe Gly Gly
        115                 120                 125

Gly Thr Lys Val Val Ile Lys Leu Ser Ala Asp Asp Ala Lys Lys Asp
    130                 135                 140

Ala Ala Lys Lys Asp Asp Ala Lys Lys Asp Asp Ala Lys Lys Asp Leu
145                 150                 155                 160

Glu Ala Ser Asp Tyr Lys Asp Asp Asp Lys
                165                 170
```

<210> SEQ ID NO 21
<211> LENGTH: 1361
<212> TYPE: DNA
<213> ORGANISM: Artificial Sequence
<220> FEATURE:
<221> NAME/KEY: Hum4 VL-UNIHOPE linker-FLAG peptide construct in pSC49FLAG
<222> LOCATION: 1..1361
<223> OTHER INFORMATION: :

<400> SEQUENCE: 21

```
ctcatgtttg acagcttatc atcgatgaat tccatcactt ccctccgttc atttgtcccc      60
ggtggaaacg aggtcatcat ttccttccga aaaacggtt gcatttaaat cttacatata     120
taatactttc aaagactaca tttgtaagat ttgatgtttg agtcggctga agatcgtac     180 gtaccaatta ttgtttcgtg attgttcaag ccataacact gtagggatag tggaaagagt     240
gcttcatctg gttacgatca atcaaatatt caaacggagg gagacgattt tgatgaaata     300
cctattgcct acggcagccg ctggattgtt attactcgct gcccaaccag ccatggccga     360
catcgtgatg acccagtctc cagactccct ggctgtgtct ctgggccaga gggccaccat     420
caactgcaag cccagccaga gtgttttata cagctccaac aataagaact acttagcttg     480
gtaccagcag aaaccaggac agcctcctaa gctgctcatt tactgggcat ctacccggga     540
atccggggtc cctgaccgat tcagtggcag cgggtctggg acagatttca ctctcaccat     600
cagcagcctg caggctgaag atgcggcagt ttattactgt cagcaatatt atagttatcc     660
```

```
tctcactttc ggcggaggga ccaaggtggt gatcaagctt agtgcggacg atgcgaaaaa      720
ggatgctgcg aagaaggatg acgctaagaa agacgatgct aaaaaggacc tcgaggttca      780
gttgcagcag tctgacgctg agttggtgaa acctgggggt tcagtgaaga tttcctgcaa      840
ggcttctggc tacaccttca ctgaccatgc aattcactgg gtgaaacaga accctgaaca      900
gggcctggaa tggattggat attttctcc cggaaatgat gattttaaat acaatgagag       960
gttcaagggc aaggccacac tgactgcaga caaatcctcc agcactgcct acgtgcagct     1020
caacagcctg acatctgagg attctgcagt gtatttctgt acaagatccc tgaatatggc     1080
ctactggggt caaggaacct cagtcaccgt ctcctcagct agcgactaca aggacgatga     1140
tgacaaataa aaacctagcg atgaatccgt caaaacatca tcttacataa agtcacttgg     1200
tgatcaagct catatcattg tccggcaatg gtgtgggctt tttttgtttt ctatctttaa     1260
agatcatgtg aagaaaaacg ggaaaatcgg tctgcgggaa aggaccgggt ttttgtcgaa     1320
atcataggcg aatgggttgg attgtgacaa aattcggatc c                         1361
```

<210> SEQ ID NO 22
<211> LENGTH: 285
<212> TYPE: PRT
<213> ORGANISM: Artificial Sequence
<220> FEATURE:
<221> NAME/KEY: Hum4 VL-UNIHOPE linker-FLAG peptide construct in
      pSC49FLAG
<222> LOCATION: 1..285
<223> OTHER INFORMATION: :

<400> SEQUENCE: 22

```
Met Lys Tyr Leu Leu Pro Thr Ala Ala Ala Gly Leu Leu Leu Leu Ala
1               5                   10                  15

Ala Gln Pro Ala Met Ala Asp Ile Val Met Thr Gln Ser Pro Asp Ser
            20                  25                  30

Leu Ala Val Ser Leu Gly Glu Arg Ala Thr Ile Asn Cys Lys Pro Ser
        35                  40                  45

Gln Ser Val Leu Tyr Ser Ser Asn Asn Lys Asn Tyr Leu Ala Trp Tyr
    50                  55                  60

Gln Gln Lys Pro Gly Gln Pro Pro Lys Leu Leu Ile Tyr Trp Ala Ser
65                  70                  75                  80

Thr Arg Glu Ser Gly Val Pro Asp Arg Phe Ser Gly Ser Gly Ser Gly
                85                  90                  95

Thr Asp Phe Thr Leu Thr Ile Ser Ser Leu Gln Ala Glu Asp Ala Ala
            100                 105                 110

Val Tyr Tyr Cys Gln Gln Tyr Tyr Ser Tyr Pro Leu Thr Phe Gly Gly
        115                 120                 125

Gly Thr Lys Val Val Ile Lys Leu Ser Ala Asp Ala Lys Lys Asp
    130                 135                 140

Ala Ala Lys Lys Asp Asp Ala Lys Lys Asp Asp Ala Lys Lys Asp Leu
145                 150                 155                 160

Glu Val Gln Leu Gln Gln Ser Asp Ala Glu Leu Val Lys Pro Gly Ala
                165                 170                 175

Ser Val Lys Ile Ser Cys Lys Ala Ser Gly Tyr Thr Phe Thr Asp His
            180                 185                 190

Ala Ile His Trp Val Lys Gln Asn Pro Glu Gln Gly Leu Glu Trp Ile
        195                 200                 205

Gly Tyr Phe Ser Pro Gly Asn Asp Asp Phe Lys Tyr Asn Glu Arg Phe
    210                 215                 220
```

Lys Gly Lys Ala Thr Leu Thr Ala Asp Lys Ser Ser Thr Ala Tyr
225                 230                 235                 240

Val Gln Leu Asn Ser Leu Thr Ser Glu Asp Ser Ala Val Tyr Phe Cys
            245                 250                 255

Thr Arg Ser Leu Asn Met Ala Tyr Trp Gly Gln Gly Thr Ser Val Thr
                260                 265                 270

Val Ser Ser Ala Ser Asp Tyr Lys Asp Asp Asp Lys
            275                 280                 285

<210> SEQ ID NO 23
<211> LENGTH: 1244
<212> TYPE: DNA
<213> ORGANISM: Artificial Sequence
<220> FEATURE:
<221> NAME/KEY: single chain pel B peptide-HLA-DRb11/a-FLAG construct
<222> LOCATION: 1..1244
<223> OTHER INFORMATION: :

<400> SEQUENCE: 23
ctcatgtttg acagcttatc atcgatgaat tccatcactt ccctccgttc atttgtcccc      60
ggtggaaacg aggtcatcat ttccttccga aaaacggtt gcatttaaat cttacatata     120
taatactttc aaagactaca tttgtaagat ttgatgtttg agtcggctga agatcgtac     180 gtaccaatta ttgtttcgtg attgttcaag ccataacact gtagggatag tggaaagagt     240
gcttcatctg gttacgatca atcaaatatt caaacggagg gagacgattt tgatgaaata     300
cctattgcct acggcagccg ctggattgtt attactcgct gcccaaccag ccatggccgg     360
ggacacccga ccacgtttct tgtggcagct taagtttgaa tgtcatttct tcaatgggac     420
ggagcgggtg cggttgctgg aaagatgcat ctataaccaa gaggagtccg tgcgcttcga     480
cagcgacgtg ggggagtacc gggcggtgac ggagctgggg cggcctgatg ccgagtactg     540
gaacagccag aaggacctcc tggagcagag gcgggccgcg gtggacacct actgcagaca     600
caactacggg gttggtgaga gcttcacagt gcagcggcga gttcatccta aggtgactgt     660
gtataagctt agtgcggacg atgcgaaaaa ggatgctgcg aagaaggatg acgctaagaa     720
agacgctaaa aaggacctcg agatcaaaga gaaacatgtg atcatccagg ccgagttcta     780
tctgaatcct gaccaatcag gcgagtttat gtttgacttt gatggtgatg agattttcca     840
tgtggatatg gcaaagaagg agacggtctg gcggcttgaa gaatttggac gatttgccag     900
ctttgaggct caaggtgcat tggccaacat agctgtggac aaagccaacc tggaaatcat     960
gacaaagcgc tccaactata ctccgatcac caatgctagc gactacaagg acgatgatga    1020
caaataaaaa taaaaaccta gcgatgaatc cgtcaaaaca tcatcttaca taaagtcact    1080
tggtgatcaa gctcatatca ttgtccggca atggtgtggg ctttttttgt tttctatctt    1140
taaagatcat gtgaagaaaa acgggaaaat cggtctgcgg gaaggaccg ggttttttgtc    1200 gaaatcatag gcgaatgggt tggattgtga caaaattcgg atcc                      1244

<210> SEQ ID NO 24
<211> LENGTH: 244
<212> TYPE: PRT
<213> ORGANISM: Artificial Sequence
<220> FEATURE:
<221> NAME/KEY: single chain pel B peptide-HLA-DRb11/a-FLAG construct
<222> LOCATION: 1..244
<223> OTHER INFORMATION: :

-continued

```
<400> SEQUENCE: 24

Met Lys Tyr Leu Leu Pro Thr Ala Ala Gly Leu Leu Leu Ala
1               5                   10                  15

Ala Gln Pro Ala Met Ala Gly Asp Thr Arg Pro Arg Phe Leu Trp Gln
            20                  25                  30

Leu Lys Phe Glu Cys His Phe Phe Asn Gly Thr Glu Arg Val Arg Leu
        35                  40                  45

Leu Glu Arg Cys Ile Tyr Asn Gln Glu Glu Ser Val Arg Phe Asp Ser
    50                  55                  60

Asp Val Gly Glu Tyr Arg Ala Val Thr Glu Leu Gly Arg Pro Asp Ala
65                  70                  75                  80

Glu Tyr Trp Asn Ser Gln Lys Asp Leu Leu Glu Gln Arg Arg Ala Ala
                85                  90                  95

Val Asp Thr Tyr Cys Arg His Asn Tyr Gly Val Gly Glu Ser Phe Thr
            100                 105                 110

Val Gln Arg Arg Val Glu Pro Lys Val Thr Val Tyr Lys Leu Ser Ala
        115                 120                 125

Asp Asp Ala Lys Lys Asp Ala Ala Lys Lys Asp Ala Lys Lys Asp
    130                 135                 140

Ala Lys Lys Asp Leu Glu Ile Lys Glu Glu His Val Ile Ile Gln Ala
145                 150                 155                 160

Glu Phe Tyr Leu Asn Pro Asp Gln Ser Gly Glu Phe Met Phe Asp Phe
                165                 170                 175

Asp Gly Asp Glu Ile Phe His Val Asp Met Ala Lys Lys Glu Thr Val
            180                 185                 190

Trp Arg Leu Glu Glu Phe Gly Arg Phe Ala Ser Phe Glu Ala Gln Gly
        195                 200                 205

Ala Leu Ala Asn Ile Ala Val Asp Lys Ala Asn Leu Glu Ile Met Thr
    210                 215                 220

Lys Arg Ser Asn Tyr Thr Pro Ile Thr Asn Ala Ser Asp Tyr Lys Asp
225                 230                 235                 240

Asp Asp Asp Lys

<210> SEQ ID NO 25
<211> LENGTH: 1244
<212> TYPE: DNA
<213> ORGANISM: Artificial Sequence
<220> FEATURE:
<221> NAME/KEY: single chain pel B peptide-HLA-DRb42/a-FLAG construct
<222> LOCATION: 1..1244
<223> OTHER INFORMATION: :

<400> SEQUENCE: 25
ctcatgtttg acagcttatc atcgatgaat tccatcactt ccctccgttc atttgtcccc      60
ggtggaaacg aggtcatcat ttccttccga aaaacggtt gcatttaaat cttacatata     120
taatactttc aaagactaca tttgtaagat ttgatgtttg agtcggctga aagatcgtac     180
gtaccaatta ttgtttcgtg attgttcaag ccataacact gtagggatag tggaaagagt     240
gcttcatctg gttacgatca atcaaatatt caaacggagg agacgatttt gatgaaata      300 cctattgcct acggcagccg ctggattgtt attactcgct gcccaaccag ccatggccgg     360
ggacacccga ccacgtttct tggagcaggt taaacatgag tgtcatttct caacgggac     420 ggagcgggtg cggttcctgg acagatactt ctatcaccaa gaggagtacg tgcgcttcga     480
cagcgacgtg ggggagtacc gggcggtgac ggagctgggg cggcctgatg ccgagtactg     540
```

```
gaacagccag aaggacatcc tggaagacga gcgggccgcg gtggacacct actgcagaca    600
caactacggg gttgtggaga gcttcacagt gcagcggcga gtctatccta aggtgactgt    660
gtataagctt agtgcggacg atgcgaaaaa ggatgctgcg aagaaggatg acgctaagaa    720
agacgctaaa aaggacctcg agatcaaaga agaacatgtg atcatccagg ccgagttcta    780
tctgaatcct gaccaatcag gcgagtttat gtttgacttt gatggtgatg agattttcca    840
tgtggatatg gcaaagaagg agacggtctg gcggcttgaa gaatttggac gatttgccag    900
ctttgaggct caaggtgcat tggccaacat agctgtggac aaagccaacc tggaaatcat    960
gacaaagcgc tccaactata ctccgatcac caatgctagc gactacaagg acgatgatga   1020
caaataaaaa taaaaaccta gcgatgaatc cgtcaaaaca tcatcttaca taaagtcact   1080
tggtgatcaa gctcatatca ttgtccggca atggtgtggg ctttttttgt tttctatctt   1140
taaagatcat gtgaagaaaa acgggaaaat cggtctgcgg gaaggaccg ggttttttgtc   1200 gaaatcatag gcgaatgggt tggattgtga caaaattcgg atcc                    1244
```

<210> SEQ ID NO 26
<211> LENGTH: 244
<212> TYPE: PRT
<213> ORGANISM: Artificial Sequence
<220> FEATURE:
<221> NAME/KEY: single chain pel B peptide-HLA-DRb42/a-FLAG construct
<222> LOCATION: 1..244
<223> OTHER INFORMATION: :

<400> SEQUENCE: 26

```
Met Lys Tyr Leu Leu Pro Thr Ala Ala Ala Gly Leu Leu Leu Leu Ala
1               5                   10                  15

Ala Gln Pro Ala Met Ala Gly Asp Thr Arg Pro Arg Phe Leu Glu Gln
                20                  25                  30

Val Lys His Glu Cys His Phe Phe Asn Gly Thr Glu Arg Val Arg Phe
            35                  40                  45

Leu Asp Arg Tyr Phe Tyr His Gln Glu Glu Tyr Val Arg Phe Asp Ser
        50                  55                  60

Asp Val Gly Glu Tyr Arg Ala Val Thr Glu Leu Gly Arg Pro Asp Ala
65                  70                  75                  80

Glu Tyr Trp Asn Ser Gln Lys Asp Ile Leu Glu Asp Glu Arg Ala Ala
                85                  90                  95

Val Asp Thr Tyr Cys Arg His Asn Tyr Gly Val Val Glu Ser Phe Thr
            100                 105                 110

Val Gln Arg Arg Val Tyr Pro Lys Val Thr Val Tyr Lys Leu Ser Ala
        115                 120                 125

Asp Asp Ala Lys Lys Asp Ala Ala Lys Lys Asp Asp Ala Lys Lys Asp
    130                 135                 140

Ala Lys Lys Asp Leu Glu Ile Lys Glu Glu His Val Ile Ile Gln Ala
145                 150                 155                 160

Glu Phe Tyr Leu Asn Pro Asp Gln Ser Gly Glu Phe Met Phe Asp Phe
                165                 170                 175

Asp Gly Asp Glu Ile Phe His Val Asp Met Ala Lys Lys Glu Thr Val
            180                 185                 190

Trp Arg Leu Glu Glu Phe Gly Arg Phe Ala Ser Phe Glu Ala Gln Gly
        195                 200                 205

Ala Leu Ala Asn Ile Ala Val Asp Lys Ala Asn Leu Glu Ile Met Thr
    210                 215                 220
```

Lys Arg Ser Asn Tyr Thr Pro Ile Thr Asn Ala Ser Asp Tyr Lys Asp
225                 230                 235                 240

Asp Asp Asp Lys

<210> SEQ ID NO 27
<211> LENGTH: 1244
<212> TYPE: DNA
<213> ORGANISM: Artificial Sequence
<220> FEATURE:
<221> NAME/KEY: single chain pel B peptide-HLA-DRb48/a-FLAG construct
<222> LOCATION: 1..1244
<223> OTHER INFORMATION: :

<400> SEQUENCE: 27

```
ctcatgtttg acagcttatc atcgatgaat tccatcactt ccctccgttc atttgtcccc     60
ggtggaaacg aggtcatcat ttccttccga aaaacggtt gcatttaaat cttacatata    120
taatactttc aaagactaca tttgtaagat ttgatgtttg agtcggctga agatcgtac     180
gtaccaatta ttgtttcgtg attgttcaag ccataacact gtagggatag tggaaagagt    240
gcttcatctg gttacgatca atcaaatatt caaacgaggg agacgattt tgatgaaata    300
cctattgcct acggcagccg ctggattgtt attactcgct gcccaaccag ccatggccgg    360
ggacacccga ccacgtttct tggagcaggt taaacatgag tgtcatttct caacgggac    420
ggagcgggtg cggttcctgg acagatactt ctatcaccaa gaggagtacg tgcgcttcga    480
cagcgacgtg ggggagtacc gggcggtgac ggagctgggg cggcctgatg ccgagtactg    540
gaacagccag aaggacctcc tcgagcagag gcgggccgcg gtggacacct actgcagaca    600
caactacggg gttggtgaga gcttcacagt gcagcggcga gttgagccta aggtgactgt    660
gtataagctt agtgcggacg atgcgaaaaa ggatgctgcg aagaaggatg acgctaagaa    720
agacgctaaa aaggacctcg agatcaaaga gaaacatgtg atcatccagg ccgagttcta    780
tctgaatcct gaccaatcag gcgagtttat gtttgacttt gatggtgatg agattttcca    840
tgtggatatg gcaaagaagg agacggtctg gcggcttgaa gaatttggac gatttgccag    900
ctttgaggct caaggtgcat tggccaacat agctgtggac aaagccaacc tggaaatcat    960
gacaaagcgc tccaactata ctccgatcac caatgctagc gactacaagg acgatgatga   1020
caaataaaaa taaaaccta gcgatgaatc cgtcaaaaca tcatcttaca taagtcact    1080
tggtgatcaa gctcatatca ttgtccggca atggtgtggg ctttttttgt tttctatctt   1140
taaagatcat gtgaagaaaa acgggaaaat cggtctgcgg gaaggaccgg gttttgtc     1200
gaaatcatag gcgaatgggt tggattgtga caaaattcgg atcc                  1244
```

<210> SEQ ID NO 28
<211> LENGTH: 244
<212> TYPE: PRT
<213> ORGANISM: Artificial Sequence
<220> FEATURE:
<221> NAME/KEY: single chain pel B peptide-HLA-DRb48/a-FLAG construct
<222> LOCATION: 1..244
<223> OTHER INFORMATION: :

<400> SEQUENCE: 28

Met Lys Tyr Leu Leu Pro Thr Ala Ala Ala Gly Leu Leu Leu Leu Ala
1               5                   10                  15

Ala Gln Pro Ala Met Ala Gly Asp Thr Arg Pro Arg Phe Leu Glu Gln
                20                  25                  30

Val Lys His Glu Cys His Phe Phe Asn Gly Thr Glu Arg Val Arg Phe
            35                  40                  45

-continued

```
Leu Asp Arg Tyr Phe Tyr His Gln Glu Glu Tyr Val Arg Phe Asp Ser
     50                  55                  60
Asp Val Gly Glu Tyr Arg Ala Val Thr Glu Leu Gly Arg Pro Asp Ala
 65                  70                  75                  80
Glu Tyr Trp Asn Ser Gln Lys Asp Leu Leu Glu Gln Arg Arg Ala Ala
                 85                  90                  95
Val Asp Thr Tyr Cys Arg His Asn Tyr Gly Val Gly Glu Ser Phe Thr
                100                 105                 110
Val Gln Arg Arg Val Glu Pro Lys Val Thr Val Tyr Lys Leu Ser Ala
            115                 120                 125
Asp Asp Ala Lys Lys Asp Ala Ala Lys Lys Asp Asp Ala Lys Lys Asp
130                 135                 140
Ala Lys Lys Asp Leu Glu Ile Lys Glu Glu His Val Ile Ile Gln Ala
145                 150                 155                 160
Glu Phe Tyr Leu Asn Pro Asp Gln Ser Gly Glu Phe Met Phe Asp Phe
                165                 170                 175
Asp Gly Asp Glu Ile Phe His Val Asp Met Ala Lys Lys Glu Thr Val
            180                 185                 190
Trp Arg Leu Glu Glu Phe Gly Arg Phe Ala Ser Phe Glu Ala Gln Gly
        195                 200                 205
Ala Leu Ala Asn Ile Ala Val Asp Lys Ala Asn Leu Glu Ile Met Thr
    210                 215                 220
Lys Arg Ser Asn Tyr Thr Pro Ile Thr Asn Ala Ser Asp Tyr Lys Asp
225                 230                 235                 240
Asp Asp Asp Lys
```

<210> SEQ ID NO 29
<211> LENGTH: 1244
<212> TYPE: DNA
<213> ORGANISM: Artificial Sequence
<220> FEATURE:
<221> NAME/KEY: single chain pel B peptide-HLA-DRb41/a-FLAG construct
<222> LOCATION: 1..1244
<223> OTHER INFORMATION: :

<400> SEQUENCE: 29

```
ctcatgtttg acagcttatc atcgatgaat tccatcactt ccctccgttc atttgtcccc      60
ggtggaaacg aggtcatcat ttccttccga aaaacggtt gcatttaaat cttacatata     120
taatactttc aaagactaca tttgtaagat ttgatgtttg agtcggctga agatcgtac     180
gtaccaatta ttgtttcgtg attgttcaag ccataacact gtagggatag tggaaagagt     240
gcttcatctg gttacgatca atcaaatatt caaacggagg gagacgattt tgatgaaata     300
cctattgcct acggcagccg ctggattgtt attactcgct gcccaaccag ccatggccgg     360
ggacacccga ccacgtttct tggagcaggt taaacatgag tgtcatttct tcaacgggac     420
ggagcgggtg cggttcctgg acagatactt ctatcaccaa gaggagtacg tgcgcttcga     480
cagcgacgtg ggggagtacc gggcggtgac ggagctgggg cggcctgatg ccgagtactg     540
gaacagccag aaggacctcc tggagcagaa gcggccgcg gtggacacct actgcagaca     600
caactacggg gttggtgaga gcttcacagt gcagcggcga gtctatccta aggtgactgt     660
gtataagctt agtgcggacg atgcgaaaaa ggatgctgcg aagaaggatg acgctaagaa     720
agacgctaaa aaggacctcg agatcaaaga gaacatgtg atcatccagg ccgagttcta     780
tctgaatcct gaccaatcag gcgagtttat gtttgacttt gatggtgatg agattttcca     840
tgtggatatg gcaaagaagg agacggtctg gcggcttgaa gaatttggac gatttgccag     900
```

```
ctttgaggct caaggtgcat tggccaacat agctgtggac aaagccaacc tggaaatcat    960
gacaaagcgc tccaactata ctccgatcac caatgctagc gactacaagg acgatgatga   1020
caaataaaaa taaaaaccta gcgatgaatc cgtcaaaaca tcatcttaca taaagtcact   1080
tggtgatcaa gctcatatca ttgtccggca atggtgtggg cttttttgt tttctatctt    1140 taaagatcat gtgaagaaaa acgggaaaat cggtctgcgg gaaaggaccg ggttttgtc    1200 gaaatcatag gcgaatgggt tggattgtga caaaattcgg atcc                    1244
```

<210> SEQ ID NO 30
<211> LENGTH: 244
<212> TYPE: PRT
<213> ORGANISM: Artificial Sequence
<220> FEATURE:
<221> NAME/KEY: single chain pel B peptide-HLA-DRb41/a-FLAG construct
<222> LOCATION: 1..244
<223> OTHER INFORMATION: :

<400> SEQUENCE: 30

```
Met Lys Tyr Leu Leu Pro Thr Ala Ala Ala Gly Leu Leu Leu Leu Ala
1               5                   10                  15

Ala Gln Pro Ala Met Ala Gly Asp Thr Arg Pro Arg Phe Leu Glu Gln
                20                  25                  30

Val Lys His Glu Cys His Phe Phe Asn Gly Thr Glu Arg Val Arg Phe
            35                  40                  45

Leu Asp Arg Tyr Phe Tyr His Gln Glu Glu Tyr Val Arg Phe Asp Ser
        50                  55                  60

Asp Val Gly Glu Tyr Arg Ala Val Thr Glu Leu Gly Arg Pro Asp Ala
65                  70                  75                  80

Glu Tyr Trp Asn Ser Gln Lys Asp Leu Leu Glu Gln Lys Arg Ala Ala
                85                  90                  95

Val Asp Thr Tyr Cys Arg His Asn Tyr Gly Val Gly Glu Ser Phe Thr
            100                 105                 110

Val Gln Arg Arg Val Tyr Pro Lys Val Thr Val Tyr Lys Leu Ser Ala
        115                 120                 125

Asp Asp Ala Lys Lys Asp Ala Ala Lys Lys Asp Asp Ala Lys Lys Asp
130                 135                 140

Ala Lys Lys Asp Leu Glu Ile Lys Glu Glu His Val Ile Ile Gln Ala
145                 150                 155                 160

Glu Phe Tyr Leu Asn Pro Asp Gln Ser Gly Glu Phe Met Phe Asp Phe
                165                 170                 175

Asp Gly Asp Glu Ile Phe His Val Asp Met Ala Lys Lys Glu Thr Val
            180                 185                 190

Trp Arg Leu Glu Glu Phe Gly Arg Phe Ala Ser Phe Glu Ala Gln Gly
        195                 200                 205

Ala Leu Ala Asn Ile Ala Val Asp Lys Ala Asn Leu Glu Ile Met Thr
    210                 215                 220

Lys Arg Ser Asn Tyr Thr Pro Ile Thr Asn Ala Ser Asp Tyr Lys Asp
225                 230                 235                 240

Asp Asp Asp Lys
```

<210> SEQ ID NO 31
<211> LENGTH: 25
<212> TYPE: PRT
<213> ORGANISM: Artificial Sequence
<220> FEATURE:
<221> NAME/KEY: UNIHOPE linker
<222> LOCATION: 1..25

```
<223> OTHER INFORMATION: :

<400> SEQUENCE: 31

Leu Ser Ala Asp Asp Ala Lys Lys Asp Ala Ala Lys Lys Asp Asp Ala
1               5                   10                  15

Lys Lys Asp Asp Ala Lys Lys Asp Leu
            20                  25

<210> SEQ ID NO 32
<211> LENGTH: 26
<212> TYPE: DNA
<213> ORGANISM: Artificial Sequence
<220> FEATURE:
<221> NAME/KEY: penP1 primer
<222> LOCATION: 1..26
<223> OTHER INFORMATION: :

<400> SEQUENCE: 32
cgataagctt gaattccatc acttcc                                          26

<210> SEQ ID NO 33
<211> LENGTH: 90
<212> TYPE: DNA
<213> ORGANISM: Artificial Sequence
<220> FEATURE:
<221> NAME/KEY: penP2 primer
<222> LOCATION: 1..90
<223> OTHER INFORMATION: :

<400> SEQUENCE: 33
ggccatggct ggttgggcag cgagtaataa caatccagcg gctgccgtag gcaataggta    60
tttcatcaaa atcgtctccc tccgtttgaa                                     90

<210> SEQ ID NO 34
<211> LENGTH: 44
<212> TYPE: DNA
<213> ORGANISM: Artificial Sequence
<220> FEATURE:
<221> NAME/KEY: penP3 primer
<222> LOCATION: 1..44
<223> OTHER INFORMATION: :

<400> SEQUENCE: 34
gctgcccaac cagccatggc cgacatcgtg atgacccagt ctcc                      44

<210> SEQ ID NO 35
<211> LENGTH: 90
<212> TYPE: DNA
<213> ORGANISM: Artificial Sequence
<220> FEATURE:
<221> NAME/KEY: penP6(-) primer
<222> LOCATION: 1..90
<223> OTHER INFORMATION: :

<400> SEQUENCE: 35
ctcttgatca ccaagtgact ttatgtaaga tgatgttttg acggattcat cgcaatgttt    60
ttatttgccg gagacggtga ctgaggttcc                                     90

<210> SEQ ID NO 36
<211> LENGTH: 23
<212> TYPE: DNA
<213> ORGANISM: Artificial Sequence
<220> FEATURE:
<221> NAME/KEY: Nco1.1 primer
<222> LOCATION: 1..23
<223> OTHER INFORMATION: :
```

```
<400> SEQUENCE: 36
tccggaattc cgtatggcaa tga                                              23

<210> SEQ ID NO 37
<211> LENGTH: 37
<212> TYPE: DNA
<213> ORGANISM: Artificial Sequence
<220> FEATURE:
<221> NAME/KEY: Nco1.3(-) primer
<222> LOCATION: 1..37
<223> OTHER INFORMATION: :

<400> SEQUENCE: 37
cttgcgtata atatttgccc atcgtgaaaa cggggggc                              37

<210> SEQ ID NO 38
<211> LENGTH: 22
<212> TYPE: DNA
<213> ORGANISM: Artificial Sequence
<220> FEATURE:
<221> NAME/KEY: Nco1.2 primer
<222> LOCATION: 1..22
<223> OTHER INFORMATION: :

<400> SEQUENCE: 38
atgggcaaat attatacgca ag                                               22

<210> SEQ ID NO 39
<211> LENGTH: 36
<212> TYPE: DNA
<213> ORGANISM: Artificial Sequence
<220> FEATURE:
<221> NAME/KEY: Nco1.4c(-) primer
<222> LOCATION: 1..36
<223> OTHER INFORMATION: :

<400> SEQUENCE: 39
cactgaattc atcgatgata agctgtcaaa catgag                                36

<210> SEQ ID NO 40
<211> LENGTH: 35
<212> TYPE: DNA
<213> ORGANISM: Artificial Sequence
<220> FEATURE:
<221> NAME/KEY: 104BH1 primer
<222> LOCATION: 1..35
<223> OTHER INFORMATION: :

<400> SEQUENCE: 40
cagccatggc cgacatcgtg atgacccagt ctcca                                 35

<210> SEQ ID NO 41
<211> LENGTH: 86
<212> TYPE: DNA
<213> ORGANISM: Artificial Sequence
<220> FEATURE:
<221> NAME/KEY: 104BH2(-) primer
<222> LOCATION: 1..86
<223> OTHER INFORMATION: :

<400> SEQUENCE: 41
aagcttgccc catgctgctt taacgttagt tttatctgct ggagacagag tgccttctgc      60 cttg gtccctccgc cgaaag                                                 86

<210> SEQ ID NO 42
<211> LENGTH: 50
```

```
<212> TYPE: DNA
<213> ORGANISM: Artificial Sequence
<220> FEATURE:
<221> NAME/KEY: 104B3 primer
<222> LOCATION: 1..50
<223> OTHER INFORMATION: :

<400> SEQUENCE: 42
gttaaagcag catggggcaa gcttatgact cagttgcagc agtctgacgc         50

<210> SEQ ID NO 43
<211> LENGTH: 99
<212> TYPE: DNA
<213> ORGANISM: Artificial Sequence
<220> FEATURE:
<221> NAME/KEY: 104B4(-) primer
<222> LOCATION: 1..99
<223> OTHER INFORMATION: :

<400> SEQUENCE: 43
ctcttgatca ccaagtgact ttatgtaaga tgatgttttg acggattcat cgctagcttt    60
ttatttgcca taataagggg agacggtgac tgaggttcc                          99

<210> SEQ ID NO 44
<211> LENGTH: 34
<212> TYPE: DNA
<213> ORGANISM: Artificial Sequence
<220> FEATURE:
<221> NAME/KEY: UNIH1 primer
<222> LOCATION: 1..34
<223> OTHER INFORMATION: :

<400> SEQUENCE: 44
cagccatggc cgacattgtg atgtcacagt ctcc                         34

<210> SEQ ID NO 45
<211> LENGTH: 71
<212> TYPE: DNA
<213> ORGANISM: Artificial Sequence
<220> FEATURE:
<221> NAME/KEY: UNIH2(-) primer
<222> LOCATION: 1..71
<223> OTHER INFORMATION: :

<400> SEQUENCE: 45
gaggtccgta agatctgcct cgctacctag caaaaggtcc tcaagcttga tcaccacctt    60
ggtccctccg c                                                       71

<210> SEQ ID NO 46
<211> LENGTH: 48
<212> TYPE: DNA
<213> ORGANISM: Artificial Sequence
<220> FEATURE:
<221> NAME/KEY: UNI3 primer
<222> LOCATION: 1..48
<223> OTHER INFORMATION: :

<400> SEQUENCE: 46
agcgaggcag atcttacgga cctcgaggtt cagttgcagc agtctgac           48

<210> SEQ ID NO 47
<211> LENGTH: 40
<212> TYPE: DNA
<213> ORGANISM: Artificial Sequence
<220> FEATURE:
<221> NAME/KEY: UNI4(-) primer
<222> LOCATION: 1..40
```

```
<223> OTHER INFORMATION: :

<400> SEQUENCE: 47
catcgctagc tttttatgag gagacggtga ctgaggttcc                           40

<210> SEQ ID NO 48
<211> LENGTH: 89
<212> TYPE: DNA
<213> ORGANISM: Artificial Sequence
<220> FEATURE:
<221> NAME/KEY: UNIHOPE primer
<222> LOCATION: 1..89
<223> OTHER INFORMATION: :

<400> SEQUENCE: 48
tataaagctt agtgcggacg atgcgaaaaa ggatgctgcg aagaaggatg acgctaagaa     60
agacgatgct aaaaaggacc tcgagtcta                                       89

<210> SEQ ID NO 49
<211> LENGTH: 89
<212> TYPE: DNA
<213> ORGANISM: Artificial Sequence
<220> FEATURE:
<221> NAME/KEY: UNIHOPE(-) primer
<222> LOCATION: 1..89
<223> OTHER INFORMATION: :

<400> SEQUENCE: 49
tagactcgag gtccttttta gcatcgtctt tcttagcgtc atccttcttc gcagcatcct     60
ttttcgcatc gtccgcacta agctttata                                       89

<210> SEQ ID NO 50
<211> LENGTH: 34
<212> TYPE: DNA
<213> ORGANISM: Artificial Sequence
<220> FEATURE:
<221> NAME/KEY: UNIM1 primer
<222> LOCATION: 1..34
<223> OTHER INFORMATION: :

<400> SEQUENCE: 50
cagccatggc cgacattgtg atgtcacagt ctcc                                 34

<210> SEQ ID NO 51
<211> LENGTH: 71
<212> TYPE: DNA
<213> ORGANISM: Artificial Sequence
<220> FEATURE:
<221> NAME/KEY: UNIM2(-) primer
<222> LOCATION: 1..71
<223> OTHER INFORMATION: :

<400> SEQUENCE: 51
gaggtccgta agatctgcct cgctacctag caaaaggtcc tcaagcttca gcaccagctt     60
ggtcccagca c                                                          71

<210> SEQ ID NO 52
<211> LENGTH: 58
<212> TYPE: DNA
<213> ORGANISM: Artificial Sequence
<220> FEATURE:
<221> NAME/KEY: SCUHPM 5.8 primer
<222> LOCATION: 1..58
<223> OTHER INFORMATION: :
```

-continued

```
<400> SEQUENCE: 52
aacagctagc tttttaggag tcatagtcct caggggagac ggtgactgag gttccttg        58

<210> SEQ ID NO 53
<211> LENGTH: 64
<212> TYPE: DNA
<213> ORGANISM: Artificial Sequence
<220> FEATURE:
<221> NAME/KEY: SCUHPM 5.2 primer
<222> LOCATION: 1..64
<223> OTHER INFORMATION: :

<400> SEQUENCE: 53
aacagctagc tttttactca tactcttcag ggtcttcagg ggagacggtg actgaggttc       60
cttg                                                                   64

<210> SEQ ID NO 54
<211> LENGTH: 105
<212> TYPE: DNA
<213> ORGANISM: Artificial Sequence
<220> FEATURE:
<221> NAME/KEY: pHIL-S1 5'-AOX1/PHOX1/MultiCloning/3'AOX1 construct
<222> LOCATION: 1..105
<223> OTHER INFORMATION: :

<400> SEQUENCE: 54
ttattcgaaa cgatgttctc tccaattttg tccttggaaa ttattttagc tttggctact       60
ttgcaatctg tcttcgctcg agaatccccc gggatcctta gacat                      105

<210> SEQ ID NO 55
<211> LENGTH: 20
<212> TYPE: DNA
<213> ORGANISM: Artificial Sequence
<220> FEATURE:
<221> NAME/KEY: TAGVLFR2 primer
<222> LOCATION: 1..20
<223> OTHER INFORMATION: :

<400> SEQUENCE: 55
tggtaccagc agaaaccagg                                                  20

<210> SEQ ID NO 56
<211> LENGTH: 22
<212> TYPE: DNA
<213> ORGANISM: Artificial Sequence
<220> FEATURE:
<221> NAME/KEY: TAGVLCDR3 primer
<222> LOCATION: 1..22
<223> OTHER INFORMATION: :

<400> SEQUENCE: 56
gtcagcarta ttatagytat cc                                               22

<210> SEQ ID NO 57
<211> LENGTH: 21
<212> TYPE: DNA
<213> ORGANISM: Artificial Sequence
<220> FEATURE:
<221> NAME/KEY: TAGVHCDR2 primer
<222> LOCATION: 1..21
<223> OTHER INFORMATION: :

<400> SEQUENCE: 57
atggattgga tattttctc c                                                 21
```

```
<210> SEQ ID NO 58
<211> LENGTH: 20
<212> TYPE: DNA
<213> ORGANISM: Artificial Sequence
<220> FEATURE:
<221> NAME/KEY: ECONOT primer
<222> LOCATION: 1..20
<223> OTHER INFORMATION: :

<400> SEQUENCE: 58
gaattcttag cggccgcttg                                               20

<210> SEQ ID NO 59
<211> LENGTH: 20
<212> TYPE: DNA
<213> ORGANISM: Artificial Sequence
<220> FEATURE:
<221> NAME/KEY: TONOCE primer
<222> LOCATION: 1..20
<223> OTHER INFORMATION: :

<400> SEQUENCE: 59
caagcggccg ctaagaattc                                               20

<210> SEQ ID NO 60
<211> LENGTH: 19
<212> TYPE: DNA
<213> ORGANISM: Artificial Sequence
<220> FEATURE:
<221> NAME/KEY: ECOVNHESEQ primer
<222> LOCATION: 1..19
<223> OTHER INFORMATION: :

<400> SEQUENCE: 60
tgcgcataga aattgcatc                                                19

<210> SEQ ID NO 61
<211> LENGTH: 92
<212> TYPE: DNA
<213> ORGANISM: Artificial Sequence
<220> FEATURE:
<221> NAME/KEY: PY49VLI primer
<222> LOCATION: 1..92
<223> OTHER INFORMATION: :

<400> SEQUENCE: 61
acatttcgaa acgatgcttt tgcaagcttt cctttccctt ttggctggtt ttgcagctaa    60
gatatctgct gacattgtga tgtcacagtc tc                                 92

<210> SEQ ID NO 62
<211> LENGTH: 36
<212> TYPE: DNA
<213> ORGANISM: Artificial Sequence
<220> FEATURE:
<221> NAME/KEY: PY523 primer
<222> LOCATION: 1..36
<223> OTHER INFORMATION: :

<400> SEQUENCE: 62
aaatggatcc tattagtcat agtcttcagg gtcttc                             36

<210> SEQ ID NO 63
<211> LENGTH: 40
<212> TYPE: DNA
<213> ORGANISM: Artificial Sequence
<220> FEATURE:
<221> NAME/KEY: PSC49VH primer
<222> LOCATION: 1..40
```

<223> OTHER INFORMATION: :

<400> SEQUENCE: 63
atgtggatcc ctattagtag gagacggtga ctgaggttcc                                  40

<210> SEQ ID NO 64
<211> LENGTH: 50
<212> TYPE: DNA
<213> ORGANISM: Artificial Sequence
<220> FEATURE:
<221> NAME/KEY: FLAGC primer
<222> LOCATION: 1..50
<223> OTHER INFORMATION: :

<400> SEQUENCE: 64
tcgagacaat gtcgctagcg actacaagga cgatgatgac aaataaaaac                        50

<210> SEQ ID NO 65
<211> LENGTH: 50
<212> TYPE: DNA
<213> ORGANISM: Artificial Sequence
<220> FEATURE:
<221> NAME/KEY: FLAGNC primer
<222> LOCATION: 1..50
<223> OTHER INFORMATION: :

<400> SEQUENCE: 65
ctaggttttt atttgtcatc atcgtccttg tagtcgctag cgacattgtc                        50

<210> SEQ ID NO 66
<211> LENGTH: 22
<212> TYPE: DNA
<213> ORGANISM: Artificial Sequence
<220> FEATURE:
<221> NAME/KEY: PENTPSEQ primer
<222> LOCATION: 1..22
<223> OTHER INFORMATION: :

<400> SEQUENCE: 66
ctttatgtaa gatgatgttt tg                                                     22

<210> SEQ ID NO 67
<211> LENGTH: 33
<212> TYPE: DNA
<213> ORGANISM: Artificial Sequence
<220> FEATURE:
<221> NAME/KEY: SC49FLAG primer
<222> LOCATION: 1..33
<223> OTHER INFORMATION: :

<400> SEQUENCE: 67
tattgctagc tgaggagacg gtgactgagg ttc                                         33

<210> SEQ ID NO 68
<211> LENGTH: 21
<212> TYPE: DNA
<213> ORGANISM: Artificial Sequence
<220> FEATURE:
<221> NAME/KEY: PENPR1 primer
<222> LOCATION: 1..21
<223> OTHER INFORMATION: :

<400> SEQUENCE: 68
aacactgtag ggatagtgga a                                                      21

<210> SEQ ID NO 69
<211> LENGTH: 20

```
<212> TYPE: DNA
<213> ORGANISM: Artificial Sequence
<220> FEATURE:
<221> NAME/KEY: PENPR2 primer
<222> LOCATION: 1..20
<223> OTHER INFORMATION: :

<400> SEQUENCE: 69
gtctccctcc gtttgaatat                                                    20

<210> SEQ ID NO 70
<211> LENGTH: 22
<212> TYPE: DNA
<213> ORGANISM: Artificial Sequence
<220> FEATURE:
<221> NAME/KEY: UHVHSEQ primer
<222> LOCATION: 1..22
<223> OTHER INFORMATION: :

<400> SEQUENCE: 70
gatgctgcga agaaggatga cg                                                 22

<210> SEQ ID NO 71
<211> LENGTH: 21
<212> TYPE: DNA
<213> ORGANISM: Artificial Sequence
<220> FEATURE:
<221> NAME/KEY: TAGVHFR4 primer
<222> LOCATION: 1..21
<223> OTHER INFORMATION: :

<400> SEQUENCE: 71
actggggtca aggaacctca g                                                  21

<210> SEQ ID NO 72
<211> LENGTH: 30
<212> TYPE: DNA
<213> ORGANISM: Artificial Sequence
<220> FEATURE:
<221> NAME/KEY: HLADA5 primer
<222> LOCATION: 1..30
<223> OTHER INFORMATION: :

<400> SEQUENCE: 72
tgacgaattc gcccaagaag aaaatggcca                                         30

<210> SEQ ID NO 73
<211> LENGTH: 30
<212> TYPE: DNA
<213> ORGANISM: Artificial Sequence
<220> FEATURE:
<221> NAME/KEY: HLADA3 primer
<222> LOCATION: 1..30
<223> OTHER INFORMATION: :

<400> SEQUENCE: 73
tcaggaattc tggaaaacgc tgaagatgac                                         30

<210> SEQ ID NO 74
<211> LENGTH: 30
<212> TYPE: DNA
<213> ORGANISM: Artificial Sequence
<220> FEATURE:
<221> NAME/KEY: HLADB5 primer
<222> LOCATION: 1..30
<223> OTHER INFORMATION: :
```

-continued

<400> SEQUENCE: 74
tgacgaattc ctgtcctgtt ctccagcatg                                        30

<210> SEQ ID NO 75
<211> LENGTH: 38
<212> TYPE: DNA
<213> ORGANISM: Artificial Sequence
<220> FEATURE:
<221> NAME/KEY: HLADB3.3 primer
<222> LOCATION: 1..38
<223> OTHER INFORMATION: :

<400> SEQUENCE: 75
gactctagac ccgggtacca atgctgggac ttcaggcc                               38

<210> SEQ ID NO 76
<211> LENGTH: 69
<212> TYPE: DNA
<213> ORGANISM: Artificial Sequence
<220> FEATURE:
<221> NAME/KEY: 0101F primer
<222> LOCATION: 1..69
<223> OTHER INFORMATION: :

<400> SEQUENCE: 76
ggtggacacc tattgcagac acaactacgg ggttggtgag agcttcacag tgcagcggcg       60
agttgagcc                                                              69

<210> SEQ ID NO 77
<211> LENGTH: 74
<212> TYPE: DNA
<213> ORGANISM: Artificial Sequence
<220> FEATURE:
<221> NAME/KEY: 0101R primer
<222> LOCATION: 1..74
<223> OTHER INFORMATION: :

<400> SEQUENCE: 77
ttaggctcaa ctcgccgctg cactgtgaag ctctcaccaa ccccgtagtt gtgtctgcaa       60
taggtgtcca ccgc                                                        74

<210> SEQ ID NO 78
<211> LENGTH: 79
<212> TYPE: DNA
<213> ORGANISM: Artificial Sequence
<220> FEATURE:
<221> NAME/KEY: DRb-3AH5' primer
<222> LOCATION: 1..79
<223> OTHER INFORMATION: :

<400> SEQUENCE: 78
gacctcctcg agcagaggcg ggccgcggtg gacacctact gccggcacaa ctacggggtt       60
ggtgaaagct tcacagtgc                                                   79

<210> SEQ ID NO 79
<211> LENGTH: 95
<212> TYPE: DNA
<213> ORGANISM: Artificial Sequence
<220> FEATURE:
<221> NAME/KEY: DRb-3AHV3' primer
<222> LOCATION: 1..95
<223> OTHER INFORMATION: :

```
<400> SEQUENCE: 79
tcaggataga ctcgccgctg cactgtgaag ctttcaccaa ccccgtagtt gtgccggcag    60
taggtgtcca ccgcggcccg cctctgctcg aggag                              95

<210> SEQ ID NO 80
<211> LENGTH: 28
<212> TYPE: DNA
<213> ORGANISM: Artificial Sequence
<220> FEATURE:
<221> NAME/KEY: SCDRA5.1 primer
<222> LOCATION: 1..28
<223> OTHER INFORMATION: :

<400> SEQUENCE: 80
ggacctcgag atcaaagaag aacatgtg                                      28

<210> SEQ ID NO 81
<211> LENGTH: 28
<212> TYPE: DNA
<213> ORGANISM: Artificial Sequence
<220> FEATURE:
<221> NAME/KEY: SCDRA3.1 primer
<222> LOCATION: 1..28
<223> OTHER INFORMATION: :

<400> SEQUENCE: 81
agtcgctagc attggtgatc ggagtata                                      28

<210> SEQ ID NO 82
<211> LENGTH: 30
<212> TYPE: DNA
<213> ORGANISM: Artificial Sequence
<220> FEATURE:
<221> NAME/KEY: SCDRB5.1 primer
<222> LOCATION: 1..30
<223> OTHER INFORMATION: :

<400> SEQUENCE: 82
ccagccatgg ccggggacac ccgaccacgt                                    30

<210> SEQ ID NO 83
<211> LENGTH: 28
<212> TYPE: DNA
<213> ORGANISM: Artificial Sequence
<220> FEATURE:
<221> NAME/KEY: SCDRB3.1 primer
<222> LOCATION: 1..28
<223> OTHER INFORMATION: :

<400> SEQUENCE: 83
cactaagctt atacacagtc accttagg                                      28

<210> SEQ ID NO 84
<211> LENGTH: 18
<212> TYPE: DNA
<213> ORGANISM: Artificial Sequence
<220> FEATURE:
<221> NAME/KEY: VLSEQ1 primer
<222> LOCATION: 1..18
<223> OTHER INFORMATION: :

<400> SEQUENCE: 84
ctattgccta cggcagcc                                                 18

<210> SEQ ID NO 85
<211> LENGTH: 18
```

```
<212> TYPE: DNA
<213> ORGANISM: Artificial Sequence
<220> FEATURE:
<221> NAME/KEY: VLSEQ2 primer
<222> LOCATION: 1..18
<223> OTHER INFORMATION: :

<400> SEQUENCE: 85
agcgtcatcc ttcttcgc                                              18

<210> SEQ ID NO 86
<211> LENGTH: 14
<212> TYPE: DNA
<213> ORGANISM: Artificial Sequence
<220> FEATURE:
<221> NAME/KEY: VHSEQ1 primer
<222> LOCATION: 1..14
<223> OTHER INFORMATION: :

<400> SEQUENCE: 86
gatgctaaaa agac                                                  14

<210> SEQ ID NO 87
<211> LENGTH: 21
<212> TYPE: DNA
<213> ORGANISM: Artificial Sequence
<220> FEATURE:
<221> NAME/KEY: VHSEQ2 primer
<222> LOCATION: 1..21
<223> OTHER INFORMATION: :

<400> SEQUENCE: 87
aggtttttat ttgtcatcat c                                          21

<210> SEQ ID NO 88
<211> LENGTH: 17
<212> TYPE: DNA
<213> ORGANISM: Artificial Sequence
<220> FEATURE:
<221> NAME/KEY: Aint1 primer
<222> LOCATION: 1..17
<223> OTHER INFORMATION: :

<400> SEQUENCE: 88
ggacgatttg ccagctt                                               17

<210> SEQ ID NO 89
<211> LENGTH: 17
<212> TYPE: DNA
<213> ORGANISM: Artificial Sequence
<220> FEATURE:
<221> NAME/KEY: Aint2 primer
<222> LOCATION: 1..17
<223> OTHER INFORMATION: :

<400> SEQUENCE: 89
caccagaccc acagtca                                               17

<210> SEQ ID NO 90
<211> LENGTH: 17
<212> TYPE: DNA
<213> ORGANISM: Artificial Sequence
<220> FEATURE:
<221> NAME/KEY: Bint1 primer
<222> LOCATION: 1..17
<223> OTHER INFORMATION: :
```

-continued

```
<400> SEQUENCE: 90
gcttcgacag cgacgtg                                                    17

<210> SEQ ID NO 91
<211> LENGTH: 17
<212> TYPE: DNA
<213> ORGANISM: Artificial Sequence
<220> FEATURE:
<221> NAME/KEY: Bint2 primer
<222> LOCATION: 1..17
<223> OTHER INFORMATION: :

<400> SEQUENCE: 91
gtacacagtc accgtag                                                    17

<210> SEQ ID NO 92
<211> LENGTH: 17
<212> TYPE: DNA
<213> ORGANISM: Artificial Sequence
<220> FEATURE:
<221> NAME/KEY: Bint3 primer
<222> LOCATION: 1..17
<223> OTHER INFORMATION: :

<400> SEQUENCE: 92
accaggaggt tgtggtg                                                    17

<210> SEQ ID NO 93
<211> LENGTH: 17
<212> TYPE: DNA
<213> ORGANISM: Artificial Sequence
<220> FEATURE:
<221> NAME/KEY: Bint4 primer
<222> LOCATION: 1..17
<223> OTHER INFORMATION: :

<400> SEQUENCE: 93
gctcaggaat cctgttg                                                    17

<210> SEQ ID NO 94
<211> LENGTH: 20
<212> TYPE: DNA
<213> ORGANISM: Artificial Sequence
<220> FEATURE:
<221> NAME/KEY: pATD-FLAG linker
<222> LOCATION: 1..20
<223> OTHER INFORMATION: :

<400> SEQUENCE: 94
ctcgagacaa tgtcgctagc                                                 20

<210> SEQ ID NO 95
<211> LENGTH: 10
<212> TYPE: PRT
<213> ORGANISM: Artificial Sequence
<220> FEATURE:
<221> NAME/KEY: pATD-FLAG' linker
<222> LOCATION: 1..10
<223> OTHER INFORMATION: :

<400> SEQUENCE: 95

Leu Glu Thr Thr Ser Ala Asp Asp Ala Ser
1               5                   10

<210> SEQ ID NO 96
<211> LENGTH: 30
<212> TYPE: DNA
```

```
<213> ORGANISM: Artificial Sequence
<220> FEATURE:
<221> NAME/KEY: pATD-FLAG' linker
<222> LOCATION: 1..30
<223> OTHER INFORMATION: :

<400> SEQUENCE: 96
ctcgagacaa ctagtgcgga cgacgctagc                              30

<210> SEQ ID NO 97
<211> LENGTH: 24
<212> TYPE: DNA
<213> ORGANISM: Artificial Sequence
<220> FEATURE:
<221> NAME/KEY: XSN primer
<222> LOCATION: 1..24
<223> OTHER INFORMATION: :

<400> SEQUENCE: 97
tcgagacaac tagtgcggac gacg                                    24

<210> SEQ ID NO 98
<211> LENGTH: 24
<212> TYPE: DNA
<213> ORGANISM: Artificial Sequence
<220> FEATURE:
<221> NAME/KEY: NSX primer
<222> LOCATION: 1..24
<223> OTHER INFORMATION: :

<400> SEQUENCE: 98
ctagcgtcgt ccgcactagt tgtc                                    24

<210> SEQ ID NO 99
<211> LENGTH: 14
<212> TYPE: DNA
<213> ORGANISM: Artificial Sequence
<220> FEATURE:
<221> NAME/KEY: pCD-1 primer
<222> LOCATION: 1..14
<223> OTHER INFORMATION: :

<400> SEQUENCE: 99
gagaattcag gtac                                               14

<210> SEQ ID NO 100
<211> LENGTH: 15
<212> TYPE: DNA
<213> ORGANISM: Artificial Sequence
<220> FEATURE:
<221> NAME/KEY: pCD-2 primer
<222> LOCATION: 1..15
<223> OTHER INFORMATION: :

<400> SEQUENCE: 100
acgtctctta agtcc                                              15

<210> SEQ ID NO 101
<211> LENGTH: 9
<212> TYPE: DNA
<213> ORGANISM: Artificial Sequence
<220> FEATURE:
<221> NAME/KEY: sdDRtrunc-1 primer
<222> LOCATION: 1..9
<223> OTHER INFORMATION: :

<400> SEQUENCE: 101 agctttaag                                                      9
```

```
<210> SEQ ID NO 102
<211> LENGTH: 9
<212> TYPE: DNA
<213> ORGANISM: Artificial Sequence
<220> FEATURE:
<221> NAME/KEY: sdDRtrunc-2 primer
<222> LOCATION: 1..9
<223> OTHER INFORMATION: :

<400> SEQUENCE: 102 ctagcttaa                                                                          9
```